United States Patent
Radford et al.

(10) Patent No.: US 6,488,675 B1
(45) Date of Patent: *Dec. 3, 2002

(54) CONTAMINATED MEDICAL WASTE DISPOSAL SYSTEM AND METHOD

(76) Inventors: Fred R. Radford, 16707 S.E. Green Valley Rd., Auburn, WA (US) 98002; Drew R. Radford, 8112-39th Ave. S.W., Seattle, WA (US) 98136; Jack D. Howard, 16911 112th Place N.E., Bothell, WA (US) 98011

( * ) Notice: Subject to any disclaimer, the term of this patent is extended or adjusted under 35 U.S.C. 154(b) by 0 days.

This patent is subject to a terminal disclaimer.

(21) Appl. No.: 09/418,895

(22) Filed: Oct. 15, 1999

Related U.S. Application Data

(63) Continuation of application No. 08/789,370, filed on Jan. 24, 1997, now Pat. No. 6,027,490.
(60) Provisional application No. 60/010,525, filed on Jan. 24, 1996.

(51) Int. Cl.[7] .................................................. A61M 1/00
(52) U.S. Cl. ........................ 604/540; 604/317; 604/541
(58) Field of Search ................................ 604/317–326, 604/540, 541; 220/770; 588/258

(56) References Cited

U.S. PATENT DOCUMENTS

| | | |
|---|---|---|
| 1,535,604 A | 4/1925 | Hendricks |
| 2,312,950 A | 3/1943 | Zimarik |
| 2,647,384 A | 8/1953 | Erlanger |
| 2,848,996 A | 8/1958 | Kowal |
| 2,896,643 A | 7/1959 | Ottoson |
| 2,936,753 A | 5/1960 | Trace |
| 2,936,757 A | 5/1960 | Trace |
| 3,014,481 A | 12/1961 | Rumble, Jr. et al. |
| 3,044,285 A | 7/1962 | Koplin |
| 3,075,524 A | 1/1963 | Clark, Jr. |
| 3,139,238 A | 6/1964 | Norstrud et al. |
| 3,163,149 A | 12/1964 | Ivey |
| 3,191,600 A | 6/1965 | Everett |
| 3,435,834 A | 4/1969 | Cooper |
| 3,578,744 A | 5/1971 | McDonald, Jr. |
| 3,645,283 A | 2/1972 | Cassells |
| 3,672,391 A | 6/1972 | Livingston et al. |

(List continued on next page.)

Primary Examiner—Kim M. Lewis
(74) Attorney, Agent, or Firm—Robert B. Hughes; Hughes Law Firm, PLLC

(57) ABSTRACT

A system for collecting, transporting and disposing of biofluids, such as those collected in a hospital or other health facility, in a manner to protect an operator and related support devices and systems from contact with potentially hazardous biofluids. The system provides a portable container adapted to be connected to the patient's suction tubes and also to the vacuum source, so that biofluid is collected in the container. The container is then moved to a base disposal location, and an outlet valve of the valve and connecting assembly of the container is connected to the base assembly, and the valve of the container moved to an open position. A sealed discharge passageway is formed, and the biofluid flows through this passageway. The valve of the container is closed, and the container removed and either disposed of, or washed, and sanitized so as to be ready for reuse. There is also provided a plug and manifold assembly to removably interfit with the container. The plug and manifold assembly can be made disposable or can be washed and disinfected for reuse.

53 Claims, 85 Drawing Sheets

U.S. PATENT DOCUMENTS

| | | |
|---|---|---|
| 3,678,955 A | 7/1972 | Nelson |
| 3,799,396 A | 3/1974 | Bender |
| 3,802,447 A | 4/1974 | Jurjans |
| 3,804,297 A | 4/1974 | Griparis |
| 3,833,001 A | 9/1974 | Abrahams et al. |
| 3,833,417 A | 9/1974 | Kleimola et al. |
| 3,881,328 A | 5/1975 | Robinson |
| 3,901,408 A | 8/1975 | Boden et al. |
| 3,916,924 A | 11/1975 | McGowan |
| 3,929,133 A | 12/1975 | Ragab |
| 4,039,351 A | 8/1977 | Butler |
| 4,090,502 A | 5/1978 | Tajika |
| 4,092,993 A | 6/1978 | Stevenson |
| 4,105,031 A | 8/1978 | Kurtz et al. |
| 4,106,155 A | 8/1978 | Fosslien |
| 4,111,716 A | 9/1978 | Stevenson |
| 4,119,114 A | 10/1978 | Bolton et al. |
| 4,135,515 A | 1/1979 | Muriot |
| 4,142,545 A | 3/1979 | Billigmeier |
| 4,144,901 A | 3/1979 | Stevenson |
| RE30,097 E | 9/1979 | Gillespie |
| 4,213,796 A | 7/1980 | Shaffer |
| 4,244,364 A | 1/1981 | Grushkin |
| 4,275,726 A | 6/1981 | Schael |
| 4,277,290 A | 7/1981 | Andrews et al. |
| 4,306,557 A | 12/1981 | North |
| 4,307,741 A | 12/1981 | Rossi |
| 4,312,463 A | 1/1982 | Daby |
| 4,319,568 A | 3/1982 | Tregoning |
| 4,344,469 A | 8/1982 | Brown |
| 4,384,580 A | 5/1983 | Leviton |
| 4,403,611 A | 9/1983 | Babbitt et al. |
| 4,417,891 A | 11/1983 | Cianci |
| 4,449,976 A | 5/1984 | Kamen |
| 4,452,268 A | 6/1984 | Icking et al. |
| 4,493,695 A | 1/1985 | Cook |
| 4,540,413 A | 9/1985 | Russo |
| 4,626,248 A | 12/1986 | Scheller |
| 4,627,833 A | 12/1986 | Cook |
| 4,642,093 A | 2/1987 | Harle |
| 4,646,786 A | 3/1987 | Herder et al. |
| 4,653,010 A | 3/1987 | Figler et al. |
| 4,673,006 A | 6/1987 | Speck |
| 4,687,121 A | 8/1987 | Copeland |
| 4,832,689 A | 5/1989 | Mauerer et al. |
| 4,838,872 A | 6/1989 | Sherlock |
| 4,863,446 A | 9/1989 | Parker |
| 4,905,325 A | 3/1990 | Colditz |
| 4,915,119 A | 4/1990 | Franklin |
| 4,923,438 A | 5/1990 | Vasconcellos et al. |
| RE33,250 E | 7/1990 | Cook |
| 4,955,391 A | 9/1990 | Parker et al. |
| 4,957,491 A | 9/1990 | Parker |
| 5,117,857 A | 6/1992 | Smith |
| 5,135,485 A | 8/1992 | Cohen et al. |
| 5,185,007 A | 2/1993 | Middaugh et al. |
| 5,242,434 A | 9/1993 | Terry |
| 5,242,435 A | 9/1993 | Murji et al. |
| 5,282,744 A | 2/1994 | Meyer |
| 5,380,308 A | 1/1995 | Gunya et al. |
| 5,401,261 A | 3/1995 | Gunya et al. |
| 5,449,009 A | 9/1995 | Kerwin et al. |
| 5,607,411 A | 3/1997 | Heironimus et al. |
| 5,620,428 A | 4/1997 | Hand |
| 5,637,103 A | 6/1997 | Kerwin et al. |
| 5,741,237 A | 4/1998 | Walker |
| 5,776,260 A | 7/1998 | Dunn et al. |
| 5,901,717 A | 5/1999 | Dunn et al. |
| 5,975,096 A | 11/1999 | Dunn et al. |
| 6,027,490 A * | 2/2000 | Radford ..................... 604/540 |

* cited by examiner

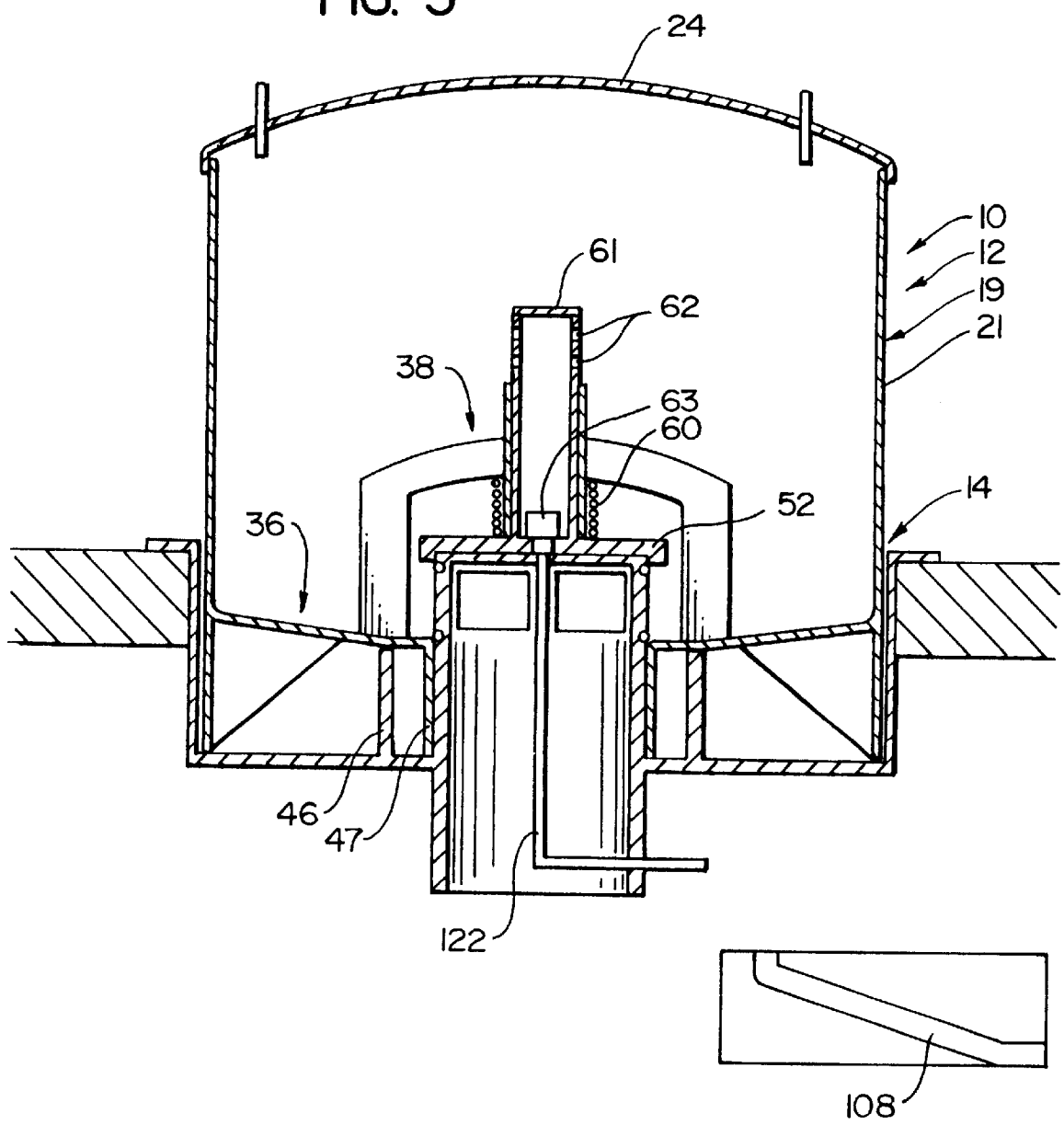

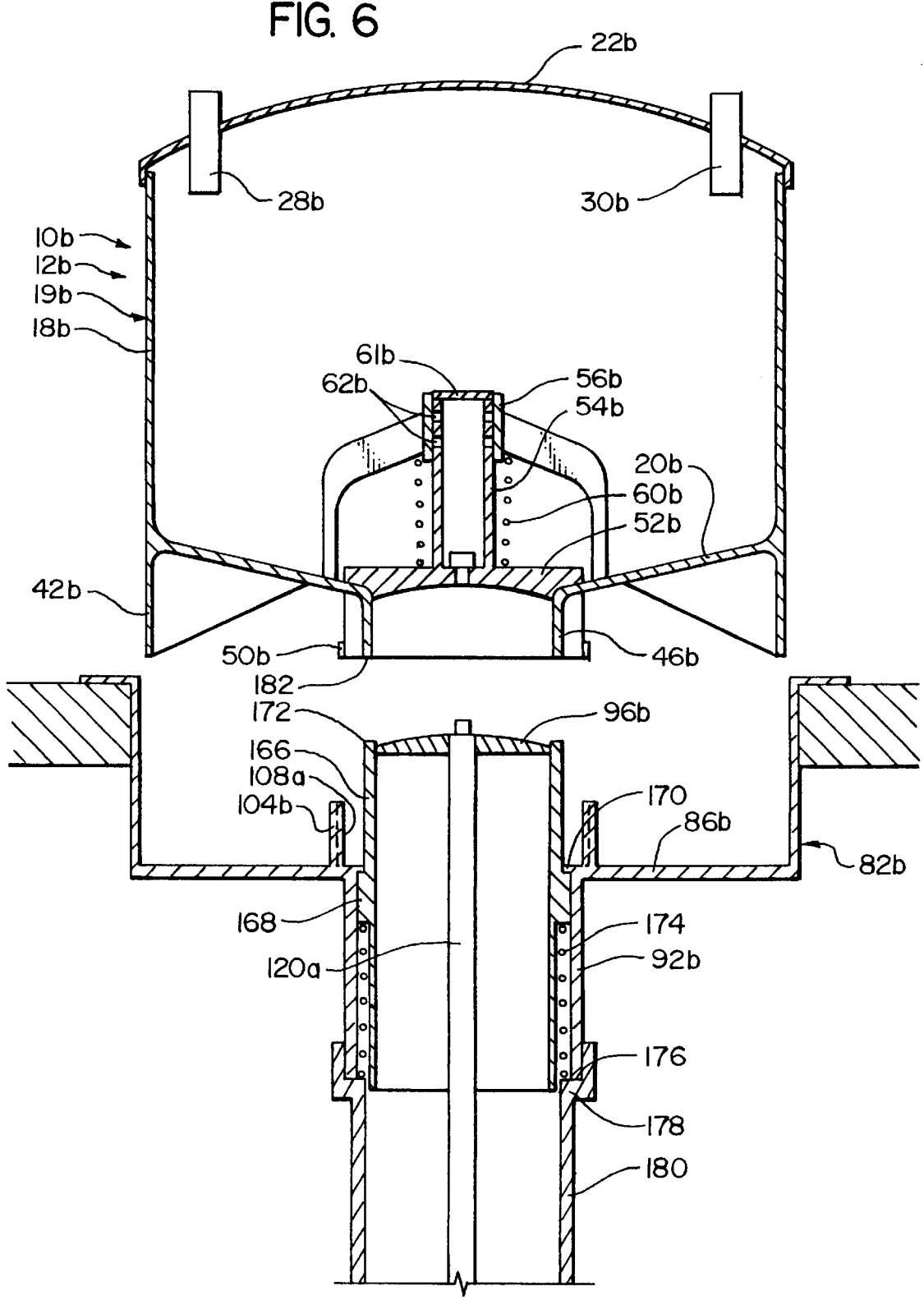

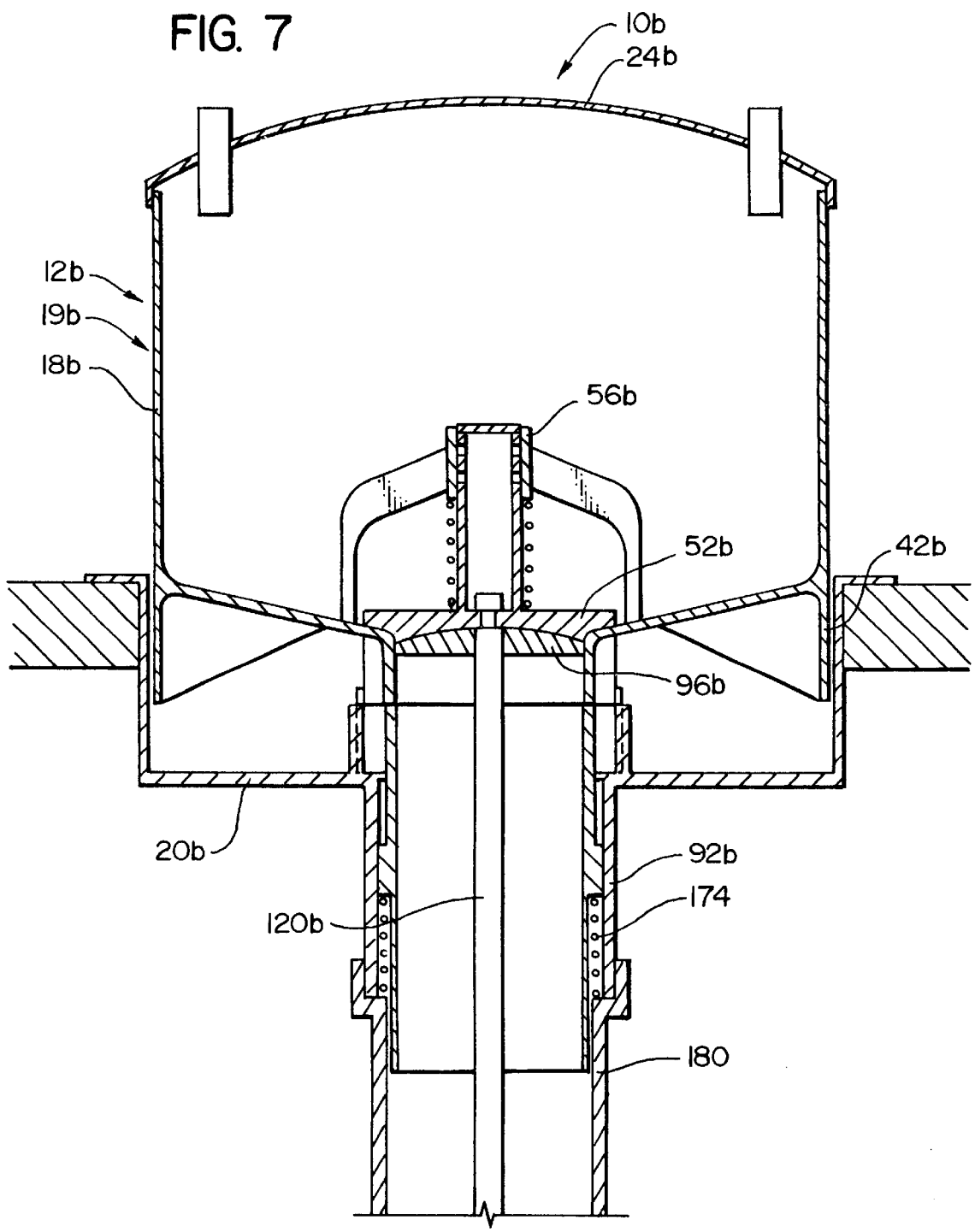

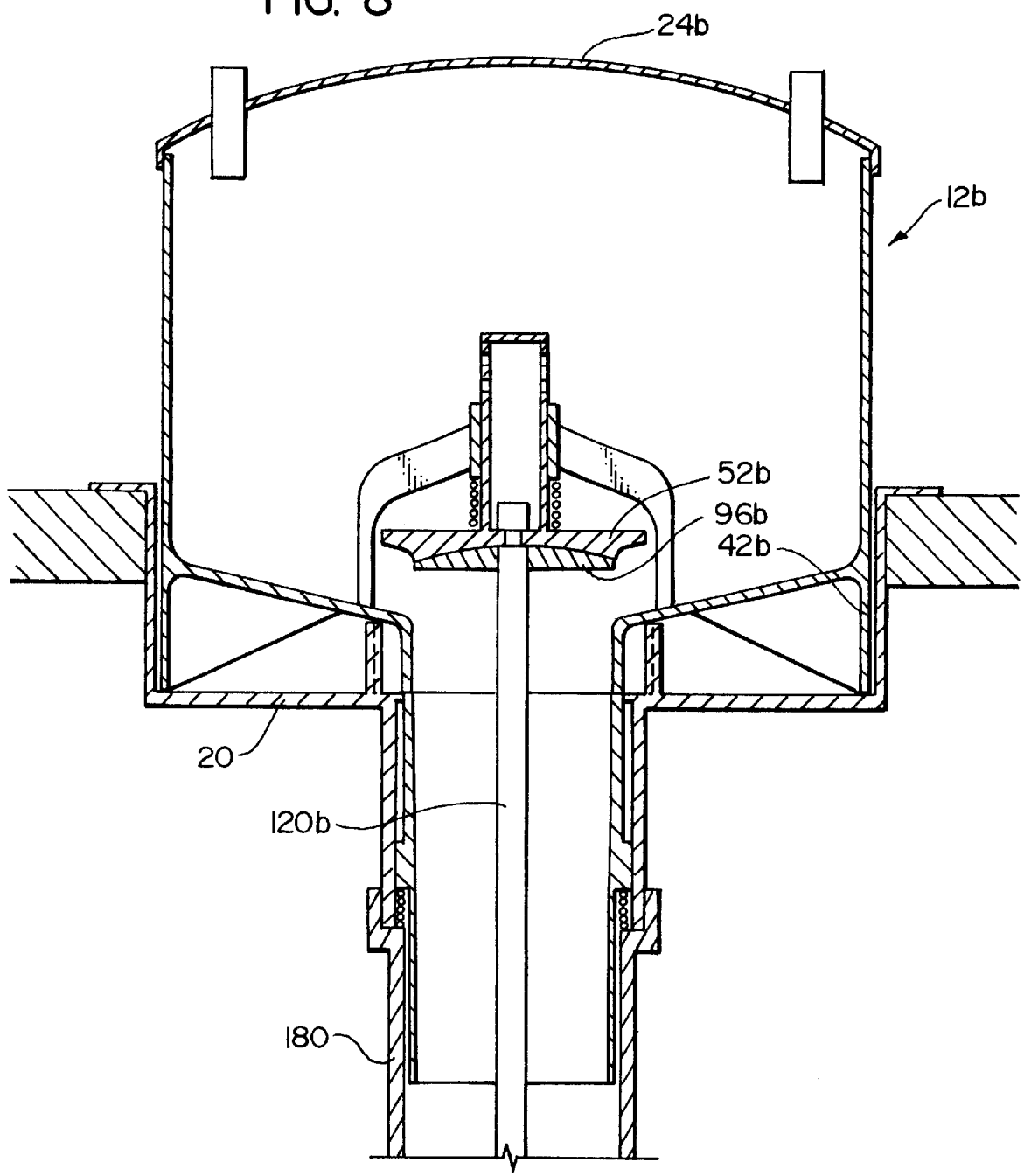

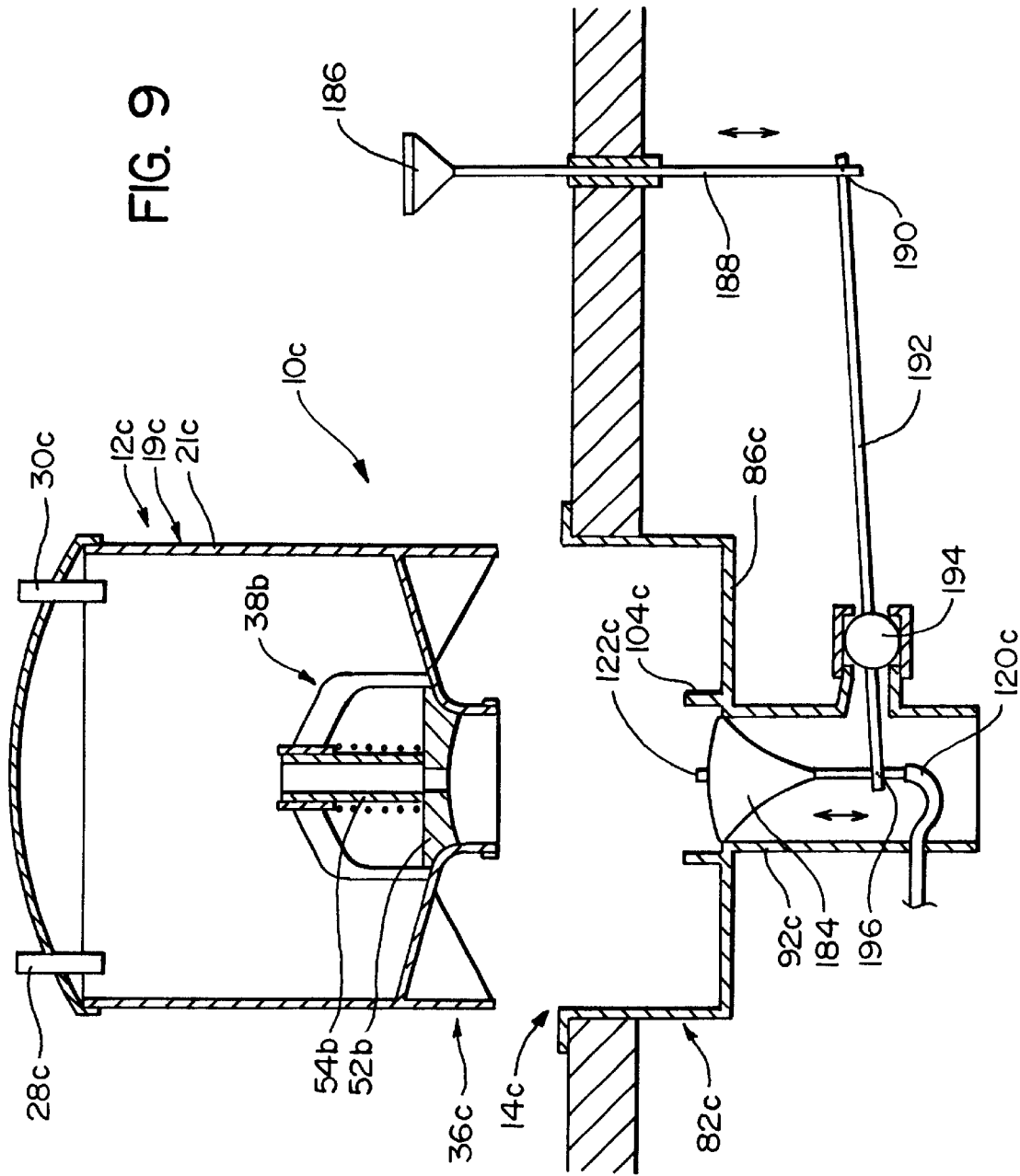

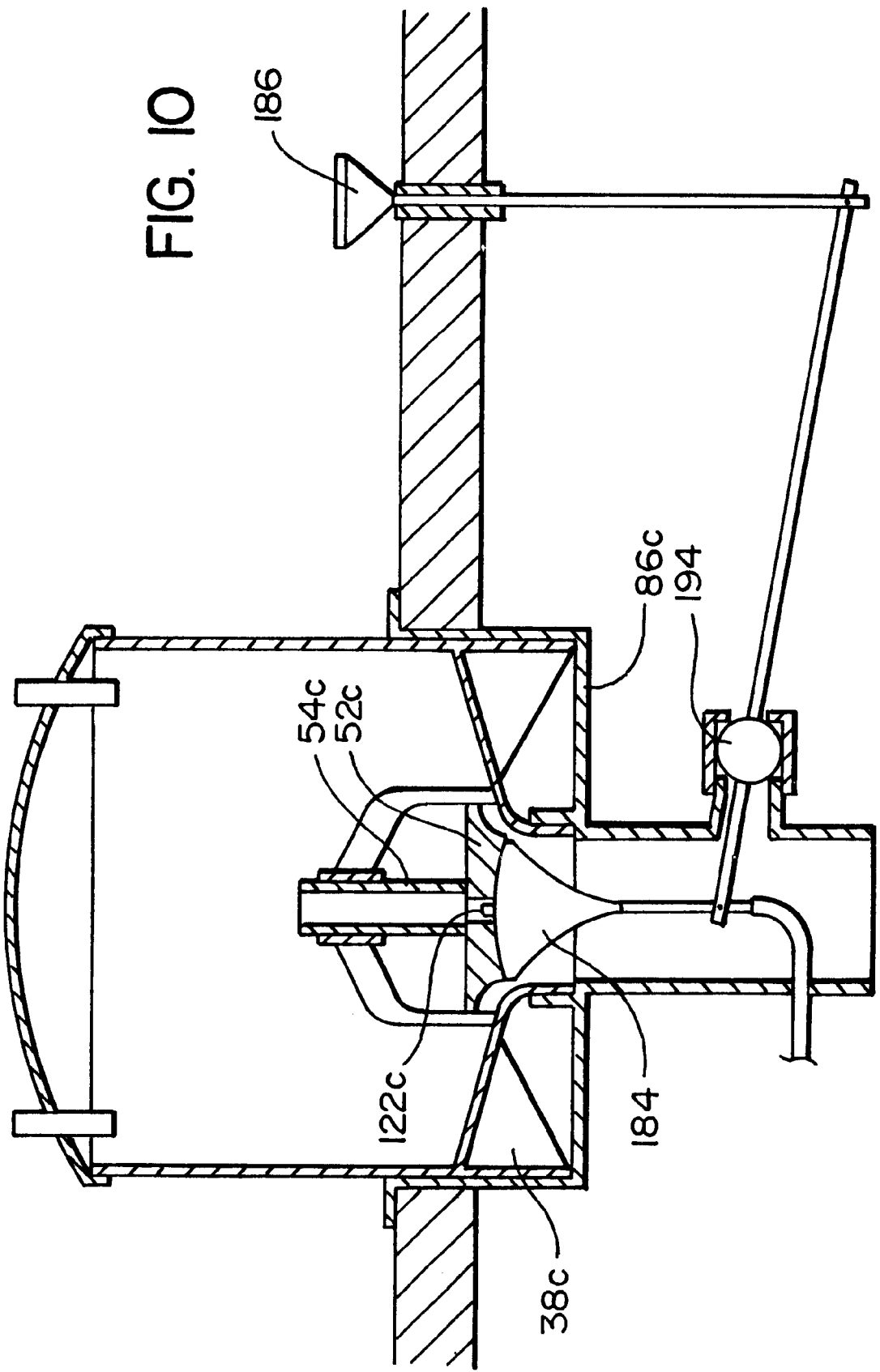

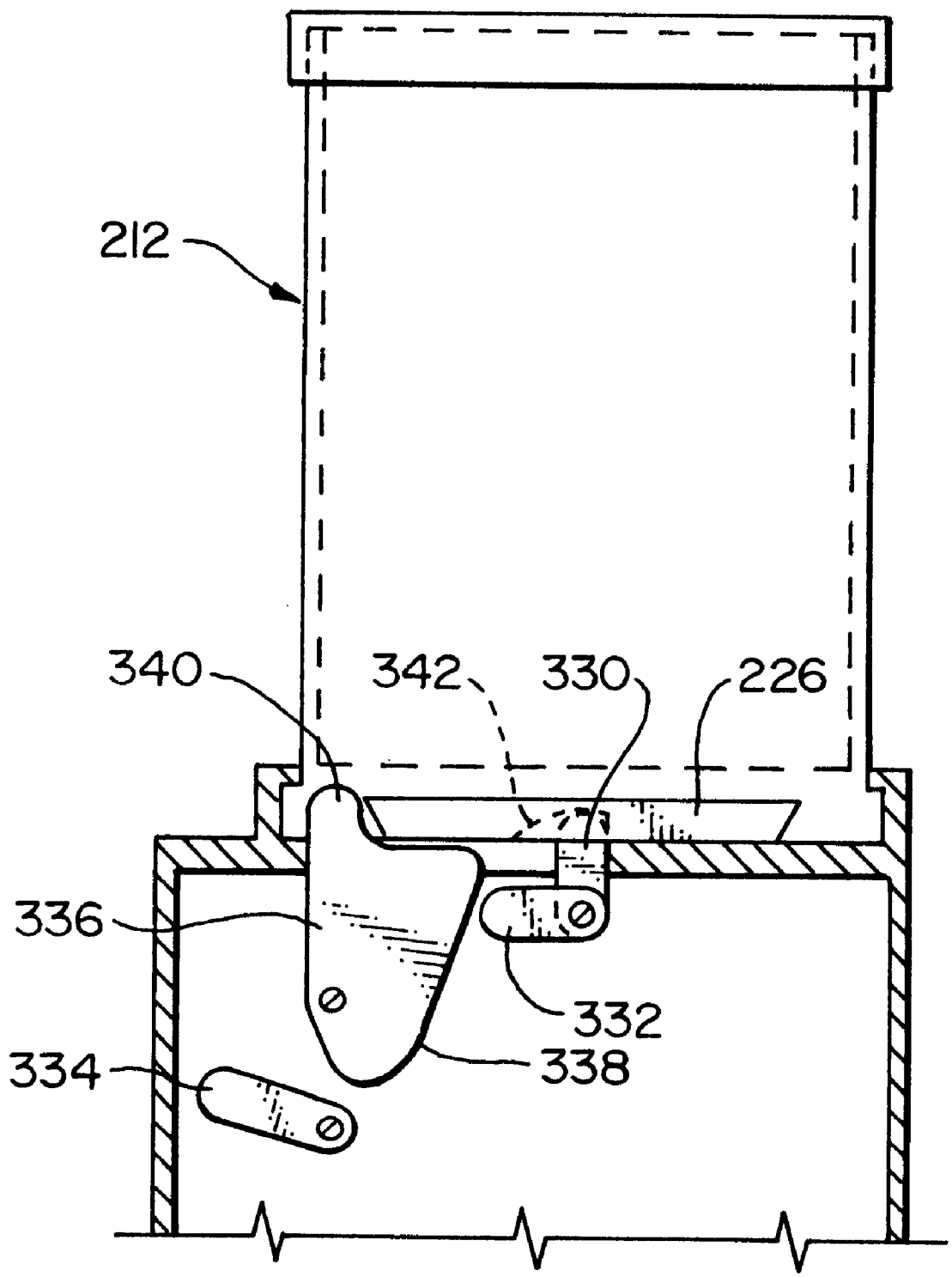

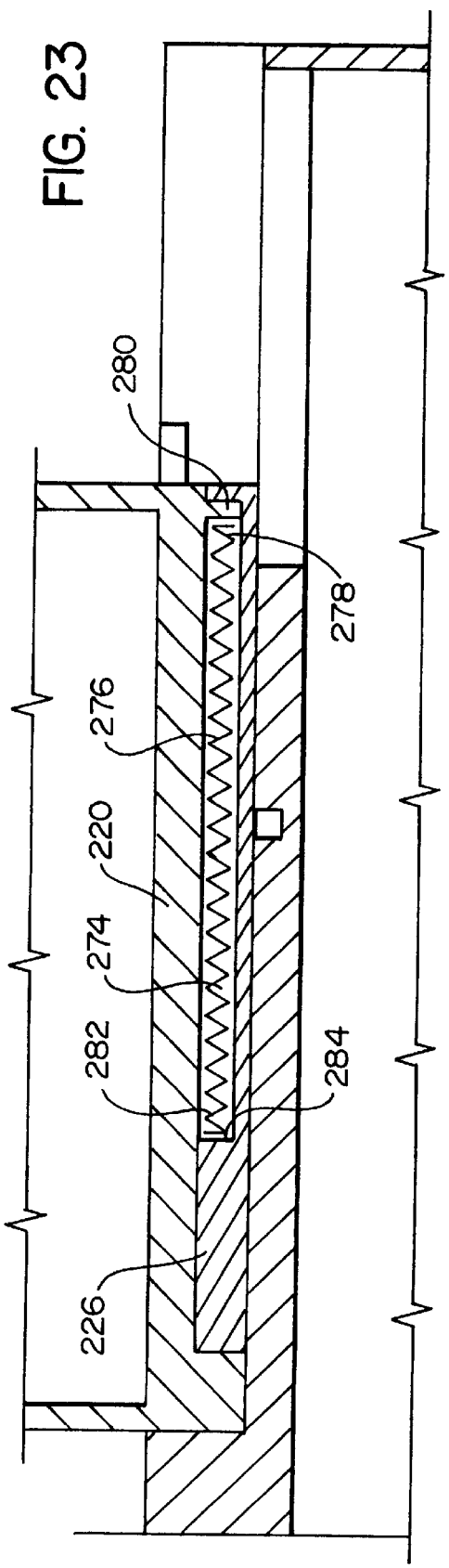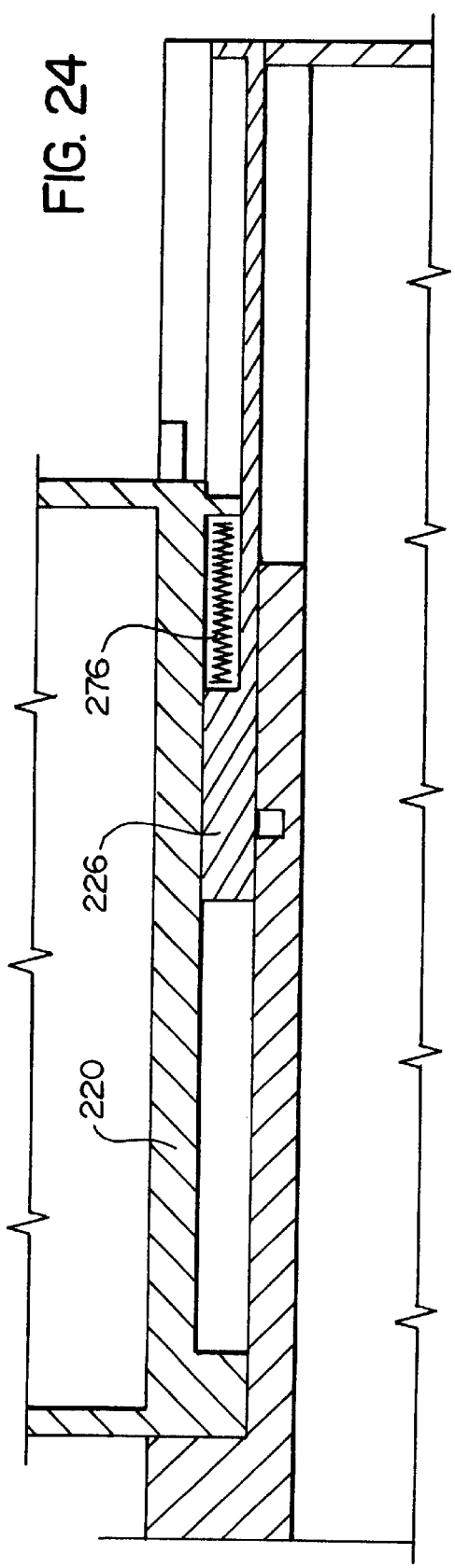

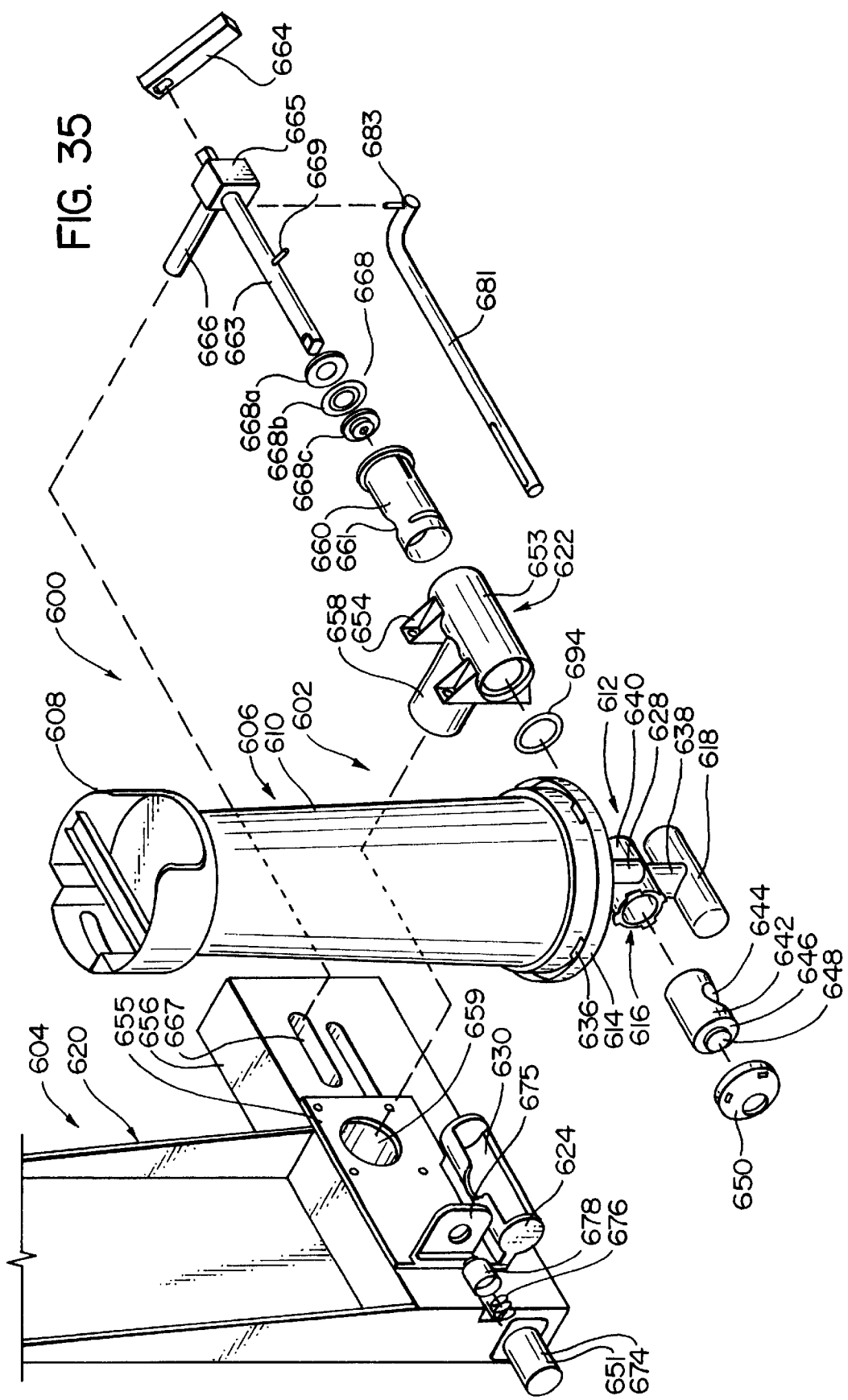

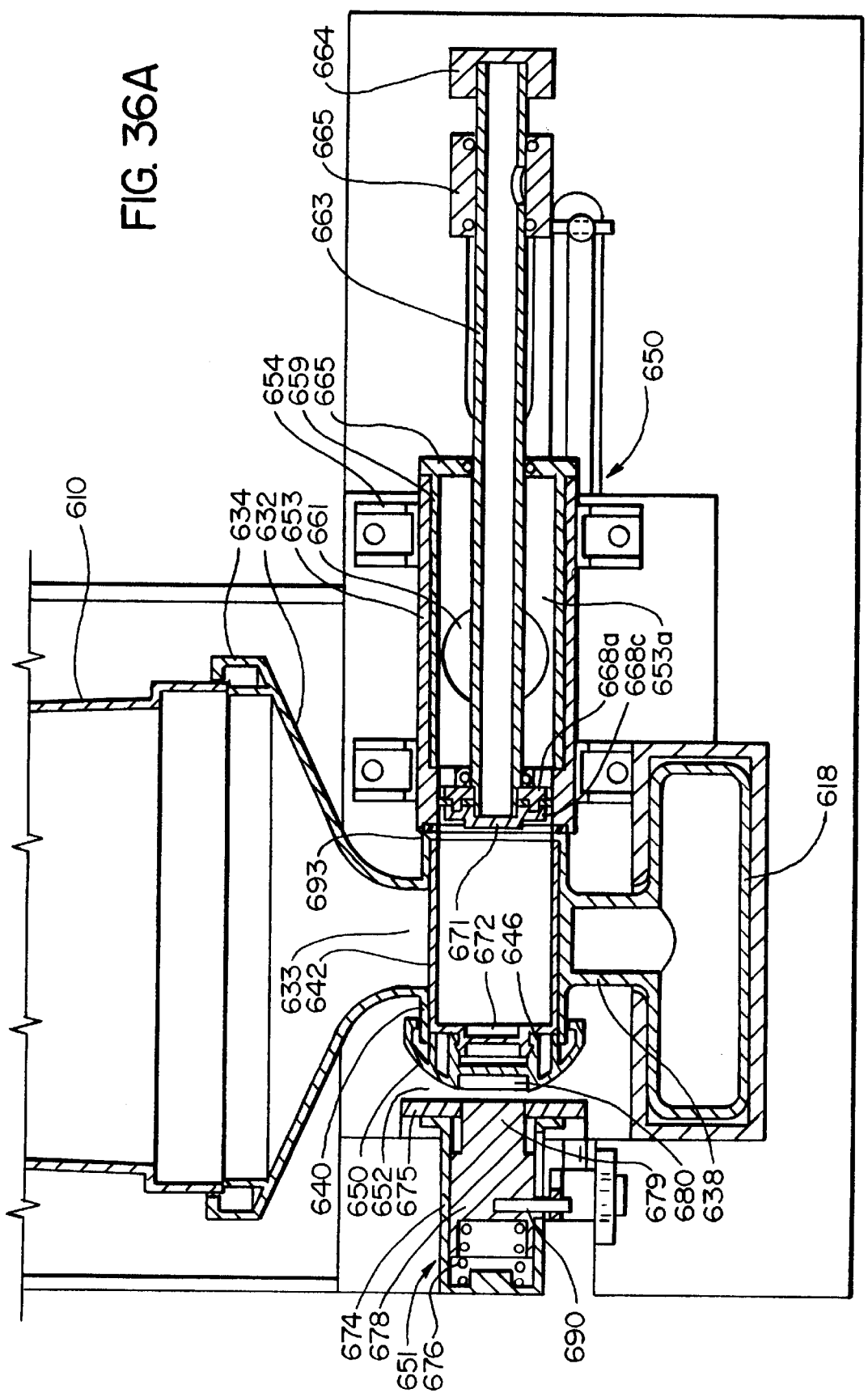

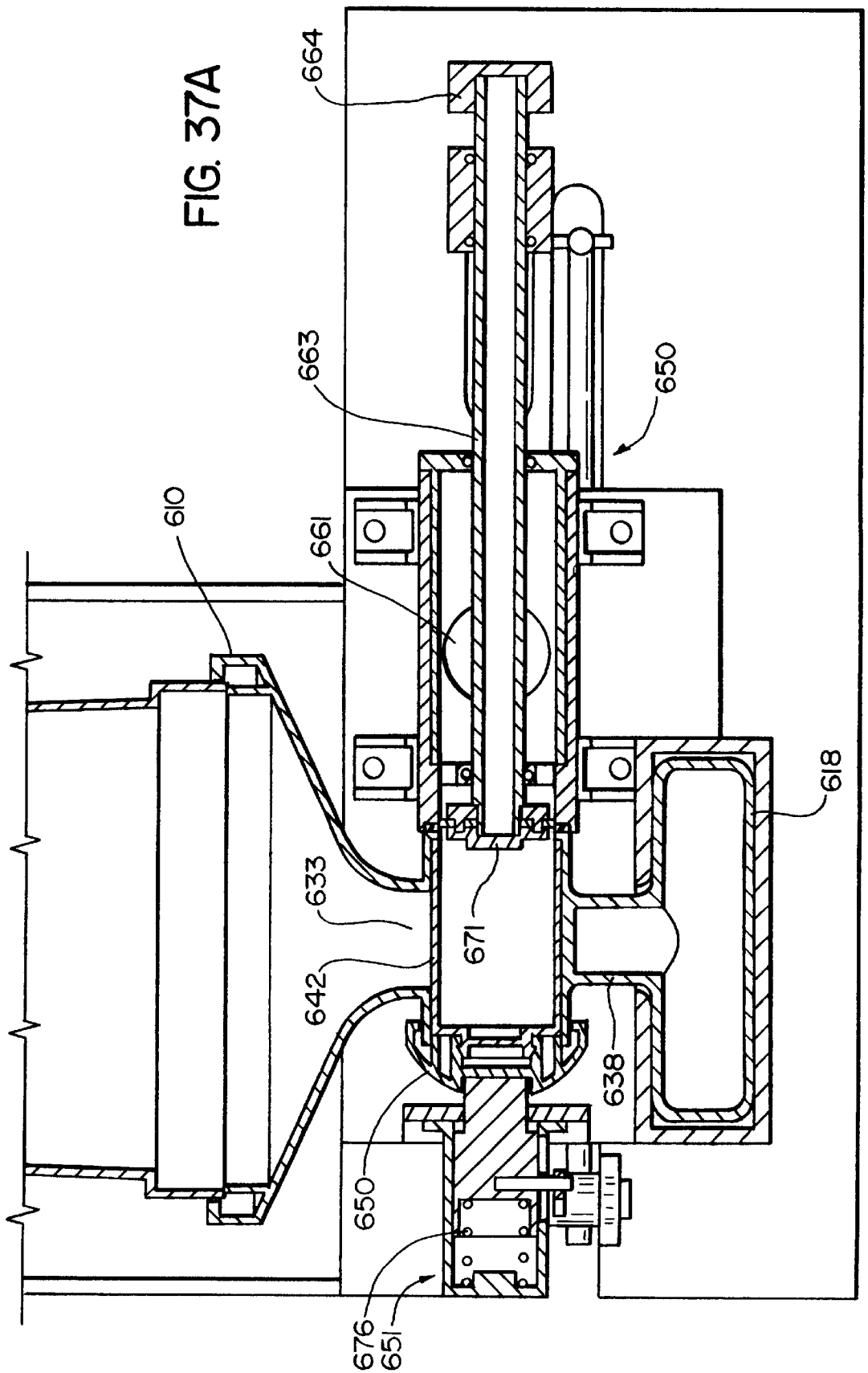

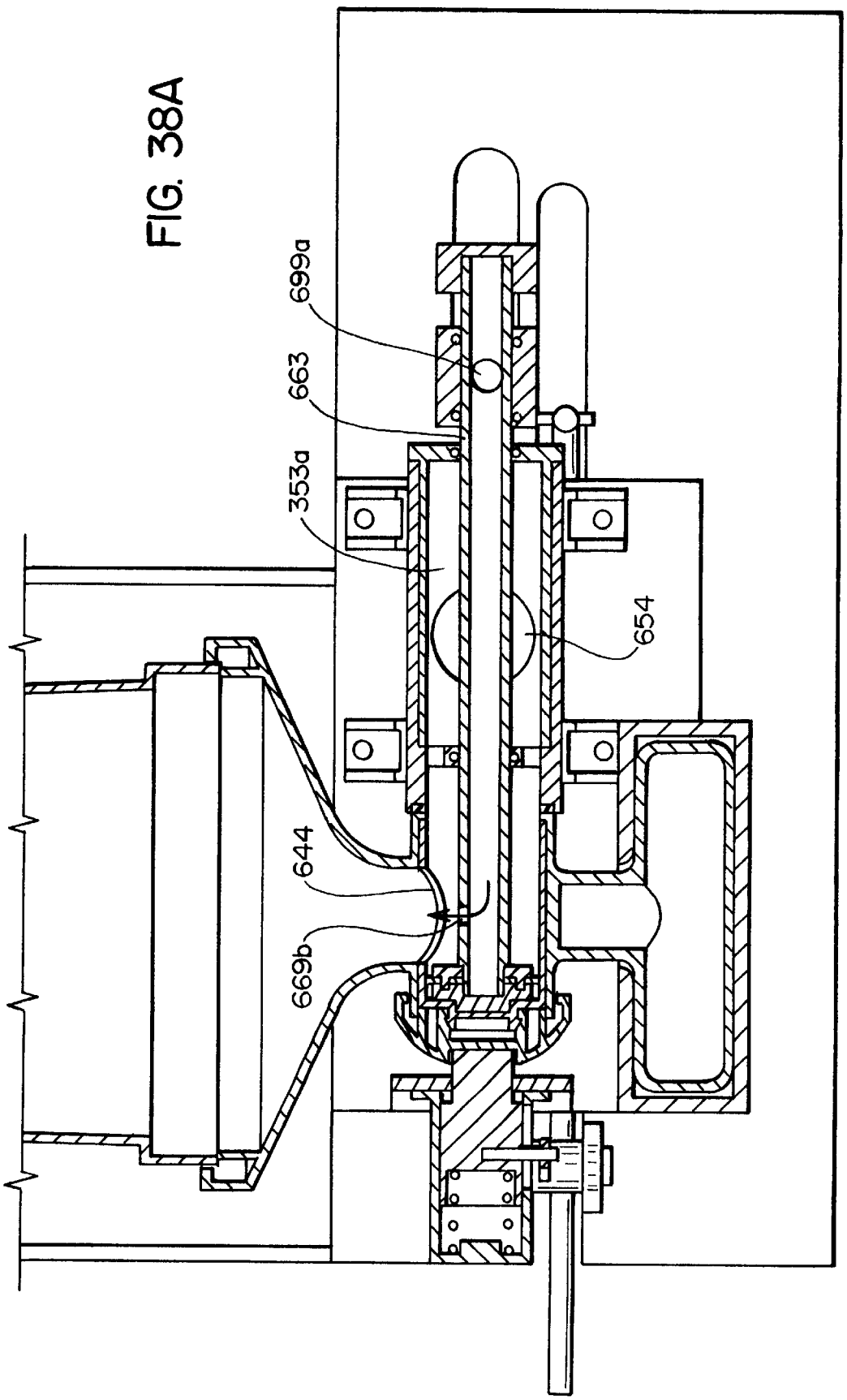

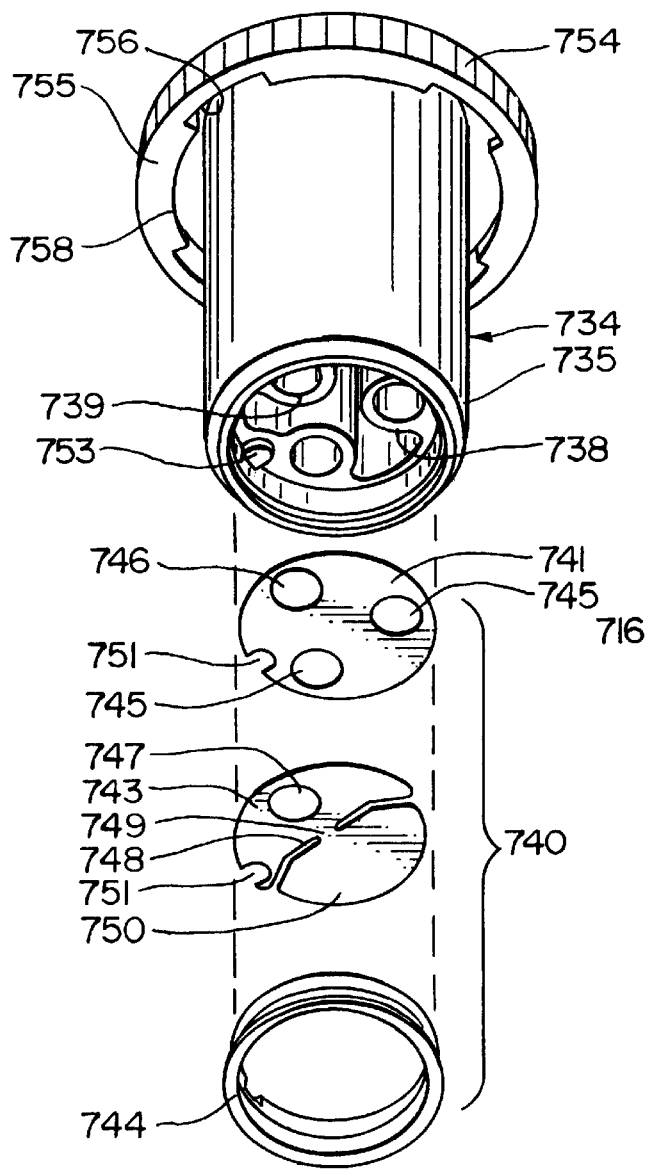
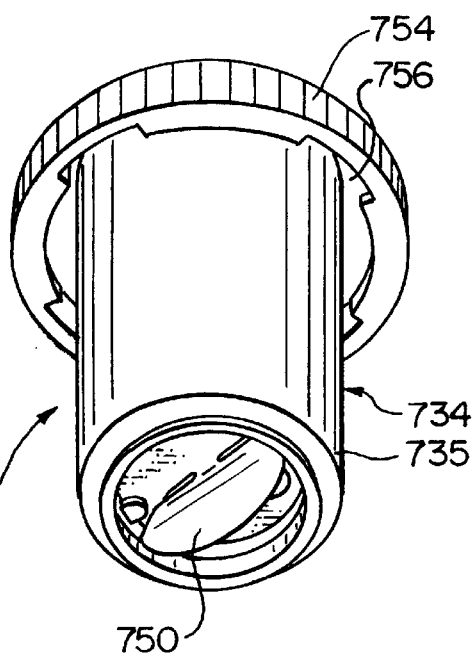
FIG. 43A
FIG. 43B

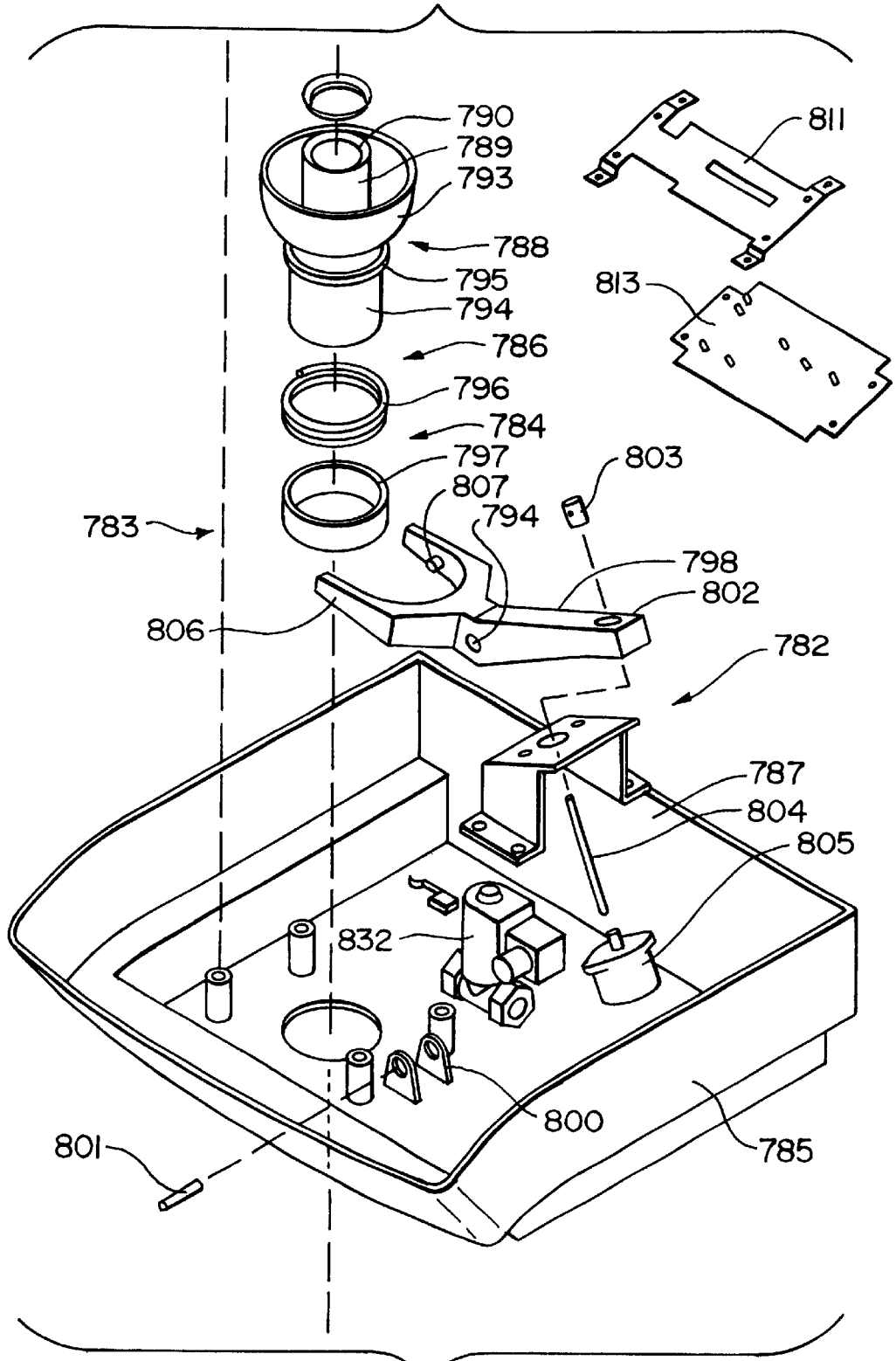

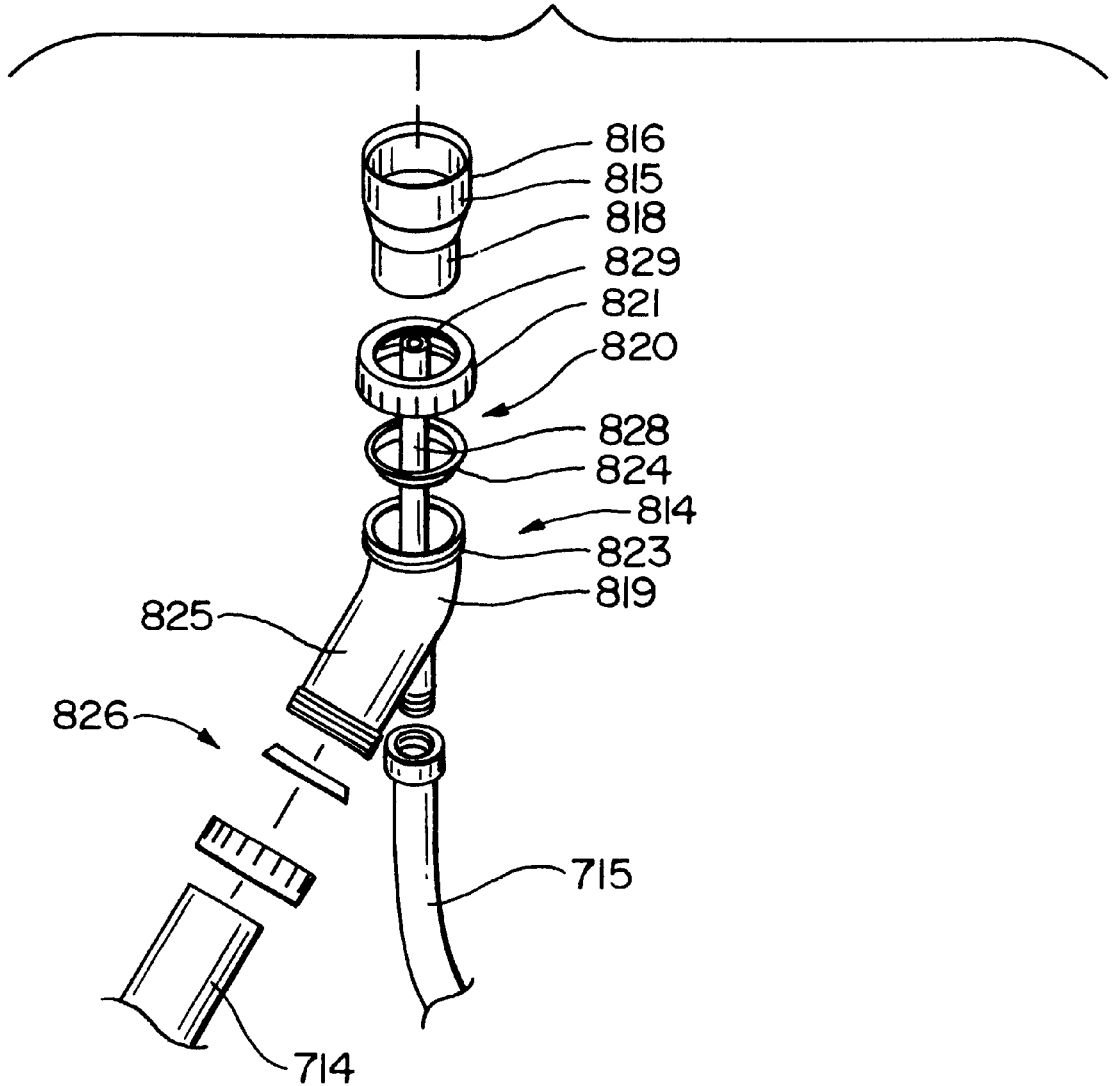

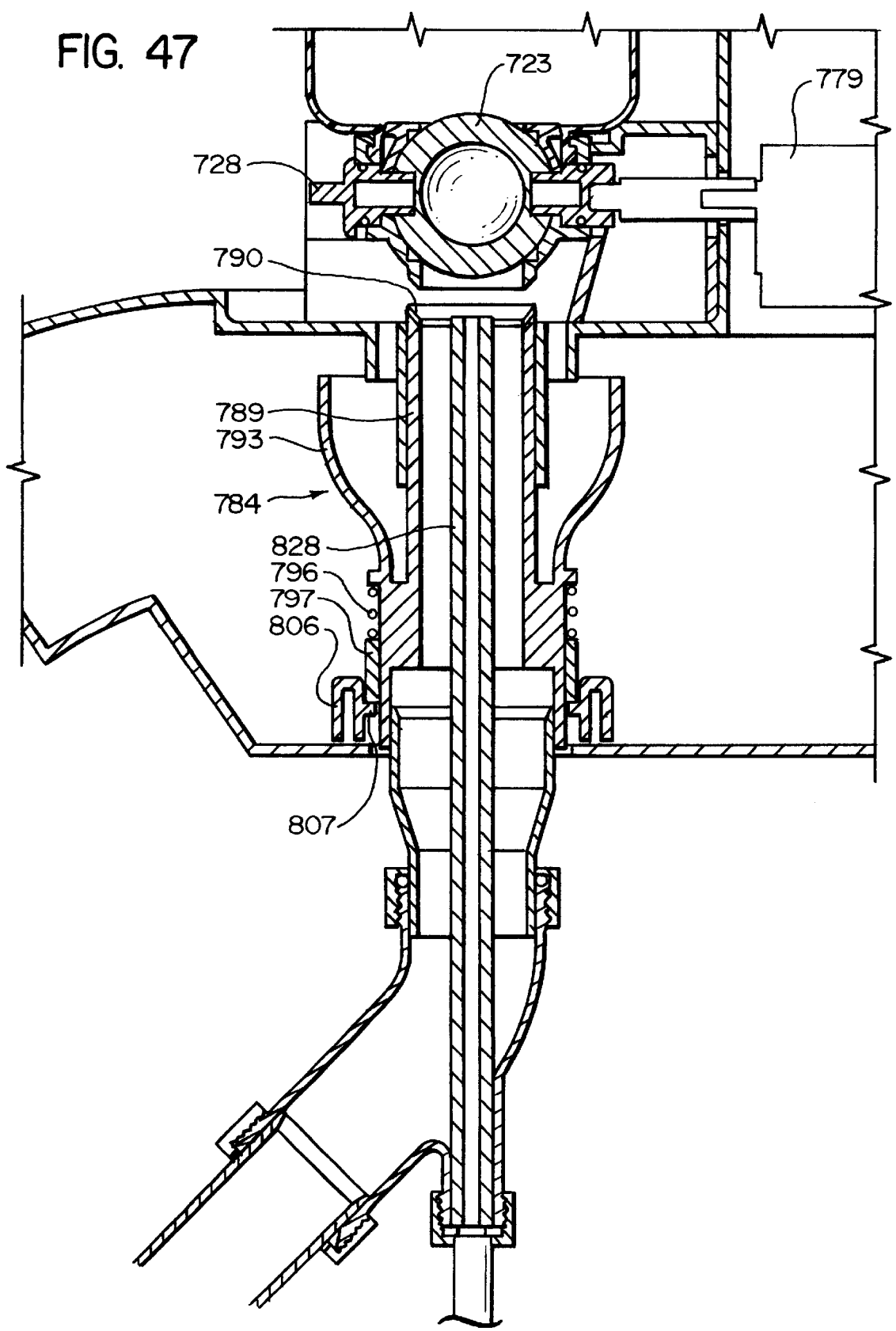

CONTAMINATED MEDICAL WASTE DISPOSAL SYSTEM AND METHOD

This application is a Continuation of U.S. patent application Ser. No. 08/789,370 filed on Jan. 24, 1997, now U.S. Pat. No. 6,027,490 which is related to, based upon and claims priority of Provisional Serial No. 60/010,525 filed Jan. 24, 1996.

FIELD OF THE INVENTION

The present invention relates to a system and method of disposing of contaminated waste, particularly medical waste, and more particularly to such a system and method where at least the main components of the system are reusable, and the waste can be safely disposed of into a conventional sewer system, or in containers which may be transported to other suitable locations (or sewers).

BACKGROUND OF THE INVENTION

It has long been a serious problem and an expensive process to collect, and dispose of, contaminated biological waste in a hospital or other health care facility, in a safe and sanitary manner. The general system which has been in use is to direct the biological waste into a disposal container at the location where it is being generated, seal this container in a manner to isolate the waste and transport each such container to a central collecting facility at the hospital, where it is possibly sterilized, after which these are then taken to a waste disposal site. The alternative is to dispose of the fluid by pouring it into sewer or toilets.

One common example of this is the collection of waste when a suctioning process is being conducted with the patient. The suctioning tube is positioned to withdraw fluid or viscous material from the patient's breathing airways and to carry this material into a container. The interior chamber of the container is connected to a vacuum source, and the material from the patient collects in the bottom of the container. Periodically, the container is disconnected from the suction tube and the vacuum source, sealed, and then taken to the collecting location in the hospital. Then another disposable container is connected to the suctioning tube and the vacuum source, with the above process being repeated. If the alternative to pour the contents out is chosen, splashing may/will endanger the person and contaminate the environment.

It has long been known in the health care field that if contaminated biological waste is delivered into a conventional sewer system, at such time as the biological waste becomes sufficiently diluted by the large volume of sewage in the system, it then becomes harmless. However, to the best knowledge of the applicants herein, in spite of the fact that this means of disposal has been known for some period of time, there has not been devised a method to make use of this in a safe and practical manner in a hospital or other health care facility.

Thus, the main method of disposing of such waste still remains to seal the collected waste in a disposable container at the location where it is generated, and then deliver this sealed and contained waste (still in a special container) to a distant disposal site for contaminated medical waste or openly pour it into common toilets or sewers. The expense associated with the first type of waste disposal system represents a substantial part of the costs for health care in hospitals and the like. And the second is a risk to both staff and patients.

A search of the patent literature has disclosed a number of patents, these being the following:

U.S. Pat. No. 5,282,744 (Meyer) discloses a system for withdrawing and disposing of dental waste. There is provided a plurality of mouth aspirators 10, and a suction is applied to a container 11 to draw the material into the container. The container is mounted to a support and drain assembly 12. There is a valve means 23 that is closed when the container is subjected to suction, and this is opened to permit the contents of the container 11 to flow into the assembly 12 and into a sewer. There is in the container 11 a liquid level sensor 26 that is connected to a relay 29 in the control panel 30 for the vacuum pump 13.

U.S. Pat. No. 4,923,438 (Vasconcellos et al) discloses a blood recovery system where there are "blood cardiotomy reservoirs" where blood is taken from the patient for subsequent reinfusion into the patient. There is a vacuum storage level with a blood aspiration port into which the blood is drawn by the vacuum. This accumulates in the upper chamber 20 which is valved to the chamber 22 by a valve 42. There is a valve 30 which is held closed at 32. Movement of a lever 34 opens the valve element 30 so that the blood drains into chamber 24 and can be drained out at 26.

U.S. Pat. No. 4,838,872 (Sherlock) discloses a blood collecting bag 16 that is provided with a drain element that is closed by a member 75. Means are provided to maintain the bag in an expanded position. The blood can be reinfused back to the patient.

U.S. Pat. No. 3,833,001 (Abrahams et al) shows a "portable, self-cleansing apparatus for aspiration and removal of sinus fluids and/or tracheal secretions, etc." Tap water is directed from a faucet through a venturi which creates a suction in the container, so that the sinus fluid or other secretions are drawn into the tube 82 and into a container. The water and collected fluids accumulate in the bottom and are ejected through a lower outlet 18 that is positioned above a drain 20 of a sink 16

U.S. Pat. No. 2,936,753 (Trace) shows a surgical drainage apparatus with a collection bag and a lower drain opening. In one embodiment (see FIGS. 6 and 7) a suction can be applied. The apparatus is arranged to prevent backward flow up the drainage tube when there is a negative pressure in the drainage tube.

U.S. Pat. No. 1,535,604 (Hendricks) shows a pan for washing dishes, and this pan is provided with a drainage valve, with a valve closure element operated by a lever system comprising members 21 and 24.

SUMMARY OF THE INVENTION

The system and method of the present invention is arranged for the collection, transport and disposal of biofluids, particularly in a hospital or other health care environment. This is done in a manner to protect the operator and related support devices and systems from contact with potentially hazardous biofluids. In this system, the biofluid vessel and other components are able to be sanitized for further reprocessing or disposal. This system is a splash free, drip free system which alleviates the problem of cross contamination, and thus alleviates at least to some extent the problem of nosocomial infections (hospital acquired infections). Further, this system alleviates to a substantially extent the problem of aerosolization of potentially hazardous biofluids. In the present system, there is provided a reusable or disposal biofluid container which serves the function of a collection, transport, and disposal vessel. This is done with an interlocking/coupling mechanism which enables a sealed path and contamination free disposal of the biofluid contents of the container when mated to an interlocking/coupling appliance of a base assembly.

The system comprises a containing assembly which in turn comprises a portable container defining a biofluid containing chamber. There is fluid inlet and outlet means to receive biofluids from a patient and direct the biofluid into the containing chamber, and also to discharge the biofluid from the chamber. The containing assembly has a container interconnecting means.

This system also comprises a base assembly, which comprises a base structure having a receiving area to receive a container in an operating position. There is also a base interconnecting means arranged to interconnect with the container interconnecting means, with the container in the operating position. Further, the base assembly has disposal means defining a disposal passageway and leading to a disposal location.

The containing assembly and the base assembly are arranged so that with the container in the operating position, and with interconnection by the container interconnecting means and the base interconnecting means, the containing assembly and the base assembly provide a discharge passageway from the chamber to the disposal passageway.

The containing assembly is positioned at a collecting location to receive biofluid, and then moved to the base assembly. The container interconnecting means and the base interconnecting means are interconnected, and the biofluid delivered to a disposal location.

The fluid inlet and outlet means provides a sealed flow passageway extending between the containing chamber and the location exterior of the container, and further comprises valve means having a closed position to block the flow passageway and an open to permit flow through the flow passageway. The inlet and outlet means comprises inlet means which defines at least one inlet passageway by which biofluid can be moved from a location exterior of the container into the containing chamber.

In some of the preferred embodiments, the fluid inlet and outlet means comprises a closure and fluid inlet device which in turn comprises a closure housing configured and arranged to be positioned in a container opening and more particularly in a valve passageway when the valve is in its open position. Also, this closure and fluid inlet device has at least one inlet passageway therein for inflow of biofluid into the chamber, and in the preferred form, there is check valve means to permit flow from an exterior location through the inlet passageway into the containing chamber, but to block flow from the containing chamber outwardly to the inlet passageway. Further, in the preferred form, this device comprises an outlet passageway permitting gaseous flow outwardly fro the containing chamber to a suction source.

In a broader sense, the closure and fluid inlet means is arranged to provide into a through opening which leads to the containing chamber, with an inlet end of the inlet means having a connecting portion adapted to be connected to a biofluid tube means to carry biofluid into the containing chamber. This closure and fluid inlet device is removably mounted in the through opening in a manner that it seals the through opening. The closure and fluid inlet device can be removed from the opening with or without a suction tube connected thereto for disposal at a disposal location. In a preferred form, this closure and fluid inlet device comprises a housing having an outer surrounding housing section which fits in sealing engagement with the through opening, and there are tubular passageway inlet means and tubular passageway outlet means positioned within the housing. A lower inlet portion of the tubular passageway outlet means is positioned below a lower outlet of the tubular passage inlet means. Also, the check valve means is positioned adjacent to the lower end portion of the tubular passageway inlet means in a manner that biofluid flowing through the tubular passageway inlet means is discharged into the container in a manner to alleviate possible outflow of biofluid particles into the tubular passageway outlet means, this being accomplished in part by the check valve means by diverting the fluid away from the inlet portion of the tubular passageway outlet means.

The check valve means comprises a flexible generally planar flap member positioned at a lower end portion of the outer housing portion, with the flap member having an opening aligned with the tubular passageway outlet means, but extending over the outlet end of the tubular passageway inlet means, and with the flap member being retained in a manner so as to be movable away from the outlet end of the tubular passageway inlet means. Also, in the preferred form, the closure and inlet means comprises a filter positioned within the closure and fluid inlet device proximate to the outlet end of the outlet means to collect biofluid which could possibly pass up through said outlet means. This filter is such that if the biofluid rises to a level where it is drawn up through the outlet passageway, the filter expands to block the outlet passageway, thus stopping the suction action of a vacuum source, and signaling that the biofluid container should be removed and emptied.

This closure and inlet means could in another arrangement be interconnected between the suction tubes from the patient and inserted in a device defining a through opening leading to a disposal passageway, thus by-passing the container. For example, the closure and fluid inlet device could lead through a passageway directly to a disposal location of the biofluid material.

Also, with the closure and fluid inlet device being removably connected, it would be possible to leave the suction tubes in place in the patient, while disconnecting the container from one container that is filled with biofluid, and inserting another container, without disturbing the suction tubes in the patient.

In several preferred embodiments, the fluid inlet and outlet means and the interconnecting means comprises a valve and connecting means mounted in operative engagement with the through opening of the container. This valve and interconnecting means comprises a valve means which in turn comprises a valve housing with a valve element being movable relative to the valve housing between an open position to provide a valve through opening from the connecting chamber, and a closed position closing the valve through opening.

The containing interconnecting mechanism is arranged to come into interconnecting engagement with the base interconnecting means so that the valve through opening is in communication with the disposal passageway of the base assembly.

In one configuration, the valve element is rotatably mounted in the valve housing and further comprises valve actuating means by which the valve element can be moved between its open and closed positions.

In several preferred embodiments, the valve element and the valve actuating means are arranged, relative to the base assembly in a manner that with the container interconnecting mechanism of the valve and connecting means being interconnected, with the base interconnecting means in an operating position, and with the valve in its open position, the container interconnecting mechanism of the valve and connecting means is not able to be moved toward a release position until the valve element has been moved to its closed position.

In one form, the valve actuating means comprises at least in part a manually operable valve handle by which the valve element can be manually moved between its open and closed position, and the system is arranged so that with the container interconnecting mechanism in operative engagement with the base interconnecting means, movement of the valve element to the closed position also moves the valve actuating means to a position to prevent disengagement of the interconnecting mechanism. In a preferred form, the interlocking means is in the interlocking position after the valve element is moved to the open position.

In some preferred embodiments, the interconnecting mechanism of the valve and connecting means and the base interconnecting means are arranged with a recess/protrusion interconnecting means, where one interconnecting portion of the interconnecting mechanism or the base interconnecting means is provided with recess means, and the other of the interconnecting mechanism and the base connecting means is provided with protruding means which come into operative engagement with the recess means. Thus, the valve and connecting means is moved rotatably relative to the base assembly to come into and out of interconnecting engagement. Also, in at least one preferred embodiment, this interconnecting action is such that the interconnecting movement of the valve and connecting means has a component of travel toward the base assembly. The valve and interconnecting means is arranged relative to the disposal means of the base assembly so that this movement of the valve and connecting assembly causes said valve and connecting means to come into sealing interengagement with the disposal means so that the valve through opening portion is connected with the disposal passageway of the disposal means in sealing isolated relationship to provide a sealed disposal path.

More particularly, the disposal means comprises a passageway defining section which is positioned to be movable along a path having a substantial alignment component axially aligned with a passageway portion defined by the passageway defining section, with the passageway defining section arranged to be urged toward a sealing position, whereby movement of the relevant connecting means toward said passageway defining section causes sealing engagement with the passageway defining section.

In these embodiments, a compression spring urges the passageway defining section toward sealing engagement, and the passageway defining section is in telescoping engagement with another tubular disposal section lending to a disposal location.

A preferred valve configuration is to provide a rotatably mounted valve element with upper and lower circumferential seal surrounding a valve through opening, and having a wiping action over the valve surface when the valve is moved from its open to closed position.

Desirably the container has two vertical side handles on opposite sides of the container particularly adapted for inverting the container and rotating the container into its interconnecting position.

In some embodiments, the container is rotated into an interlocking position. In other embodiments the container assembly and base assembly have slideway interconnecting means another embodiment has a handle means on the container assembly so that the container assembly can be mounted to the base assembly by the handle means and rotated to an inverted position relative to the base assembly. In another arrangement there are in interengaging sleeve sealing means between the container assembly and the base assembly. The valve element is actuated either by the stationary member in the base assembly, or by a selectively operable valve actuator. Also, in some embodiments, the valve element is provided with spring means to urge it toward its closed position.

There is an irrigating system comprising irrigating tube means positioned to discharge irrigating liquid through inter surface portions of the base assembly and the container to disinfect these with an irrigating liquid. Also, a closure lid can be placed over the base assembly and the interior surfaces of the base assembly irrigated. Also the container has a pyramid shaped bottom wall to facilitate dispersion of the irrigating fluid in the container, and to enhance liquid level reading of the biofluid in the container. Additional features of the present invention will become apparent from the following detailed description.

BRIEF DESCRIPTION OF THE DRAWINGS

FIG. 5 is a view similar to FIGS. 3 and 4, but showing the container assembly fully connected to the base assembly in a manner that the waste material in the container assembly is being emptied into the base assembly;

FIGS. 6, 7 and 8 are longitudinal sectional views of a third embodiment of the present invention, these showing three different positions of the second embodiment, similar to the operating positions of FIGS. 3, 4 and 5 of the first embodiment;

FIG. 9 is a longitudinal sectional view of a fourth embodiment of the present invention, showing the container assembly in a position above the base assembly, to be moved into engagement with the base assembly;

FIG. 10 is a longitudinal sectional view similar to FIG. 9, but showing the container assembly in its operating position and the drain plug having been moved upwardly to open the valve plug so that the waste material within the container assembly flows into the base assembly;

FIG. 19 is a view similar to FIGS. 16 and 18, showing the interlock control mechanism in an operating position where the valve member can be moved to empty the contents of the container;

FIG. 23 is a sectional view showing a spring mechanism of the container assembly holding the valve member in a closed position;

FIG. 24 is a view similar to FIG. 23, showing the valve member being moved to the open position, against the urging of the spring member;

FIG. 35 is an isometric exploded view, showing various components of the container assembly and the base assembly;

FIG. 36A is a sectional view, taken along a vertical plane parallel to a longitudinal axis of the valve actuating and discharge section and the valve of the container assembly;

FIG. 37A is a sectional view similar to FIG. 36B, but showing the valve actuating and discharge section in a second position during its operation;

FIG. 38A is a view similar to FIGS. 36A and 37A, but showing the valve actuating and discharge section in the discharge position;

FIG. 43A is an isometric exploded view of the closure and inlet device;

FIG. 43B is an isometric view of the closure and inlet device of FIG. 43A in its assembled position;

FIG. 47 is a sectional view similar to FIG. 46A, but taken along a section rotated 90° with respect to 46A;

DESCRIPTION OF THE PREFERRED EMBODIMENTS a) First Embodiment

FIGS. 1 through 5 show the system 10 of the first embodiment of the present invention. As shown in FIGS. 2–5, this comprises two main components, namely a portable container assembly 12 to collect the contaminated material, and a base assembly 14 to receive the material from the container assembly 12.

Figure 1:
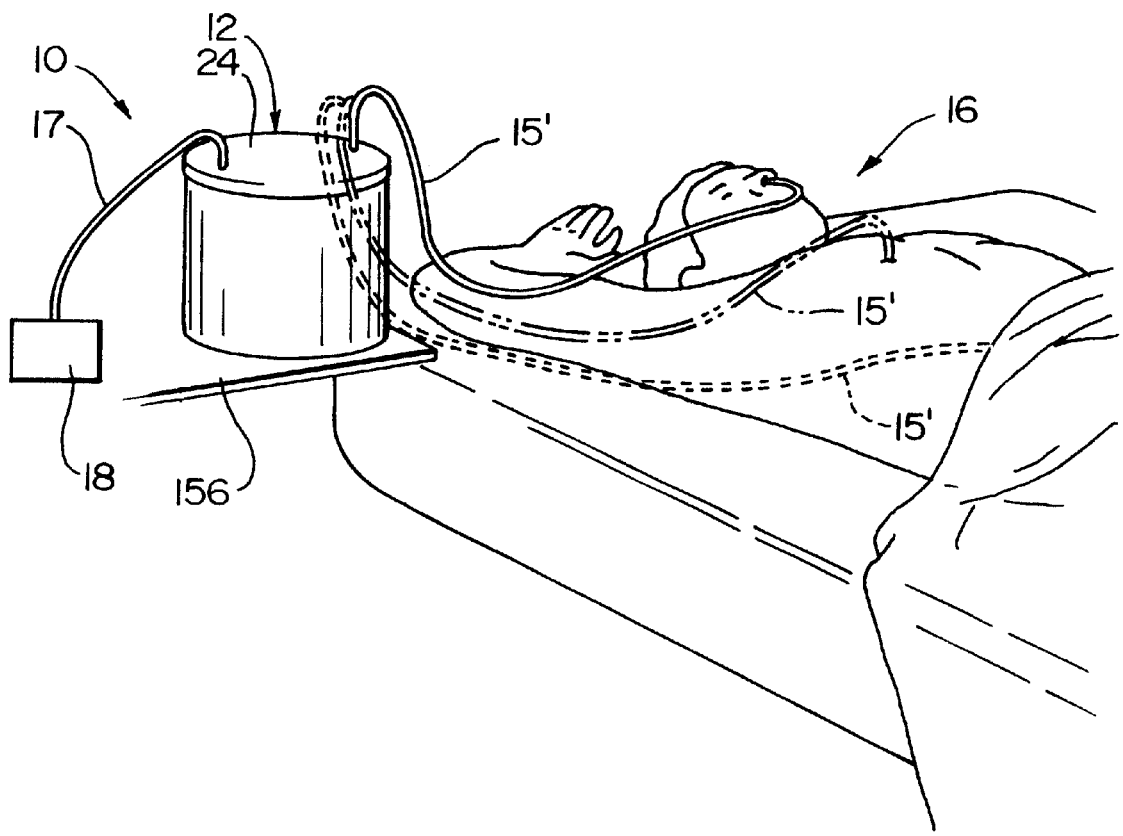
FIG. 1 illustrates the container assembly of the present invention in its operating position near a patient, with the container assembly being connected to a vacuum source and also three examples of suction tubes to collect waste material from the patient through the suction tubes.

Initially, as shown in FIG. 1, the container assembly 12 is placed near the patient from whom the waste material (i.e. body fluid or viscous material of some sort) is being collected. An inlet end of a suction tube 15 is inserted into a body cavity of the patient 16 or to another device which is otherwise operatively connected to the patient, with the other end of the suction tube 15 being connected to the assembly 12. Then the vacuum line 17 is connected between a suitable vacuum source, (schematically illustrated at 18) and to the container 12. As the vacuum is applied, the waste material is drawn from the patient through the suction tube 15 and into the containing portion of the containing assembly 12. It is to be understood that the suction tube 15 could be applied for various applications, such as being positioned in a chest cavity, possibly to collect urine, or other body cavities for example for wound drainage. Accordingly, three such suction tubes are illustrated schematically and designated 15'.

Then after a sufficient amount of the waste material from the patient has been collected so that the container assembly 12 should be emptied, the container assembly 12 is disconnected form the suction tube 15 and from the vacuum source 18 and carried to the base assembly 14 (FIG. 2), which would normally be at a fixed location on a counter top or the like and interconnected with the main sewer system of the hospital or health facility. Then the container assembly 12 is interconnected with the base assembly 14 in a manner that the contaminated material is safely delivered into the discharge passageway of the base assembly for safe disposal in the sewer system.

To proceed with a more detailed description of the present invention, the container assembly 12 comprises a container 19 defining a containing chamber 20 and having a cylindrical sidewall 21 and a bottom wall 22 that slopes downwardly and inwardly toward a bottom central discharge opening 23. The container 19 has a lid 24 which in this particular design is formed in a slightly upwardly convex curve. The lid 24 has a peripheral downwardly extending lip 25 which fits in sealing engagement around the upper edge 26 of the sidewall.

The lid 24 is formed with a pair of fittings 28 and 30, respectively. The fitting 28 is an inlet fitting which may of itself be of conventional design, and it is adapted to be connected to a discharge end of a suction tube 15. The fitting 30 is a vacuum tube fitting adapted to be connected to an inlet end of a vacuum tube 17. This fitting 30 also, of itself, may be of conventional design. Since the fittings 28 and 30 can be of conventional design, these will not be shown or described in detail herein.

The lower part of the container 19 is formed with a discharge connecting section 36 which is arranged to interfit with the base assembly 14 in a manner to securely hold the container assembly 12 in place during discharge of the waste material (i.e. waste fluid) and also to isolate the waste fluid from the surrounding environment during the discharge operation. Also, the container assembly 12 comprises a valve assembly 38, this valve assembly being mounted to the bottom wall 22 at a lower central location. The container assembly 12 is further provided with an irrigating system 40 which (with the container assembly 12 in its discharge position in the base assembly 14) functions to direct an irrigating/cleaning liquid into the container 19 subsequent to discharge of the waste material to wash the remaining waste material from the container assembly 12 and through the base assembly 14.

To describe the discharge connecting section 36 in more detail, it comprises a lower perimeter base member 42 which in this particular embodiment is formed as a downward extension of the container sidewall 21 so as to take the form of a circumferential downwardly extending perimeter flange. The lower edge 44 of the container base 42 is at a sufficiently low elevation so as to be able to support the container assembly 12 on a flat surface.

The connecting section 36 further comprises a pair of concentric cylindrical locating/sealing sleeves 46 and 47 concentrically located about a longitudinal center axis 48 of the container assembly 12. The upper edge of the inner sleeve 47 defines the lower container opening 23. The lower end of the outer locating/sealing sleeve 46 is formed with locking fingers 50 by which the assembly 12 can be securely connected to the base assembly 14. The functions of these components 42, 46, 47 and 50 will be described later herein in more detail.

The aforementioned valve assembly 38 comprises a disk shaped valve plug 52 that is connected to an upwardly extending tubular valve stem 54 that is in turn mounted within a mounting cylinder 56 which in turn is mounted to a pair of arms 58 that connect to the bottom wall 22. There is a compression spring 60 mounted around the valve stem 54 and sleeve 56, with its pressing against the valve plug 52 to urge the plug 52 and the stem 54 to their down position and with the upper end of the spring bearing against the arms 58.

The upper end of the tubular valve stem 54 is closed by an end cap 61. The upper sidewall portion of the stem 54 has a plurality of nozzle openings 62 spaced circumferentially around the stem 54 so that water/disinfectant can be sprayed upwardly through the stem 54 and outwardly through the openings 62 to clean the inside of the container 19. At the lower end of the stem 54, there is a check valve 63 which permits flow of liquid upwardly through a center opening 65 in the plug 52 so that water/disinfectant can flow upwardly into the interior of the tubular stem 54 and outwardly through the irrigation vents 62.

There will now be a more detailed description of the base assembly 14. In the particular embodiment shown herein, this base assembly 14 is shown mounted in a cutout 78 in a conventional counter top 80. More particularly, this base assembly 14 comprises a base housing 82 which is made up of a cylindrical sidewall 84 and a base floor 86 fixedly connected to (or formed integrally with) lower edge of the sidewall 84. The sidewall 84 is snugly positioned within the cutout 78, and is formed with an outwardly extending perimeter mounting flange 88 that extends a short distance over the perimeter edge 89 of the upper surface 90 of the counter top 80.

At the middle of the base floor 86 there is a drain pipe 92 which is formed integrally with (or fixedly connected to) the base floor 86. This drain pipe 92 has an upward cylindrical extension 94 that is in turn connected to a top disk shaped cover or cap 96. The upper part of the extension 94 has a plurality of drain windows 98 around the circumference thereof, and there is one seal ring 100 located above, and a second seal ring 102 located below, the set of drain windows 98. The seals 100 and 102 act as "cleaning seals". The base housing 82 also has a mounting cylinder 104 that is fixedly connected to (or formed integrally with) the floor 86. This mounting cylinder 104 and the lower part of the upward cylindrical extension 94 define an annular recess 106 to receive the aforementioned locating/sealing sleeve of the container assembly 12. The mounting cylinder 104 has a set of interior keyways 108 (see FIG. 3A) to engage the fingers 50 of the locating/sealing sleeve 46.

The lower part of the cylindrical extension 94 has formed therein a plurality of inwardly extending scupper openings 110 to drain liquid from the recess 106 into the discharge passageway 112 defined by the drain pipe 92. Also, the lower part of the mounting flange 104 has a plurality of scupper openings 114 arranged to receive liquid flow from the area above the floor 86 surrounding the flange 104.

Positioned within the drain pipe 92 is a vertically aligned irrigation tube 120, the upper end nozzle 122 of which extends a short distance above the upper end of the cylindrical extension 94. The lower end of this irrigation tube 120 connects to a laterally extending tube 124 that extends through the wall of the drain pipe 92 in a manner to make a seal therewith. This tube 124 is connected through a valve 126 to a suitable source of irrigating liquid, such as plain water or water which has dissolved therein a sanitizing/cleaning agent or agents.

Also, there is provided for the base assembly 14 (FIG. 2) a removable cover 142 having a peripheral downwardly extending attachment lip 144 which fits circumferential around an upstanding flange 146 that is fixedly connected and upstanding from the housing sidewall 84. With the cover 142 in place, the lip 144 snugly engages the flange 146 to enclose the entire base assembly 14, except for the peripheral mounting flange 88. The cover 142 has a moderate upward convex curve so that the center portion is raised a moderate amount.

Mounted to the lower inside surface portion of the cover.142 is a suitable liquid deflecting device 148 that is positioned above the upper end outlet 122 of the irrigation tube 120. Thus, with the cover 142 in place, by operating the valve 126 for the irrigation tube 120, the irrigating liquid can be sprayed upwardly to strike the deflecting device 148, which in turn disperses the liquid so that it sprays around the interior of the base housing 82 and flows into and around the various components of the base assembly 14. This irrigating liquid then flows through the scupper openings 114 and 110 and out the drain pipe 92.

There is also provided for the container assembly 10 a lower end cap or cover 150 having an upstanding circumferential lip or flange 152. This end cap 150 is placed over the bottom of the container 12, with the lip 152 fitting snugly around the lower edge portion of the lower container base 42.

To describe now the operation of the present invention, reference is again made to FIG. 1 which illustrates the patient 16 in bed, having the suction tube 15 extending from the person to the container assembly 12 which is placed on an adjacent support surface shown somewhat schematically at 156. The vacuum tube 17 is connected to the vacuum source, shown schematically at 18. The lid 24 for the container 12 is positioned securely over the top of the container 12. Also, the bottom end cap or closure lid 150 is securely mounted over the bottom end of the container 12.

The suctioning of the patient proceeds in the normal manner, in that the vacuum source 18 creates a reduced pressure in the containing chamber 20, defined by the container 19. The fluid or viscous material that is withdrawn from the patient's breathing cavity or other part of the body passes through the suction tube 15 and flows into the container 19. It is be understood, of course, this is a rather simplified illustration of the medical procedure involved and there would likely be other controls, and other apparatus associated with this overall procedure. Also, while the apparatus 10 is being shown used in conjunction with a suction tube 15, as indicated previously it could also be used in conjunction with other devices which carry medical waste material.

When a sufficient amount of waste material has been collected in the container 19 so that it is now desired to empty the container, then the suction tube 15 (or other tube) is disconnected from the fitting 28 in the container lid 24, and this can be accomplished in a conventional manner. In like manner, the vacuum tube 17 is disconnected from the fitting 30, with this also being able to be accomplished in a conventional manner. The two fittings 28 and 30 could be self closing upon withdrawal of their respective tubes 15 or 17. Alternatively, these fittings 28 and 30 could be manually closed or have a closure member placed thereon.

It will be noted that the contaminated (or possibly contaminated) waste material from the patient remains securely contained within the chamber 20. The valve plug 52 is held in its closed position by the action of the spring 60. As a further precaution, the lower end cap or lid 150 is positioned over the bottom end of the container 19.

The containing assembly 12 is then taken to a disposal location where the base assembly 14 is located. This disposal location could even be, for example, at a counter located in the very same room in which the patient 16 is being treated. The container assembly 12 has the lower end cap 150 removed from the container 19, and the cover 142 is removed from the base housing 82.

Figure 3:
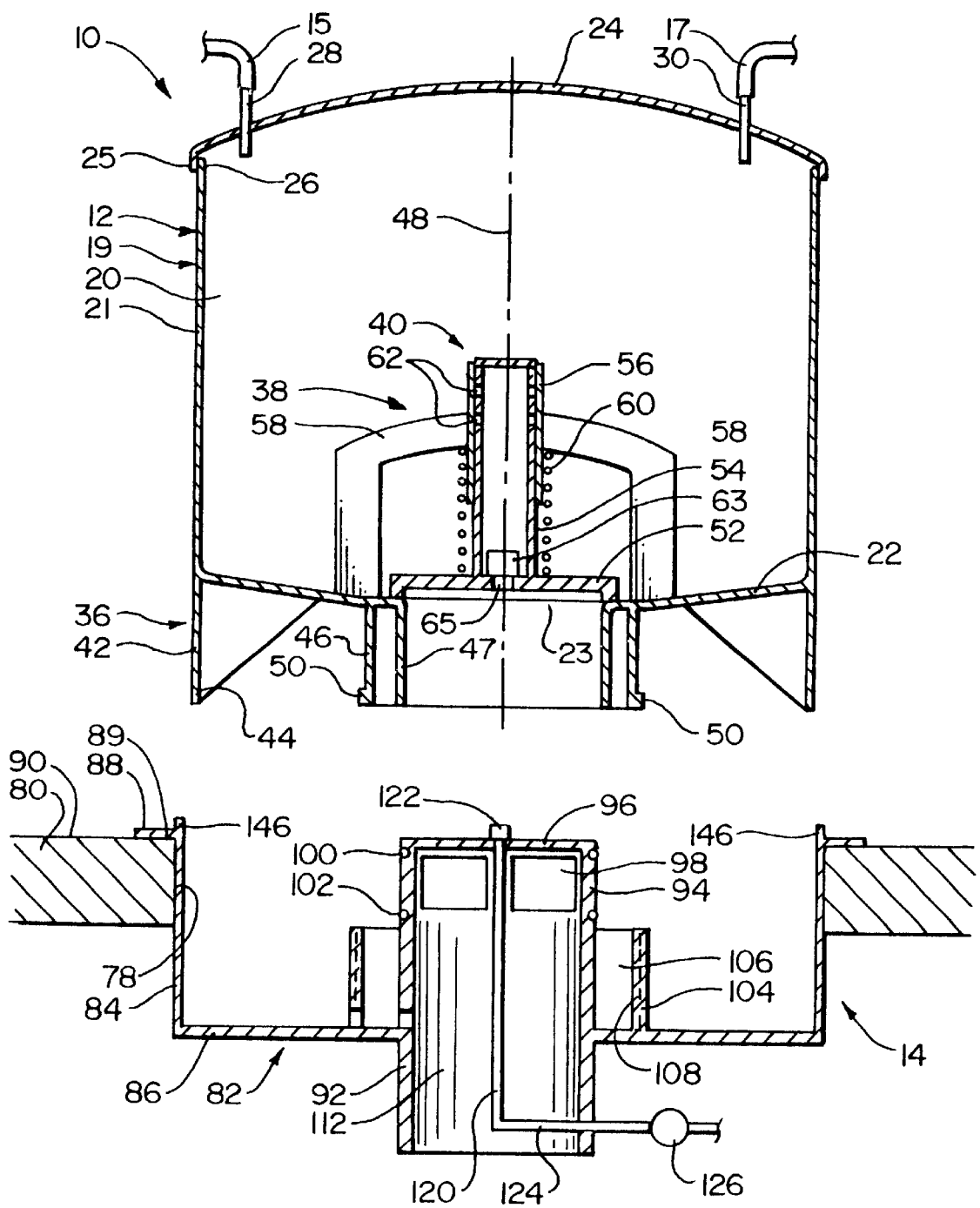
FIG. 3 is a longitudinal section view showing the container assembly in position to be lowered into a connecting location with the base assembly.
Figure 3A:
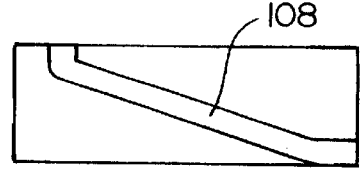
FIG. 3A is a side elevational view showing a retaining keyway.

Then the container assembly 12 is positioned immediately above the base assembly 14, as shown in FIG. 3. The container assembly 12 is then lowered downwardly with the cylindrical base 42 fitting closely within the inside surface of the base housing sidewall 84.

Figure 4:
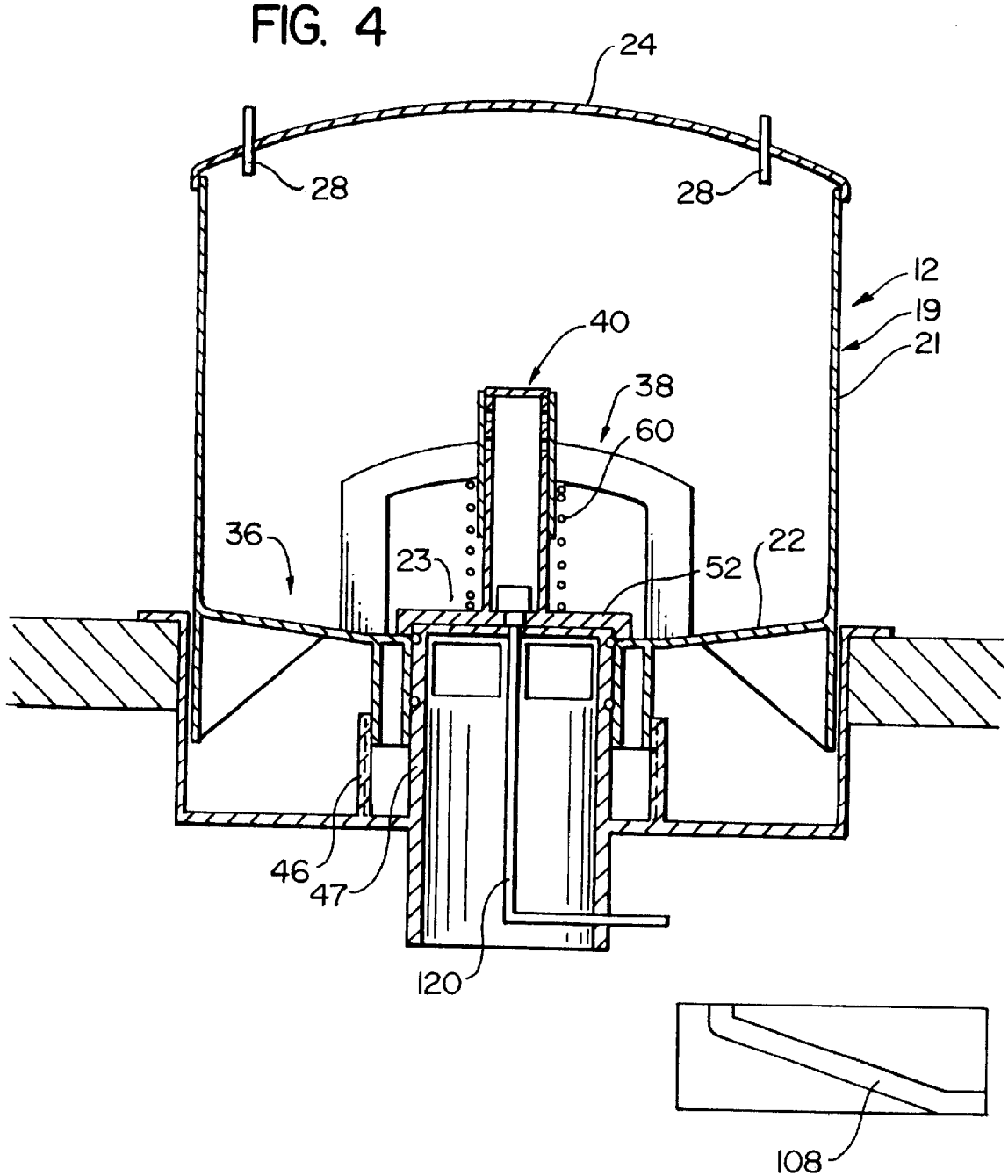
FIG. 4 is a view similar to FIG. 3, but showing the container assembly having been lowered toward its connecting position with the base assembly, and coming into engagement therewith.

When the container 12 reaches the position shown in FIG. 4, the inner locating/sealing sleeve 47 has moved downwardly around the upper part of the cylindrical extension 94. Also, the locating/sealing sleeves 46 47 are just beginning to enter the annular recess 106 defined by the mounting cylinder 104 and the cylindrical extension 94. At this point, the top wall or cap 96 engages the valve plug 52 to move the valve plug 52 upwardly out of sealing engagement with the containers bottom wall 22.

When the fingers 50 begin to engage the keyways 108, the locating flange 104, then the entire housing 16 is rotated to cause the fingers 50 and keyways 108 to come into full locking engagement as the housing 16 moves further downwardly with further rotation. As the inner locating/sealing sleeve 47 continues to move downwardly, its upper edge moves downwardly beyond the location of the drain windows 98 so that these drain windows 98 become opened to the interior chamber 20 of the container 19. Then the waste material in the chamber 20 of the container 16 flows through the windows 98 and out the passageway 112 defined by the drain pipe 92.

After the waste material in the chamber 20 has all substantially flowed through the windows 98 and through the drain pipe 92, the next step is to initiate the irrigation process. It will be noted that when the container assembly 12 is moved to its fully engaged downward position, in the base assembly 14, the upper nozzle end 122 of the irrigation tube 120 fits snugly within the opening 65 leading into the check valve 63, thus establishing a fluid connection between the tube 120 and the vent openings 62.

Then, when the irrigation valve 126 is opened, the irrigating liquid flows through the tube 124, upwardly through the tube 120 and through the opening and through the check valve stem passageway to flow outwardly through the vent openings 62 to spray outwardly within the chamber 20.

After the irrigation process is completed, the irrigation valve 126 is then closed. The container assembly 12 is rotated a sufficient number of revolutions to disengage the fingers 50 from the keyways 108 in the mounting cylinder 104. Just prior to the time that the disengagement is completed, the valve plug 52 has been moved by the spring 60 downwardly into its closed position to close the opening 23 leading into the locating/sealing sleeve 47. With the containing assembly 12 totally removed from the base assembly 14, the bottom closure lid or cap 150 is then placed over the lower end of the container 116.

At this point, the cover 142 for the base assembly 14 is placed over the base assembly 114 with the lip 144 making a seal with the flange 146. Then the irrigation valve 126 is again opened to cause the irrigating liquid to flow out the end 122 of the tube 120 to engage the deflecting device 148. This causes the irrigating liquid to be circulated over the surfaces of the base assembly 14. The irrigating liquid thus becomes dispersed throughout the interior of the base housing 82 and the components contained therein, and also against the bottom surface of the lid 142.

Then the container assembly 12 is returned to the location of the patient and is reconnected to the suction tube 15 and vacuum tube 17.

b) Second Embodiment

Figure 5A:
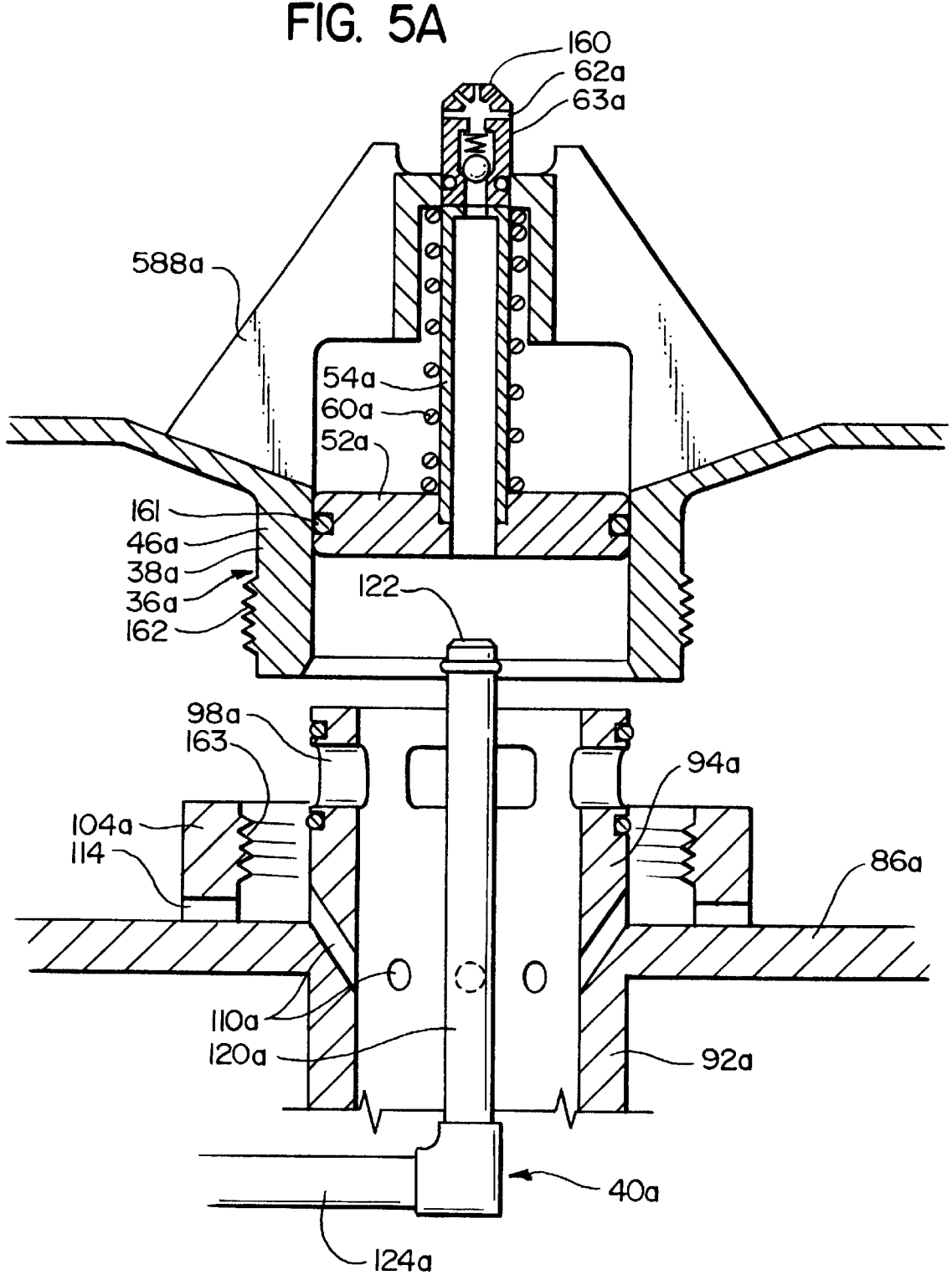
FIG. 5A is a longitudinal sectional view of a second embodiment of the present invention.

A second embodiment of the present invention is shown in FIG. 5A. This second embodiment is rather similar to the first embodiment, and components of this second embodiment which correspond to components of the first embodiment, will be given like numerical designations, with an "a" suffix distinguishing those of the second embodiment.

In this second embodiment, the check valve 63a and the vent openings 62a are combined in a single unit which is placed at the top of the valve stem 54a.

Thus, the vent openings 62a are made as nozzle openings in an end nozzle member 160. The check valve 63a is positioned in the passageway immediately leading into the nozzle member 160.

Another difference is that the plug element 52a is positioned within the upper end of the sleeve 46a (which actually combines the sleeves 46 and 47 of the first embodiment). There is an O-ring seal 161 which seals the perimeter surface of the plug 52a with the inside surface of the sleeve 46a.

This is a "cleaning seal" as it wipes off any residual liquid material on the inner surface of sleeve 46a.

A third difference is that the locating/sealing sleeve 46a has exterior threads 162 formed thereon, and these threaded engage the threads 163 in the inner surface of the outer mounting sleeve 104a.

In other respects, the embodiment of FIG. 5A is substantially the same as the embodiment shown in FIGS. 1 through 5. Accordingly, only those portions of the second embodiment which differ from the first embodiment are shown in FIG. 5A, and there is no additional description of those components other than those illustrated in FIG. 5A.

It is believed that the mode of operation of the second embodiment shown in FIG. 5A is readily understandable from prior description presented with respect to the first embodiment.

c) Third Embodiment

A third embodiment of the present invention will now be described with reference to FIGS. 6 through 8. Components of the third embodiment which are similar to the components of the first and second embodiments will be given like numerical designations, with a "b" suffix distinguishing those components of the second embodiment.

As in the first two embodiments, the container assembly 12b comprises a container 19b having the side wall 21b, lid 24b and container base 42b, configured substantially the same as in the first embodiment. Also, the valve assembly 38b comprises (as in the first embodiment) a valve plug 52b, stem 54b, mounting cylinder 56b and a compression spring 60b. However, the configuration and function of the locating/sealing sleeve 46b differ somewhat from the first embodiment in that this sleeve 46b does not simply fit into a recess, but actually engages a moveable sleeve in the base assembly 14b so as to provide an opening.

With regard to the base assembly 14b, the overall configuration is similar to the base assembly 14 of the first embodiment, in that there is the base housing 82b, and also the mounting flange 104b. However, the cap 96b is not mounted to a stationary cylindrical extension such as shown at 94 in the first embodiment. Rather, the cap 96b is mounted to the upper end of the irrigation tube 120b. The perimeter of this cap 98 acts as a cleaning seal to the inner surface of cylinder 46b. There is a stationary drain pipe 92b, and positioned within this drain pipe 92b is a moveable drain sleeve 166. This drain sleeve 166 has an outwardly stepped middle portion at 168, and the upper edge of this stepped portion 168 engages a locating lip 170 at the floor 86b to limit its upward movement to an upper position so that the upper end edge 172 of the sleeve fits around the end cap 96b.

There is a compression spring 174 surrounding the lower part of the sleeve 166 and bearing against the stepped expanded portion 168. The lower end of the spring 174 bears against a lower circumferential shoulder 176 formed at a juncture location 178 of a lower drain pipe section 180 that is a downward extension of the drain pipe 92b.

Figure 2:
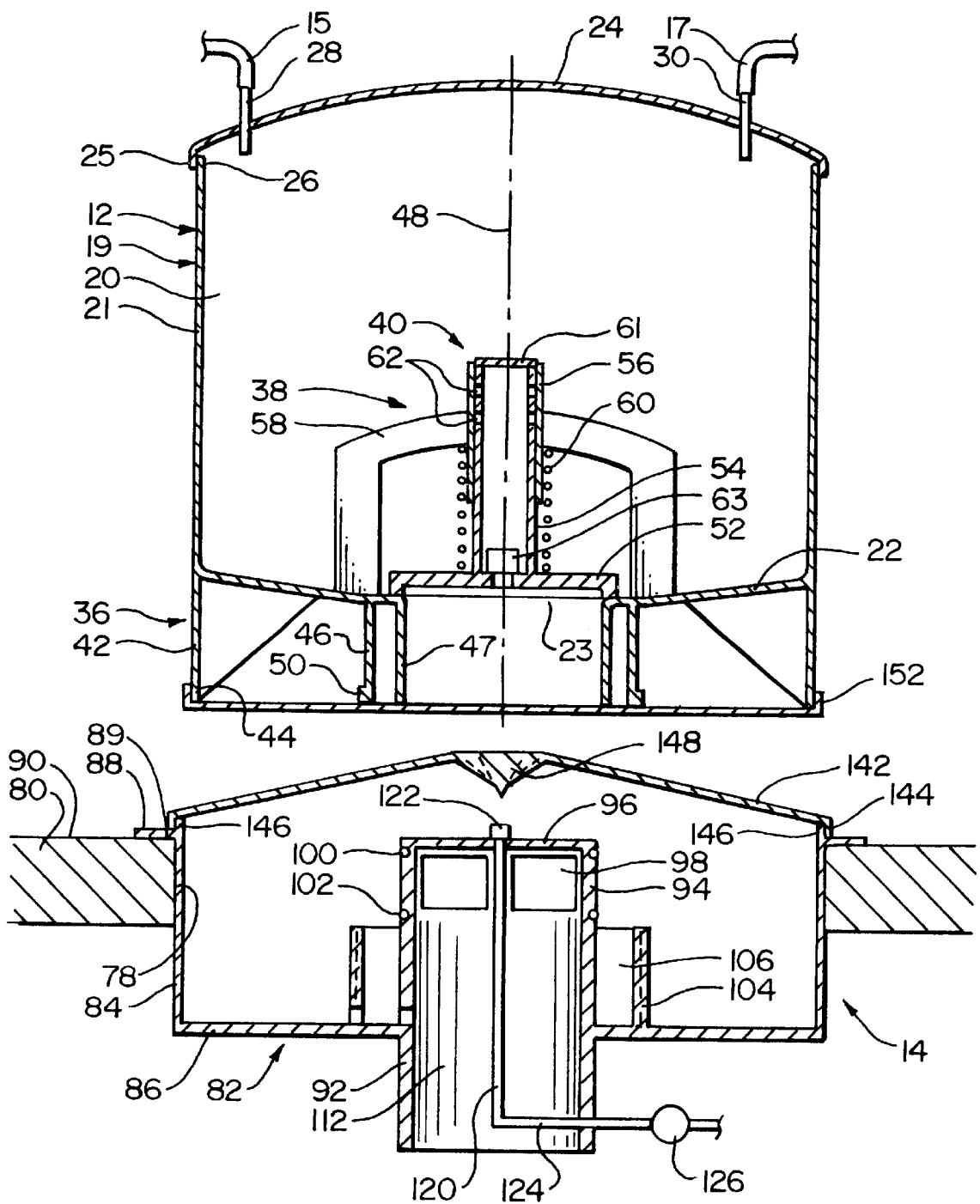
FIG. 2 is a longitudinal sectional view showing one embodiment of a container assembly and a base assembly of the present invention, spaced from one another, with the container assembly having a lower cover closing the bottom of the container assembly, and the base assembly having a top cover placed thereon.

The operation of this third embodiment proceeds as follows. First, the collecting assembly 12b with waste material therein is moved from its collecting location and is positioned above the base assembly 14b, as shown in FIG. 6, in substantially the same manner as shown in FIG. 2 relative to the first embodiment. Then the container assembly 12b is moved downwardly toward the position of FIG. 7. Initially, the downwardly facing edge surface portion 182 of the sleeve 46a engages the upper edge portion 172 of the sleeve 166 and moves the sleeve 166 downwardly against the urging of the spring 174 forming a sealed bio-fluid path. At this time the cap 96b moves upwardly within inner surface of the sleeve 46b engages an outer circumferential edge 183 of the cap 96b. When the container 17b reaches the position of FIG. 7, the cap 96b now engages the valve plug 52b. Surfaces 172 and 182 when in contact form a sealed passage comprised of cylinders 46b and 166.

Further downward movement of the container assembly 12b lifts the valve plug 52b off of the upper edge portion of the locating/sealing sleeve 54a so as to create a discharge flow path for the material in the chamber 20b of the container 19b. At this point, the fingers 50b and the related keyways are beginning to come into engagement so the container 16a is rotated a sufficient angular distance so as to cause proper engagement of the fingers 50b in the keyways.

With the container assembly 12b properly secured to the base assembly 14b, the container assembly is in the position of FIG. 8, and the flow of the medical waste material flows from the container 19b until the discharge is substantially complete. Then the irrigation operation can proceed as described previously with regard to the second embodiment. The removal of the containing assembly 12b and the further irrigation of the base assembly 14b can proceed in the manner described above relative to the first embodiment.

d) Fourth Embodiment

A fourth embodiment of the present invention will now be described with reference to FIGS. 9 and 10. Components of this fourth embodiment which are similar to components the prior three embodiments will be given like numerical designations, with a "c" suffix distinguishing those of this fourth embodiment.

The entire container assembly 12c is constructed in substantially the same manner as the container assembly 12b of the third embodiment. However, the function of the locating/ sealing sleeve 46c differs from the second embodiment in that this sleeve 46c simply fits within a mounting flange 104c of the base assembly 14c. Also, in this fourth embodiment, there is not (as in the first embodiment) the fixed cylindrical extension 94. Nor is there (as in the third embodiment) the moveable sleeve 166.

Rather, in this fourth embodiment there is provided a drain plug 184 which closes the upper end of a drain pipe 92c which extends downwardly from the base floor 86c. This drain plug 184 can be moved between its down closing position (shown in FIG. 9) upwardly to an open position (shown FIG. 10) by operation of a positioning handle 186.

The movement of the drain plug 184 can be accomplished through a mechanism which overall is somewhat similar to one that occurs commonly in bathroom fixtures in the United States. The handle 186 is connected to a downwardly extending rod 188 which is in turn is connected to one end 190 of a laterally extending rod 192 which is pivotally mounted about a ball 194 and has an opposite end 196 attached to the plug 184. Thus downward movement of the handle 186 rotates the rod 192 about the ball 194 as a fulcrum to lift the rod end 196 and lift the plug 184.

The operation of this fourth embodiment proceeds as follows. First, the container assembly 12c is positioned above, and in line with, the base assembly 14c in the same manner as described relative to the prior three embodiments. Then the interconnection of the two assemblies 12c and 14c is accomplished in generally the same manner as described with regard to the prior three embodiments, except that during the interconnecting process, there is no opening of a flow passage for the waste material in the chamber 20c. Rather, when the interconnection of the assemblies 12c and 14c is completed, the valve plug 52c becomes positioned in contact with the base plug 184, but the valve element 52c still remains in its closed position.

Then the handle 186 is depressed to raise the plug 184, and this in turn lifts the valve element 52c of its seat, so as to create a drain path for the waste material. When the discharge of the waste material into the drain pipe 92c is substantially completed, then the irrigation is accomplished in generally the same manner as described above with regard to the prior three embodiments.

e) Fifth Embodiment

Figure 11:
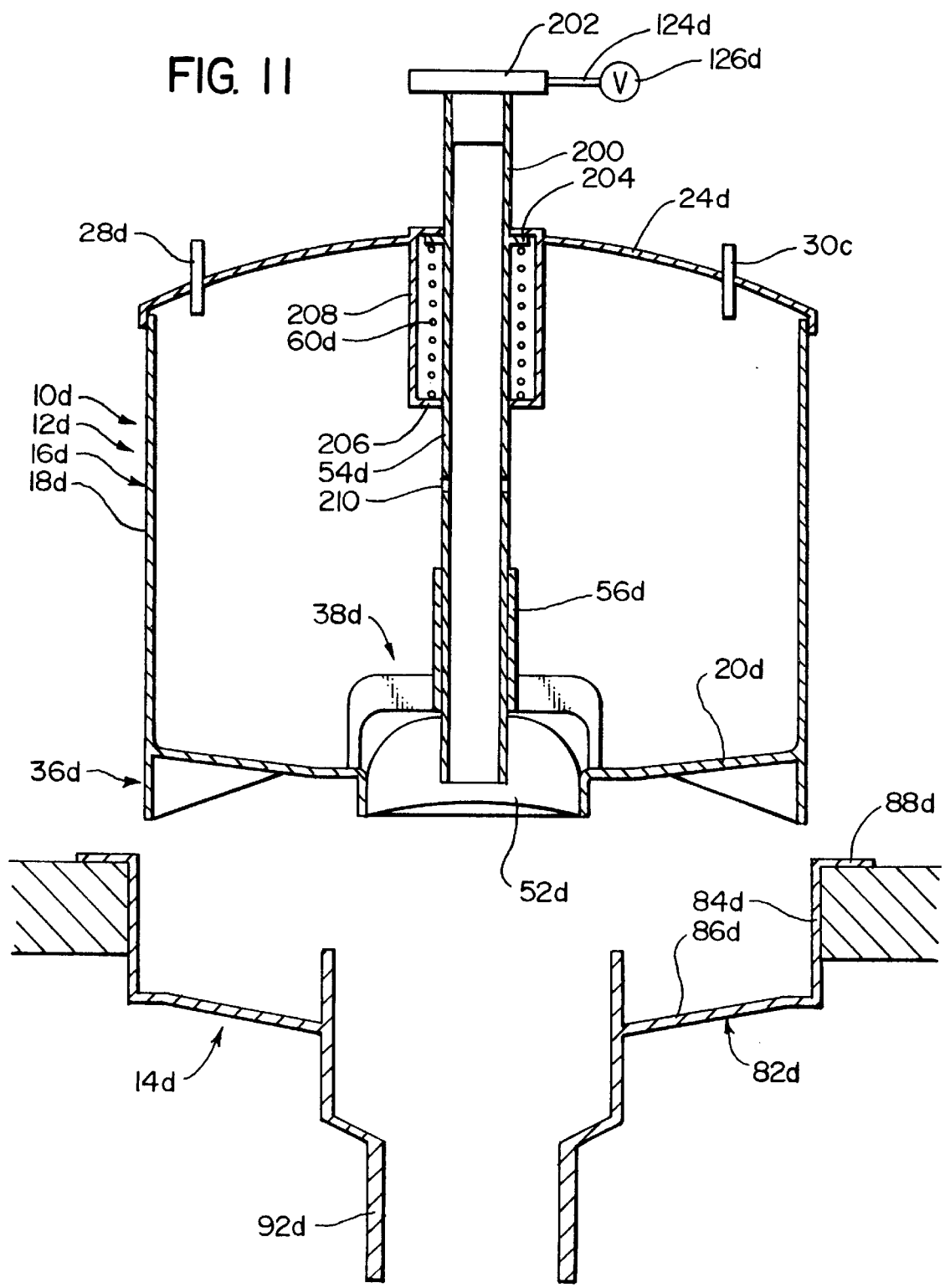
FIG. 11 is a longitudinal sectional view of a fifth embodiment, showing the container assembly in a position to be lowered into engagement with the base assembly.
Figure 12:
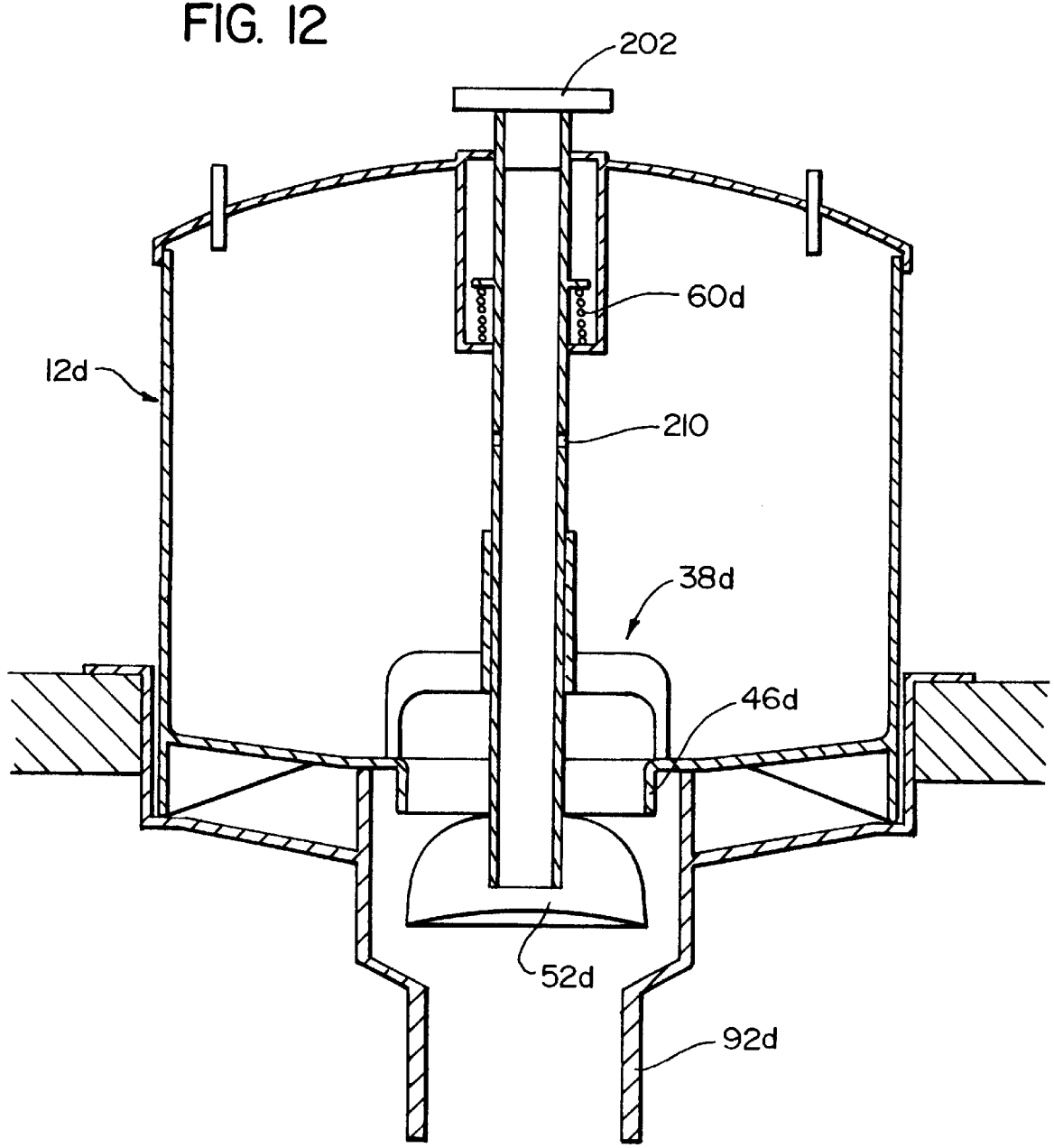
FIG. 12 is a view similar to FIG. 11, but showing the valve plug being moved to a lower position to open the containing chamber of the container assembly so that the waste material flows into the base assembly.

A fifth embodiment of the present invention will now be described with reference to FIGS. 11 and 12. Components of this fifth embodiment which are similar to the components of the prior three embodiments will be given like numerical designations with a "d" suffix distinguishing those of the fifth embodiment.

The container assembly 12d of this fifth embodiment is similar to the prior embodiments in that there is a housing 19d, with a lid 24d having the fittings 28d and 30d, and there is a valve assembly 38d having a valve plug 52d, a valve stem 54d, a mounting cylinder 56d and a compression spring 60d. However, the container assembly 12d differs in that the valve stem 54d has an upward extension 200 that extends through the container lid 24d. At the upper end of the extension 200, there is an actuating handle 202 by which the valve stem 54d can be depressed. The extension 200 has a bearing collar 204 fixedly attached to the extension 200, and the compression spring 60d pushes against this collar 204 and against a lower wall 206 of a housing 208 in which the compression spring 60d is positioned.

The opening of the valve plug 52d in this fifth embodiment differs from the prior embodiment in that by depressing the handle 202, the valve plug 52d is pushed downwardly out of its closure position relative to the locating/sealing sleeve 46d. Thus, when the container assembly 12d is in its fully interconnected position with the base assembly 14d, the handle 202 is depressed until the valve plug 52d is in its full open position (See FIG. 12). Then the handle 202 is rotated so that the bearing member 204 comes into engagement with a catch mechanism within the housing 208 to hold the valve stem 54d in its down position, thus maintaining the valve plug 52d in its open position.

When the drainage is substantially completed, then the irrigation valve 126d is opened to cause flow of the irrigating liquid through the conduit 124d to flow inside of the valve stem 54d and flow outwardly through irrigation vents 210. When the irrigation is complete, the handle 202 is rotated so as to release the valve stem 54d, and the spring 60d raises the valve stem 54d to bring the plug 52d back to its closed position.

Figure 13:
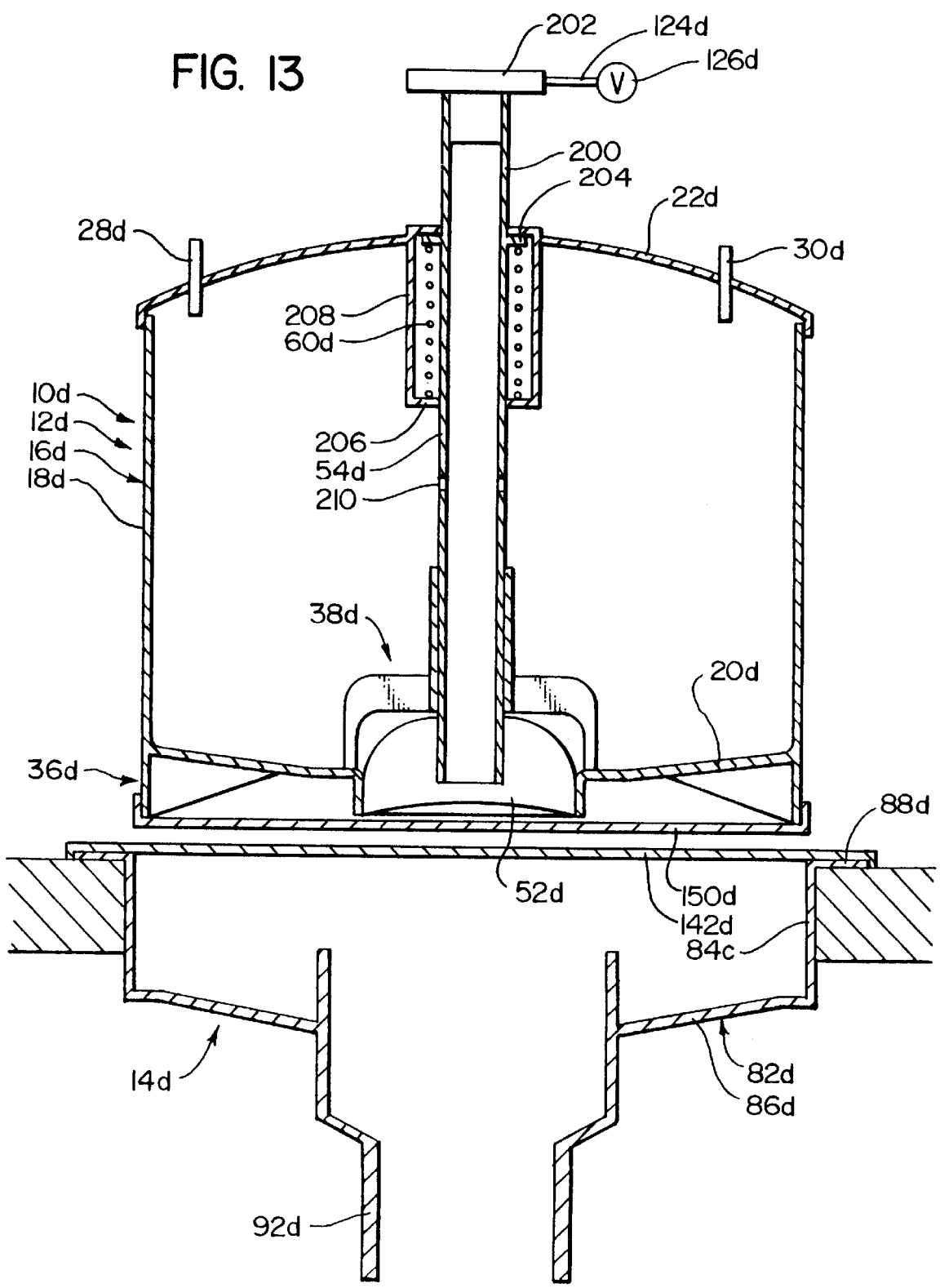
FIG. 13 is a view similar to FIGS. 11 and 12, but showing the container assembly having been moved out of engagement, with a lower lid being placed on the container assembly and a cover being placed over the base assembly.

FIG. 13 shows the fifth embodiment with the lid 150d closing the bottom of the container assembly 12d, and the lid 142d closing the base assembly 14d.

It is believed that other features of this fifth embodiment are apparent from the descriptions of the first embodiment. Accordingly, there will be no attempt to describe these in any further detail herein.

f) Sixth Embodiment

A sixth embodiment of the present invention is shown in FIGS. 14 through 24. In describing this sixth embodiment, for clarity and ease of description, there will be no attempt to equate or relate components of the sixth embodiment with various components of the five prior embodiments, by giving like numerical designations. Rather, a new set of numerical designations will be used.

The overall system of this sixth embodiment is generally designated 210, and it comprises a container assembly 212 and a base assembly 214. The container assembly 212 comprises a container 216 which comprises four side walls 218 and a bottom wall 220 to define a containing chamber 221.

There is a lid 222 which encloses the chamber 221, and there is an outlet opening 224 formed in the bottom wall 220. A slide valve 226 is mounted to the bottom wall 220 of the container 216.

The base assembly 214 comprises a housing structure 228 which in turn comprises a top plate in the form of a counter-top 230, and a containing structure 232 positioned below the counter top 230. The forward upper middle portion of the counter top 230 is recessed to form a slideway 234 to receive the lower part of the container 212. Leading downwardly from the slideway 234 is a drain pipe 236 which has an upper opening 238 which communicates directly to the open area of the slideway 234.

The base assembly 214 also comprises an irrigation/disinfectant system 240, which compromises a water line 242, leading through a check valve 244 and then to an on/off valve 246. From the on/off valve 246 the line continues at 248 to lead into the passageway 250 defined by the drainpipe 236, and leads to an upwardly directed discharge nozzle 252. The discharge nozzle 252 is positioned centrally in the passageway 250 just below the inlet openings 238 of the drain pipe 236. Also, there is a container 254, which has a disinfectant and which connects through a feed pipe 256 that leads into the water line 248 a short distance downstream of the outlet nozzle 252.

The base assembly 214 also comprises an operating and interlock control means 258, which will be described more completely later herein.

To turn our attention back to the container assembly 212, the lid 222 has two fittings, one at 260 to connect to a suction line, and another at 262 to connect to a vacuum source. As indicated previously, these fittings 260 and 262 are, or may be, of conventional design.

Figure 16:
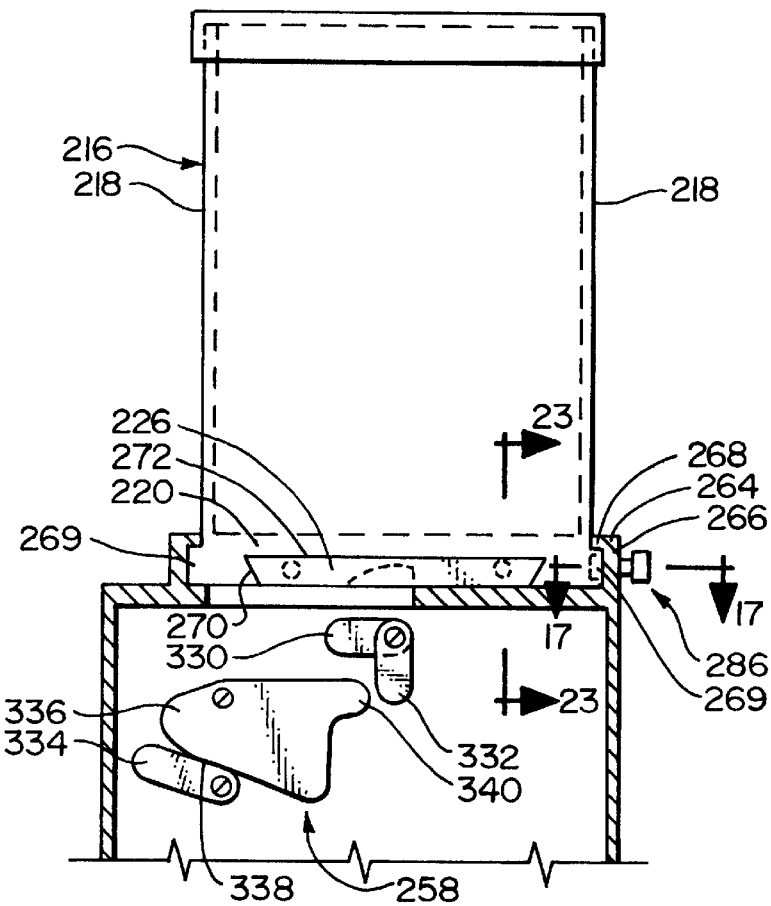
FIG. 16 is a sectional view taken along line 16—16 of FIG. 15.
Figure 18:
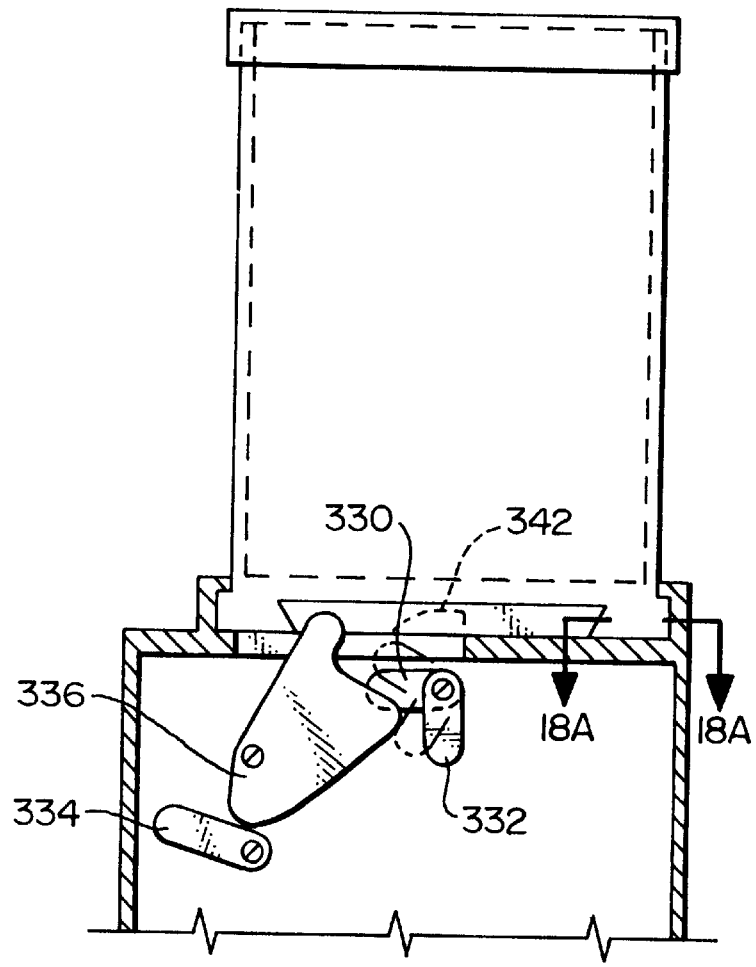
FIG. 18 is a view similar to FIG. 16, but showing the interlock control means in an intermediate position.

As can be seen in FIGS. 16, 18 and 19, the aforementioned slideway 234 comprises two side members 264, each comprising a side plate portion 266 and a laterally and inwardly extending upper flange or lip 268. The bottom wall 220 of the container 216 extends laterally outwardly a short distance to form two elongate side protrusions 269 which fit in the two recesses defined by the members 264.

Figure 14:
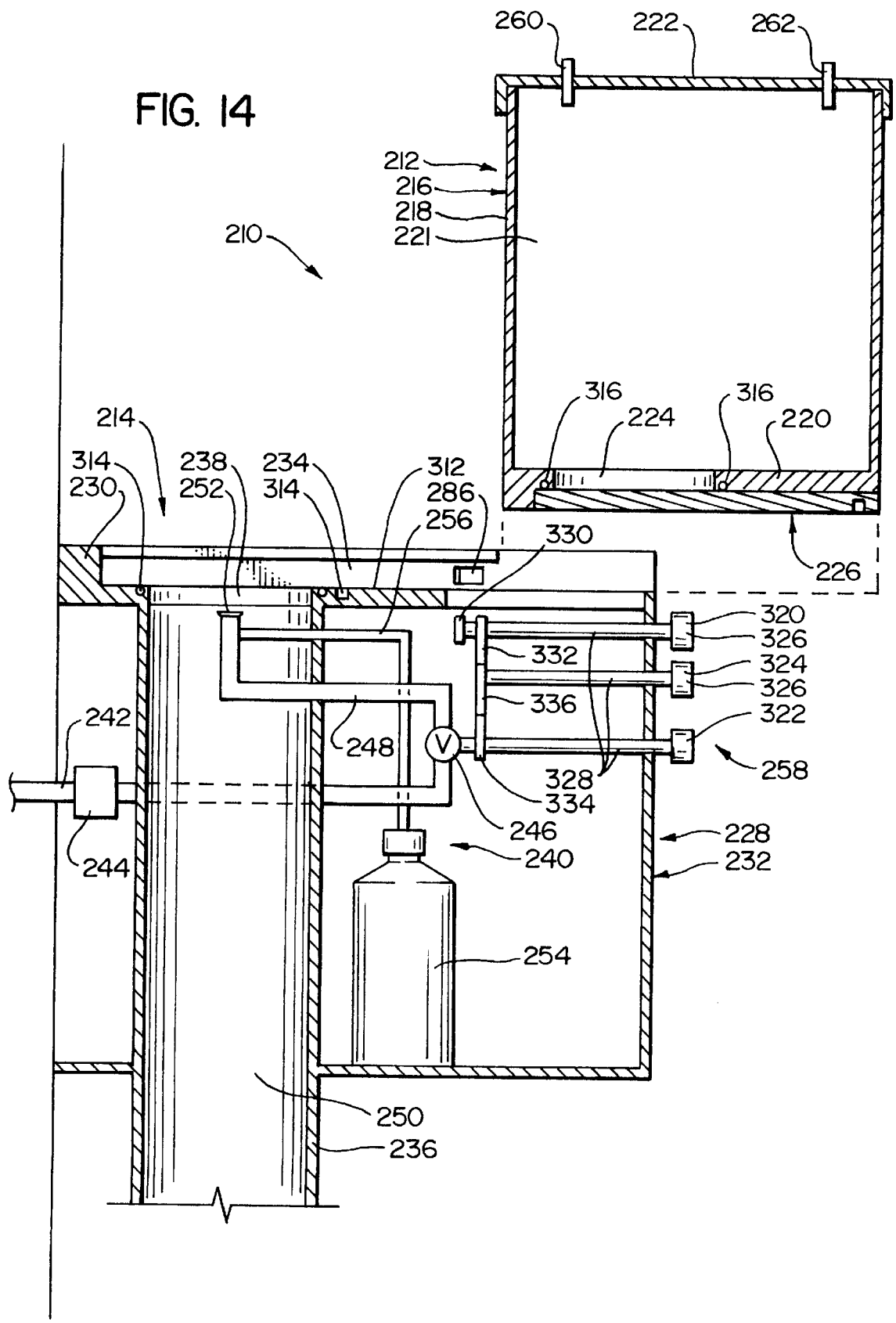
FIG. 14 is a side view, drawn partly in section, of a sixth embodiment of the present invention, with the container assembly being about to be moved into its engaged position with the base assembly.
Figure 15:
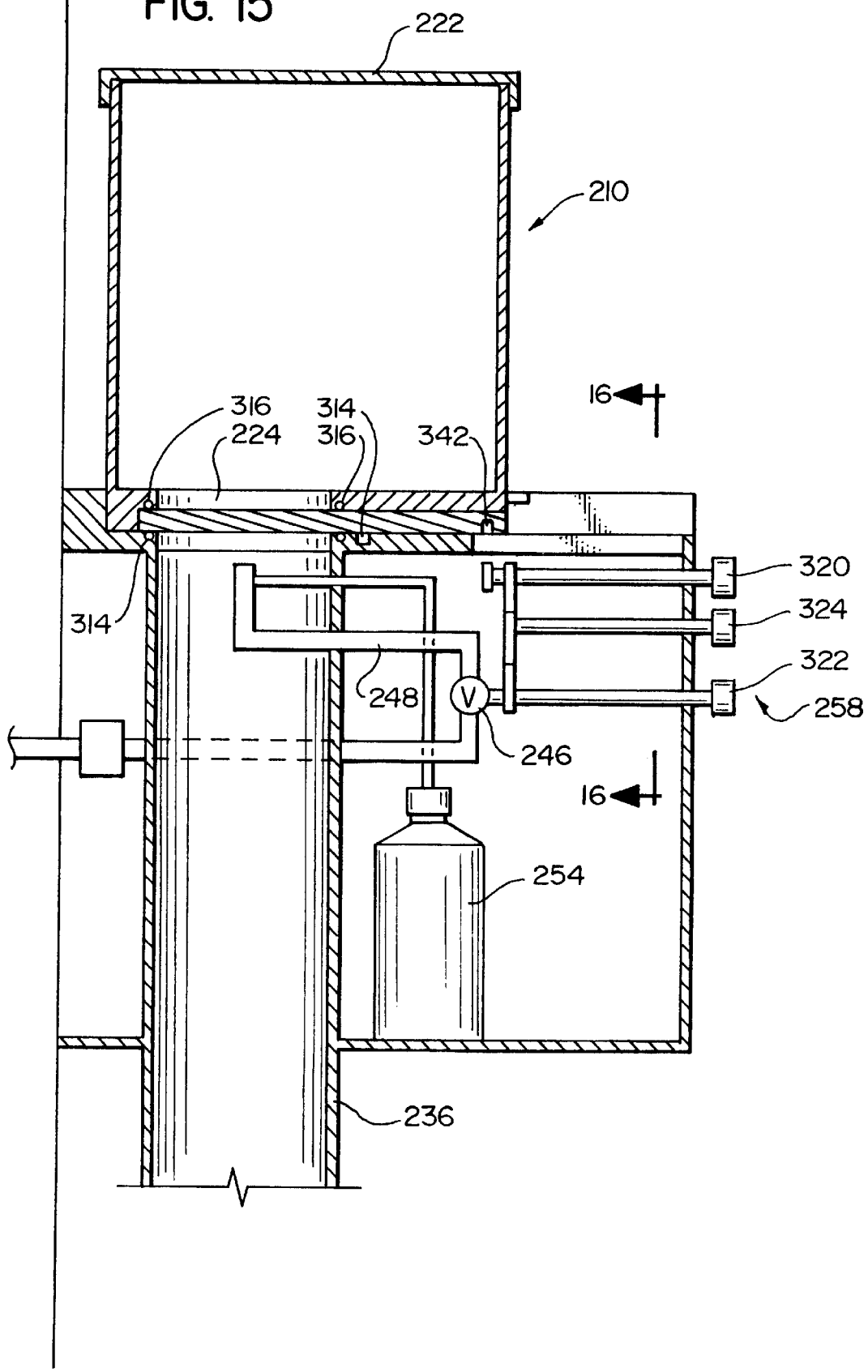
FIG. 15 is a view similar to FIG. 14, showing the container assembly in engagement with the base assembly.

As can be seen in FIGS. 14 and 15, the container assembly 212 is placed in its operating position in its slideway 234 by first positioning the container assembly 212 in a position shown in FIG. 14, where the container assembly 212 is above and to the right of the counter top plate 230. Then the container assembly 212 is lowered so that the left side thereof (as seen in FIGS. 14 and 15) has the side portions 269 of the bottom wall 220 aligned with the recesses defined by the members 264. The container assembly 212 is then moved to the left (as viewed in FIGS. 14 and 15 to move the container assembly 212 into the disposal operating position of FIG. 15.

To discuss further details of the structure of the container assembly 212, in viewing FIGS. 16, 18 and 19, it can be seen that the configuration of the slide valve 226 is that of a generally flat plate having its side edges 270 slanted so that the cross-sectional configuration is that of an isosceles trapezoid with the longer base 272 of the trapezoid being positioned upwardly. The bottom wall 220 is recessed to provide a matching trapezoidal slideway in which to receive the slide valve plate 226.

The slide valve plate 226 is spring loaded so as to be urged toward its closed position. The manner with which this is done can best be seen with reference to FIGS. 23 and 24. At two laterally spaced locations, the slide valve 226 is formed with two elongate slots 274, each of which has positioned therein a related compression spring 276. The front or the right hand end 278 of each compression spring abuts against a finger 280 that is attached to the bottom wall 220 of the container 216. The opposite end 282 of each spring member presses against an end wall portion 284 of its related slot 274. As can be seen in FIG. 24, when the slide valve 226 is moved to the right, as seen in FIG. 24, the two springs 274 become compressed, thus urging the slide valve 226 back to its closed position.

Figure 17A:
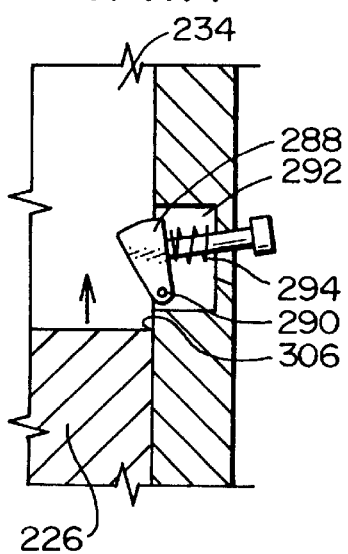
FIGS. 17A, 17B and 17C are three sequential drawings showing the operation of a retaining device to maintain the container assembly in its engaged position in the base assembly.
Figure 17B:
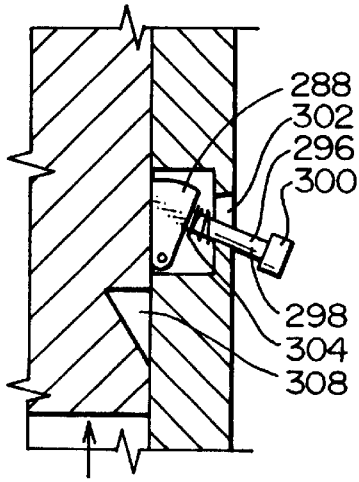

When the container assembly 212 in its disposal operating position (see FIG. 15) in the slideway 234 of the base structure 214, for safety reasons it is desirable that this container assembly remains in that operating position until the person who is discharging the waste material from the container assembly 212 consciously wishes to remove the container assembly 212 from the position of FIG. 15. Accordingly, as can be seen in FIGS. 17A, B and C there is provided a manually operable retaining device 286. As can be seen in FIG. 16, this retaining device 286 is mounted in one of the side wall members 264 of the counter top plate 230. This retaining device 286 comprises a locking element 288 which is pivotally mounted at a pivot location 290 so as to be moveable between two positions, namely a retracted position where it is positioned entirely within a recess 292 formed in the side member 264, and a locking position where it extends outwardly from the recess 292. There is provided a compression spring 294 which urges the locking member 288 to its outwardly extending locking position.

There is a manually operated lever 296 comprising a finger 298 connecting to the locking member 288, and a small knob 300 on the end of the finger 298. This finger 298 extends through a side opening 302 in the side wall portion 266.

Figure 17C:
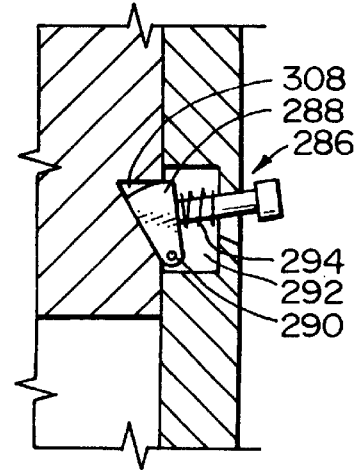

To describe the operation of this retaining member 286, as can be seen in FIG. 17A, when the bottom wall 220 of the container 216 is being moved into the slideway, the leading side edge of the wall 220 engages the locking member 288 to press it inwardly to the position of 17B so that the bottom wall 220 can pass by. When the container assembly 212 is all the way into the slideway 234 in its disposal operating position, then a triangularly shaped slot 308 comes into alignment with the locking member 288, which then springs out into its engaged position as shown in FIG. 17C, thus locking the container assembly 212 in the position of FIG. 15. Therefore, the locking device 286 must be manually moved to its non retaining position by grasping and manipulating the knob 300.

It will be noted that the upwardly facing lower surface 312 of the slideway 234 is formed with suitable seal members surrounding the discharge opening 236. These seals can be seen and are designated 314 (See FIG. 15). Also, the bottom wall 220 has provided at its lower surface surrounding seals 316 which surround the discharge opening 224 in the bottom wall 220.

The operating interlock means 258 comprises three mechanical control members (See FIG. 14). First there is a valve control member 320 which is manipulated to engage the slide valve 226 and move the slide valve to its open position. Second, there is a wash/disinfectant lever number 322 which operates the valve 246 to spray the wash/disinfectant liquid out the nozzle 252. Third, there is an interlock lever 324 which is arranged to ensure that the container assembly 212 is properly positioned during the operation and also ensure that the timing of operating the control levers 320 and 322 is correct. Each of the levers 320, 322 and 324 comprises an operating handle 326 which can be manually grasped and rotated, and a related shaft 328 connected to its knob 326. The valve control lever 320 has at its rear end an operating finger 330 fixedly connected to its related shaft 336 and an interlock finger 332 also fixedly connected to its shaft 328 and positioned at approximately a right angle relative to the finger 330 at a more forward location.

The water/disinfectant operating lever 322 has its shaft 328 operatively connected to the valve 246 so that rotation of the shaft 228 turns the valve 246 on and off. The wash/disinfectant lever 322 also has its own interlock finger 334 fixedly connected to its related shaft 328 and extending radically outwardly.

The interlock lever 324 has fixedly connected to its related shaft 328 an interlock member 336 (See FIG. 16) which is positioned in the same transverse plane as the fingers 332 and 334 and is arranged to interact with both of those fingers 332 and 334 to ensure proper operation.

To describe the operation of the operating and interlock means 258, reference is first made to FIGS. 14, 15 and 16 which show the operating and interlock means 258 in its non-operating release position. In this position, the container assembly 212 can be moved into and out of its disposal operating position relative to its base assembly 214. Also, in this first non-operating position, the valve control lever member 320 is retained in its non-engaged position, and the water/disinfectant valve 322 is maintained in its non-operating position so that the valve 246 remains closed. The reason for this is as follows. As can be seen in FIG. 16, the interlock member 336 is positioned so that it has a surface portion 338 which engages the finger 334 of the water/disinfectant lever 324 so that the lever 332 can not be rotated clockwise (as seen in FIG. 16) to open the valve 246. Also, the interlock member 236 has a protruding portion 340 which is positioned (as seen in FIG. 16) so that the interlock finger, cannot be rotated clockwise to raise the operating finger 330 of the valve control lever 320 upwardly into an engaged position. Further, the interlock member 336 is positioned so that it is entirely below the slideway 234 so that it will not obstruct the slideway 234.

Let us now assume that the container assembly 212 has been positioned so that its lower wall 220 is aligned with the slideway 324 and the container assembly is moved into the slideway 234 so as to be in its disposal operating position as shown in FIG. 16 and also in FIG. 18. Let us also assume that it is also desired to open the slide valve 226 so as to open the bottom discharge opening 224 of the bottom wall 220 of the container 216. The first step is to rotate the lever to 324 in a counterclockwise direction (as seen in FIG. 16) so as to move the interlock member 336 from the position of FIG. 16 through the position of FIG. 18 to the position of FIG. 19. It will be noted that in the position of FIG. 18, the interlock number 336 is still in a position where it blocks the interlock finger 334 of the water/disinfecting lever 322 and also prevents the rotating of the valve lever 320 upwardly and clockwise into its operation positions. When the interlock number 336 is moved further, so that it is in the position of 319, it will be noted that its surface 338 has moved free of the locking finger 334, and that the interlock member 336 is now moved away from the locking finger 332. Thus, in this position, the valve control member 320 can be rotated 90° so that its actuating finger 330 extends upwardly into a matching recess 342 in the forward bottom portion of the slide valve 226. Also, as can be seen in FIG. 19, the protrusion 340 on the interlock member 336 has now moved away from the slideway valve 226 and is positioned in front of the bottom wall 220 of the container assembly 212 so that in this position, the container assembly 212 cannot be moved out of its operating position in the base assembly 214.

Figure 20:
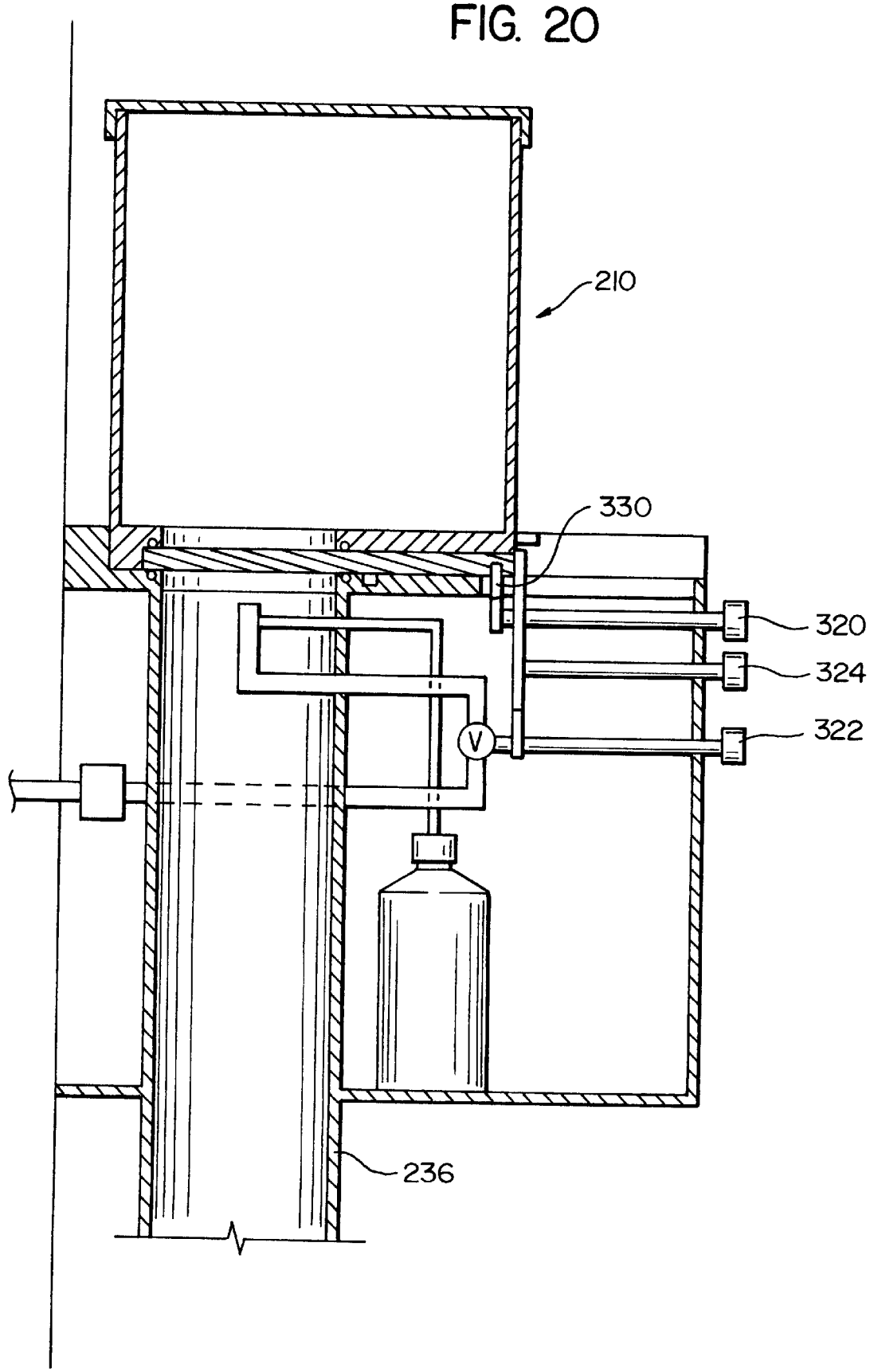
FIG. 20 is a view similar to FIG. 15, showing the valve member of the containing assembly being engaged to be moved to its open position.
Figure 21:
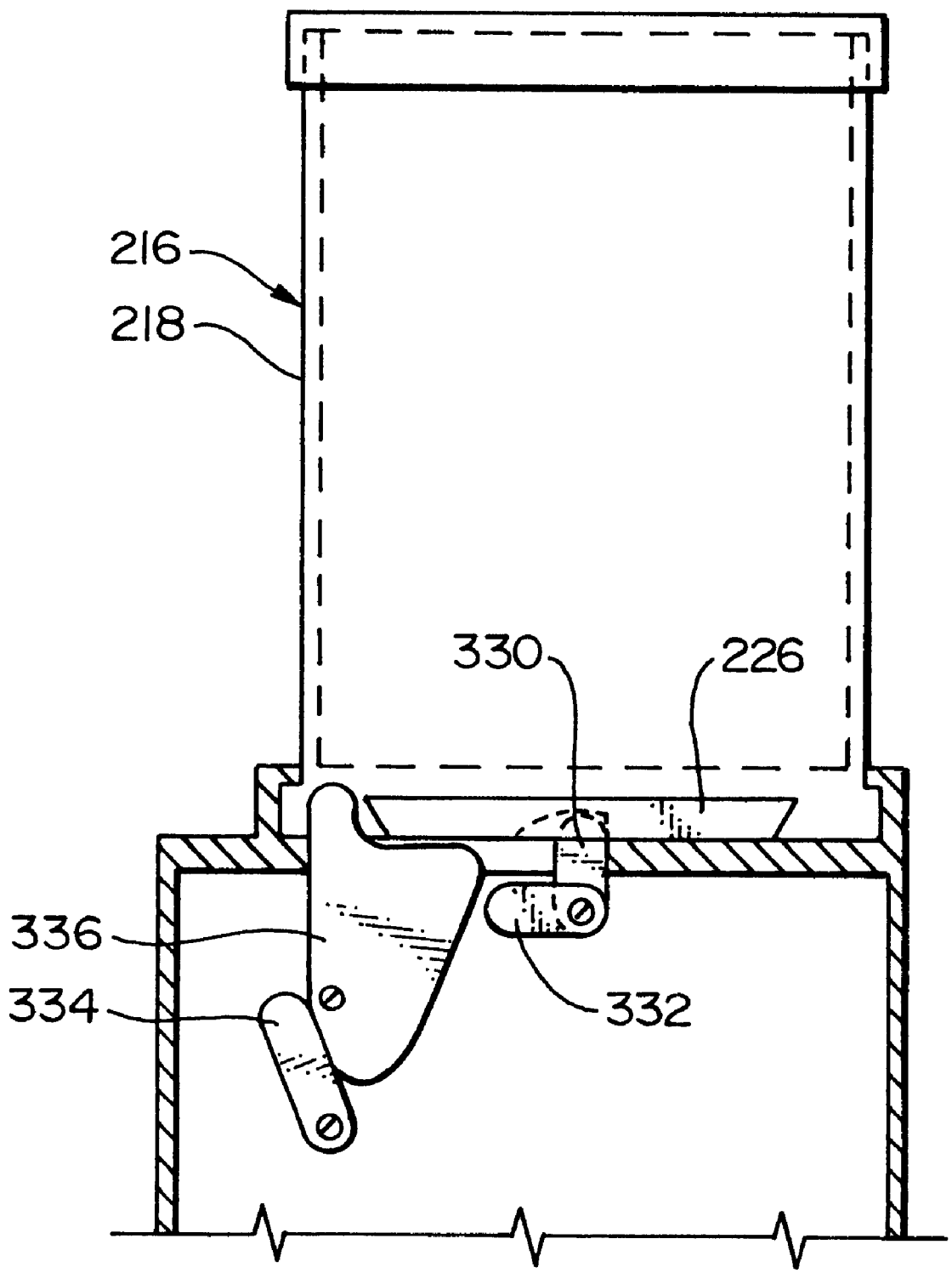
FIG. 21 is a view similar to FIGS. 16, 18 and 19, but showing the wash/disinfectant lever having been moved to its operating position.
Figure 22:
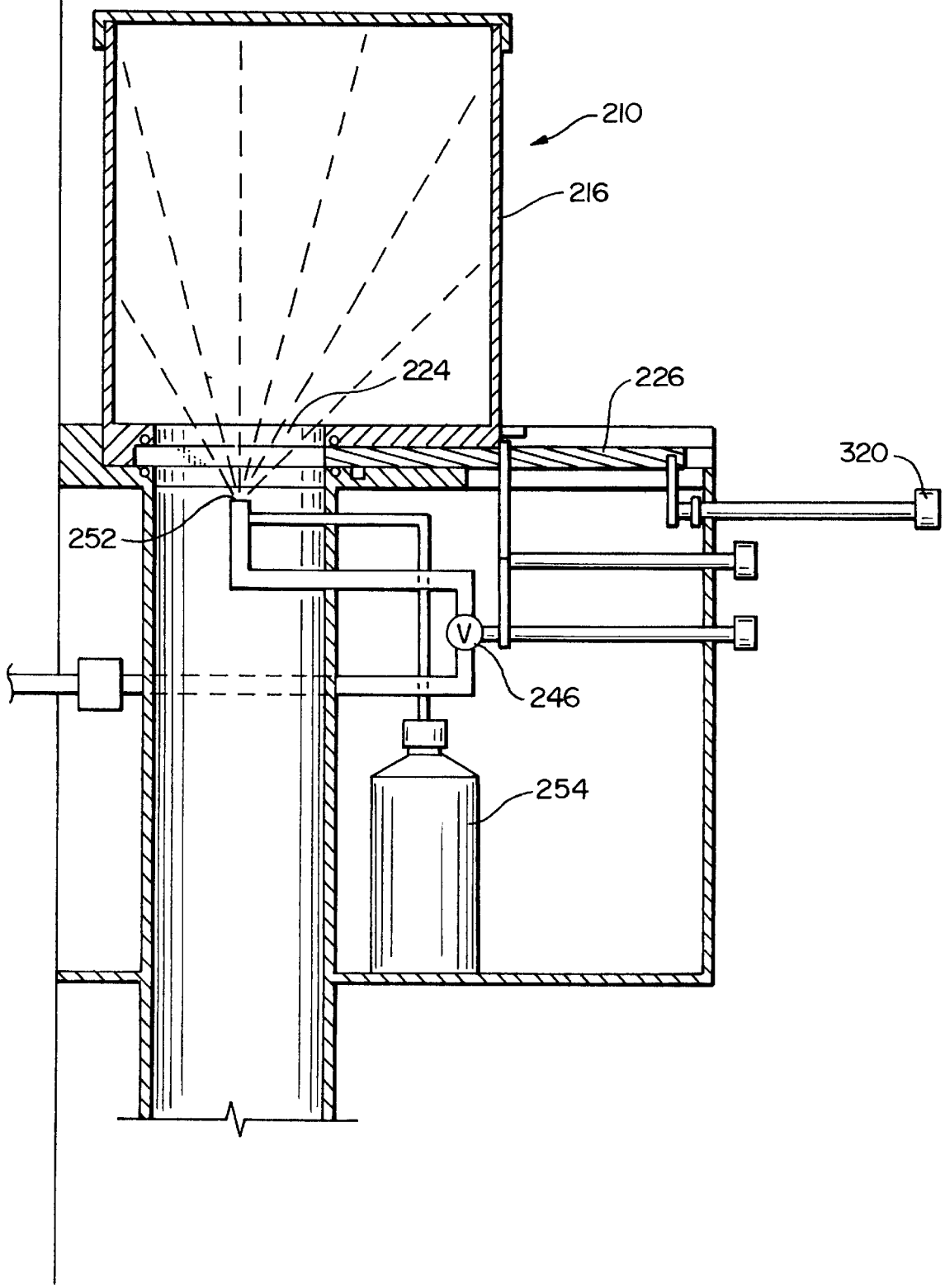
FIG. 22 is a view similar to FIG. 20, showing the wash/disinfectant liquid being sprayed into the interior of the container.

In this position, the valve lever 320 can be pulled forwardly from the position of FIG. 20 to the position of FIG. 22 to withdraw the slide valve 226 so as to open the container opening 224 to permit the contents of the container 216 to flow into the drainpipe opening 238 and down the drainpipe passageway 250. Also, in that position the water/disinfectant operating member 322 can be rotated to open the valve 246 to spray the water/disinfectant upwardly into the container chamber 221. Further, when the slide valve 226 is moved back to its closed position, the valve 246 can also be opened to spray the bottom surface of the valve 226 that is over the drain pipe opening 238.

With the foregoing in mind, let us now review the overall operation of this sixth embodiment.

Initially, the container assembly 220 is positioned near the patient as illustrate in FIG. 1. The suction fitting 260 is connected to the suction tube which is in turn operatively connected to the patient and the other fitting 262 is connected to the vacuum line. The slide valve 226 is urged by its springs 276 into the closed position, as shown in FIG. 14. As show herein, the slide valve 226 does not have any handle or other protuberance which could readily be grasped to move the valve 226 to its open position. To ensure that the valve 226 remains closed while waste material is being collected, and while the container assembly 212 is being moved from one location to the next, there can also be provided a locking mechanism which must be consciously manipulated to a release position before the valve 226 can be moved. For example, a device such as shown in FIGS. 17 A, B and C could also be provided to interconnect the valve 226 with the bottom wall 220, with this device being actuated to its release position when the containing assembly 212 is moved into the slideway 224.

Figure 18A:
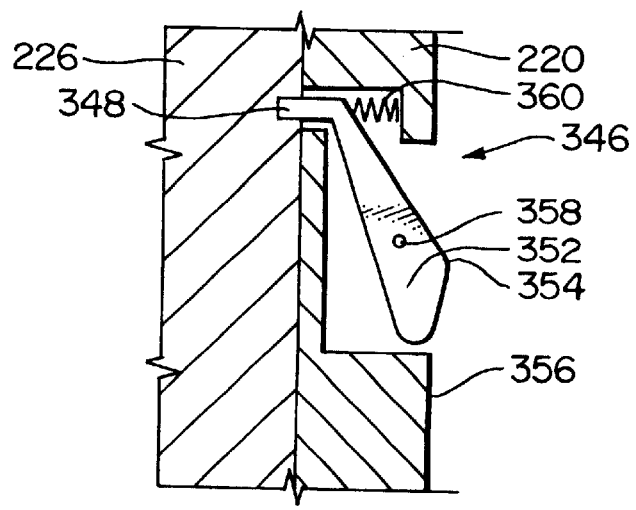
FIG. 18A is a sectional view taken at line 18a—18a of FIG. 18 showing a valve retaining and release mechanism.

Such a device is shown schematically at 346 (See FIG. 18A) where there is a locking finger 348 positioned in a recess 350 and extending into a matching recess in the valve number 226 in a locking position. There is an actuating lever arm 352 which has a slanted outwardly extending cam face 354 which normally extends a short distance outwardly from the lateral sidewall portion 356 of the bottom wall 220. This lever arm 352 is pivotally connected at a central location 358, and a compression spring 360 urges the lock finger 348 into its locking position. However, when the containing assembly 212 is moved into the slideway 218, the adjacent sidewall portion 266 presses against the cam surface 54 to move the lever 252 and retract the lock pin 348.

Thus, when the container 216 is sufficiently full of the waste material so that it would be emptied, the valve number 226 remains secure in its closed position. The suction tube and the vacuum tube are removed from their respective fittings 260 and 262, and the entire container assembly 212 is then moved to the disposal location where the base assembly 214 is located.

As shown in FIG. 14, the waste disposal opening 238 is open. However, it is to be understood that an appropriate cover device could be utilized to close the drain pipe opening 238 when it is not in use. For example, there could be a slideway cover mounted in the slideway 234 and also provided with a spring mechanism (similar to that shown in FIGS. 23 and 24) so that this cover would be urged to its closed position. Then the movement of the container assembly 212 in the slideway 234 would push the cover rearwardly away from the drain opening 238, with the slide valve then being positioned over the drain opening 238.

As described previously, the container assembly 212 with the contained waste material is initially positioned as shown in FIG. 14, then moved a short distance downwardly so that the bottom wall 220 is aligned with the slideway 234.

The container assembly 212, being in alignment with the slideway 234, is then moved fully into the slideway 234 to its disposal operating position as shown in FIG. 15. At this time, the retaining mechanism 286 will have first been moved out of the way to the position of 17B, and then the locking element 288 moves out into its locking position in the recess 308 (see FIG. 17C).

The next step is to move the slide valve 226 to its open position as shown in FIG. 22. To accomplish this, the first step is to rotate the interlock lever 324 approximately 90° counterclockwise so that its interlock member 336 moves from the position of FIG. 16, through the position of FIG. 18, to the position of FIG. 19. In the position of FIG. 19, three things have been accomplished by movement of this interlock member 336. First, the protruding portion 340 of the interlock member 336 is positioned so that it is out of the way of the slide valve 226 and is positioned in front of the left part of the bottom wall 220. Thus, the container assembly 212 is securely held in its operating position, and the slide valve 226 can be moved forwardly to its open position. Second, the interlock member 340 has moved out of its obstructing position relative to the locking finger 332 so that the slide valve lever member 320 can be rotated 90° in a clockwise direction. Third, the interlock member 336 has moved out of the way of the locking finger 334 so that the wash/disinfectant valve 322 can be operated.

The next step is to rotate the slide valve operating member 320 90° clockwise from the position of FIGS. 16 and 18 to the position of FIG. 19. In this position, the actuating finger 330 is positioned in the slide valve recess 342. Then the slide valve operating member is pulled from the position of FIG. 20 forwardly to the position of FIG. 22. This moves the slide valve 226 from its position where it covers the opening 224 in the bottom wall 220 so that the waste material that has been collected in the container flows out the opening 224, through the drain pipe inlet 238 and down the drain pipe passageway 250.

When the drainage of the waste material into the drain pipe 236 has been completed, the wash/disinfectant operating lever 322 is rotated to open the valve 246 to cause the wash water to flow from the line 242, through the check valve 244, through the valve 246, through the line portion 248 and out the nozzle 252. At the same time, the disinfectant from the container 254 can be injected into the line 248 to cause the disinfectant to mix with the wash water and be sprayed into the interior of the container 216, as shown in FIG. 22. When the washing is complete, the slide valve lever 320 is released, and the action of the springs 276 (see FIGS. 23 and 24) and move the slide valve 226 back to its closed position. If desired, the wash/disinfectant valve 246 could also be operated to wash off the exposed bottom surface portion of the slide valve 226.

To remove the container assembly 212, first the slide valve control lever 320 is rotated 90° counterclockwise back to the position of FIG. 16. Then the interlock lever 324 is rotated counterclockwise to move the interlock member 336 to the position of FIG. 16. The wash/disinfectant control lever 322 would have already been rotated counterclockwise to its closed position for its related valve 246.

The lock release member for the locking device 286 is pulled outwardly (see FIGS. 17A–17C), and then the container assembly 212 is moved out of the slideway 234. The container assembly 212 is returned to its location proximate to the patient and then again hooked up to the suction and vacuum lines.

g) Seventh Embodiment

Figure 25:
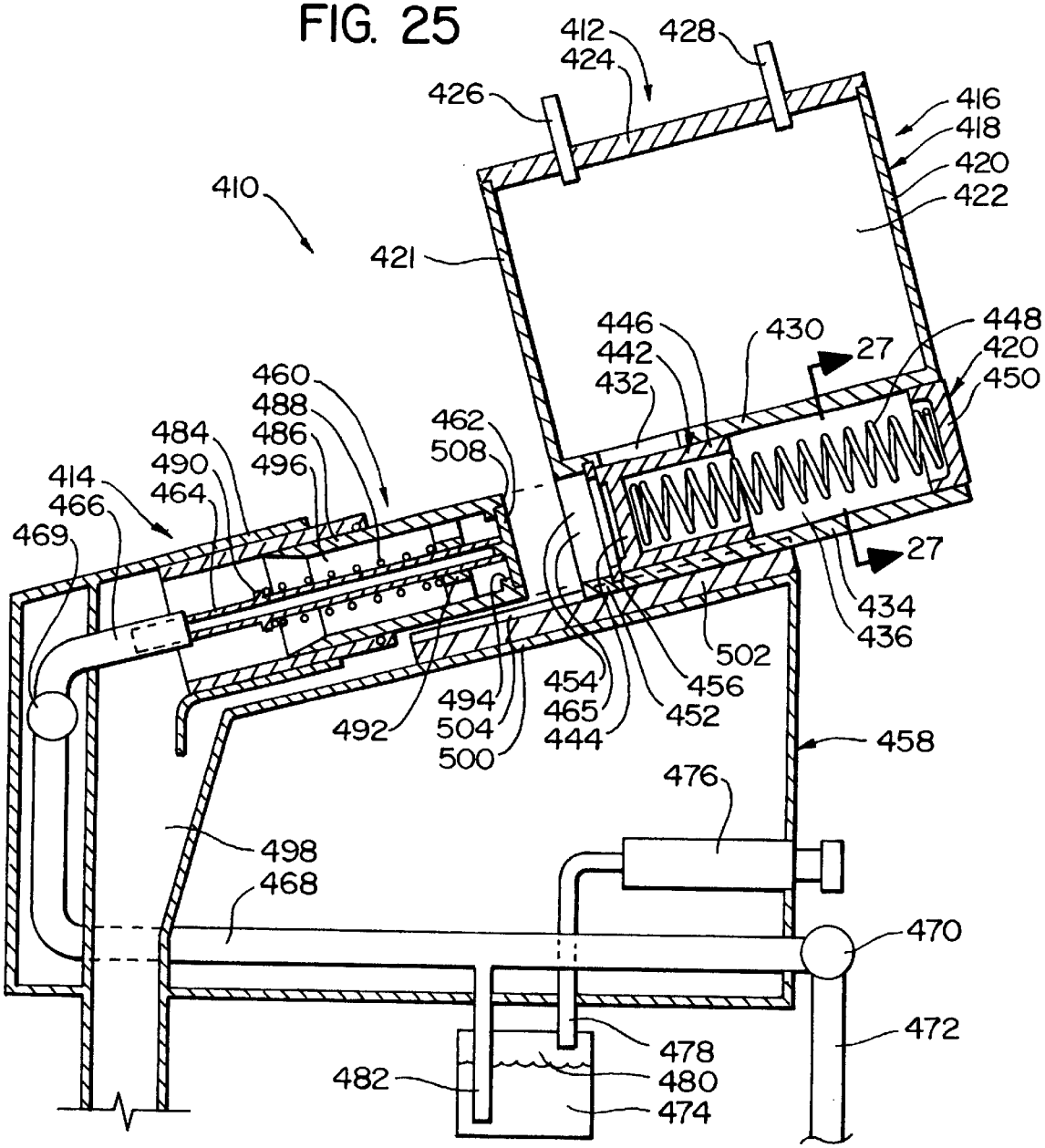
FIG. 25 is a vertical longitudinal sectional view of a seventh embodiment of the present invention, with the container assembly being in a position to be moved into engagement with the base assembly.
Figure 26:
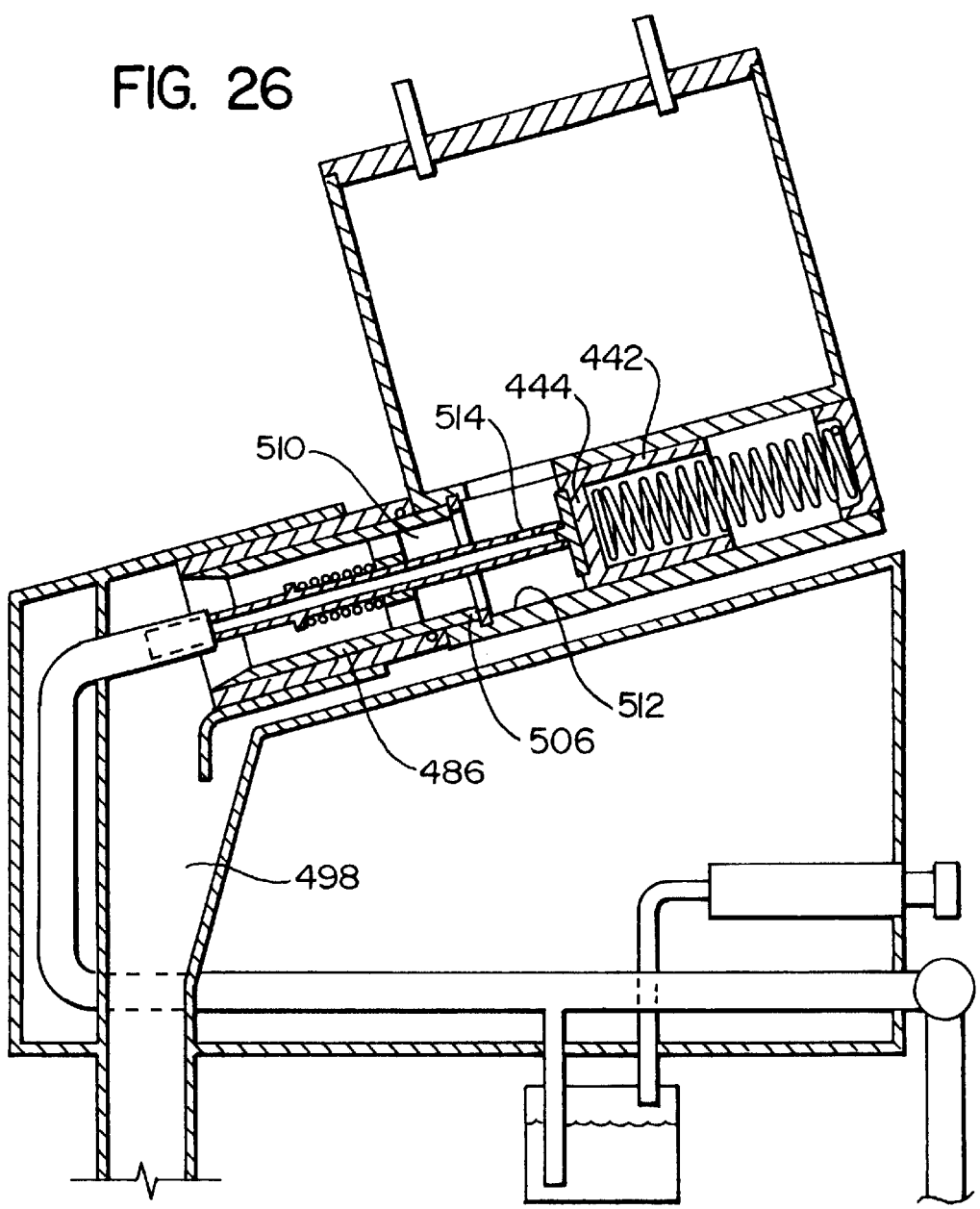
FIG. 26 is a view similar to FIG. 25, but showing the container assembly having been moved into its operating position to empty its contents into the base assembly.
Figure 27:
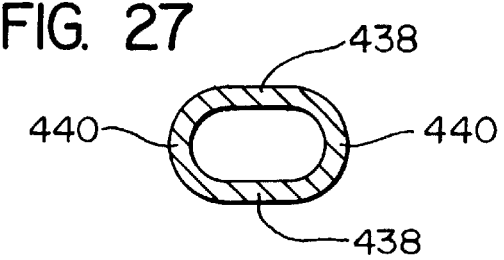
FIG. 27 is a sectional view taken along line 27—27 of FIG. 25, showing the cross section of the valve housing.

FIGS. 25, 26 and 27 disclose this seventh embodiment of the present invention. The system 410 of the seventh embodiment comprises a container assembly 412 and a base member 414, the container assembly 412 comprises a container 416 having an upper containing section 418, and a lower valve section 420, the containing section 418 comprises four sidewalls 421 defining a containing chamber 422, and a top cover 424 having a suction tube connection 426 and a vacuum tube connector 428. The containing section also has a bottom wall 430 having at its forward middle portion a discharge opening 432.

The valve section 420 comprises a valve housing 434 defining a valve chamber 436 which in transverse section has, the configuration of a flattened circle having a planar upper and lower portions 438 and semicircular end sections 440 (See FIG. 27). There is a valve element 442 slide mounted in the chamber 436. This valve element 442 comprises a forward closure wall 444 having the same configuration as the chamber 436, and also a rearwardly extending circumferential wall 446, also having a cross section matching that of the chamber 436 fitting snugly in the chamber 436. Also positioned in the chamber 436 is a compression spring 448, which bears against a rear plug member 450 that closes the rear end of the chamber 436. The valve housing 434 has a forward flange 452 which defines a forward entry portion 454 having the same cross sectional area as the chamber 436. Positioned at the rear of inner part of this entry portion 454 is an inwardly extending circumferential lip 456 which serves as a stop member to engage the outer edge portion of the front wall 444 of the valve element 442.

In FIG. 25, the container assembly 412 shows the valve element 442 in its closed position where the upper part of the sidewall 446 totally closes the discharge opening 432. The waste material is contained in the chamber 442 which is above the discharge opening 432.

The base assembly 414 comprises a base housing 458. At the upper end of the base housing 458 there is a valve actuating and drain mechanism 460 which comes into operative engagement with the valve section 420 to move the valve element 442 rearwardly to its open position, and also to form a closed drain passageway with the discharge opening 432. This mechanism 460 comprises a valve operating member that comprises a rearwardly facing valve opening plate 462 that is mounted by a tubular rod 464 at a fixed portion. This plate is configured to match, and fit within, a shallow recess 465 formed in the front face of the valve wall 444. This rod 464 is in turn connected to a discharge end 466 of a water pipe 468 which connects through a check valve 469 to a valve 470 that in turn connects to a water supply line 472. There is also a supply of disinfectant at 474. To inject the disinfectant 474 into the water line, there is provided a manually operated pump member 476 that pumps pressurized air through a tube 478 into an upper area 480 of the disinfectant container, this causing the disinfectant to flow under pressure into an outlet tube 482 and into the line 468.

To return to our description of the valve actuating and drain mechanism 460, this mechanism 460 comprises a stationary sleeve 484 in which is positioned an inner sleeve 486 that is slide mounted within the outer stationary sleeve 484. A compression spring 488 is positioned around the aforementioned stem 464, with the rear end of the spring 488 bearing against a stop member 490 on the stem 464, and with the forward end of the spring 488 bearing against an inner portion of a spider member 492 which is fixedly attached to the inner movable sleeve 486 and slide mounted around the stem 464. The inner forward surface portion of the moveable sleeve 484 has an inwardly extending lip 494 which engages the front plate member 462 to limit the forward movement of the sleeve member 486. The moveable sleeve member 486 and the stationary sleeve 484 collectively define a drain passageway 496 that leads into a rear downwardly extending drain passageway 498. The sleeve 486 has a cross sectional configuration matching that of the recess 454 so that the front end of the sleeve 454 forms a seal when positioned in the recess 454.

The base housing 458 has an upper support plate portion 500 which slopes at a moderate angle in a downward and forward direction. Mounted on this support plate 500 is a guide plate 502 defining a slideway 504 which in turn engages a matching plate which is fixedly attached to the valve lower part of the valve housing 434 on opposite sides thereof. To place the container assembly 412 in its operating position relative to the base assembly 414, the locating plate on the bottom of the container assembly 412 is placed in alignment with the slideway 504 and moved so that the plate comes into engagement with the slideway 504.

To describe the overall operation of this seventh embodiment, the container assembly 412 is initially placed at a location near the patient to receive the waste material as described previously herein. When the container assembly 412 is to be emptied, the suction tube and the vacuum tube are removed from their respective connectors 426 and 428, and the container assembly 412 with the waste material positioned in the chamber 422 is carried to the disposal location where the base assembly 414 is located. In this closed position, as shown in FIG. 25, the upper part of the valve sidewall 446 totally closes the discharge opening 432. Also, the perimeter portion of the front plate 444 engages the stop member 456 so as to form a tight seal (the stop member 456 also functioning as a seal).

To discharge the waste material from the container 418, the container assembly 412 is placed in alignment with the valve actuating and drain mechanism 460 as shown in FIG. 25. In this position, the locating plate at the lower part of the container assembly 412 is in alignment with the slideway 504, the container assembly 412 is moved forwardly so that the locating plate of the container assembly 412 enters into the slideway 504.

The forward recess area 454 moves over the outside forward surface portion of the moveable sleeve 486, and the front edge 508 of the sleeve 486 comes into engagement with the stop member 456 which also functions as a seal to form a seal with this forward edge portion 458. With a slight amount of further forward movement of the container assembly 412, the stationary plate 462 comes into engagement with the front wall 444 of the valve element 442 to fit within the front wall recess 465. As forward movement of the container assembly 412 continues, the stationary plate 462 pushes the valve element 442 rearwardly against the urging of the compression spring 448. At the same time, the stop member 456 pushes the moveable sleeve 486 rearwardly so that it slides rearwardly into the stationary sleeve 484.

This rearward movement continues until the forward edge portions of the lower front wall portion of the forward wall 420 and the forward edge of the valve housing 424 come into engagement with the front edge of the stationary sleeve 484, thus arriving at the position of FIG. 26. It can be seen in this position that the front wall 444 of the valve element 442 has moved completely away from the discharge opening 432. This causes the container waste material to flow through the discharge opening 432 and into the discharge passageway 510 that is formed by the surface portion 512 of the valve housing 434 which is (as shown in FIG. 26)

forwardly of the wall 444 of the valve member 442, then through the moveable sleeve 486 and into the main drain passageway 498.

When the draining of the waste material is substantially complete, the water valve 470 is opened and water flows through the tube 468 and into the interior passageway defined by the stem 464. There are vent openings 514 formed in the forward part of the stem 464, and the wash water flows out these vent openings 514 into the chamber 422. Also, the disinfectant can be fed into the water line 466 to mix with the wash water.

To move the container assembly 412 out of engagement with the base assembly 414, the person simply grasps the containing section 416 and pulls the entire assembly 412 rearwardly. When the assembly 412 is being moved rearwardly, the moveable sleeve 486, due to the urging of the spring 488, moves with the assembly 412, with the forward portion of the sleeve 486 still forming a seal with the extension portion 452 of the valve housing 434, and also forming a seal with the seal/stop member 456. At the same time, the valve element 442 is being moved forwardly in its valve chamber 436, due to the urging of the spring 448. At a certain relative position between the assemblies 412 and 414, the front wall 444 comes into sealing engagement with the seal/stop member 456. Very shortly after that, the forward edge 506 of the moveable sleeve 486 moves away from the seal/stop member 456 so that the forward edge portion of the sleeve 486 is positioned around the stationary plate 462. This encloses the drain passageway 510 that is positioned within the valve actuating and draining mechanism 460.

With the container assembly 412 completely separated from the base assembly 414, the valve element 442 has returned to its forward position so that the valve sidewall 446 totally closes off the discharge opening 432. In addition, the valve forward wall portion 444 makes seal with the seal/stop member 456. The container assembly 412 is then returned to its prior location where it is near the patient to receive further waste material that is suctioned or otherwise removed from the patient and delivered into the containing chamber 422.

h) Eighth Embodiment This eighth embodiment is similar to the seventh embodiment shown in FIGS. 25. Some of the components of this eighth embodiment which are similar to corresponding of the seventh embodiment will be given like numerical designations, with a "a" suffix distinguishing those of the eighth embodiment.

Figure 28:
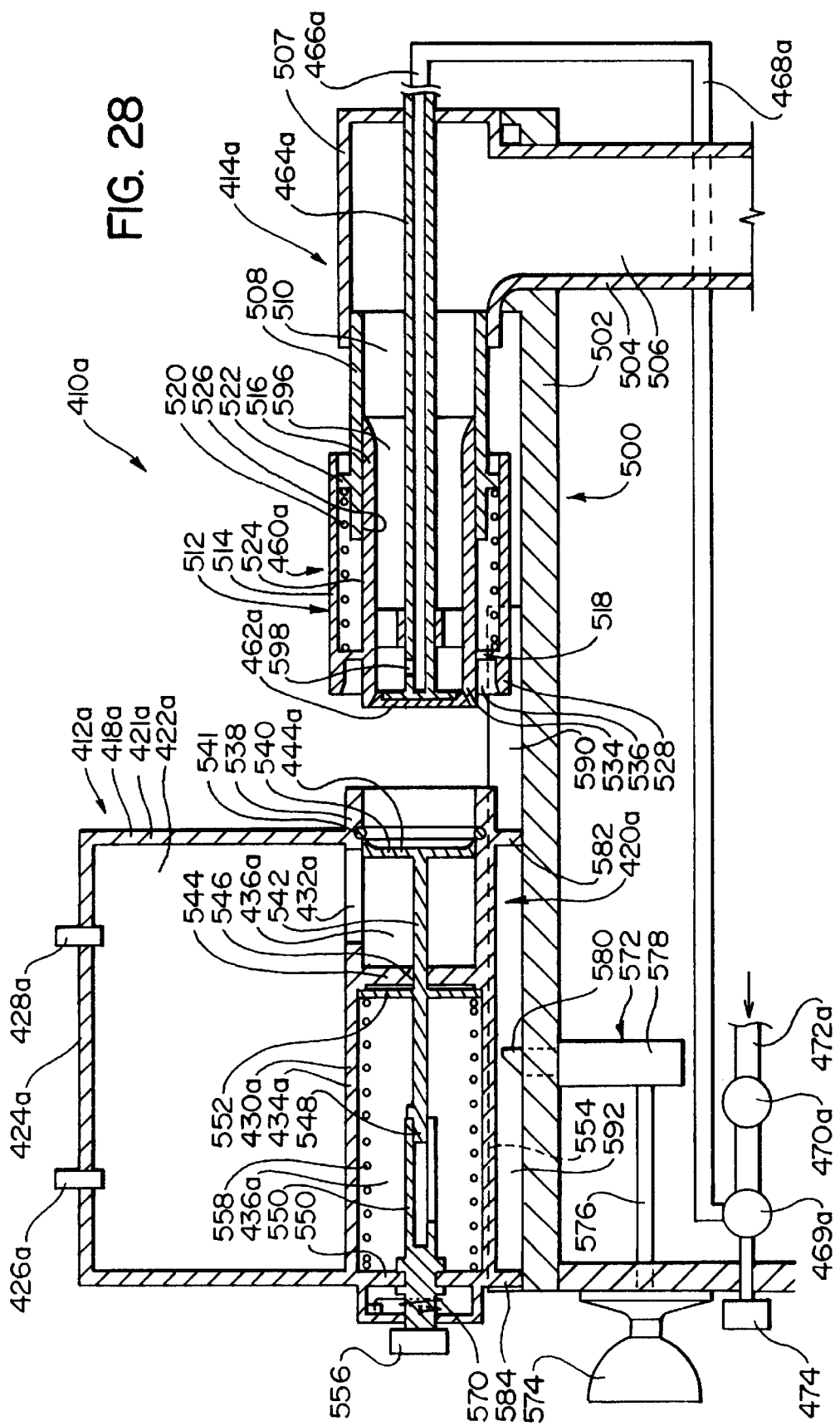
FIG. 28 is a longitudinal, vertical sectional view of an eighth embodiment of the present invention, showing the container assembly being in a position to be put into engaged position with the base assembly.

Reference is first made to FIG. 28. As in the seventh embodiment, the apparatus 410a comprises a collecting assembly 412a and a base assembly 414a. The collector assembly 412a comprises a containing section 416a which in turn comprises an upper container section 418a and a lower valve section 420a. The containing section 418a comprises four sidewalls 421a defining a containing chamber 422a. There is a lid 424a closing the chamber 422a, and positioned in this lid 424a are two connectors 426a and 428a to connect to, respectively, a suction tube and a vacuum tube.

The containing section has a bottom wall 430a and at the forward part of the bottom wall 430a there is a discharge opening 432a formed in the bottom wall 430a. The valve section 420a comprises a valve housing 434a defining a valve chamber 436a. There is a valve element 442a which comprises a forward wall 444a.

As in the prior embodiment, the base assembly 414a comprises a valve operating and drainage mechanism 460a. This comprises a front stationary wall member 462a which is fixedly connected to a tubular stem 464a that in turn connects to an inlet end 466a of a water line 468a that connects through a check valve 469a and thence to a water valve 470a that connects to a water inlet line 472a. As in the seventh embodiment, there can also be provided a source of disinfectant 474 and also means for directing the disinfectant into the water line. Some of the remaining components in this eighth embodiment have some structural and functional differences from the components of the seventh embodiment so that the prior pattern in describing this eighth embodiment of giving like numerical designations with an "a" suffix following such numerical designations will not be used to describe the additional components. Rather, new numerical designations will be given.

The valve actuating and draining mechanism 460a further comprises a stationary housing 500 that is mounted on a stationary platform 502 which can be a table top or a counter top. This table top 502 has an opening to receive a drain pipe 504 defining a drain outlet passageway 506. There is an upper housing portion 507 that has mounted within it a stationary sleeve 508 which defines a horizontally extending drain passageway 510 which leads rearwardly into the drain passageway 506.

Mounted to the forward end of the fixed sleeve section 508 is a forward moveable sleeve section 512. This sleeve section 512 comprises an outer sleeve member 514 and an inner sleeve member 516, with these two sleeve members 514 and 516 being joined to one another by a forward annular wall section 518.

The moveable sleeve 512 section is urged to its forward position by means of a compression spring 520 that is mounted within, and closely adjacent to, the inner surface of the outer sleeve 514. The rear end of this spring 520 that bears against an annular shoulder 522 extending radially outwardly from the fixed sleeve section 508, while the forward end of the spring 520 bears against the aforementioned wall 518. The outer surface 524 of the inner sleeve 516 fits against, and slides against, the inner surface 526 of the fixed sleeve 508. Also, the moveable sleeve section 512 further comprises a forward sleeve extension 528 which is connected by its rear end to the forward outer surface portion of the outer sleeve section 514. The forward extension 528 forms with a forward extension 534 of the inner sleeve an annular recess 536. This annular recess 536 receives a forward circumferential edge portion 538 of the aforementioned valve housing 434a.

The valve section 420a will now be described in more detail. The valve element of this eighth embodiment, instead of comprising a forward plug and rearwardly extending sleeve, as in the seventh embodiment, comprises a forward plug 540 that is mounted to a rod 542 which extends rearwardly through a stationary barrier wall 544 formed across the valve.housing 434a, with this wall 544 making a seal at 546 with the rod 542.

The rear end 548 of this rod 542 is positioned within a sleeve 550 which is rotatably mounted in the rear part of the valve housing 434a. At about its mid-length, there is fixedly connected to the rod 542 a pair of radially extending fingers 552 which extend into related slots 554 that extend longitudinally in the valve wall rearwardly from the barrier wall 544. These fingers 552 position the rod 544 and prevent the rod 544 from rotating within the valve housing 434a.

The sleeve 550 extends through a rear wall 554 of the valve housing 434a and is fixedly connected to a control knob 556.

Figure 29:
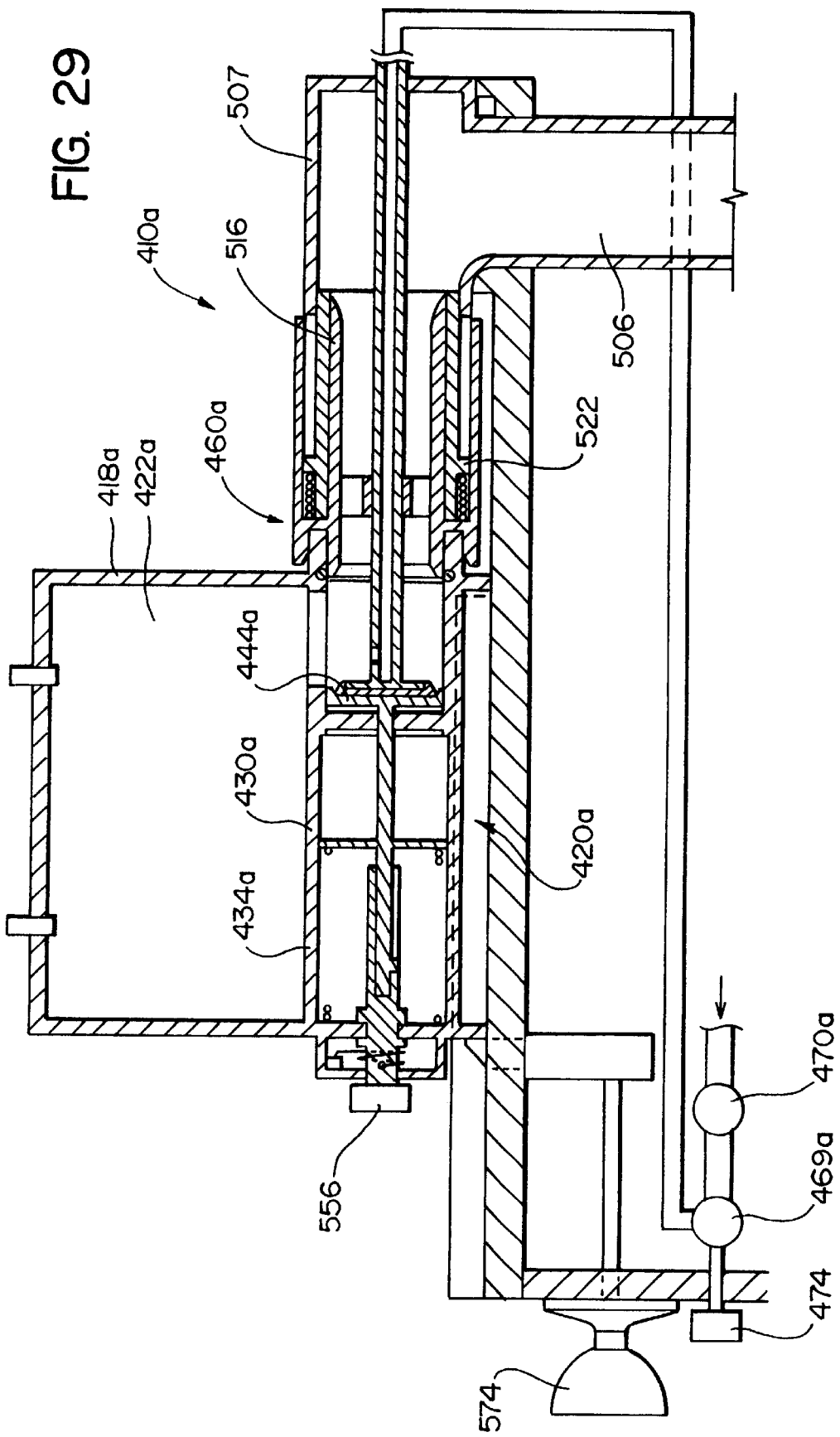
FIG. 29 is a view similar to FIG. 28, showing the container assembly in its operating position relative to the base assembly.
Figure 30:
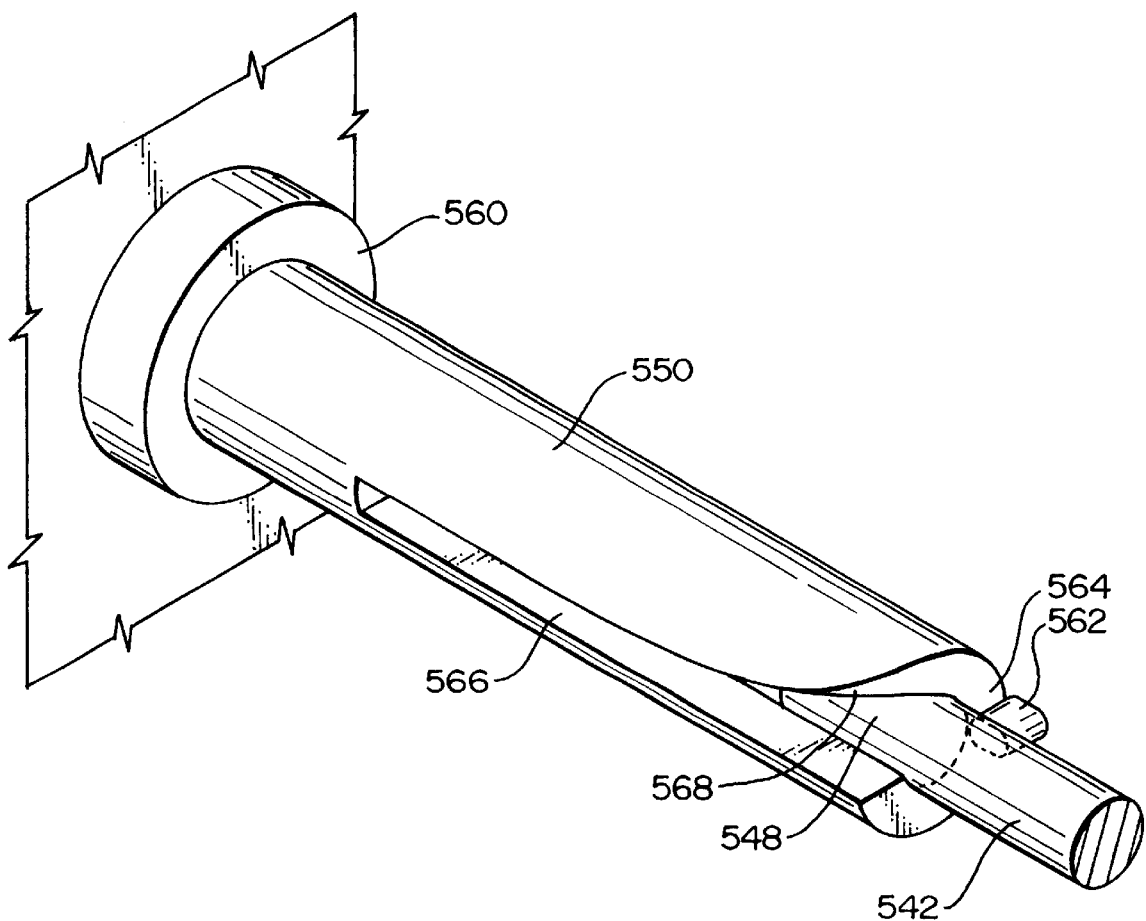
FIG. 30 is an isometric view of a valve locking mechanism of the eighth embodiment.

The purpose of this control knob 556 and the positioning sleeve 550 is to lock the valve plug 540 in its forward closed position, as shown in FIG. 30, or permit the valve plug 540 to be moved rearwardly in the valve housing 434a. There is a compression spring 558 which is positioned within the rear part of the valve housing 534a adjacent to its inside surface, and this spring 558 bears against the aforementioned positioning fingers 552. Thus, the rod 554 and the valve plug 540 attached thereto are both urged to the right, as seen in FIGS. 28 and 29 to the closed position of the valve plug 540.

Attention is now directed to FIG. 30 which shows the aforementioned sleeve 550 which is connected to the knob 556. As indicated previously, the end portion 548 of the rod 542 is positioned in the sleeve 550, which in turn is rotatably mounted by a pair of collars, one of which is shown at 560 in FIG. 30, and both of which are shown in FIGS. 28 and 29.

The rod 552 has fixedly connected to it a short distance forwardly of the rear end of the rod 542 a locking finger 562 which extends radially a short distance from the rod 562. In the position of FIG. 30, the knob 556 has been rotated to a position where the finger 562 rests against a flat locking surface 564 which is transversely aligned relative to the longitudinal axis of the rod 542 and the sleeve 550. The sleeve 550 is formed with a longitudinal slot 566, with the forward end of this slot having one of its side surfaces 568 slanting from the longitudinal axis so as to slant in a circumferential direction toward the flat locking surface 564.

It is apparent from viewing FIG. 30 that as the sleeve 550 is rotated counterclockwise (as seen in FIG. 30), the surface 564 moves by the locking finger 562 until the transitioning surface portion 568 encounters the finger 562. A small amount of further rotation brings the finger 562 in alignment with the slot 566. At that position, the rod 542 can move rearwardly into the sleeve 550. As is evident from the prior description, this would occur when the valve plug or plate 540 is moved rearwardly in the chamber 536a.

The knob 556 is mounted in a manner that it is urged by a spring shown somewhat schematically at 570 to rotate toward the locking position as shown in FIG. 30. In the locking position of FIG. 30, the valve plate or plug 540 closes off the valve chamber 436a to prevent any leakage or outflow of the waste material in the chamber 422a.

When the container assembly 412a is functioning as a container, either at the location of the patient or when it is being carried or otherwise moved to the disposal location, the knob 556 is turned to the full locking position where locking finger 562 is positioned well onto the flat locking surface 564.

Then when the container assembly is placed in its position where it is to be moved into disposal operating engagement with the base assembly 414a, the knob 556 is rotated to bring the sleeve 550 so that the slot 556 is in alignment with the locking finger 562. This permits the valve element 540 to be moved to its retracted position to open the opening 432a.

In the event that the person operating the system removes the container assembly 412a out of engagement with the base assembly 414a, but neglects to manually rotate the knob 556 to its full lock position, the container assembly 412a is arranged so that the springs will automatically move the sleeve 550 to a single locking position. First, the spring 558 urges the valve element 540 to its forward position, thus carrying the rod 542 to its forward position. At the same time, the spring 570 urges the knob 556 to its locking position, thus moving the locking finger 562 at least part way along the surface 568 where it retains the rod 542 in its forward position where the valve plate 540 is in its closed position.

With reference to FIGS. 28 and 29, there is further provided a retaining latch assembly 572, which can be of conventional design, such as a latching assembly which would be used in a door. As shown herein, this latching assembly 572 comprises an operating handle 574 which could simply by a conventional door knob, which connects to a shaft 576 that in turn connects to the latching mechanism 578. The actual latch 580 extends a short distance above the counter top 502.

The containing assembly 412a is provided with mounting plates 582 and 584. As the container assembly 412a is moved to the right from the position of FIG. 28 to the position of FIG. 29, the rear support plate 584 passes over the latch 580 so as to depress it. Then as soon as the support plate 584 proceeds a short distance further, the latch 580 snaps up, as shown in FIG. 29, to hold the container assembly 412a in its disposal operating position.

The housing structure 500 of the base assembly 414 is provided with a pair of upstanding flanges 590 which define a slideway 592 to guide the container assembly 412a as being moved into its operating disposal position relative to the base assembly 414a.

To describe the operation of this eighth embodiment, it is apparent from comparing the eighth embodiment with the seventh embodiment that the basic mode of operation of this eighth embodiment is rather similar to that of the seventh embodiment.

Thus, the container assembly 412a is positioned in the slideway 592 where it is aligned with the base assembly 414a. Previously, the container assembly 412a has been moved from its location next to the patient, and it has a quantity of waste material contained therein, which is to be disposed of. As in the seventh embodiment, the container assembly 412a is moved so that initially the extension 538 of the container assembly 412a enters into the recess 536 at the forward part of the double sleeve member 512 to form a seal. Also, the stationary wall member 462a engages the valve plug 540a to move it rearwardly.

As described in connection with the seventh embodiment, this causes the flow of the waste material into the passageway portion 596 defined by the inner sleeve member 516 and thence into the discharge passageway 506. After the discharge of the material, water/disinfectant is directed through the line force 468a and through the stem 464a to exit through the vent openings 598 to clean/disinfectant the interior of the container 418a and the other exposed surfaces of the container assembly 412a.

When the cleaning step is completed, then the container assembly 412a is moved to the left, back to the position of FIG. 28. The moveable sleeve section 518 moves forwardly to its position to seal with the plate member 462a. Also, the valve plate or plug 540 moves forwardly to its sealed position. The knob 556 is moved to the locking position, and the container assembly 412a is moved back to its collecting location to collect more waste material.

i) Ninth Embodiment

Figure 31:
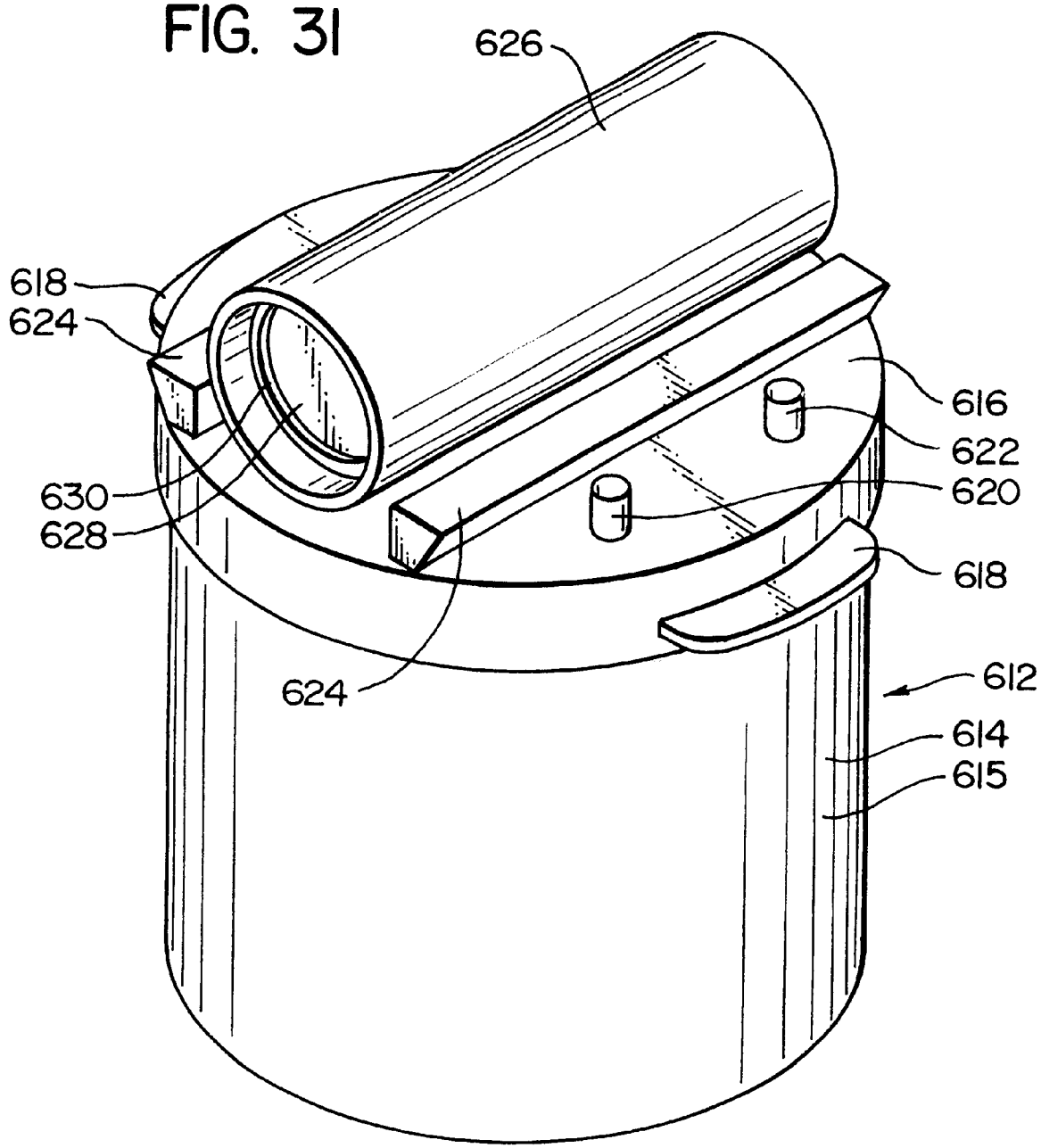
FIG. 31 is an isometric view of the containing assembly of a ninth embodiment of the present invention.

A ninth embodiment of the present invention is illustrated in FIG. 31. The operating components of this ninth embodiment are substantially the same as in the eighth embodiment. However, instead of placing the valve section at the bottom of the container, this valve section is placed on the cover of the container. The opening that leads from the container is not formed in the container bottom wall, but rather is formed in an opening in the cover.

To describe this specifically, with reference to FIG. 31, there is a container assembly 612 which comprises a cylindrical container 614 comprising a cylindrical side wall 615 and a closed bottom which is formed integrally with the sidewall 614 (this bottom wall not being shown). There is a top cover 616 which threadedly engages the container 614 in a manner to form a tight seal. Side handles 618 are provided on the cover so that the cover 616 with the container 614 can be manually moved to a disposal location.

Formed on the cover are the two connecting members 620 and 622 to connect to the suction tube and the vacuum tube. Also, there are provided two guide bars 624 which enable the container assembly 612 to be mounted in a slideway adjacent to a corresponding base assembly, such as shown in the embodiments described earlier herein.

The entire valve section is designated 626, and this can be substantially the same as the valve section 420a of the eighth embodiment. As shown herein, there is a front valve plug 628 which bears against a peripheral stop member and seal 630.

In operation, when the container assembly 612 is collecting waste, it is positioned as shown in FIG. 31, with the cover located upwardly. After the container assembly 612 is moved to the disposal location, it is turned upside down so that the cover 616 is facing downwardly. The guide bars 624 are aligned with a slideway in the base structure, and then the container assembly 612 is moved into engagement with the base assembly and operated in substantially the same manner as described previously herein.

It is to be recognized that various modifications could be made to the present invention without departing from the basic teachings thereof. Also, it is to be recognized that the various features shown in the embodiments of this invention could in many instances be transferred from one of the embodiments to the other. For example, there are in some of the embodiments provided safety or reliability features which are shown in one embodiment and not in the other. These of course be used in the embodiments where they are not actually shown. Also, corresponding components which could serve similar functions in the various embodiments have in some of the embodiments somewhat different configurations. It is evident that structural and functional features of these components could be transferred over to other embodiments to form various combinations of these features.

j) Tenth Embodiment

A tenth embodiment of the present invention is shown in FIGS. 32–39. The system of this tenth embodiment is similar to the ninth embodiment, in that the discharge valve section is placed in the cover of the container, so that the discharge opening is also located at the top of the container.

Figure 32:
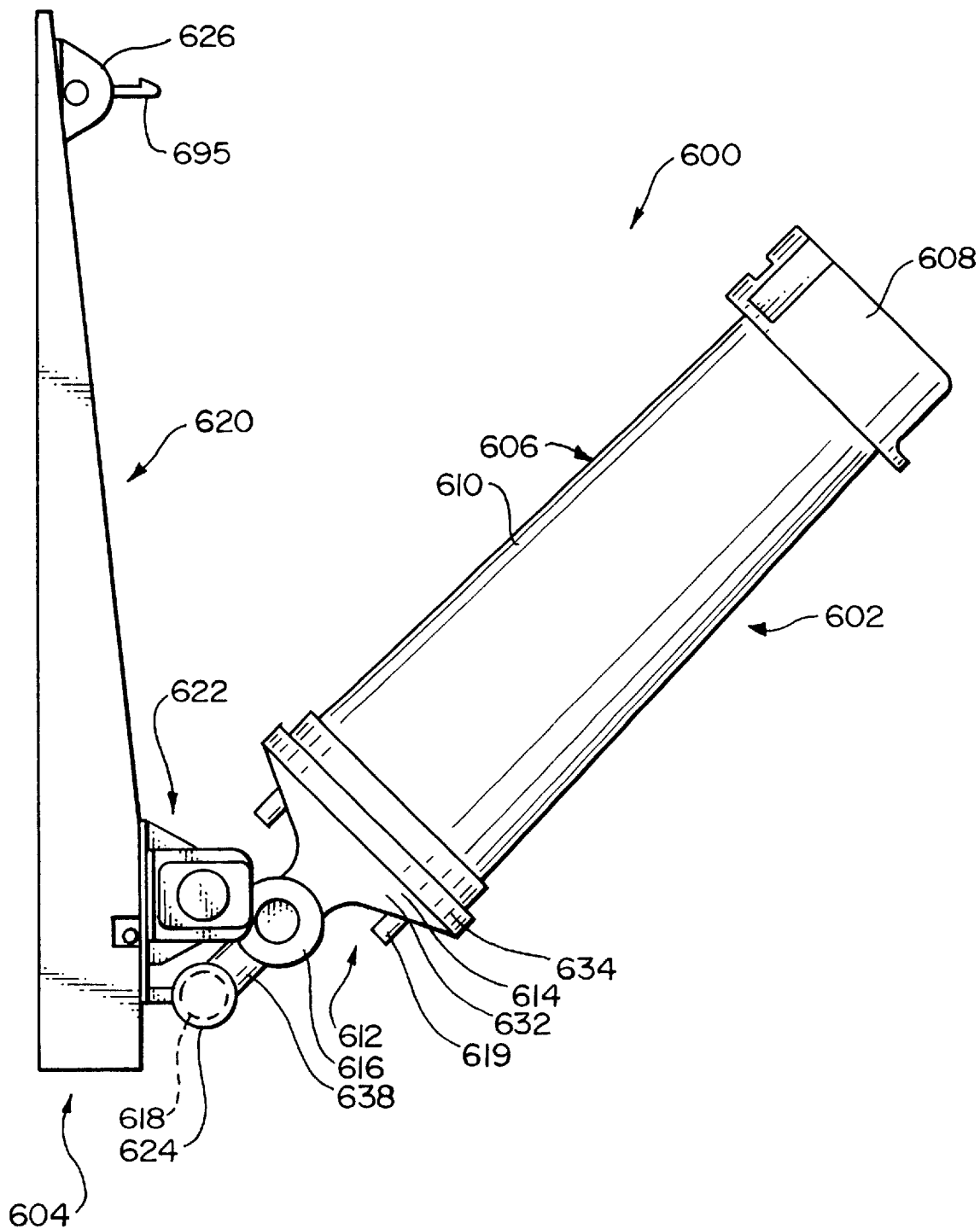
FIG. 32 is a side elevational view of a tenth embodiment of the present invention, showing the container assembly being mounted to the base assembly.

With reference to FIG. 32, the system 600 of this tenth embodiment comprises a container assembly 602 and a base assembly 604. The container assembly 602 in turn comprises a container 606 having a bottom wall portion 608 and a cylindrical sidewall 610.

The container assembly 602 in addition comprises a valve closure portion 612 which comprises a lid 614, a discharge valve 616 mounted to the top,part of the lid, and also a mounting handle 618 connected to and positioned above the valve 616. The connectors or fittings 619 for the suction tube and vacuum line containers are formed in the lid 614.

The base assembly 604 comprises housing structure 620, a valve actuating and discharge section 622, a lower container mounting device 624 which engages the mounting handle 618, and an upper catch device 626 which connects to the bottom wall portion 608 of the container 606.

When the container assembly 602 is positioned near the patient to collect the biofluids from the patient, the container assembly is upright with the bottom wall portion 608 resting on a lower support, and the suction tubes and the vacuum line are connected to fittings in the lid 614 as described in the earlier embodiments. The container assembly 602 in its upright biofluid collecting position adjacent the patient is not shown, since this operating position is apparent from the description of the earlier embodiments.

After the biofluids have been collected from the patient, the suction tubes and the vacuum line are disconnected from their respective fittings 619, and these openings 628 are closed in some suitable manner. This could be accomplished by inserting a plug or a cap on each of the fittings 619, or by incorporating an automatic closure mechanism in each fitting 619, or a combination of both of the above.

Figure 33:
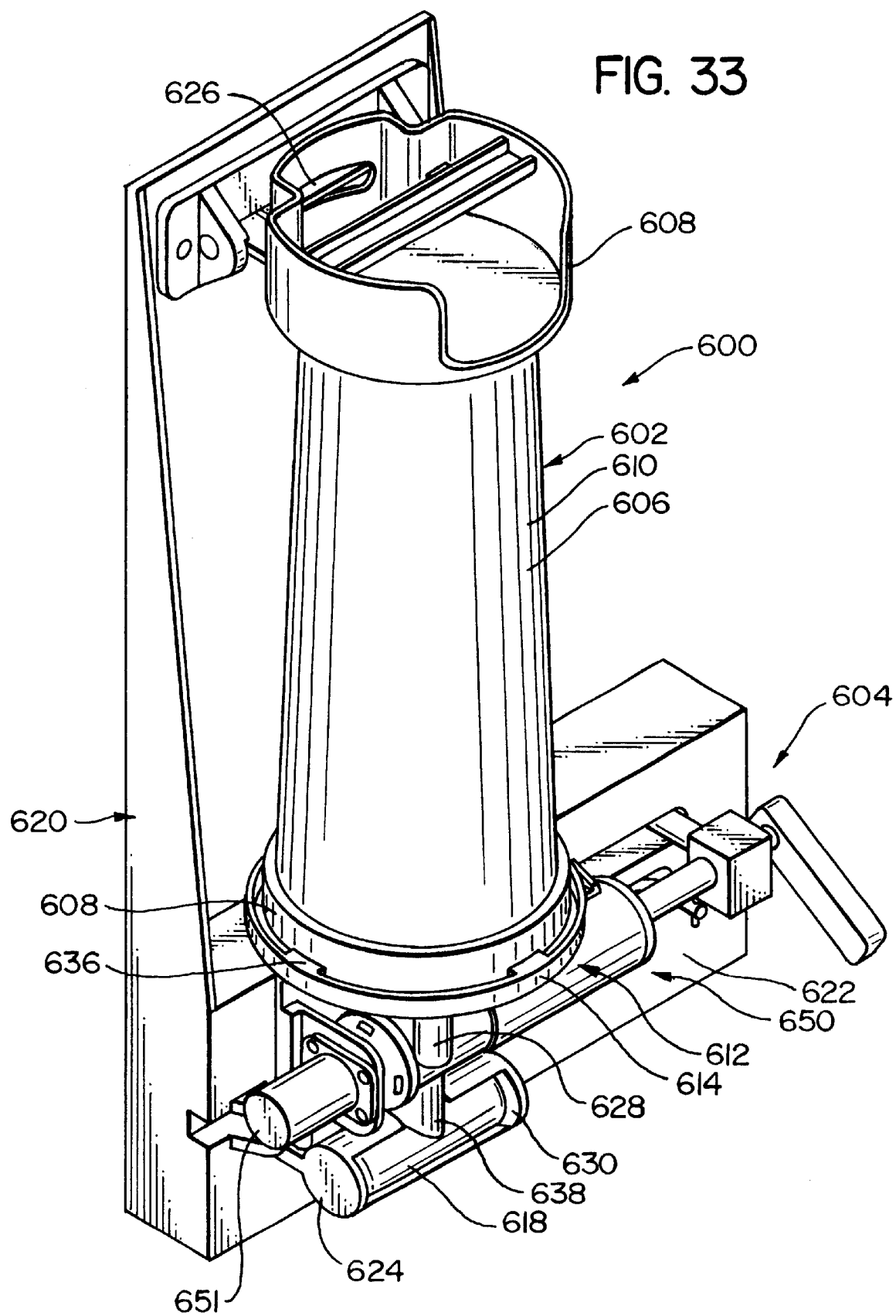
FIG. 33 is an isometric view showing the container assembly mounted to the base assembly in an operating position.

Then the container assembly 606 is carried by the handle 618 to the disposal location where the base assembly 604 is located. The container assembly 602 is rotated 90° to a horizontal position, and the handle 618 is inserted into a front opening 630 of the mounting device 624 and rotated upwardly as shown in FIG. 32. When the container assembly 602 has been rotated to the vertical position as shown in FIG. 33, the bottom wall portion 608 comes into engagement with the upper catch device 626 to retain the container assembly connected to the base member in its operating position so that the fluid in the container 606 can be discharged to the disposal location.

The valve/closure portion 612 will now be described with reference to FIGS. 33, 35, 36A, 36B and 36F. As indicated above, this valve/closure portion comprises a lid 614, the valve 616, and the mounting handle 618.

The lid 614 can be of conventional construction comprising a main cover portion 632 having a central discharge opening 633 and a perimeter flange 634. The lid 614 can be detachably connected to the upper edge of the container 612 in a conventional manner by use of tabs (abutments) 636 that could be positioned underneath an upper perimeter connecting flange of the container 610 having slots therein by which the lid could be positioned to cause the tabs 636 to move downwardly through the openings, with the lid being turned laterally to fasten it to the container 610. The handle 618 is cylindrically shaped, and is connected by a center mounting arm 638 to the outer housing of the valve 616.

The valve 616 comprises a cylindrical valve housing 640 in which is mounted a cylindrical valve sleeve 642 which is the valve element. This sleeve 642 has a cylindrical opening 644 formed in the cylindrical sidewall of the sleeve 642 and an end closure member 646, having an end connecting fitting 648. An end cap 649 connects to the valve housing 640. The end of the valve housing 640 opposite from the end cap 649 is open, and also the adjacent end of the valve sleeve 642 is open.

The valve actuating and discharge section 622 comprises two parts, namely an actuating section 650 and a retaining section 651. The actuating section 650 and retaining section 651 are spaced from one another to provide a recess 652 therebetween to receive the valve 616 of the container assembly 602.

The actuating section 650 of the valve actuating and discharge section 622 comprises an outer cylindrical housing 653 (see FIG. 36A and 35 which has a housing chamber 353a and which is mounted by brackets 654 to a plate 655 which is in turn connected to a rectangular block 658 which comprises the lower part of the aforementioned housing member 620. Extending laterally and rearwardly from the actuating housing 653 is a tubular discharge member 658 that fits within a recess 659 in the housing block 656, this discharge member 658 leading to a suitable drain connection that empties into a sewer or other discharge area (See FIG. 35).

Fixedly positioned within the actuating housing 653 is a positioning sleeve 660 which has a cylindrical side opening 661 which is aligned with the opening 659.

There is an actuating rod 663 which extends through an end wall 665 of the valve sleeve 660. On one end of the actuating rod 663 there is an laterally extending operating handle 664, and the actuating rod 663 is connected to a positioning member 665 rotatable with, but axially fixed with respect to, the handle 664. This positioning member 664 in turn has a laterally extending positioning rod 666 that fits in a matching positioning slot 667 formed in the block 656. At the end of the rod 663 opposite from the handle 664 there is a plug and actuating element 668, made up of a rear bearing member 668a, a middle seal 668b, and a front cylindrical valve engaging member 668c. This valve plug and actuating device 668 is fixedly mounted to the rod 663 and functions to engage the end closure wall 646 of the valve member 642 to rotate the valve element 642 between its open and closed position, and also to close the inner end of the valve housing 653.

The rod 663 has a laterally extending positioning finger 669 that engages a Z shaped positioning slot 670, comprising two end circumferentially aligned portions 670a and 670b, connected by a central longitudinally aligned portion 670c. To describe briefly the function of this slot 670 and the related actuating finger 669, the initial circumferentially aligned slot portion 670a functions to receive the pin 669 to prevent axial movement of the rod 663 in its position of FIG. 36B. When the handle 664 is rotated upwardly a short distance, the finger 669 comes into alignment with the longitudinally aligned slot section 670c which permits the rod 663 to be moved axially so that the end valve engaging portion 668 moves through the valve sleeve 642 and comes into mating engagement with the valve sleeve end wall 646.

In this position, the positioning finger 669 has come into alignment with the slot portion 670b to permit further rotational movement of the handle 664 and of the rod 663 to rotate the valve sleeve 642 to cause the valve sleeve opening 644 to come into alignment with the discharge opening 639 in the lid 614.

To describe briefly the function of the components described thus far with respect to the actuating section 650, let us first assume that the container assembly 602 has biofluid therein and has been placed in its operating discharge position as shown in FIG. 33. In this position, the actuating rod 663 is initially in a retracted position within the housing 653 to leave the space 652 between the actuating section 650 and the retaining section 651 open.

Also the plug and actuating device 668 closes the inner end of the valve housing 653. The next step is to move the actuating rod 663 inwardly so that the plug and actuating device moves through the valve sleeve 652 to cause an end protruding portion 671 coming into mating engagement with a recess 672 formed in the end wall 646 of the sleeve 642 (See FIG. 38A). Both the protruding portion 671 and the socket 672 have a flat edge portion so that rotation of the rod 663 will cause the valve sleeve 642 to rotate and cause the valve sleeve opening 644 to come into alignment with the discharge opening 633 in the lid 614. This is accomplished as indicated before, by rotating the handle 664 upwardly from the position in FIG. 36B, then moving the rod 663 laterally so that the locating pin 669 is traveling through the longitudinally aligned recess portion 670c to then become aligned with the recess 670b. Then the handle 664 is rotated to cause the valve sleeve 642 to rotate and bring the opening 644 into alignment with the lid opening 633.

The retaining section 651 of the valve actuating and discharge section 622 works in cooperation with the actuating housing 653 to retain the container 606 in its operating position of FIG. 33. This retaining section 651 is, as indicated before, on the opposite side of the actuating section 650 relative to the receiving area 652 into which the valve 616 becomes positioned.

This retaining section 651 comprises a cylindrical socket defining member 674 which is mounted to a locating member 675 mounted to the housing block 656. Positioned within the socket defining member 674 is a compression spring 676 that engages a retaining member 678 positioned for longitudinal movement in the member 674. This retaining member 678 has a forward protruding portion 679 that engages a matching recess 680 in the end cap 650 that connected to the valve housing 640.

To move the retaining section 671 into its engaged position with the valve 616, there is provided a retaining rod 681 having a first end 683 thereof attached to the aforementioned block 665 that is rotatably mounted to the rod 663 but axially fixed thereon. The arrangement and operation of this retaining rod 681 can best be seen with reference to FIG. 36F.

At the opposite end 684 of the retaining rod 661 there is an elongate slot 685 which engages a finger 686 of an arm 688 pivotally mounted at its center location 689 to the housing block 656.

Figure 36B:
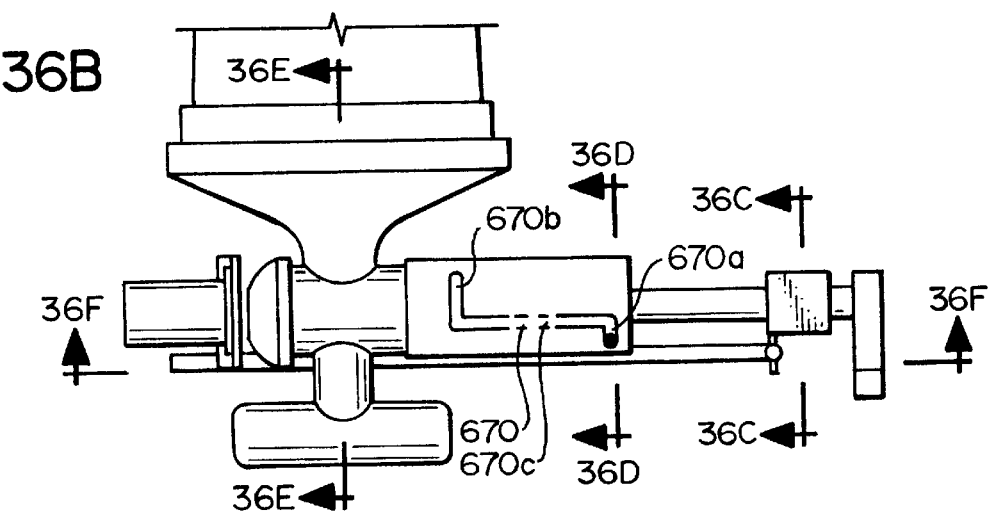
FIG. 36B is a side elevational view, showing substantially the same components as in FIG. 36A, but not in cross section.
Figure 36C:
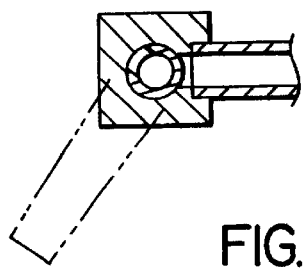
FIGS. 36C, 36D, 36E and 36F are views taken along the section lines having the same numerical designations and shown in FIG. 36B.
Figure 36D:
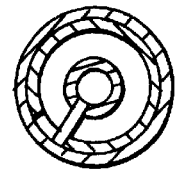
Figure 36E:
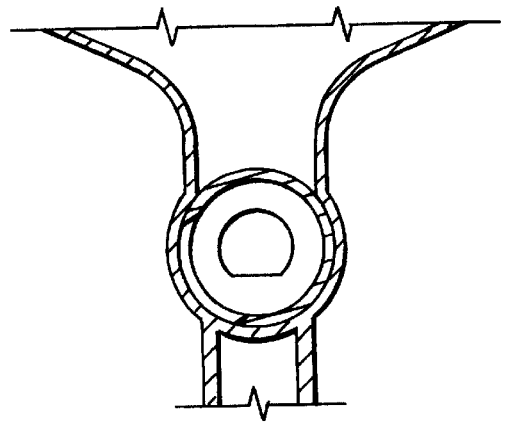
Figure 36F:
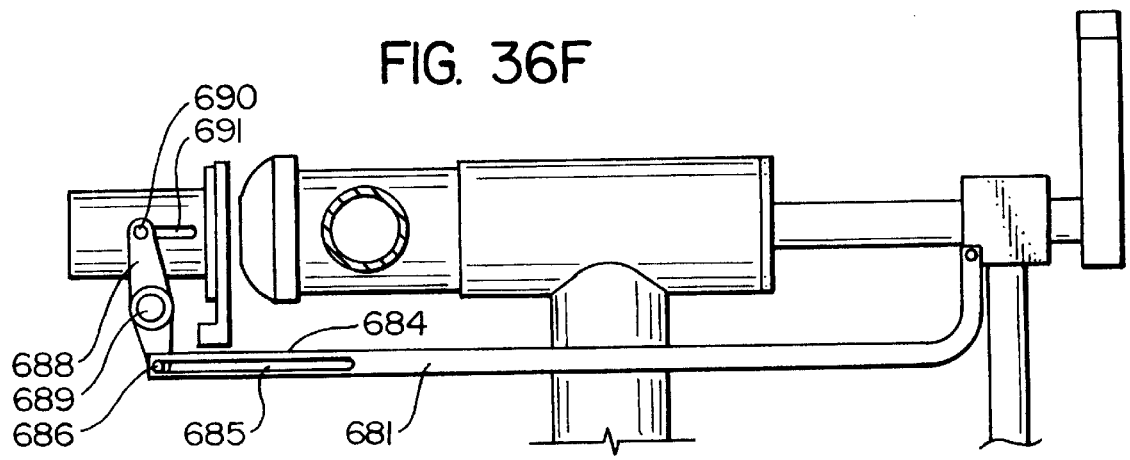

When the handle 664 is in its fully retracted position, as in FIG. 36B, the retaining rod 681 is positioned as shown in 36F, and it can be seen that the arm 668 is held in a position where it holds the retaining member 678 in its retracted position against the urging of the compression spring 668 (See FIG. 36A). The retaining member 678 is connected to the end of the arm 688 by means of a pin 690 at the opposite end of the arm from the pin 668. The pin 690 is moveable through a slot 691 in the socket defining member 674. It can be seen, with reference to FIG. 36F, that as the retaining rod 681 is moved to the left (as see in FIG. 36F), the pin 690 is moved to the right to permit the compression spring 676 to push the retaining member 678 into engagement with the end cap 650. This in turn causes the opposite end 693 of the valve housing 640 to come into sealing engagement with the adjacent circumferential edge of the actuating housing 653. Thus, it can be seen that the valve housing 640 is sealed at one end by the cap 650, and sealed at the other end to the actuating valve housing 653. An O ring seal 694 is positioned in the circumferential inner end of the actuating housing 653.

Figure 39:
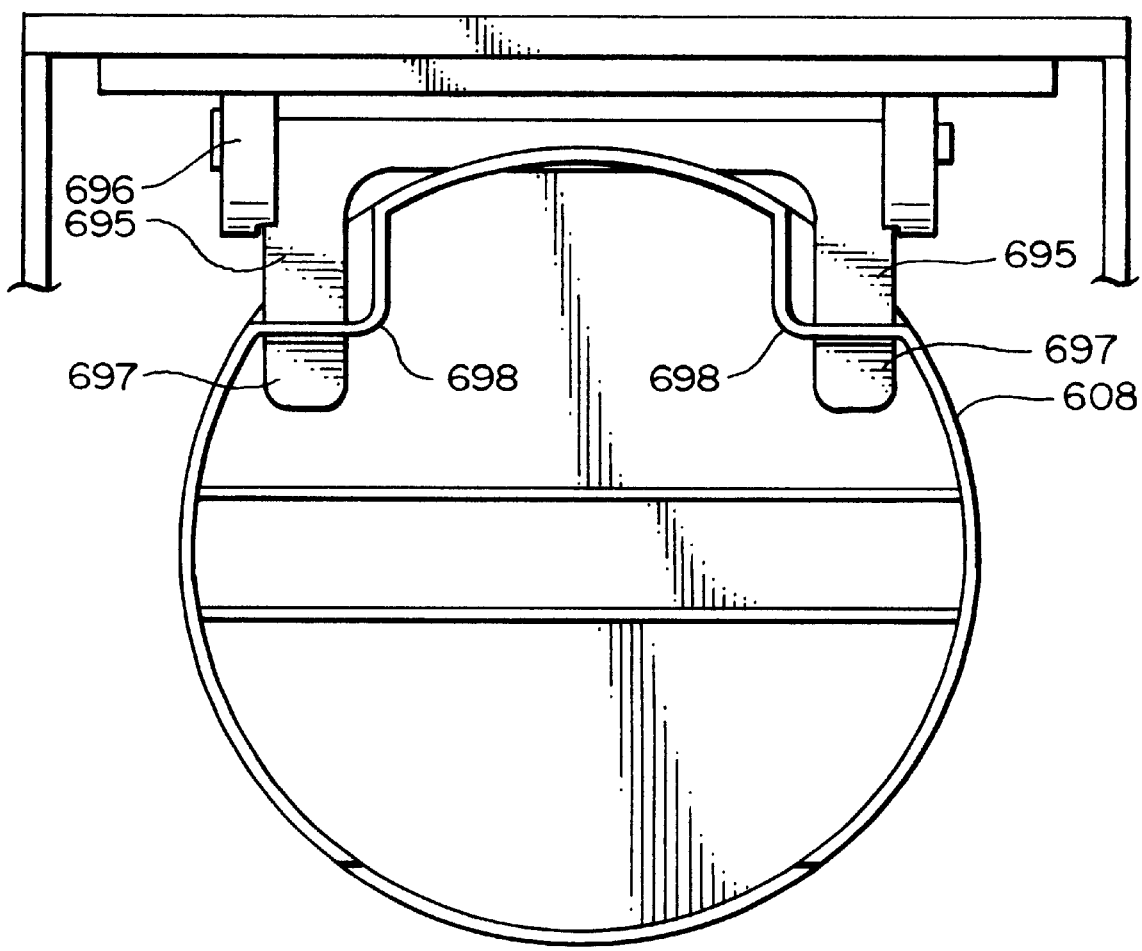
FIG. 39 is a top plan view showing the top end of the container assembly and base assembly in the operating position of FIG. 33.

The aforementioned upper catch device 626 can best be seen in FIG. 39. This comprises a pair of spring fingers 695 mounted to a bracket 696. The spring fingers have end tabs 697 that engage retaining portions 698 that have been formed from a cylindrical wall of the bottom wall portion 608 of the container 606. It is evident that as the container 606 is swung upwardly to its operating discharge position, the spring fingers 665 deflect downwardly to permit the retaining portion 698 to move into the retaining position, after which the spring fingers move upwardly to engage the member 698 to hold the container 606 in place.

Let us now describe the overall operation of this tenth embodiment 600. Initially, as indicated previously, the container assembly 602 is placed adjacent to the patient, and the suction tubes and vacuum line are attached as in the prior embodiments, and the suctioning of the patient and the collection of the fluids is accomplished as indicated previously with respect to previously described embodiments. In this position, the valve 616 remains in its closed position. When the container 606 has received a sufficient quantity of biofluids, the suction tubes and vacuum line are disengaged from the connection fittings 628 which are then closed in a suitable manner. The valve 616 still remains in its closed position. The containing assembly 602 is carried by the handle 624 to a location of the base assembly 604.

Figure 34:
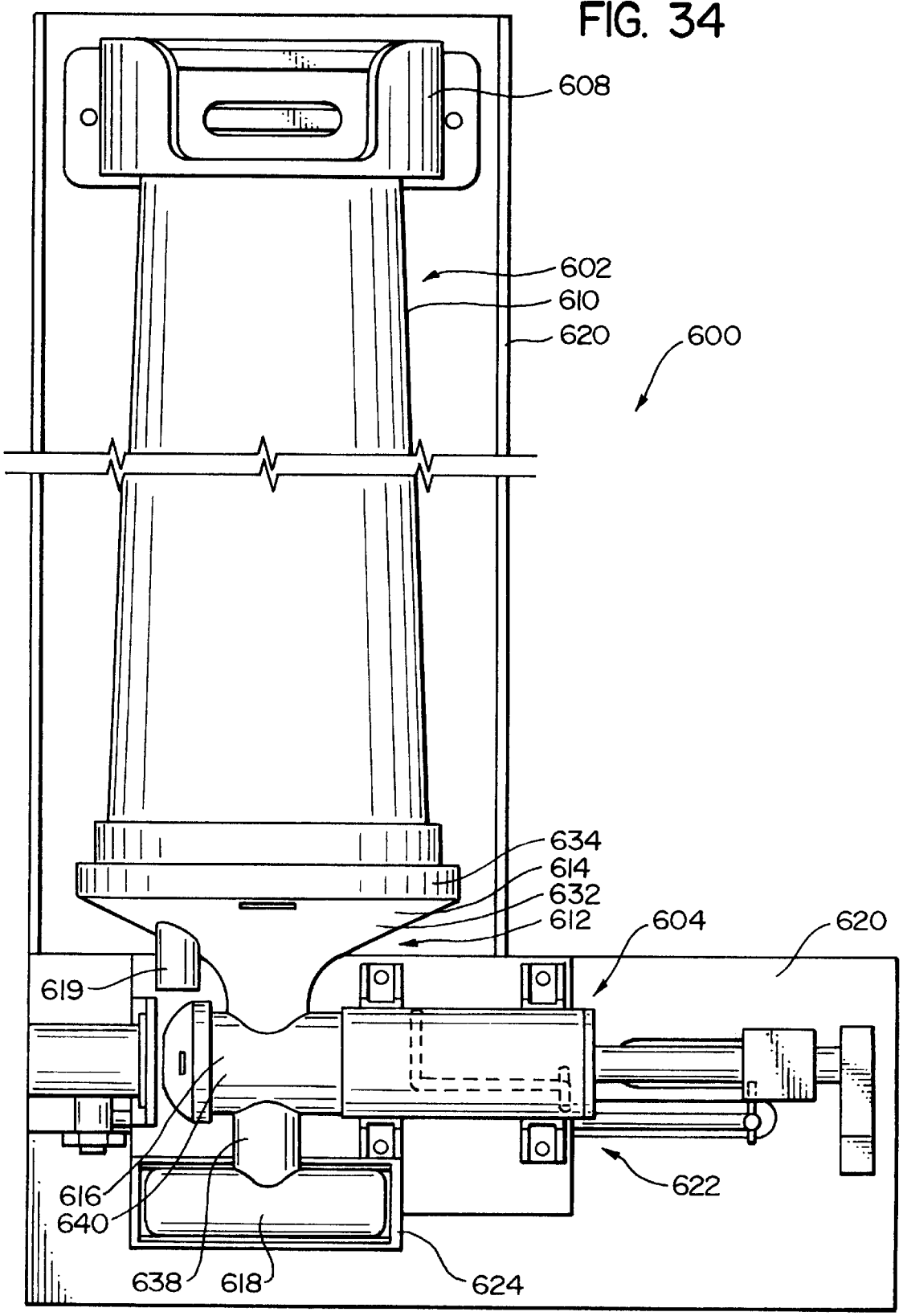
FIG. 34 is a front elevational view of the system as shown in 34.

Initially, the base assembly 604 is positioned as shown in FIG. 36A, FIG. 36B, and in FIG. 34. In this position, the actuating rod 663 is at its fully retracted position, and the locating pin 669 on the rod 663 is positioned at the lower part of the slot portion 670a (see FIG. 36B).

At this same time, the rod 663 is positioned so that the retaining rod 681 is positioned as shown in 36F, so that the arm 668 has the pin 690 positioned as shown in FIG. 36A so that the retaining element 678 is located in the left hand position (see FIG. 36A). This causes the retaining section 651 and the actuating section 650 to be spaced sufficiently far apart from each other so that the valve 616 of the container assembly 602 can be moved into the area 652.

As indicated previously, to insert the container assembly 602 into its operating position relative to its base assembly 604, the container 606 is positioned horizontally, and the handle 618 is moved into the lateral recess 630 in the lower mounting device 624. The container 606 is then rotated a further 90° upwardly into its operating position where the retaining member 626, by means of its spring fingers 695, engages the retaining members 698 of the bottom portion 608 of the container 606.

In this position, as can be seen in 36A, the end plug and actuating portion 668 of the rod 663 is positioned in the inner circumferential edge portion of the actuating housing 653, so that the chamber 653a within the housing 653 remains closed, thus keeping the opening 659 in the block 656 leading to the disposal location isolated.

Figure 37B:
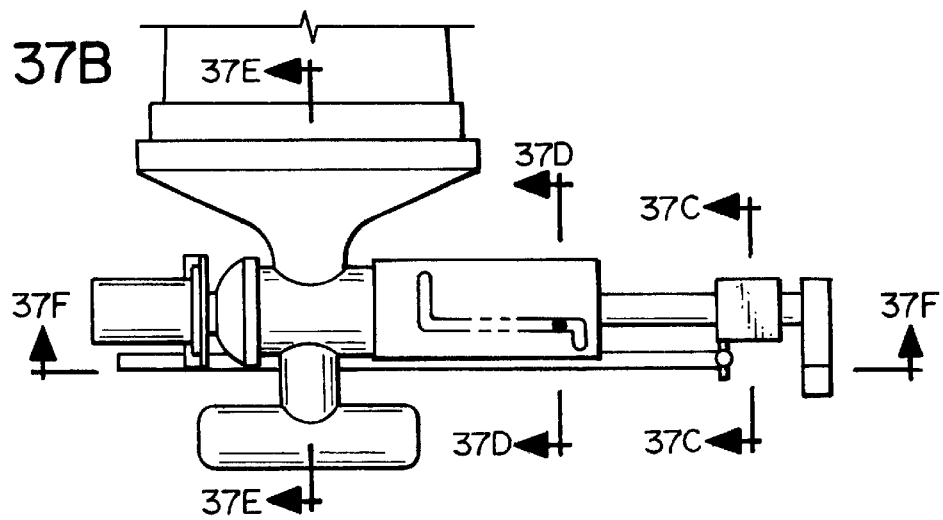
FIG. 37B is a view similar to FIG. 36B, but showing the valve actuating and discharge section in the operating position of FIG. 37A.
Figure 37C:
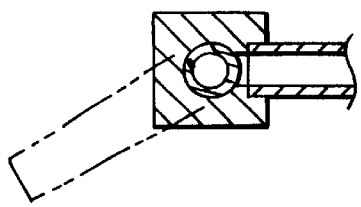
FIGS. 37C, 37D, 37E and 37F are views taken along the section lines shown in FIG. 37B having the same numerical designations.
Figure 37D:
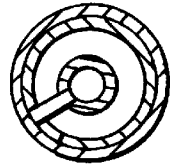
Figure 37E:
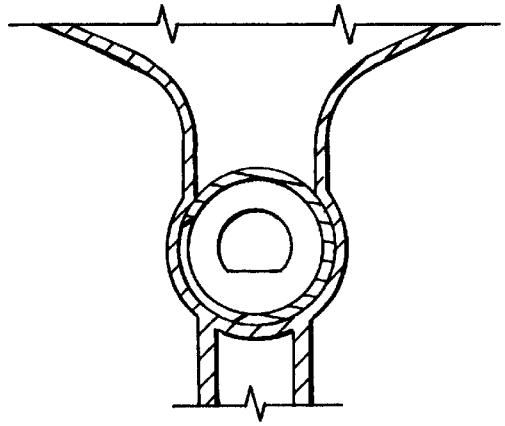
Figure 37F:
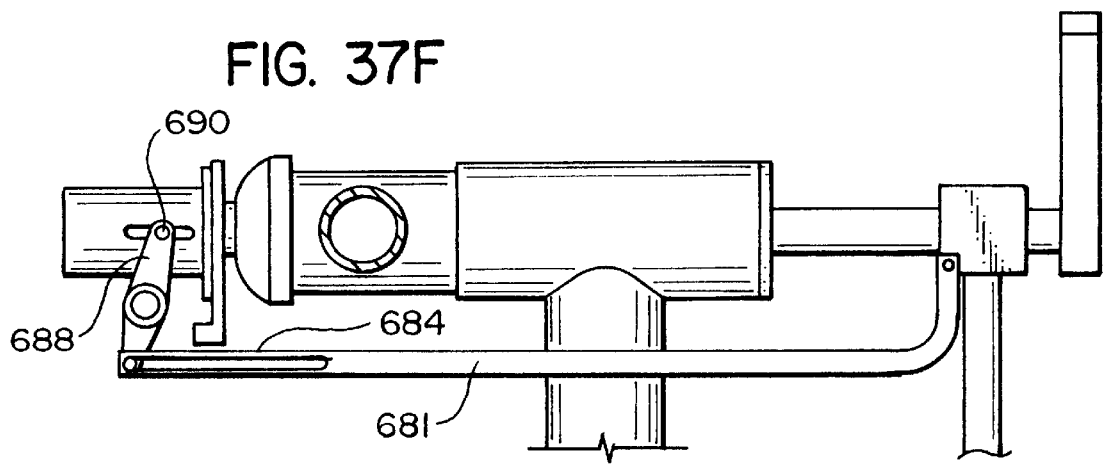

To initiate the disposal process, the handle arm 664 is raised from the position of 36B to move the positioning pin 669 upwardly to be aligned with the longitudinal slot portion 670c, and the handle 664 is moved laterally and inwardly. When the pin 669 reaches the position shown in FIG. 37B, it can be seen that the retaining rod 681 has moved a short distance to the left, as shown in FIG. 37F, which permits the retaining member 678 to move inwardly to engage the end cap 650 in a retaining position, and also to cause the opposite circumferential edge of the valve housing 643 to come into sealing engagement with the adjacent circumferential edge of the actuating housing 653. The handle 664 is moved further laterally to the left until it arrives at the inward end of the slot portion 370c so as to come into alignment with the circumferential extending slot portion 370b. This is the position shown in 378a and 378b. It can be seen the protruding portion 671 of the member 668 interfits with the recess 672 in the valve sleeve end wall 646. As indicated previously, the protrusion 671 and the recess 672 have flattened portion so that rotation of the rod 663 causes rotation of the valve sleeve 642. Thus, as the handle 664 is moved upwardly, to rotate the valve sleeve 642, the pin 669 moves upwardly in a slot portion 370b. When the pin 669 reaches the upper end of the slot portion 370b, the valve sleeve 642 has been rotated 90° to its open position, so that the valve sleeve opening 644 is in alignment with the discharge opening in the lid 14. Since the actuating rod end member 668 has moved to the left to the position of FIG. 38, there is now a through passageway from the interior of the container 606, through the valve opening 644, through the chamber defined by the valve sleeve 642 into the actuating housing chamber 353a, and through the disposal opening 659 to the disposal location.

Figure 38B:
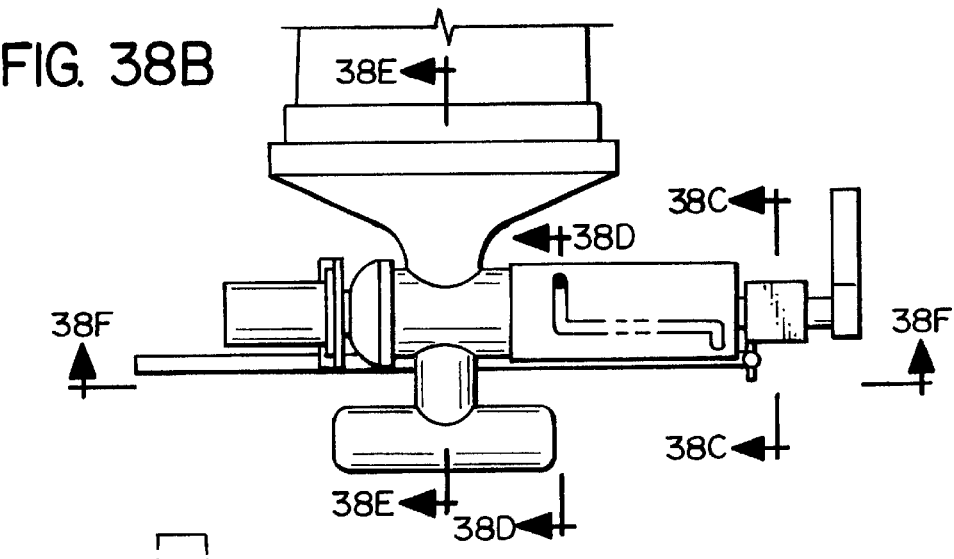
FIG. 38B is a view similar to FIGS. 36B and 37B, showing the valve and actuating system in the position of FIG. 38A.
Figure 38C:
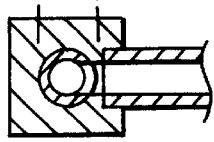
FIGS. 38C, 38D, 38E and 38F are views taken along the section lines in FIG. 38B having corresponding numerical designations.
Figure 38E:
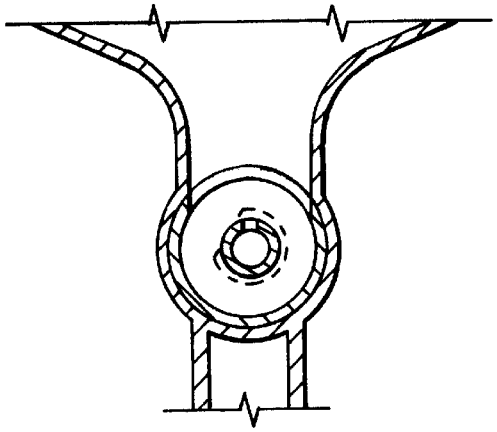
Figure 38D:
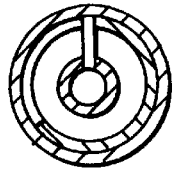
Figure 38F:
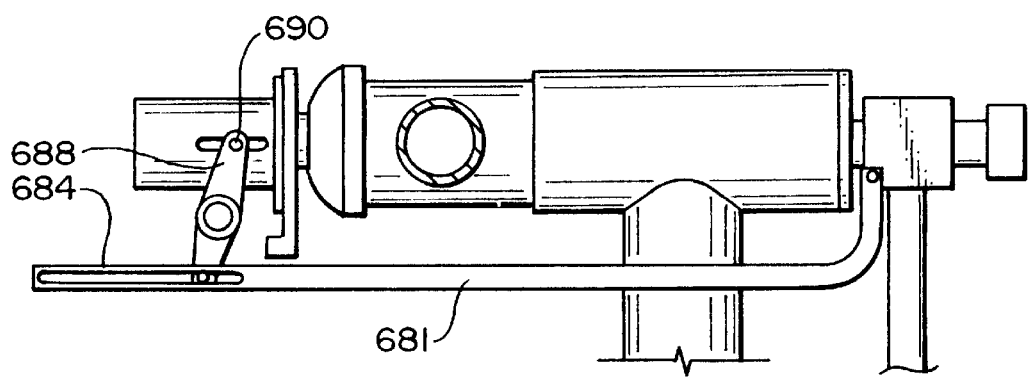

After the contents have been emptied from the container 608, then a disinfectant irrigating process can be accomplished as described in prior embodiments. To accomplish this, there is an inlet opening 699a provided in the rod member 663, and a liquid outlet opening 669b positioned (as shown in FIG. 38A) beneath the valve sleeve opening 644 to spray the cleaning and disinfectant liquid into the container.

The container assembly 602 is removed from the base assembly 604 by simply performing the above steps in reverse. This is accomplished by moving the lever 664 downwardly, then to the right, then downwardly again to be held in its release position. This motion causes the valve sleeve 644 to be rotated 90° to its closed position, also retracts the rod end member 668 to its position where the member 668 closes the actuating housing chamber 353a, and causes the retaining rod 681 to retract the retaining element 679 out of engagement with the end cap 650 of the valve housing 640. Then the container assembly 602 can be rotated 90° downwardly so that the container can then be moved laterally to disengage the handle 618 from the mounting device 624. The containing assembly is then returned to the collecting location adjacent to the patient, and the suction tubes in the vacuum line are reattached.

k) Eleventh Embodiment

Figure 40:
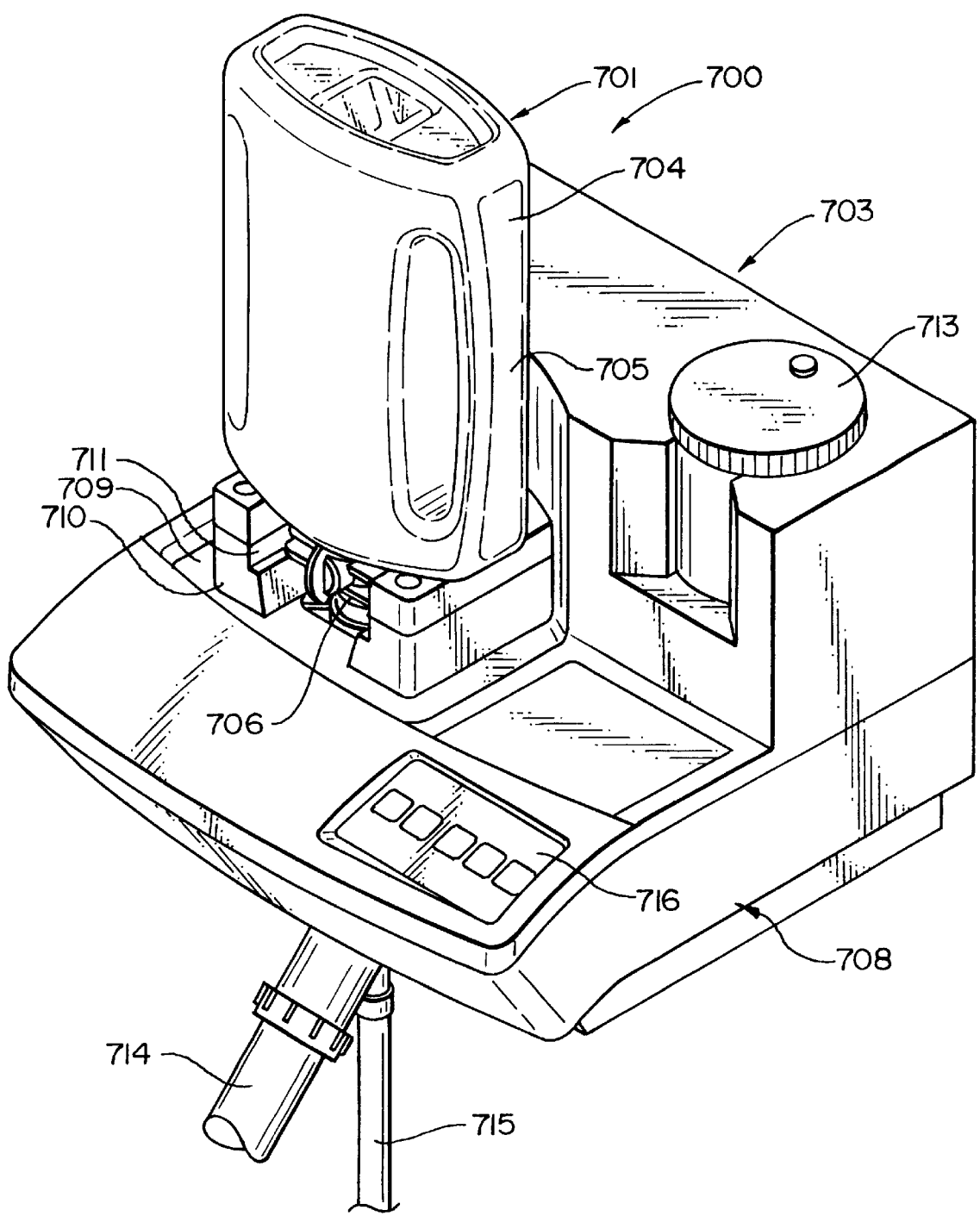
FIG. 40 is an isometric view of an eleventh embodiment of the present invention, showing the container assembly in its disposal operating position mounted to the base assembly.

The eleventh embodiment of the present invention is shown in FIGS. 40 through 51. With reference to FIG. 40, the two main components of the system 700, namely the container assembly 701 and the base assembly 703, are shown interconnected to one another in an operating discharge position where the biofluid collected in the container assembly 701 can be discharged to the base assembly 703.

Figure 41:
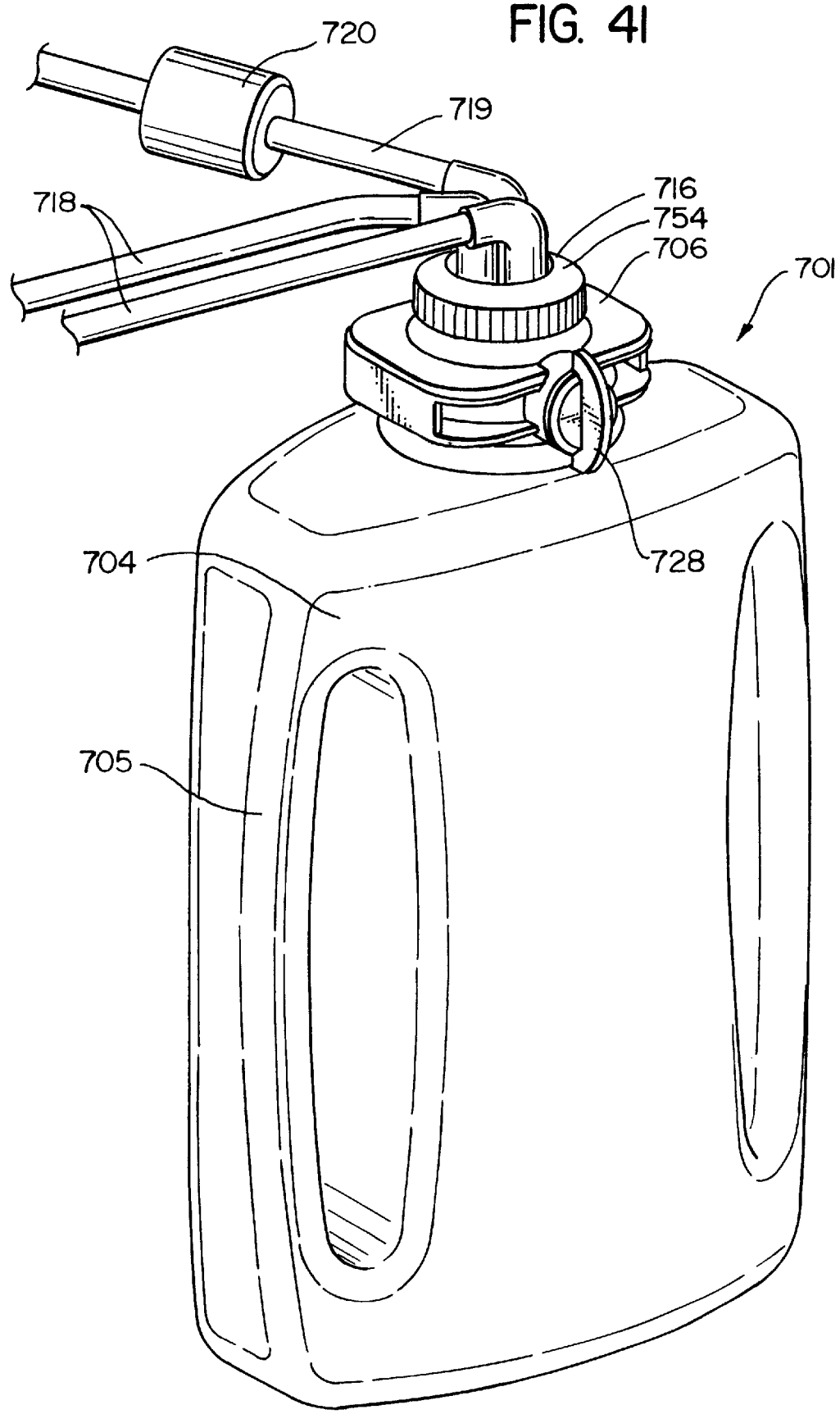
FIG. 41 is an isometric view of the container assembly of the eleventh embodiment in its collecting mode of operation.

In FIG. 41, the container assembly 701 is shown in its biofluid collecting position. The container assembly 701 comprises a container 704 having two longitudinally aligned side handles 705, and a valve and connecting assembly 706. As in the ninth and tenth embodiment, the container assembly 701 of this eleventh embodiment is arranged so that the valve and connecting assembly 706 is mounted to the top of the container 704, so that in the collecting position where the containing assembly 701 is positioned near the patient to be collecting the fluids, the containing assembly 701 is upright as shown in FIG. 41, then it is inverted to be placed in its discharge position as shown in FIG. 40.

With further reference to FIG. 40, the base assembly 703 comprises a base housing 708 defining a container mounting portion 709 in the form of a slideway comprising two laterally spaced slideway members 710 having inwardly facing slots 711.

Also, in FIG. 40 there is shown part of a disinfectant assembly 713. A disposal line 714 extends downwardly from the base housing 708 and a water line 715 extends upwardly into the base assembly 703 to provide the washing and disinfectant function as in the prior embodiments. At the front right hand upper surface of the housing 708, there is a control panel 716.

Reference is made to FIG. 41 which shows the container assembly 701 in its collecting mode where it is positioned near the patient, and collecting biofluids from the patient. In addition to the valve and connection assembly 706, there is positioned at the top of the container a plug and manifold assembly 716. This plug and manifold assembly is used with the containing assembly 701 in the collecting mode of operation, and one of its main functions in this collecting mode is to provide a very effective and convenient means for connecting the suction tubes 718, and also the suction line 719 with the interior of the container 704, and also disconnecting the same. The suction tube 719 has a filter 720. This assembly 716 will be described later herein. This assembly 716 can be considered a sealed closure member for the container and a fluid inlet means, plus serving the function of an outlet to the vacuum sources.

Figure 42:
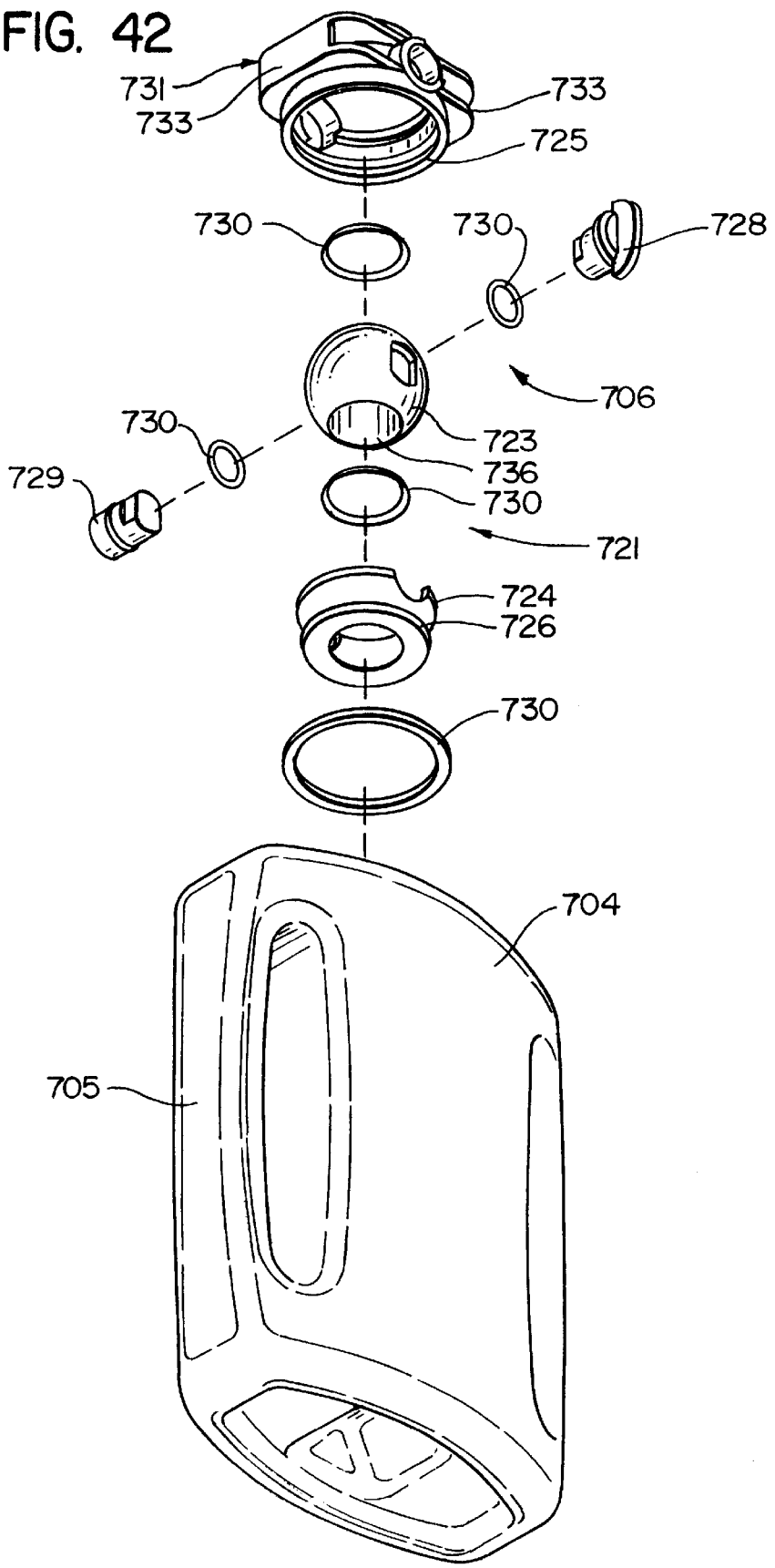
FIG. 42 is an isometric exploded view of the container assembly, showing the container and the valve and connecting assembly.

In FIG. 42, the valve and connecting assembly 706 is shown in an isometric exploded view, and is also shown assembled in FIG. 44, in a longitudinal sectional view.

The valve in the valve and connecting assembly is designated 721 and it comprises a ball valve element 723 rotatably positioned in the valve housing 724 comprising upper and lower valve housing sections 725 and 726. There is a valve handle 728 fitting in a mating recess of one side of the valve, and on the opposite side a valve drive connector 729 by which the ball valve can be rotated by a motor (to be hereinafter described) or manually. Suitable seals are provided at 730.

The connecting portion 731 of the valve and connecting assembly 706 is made integral with the upper housing section 725 and comprises a pair of mounting members 733, each having a rectangular configuration with rounded corners, and extending laterally from the upper part of the upper valve housing section 725. These two mounting members 733 engage the two slide mounting members 710 by fitting in the slideway slots 711.

Figure 44A:
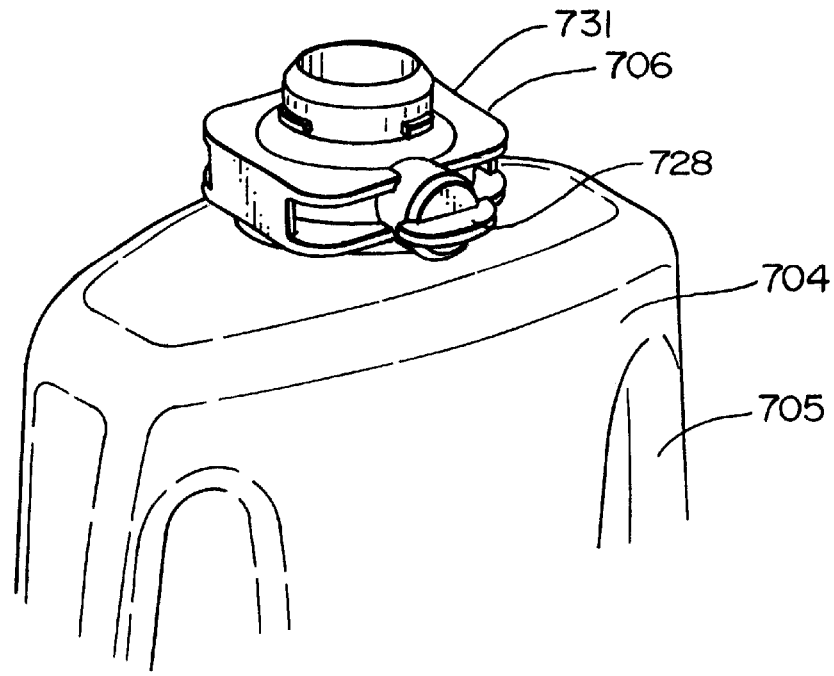
FIG. 44A is an isometric view of the upper portion of the container, with the valve and connecting assembly mounted thereto.
Figure 44B:
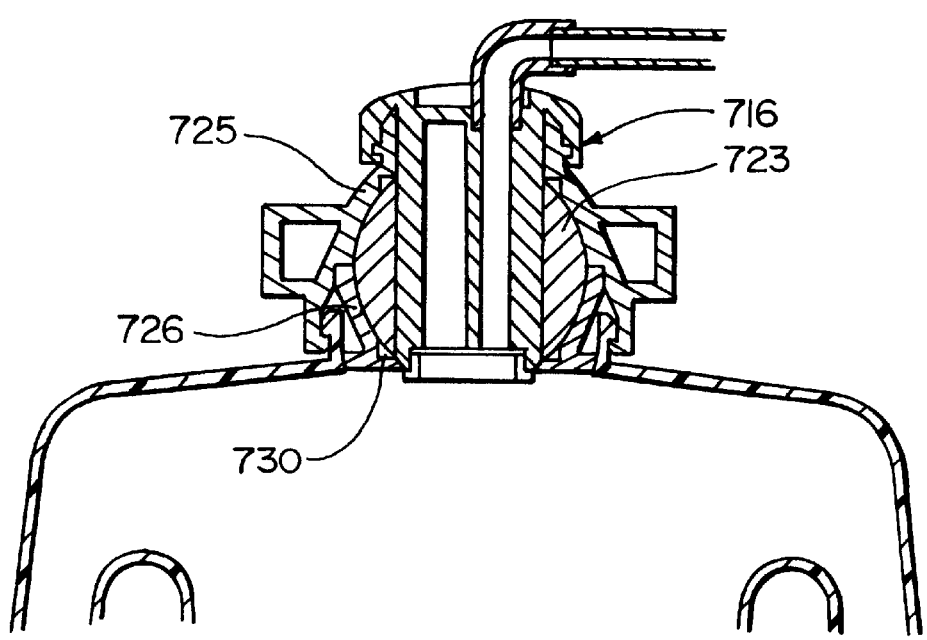
FIG. 44B is a sectional view showing the valve and connecting assembly with the closure and inlet device mounted therein.

The plug and manifold assembly 716 is shown in FIGS. 43A (in an exploded view), and 43B (assembled), and is further shown in longitudinal cross section in FIG. 44B (positioned within the valve and connecting assembly 706). This plug and manifold assembly 716 comprises a main body 734 formed integrally with plastic or some other suitable material. This main body portion 734 has an outer cylindrical portion 735 having a diameter which is very nearly the same dimension as the cylindrical flow passageway 736 of the ball valve element 723, so as to be able to fit snugly therein.

As can be seen in FIG. 44B, when the plug and manifold assembly 716 is in its operating position, the cylindrical body portion 735 fits within the opening 736 of the ball valve 723 which is in its open position, so that the biofluid can be directed from the suction lines 718 into the interior chamber of the container 704.

The body 734 is formed with three cylindrical tubular portions inside the outer body portion 735, two of these being tubular portions 738 connecting to the suction tubes 718, and the third tubular portion 739 connecting to the suction line 719. These tubular portions 738 and 739 are formed integrally inside the cylindrical housing portion 735 and extend longitudinally therein.

At the lower end of the cylindrical portion 735 there is provided a check valve assembly 740 which comprises a circular plate 741, a circular flap member 743 and a retaining ring 744. The plate 741 has three openings, namely two openings 745 that are aligned with the lower ends of the two tubular portions 738 that connect to the suction tubes 718, and a third opening 746 that is aligned with the tubular portion 739 that connects to the vacuum line 719.

The flap member 743 has a single opening 747 aligned with the opening 746 and is thus aligned with the tubular portion 749. The flap member 743 is made of moderately flexible material, such as mylar, and is partially split at 748 along a its diameter, leaving a connecting tab 749 which connects to a flap portion 750 that functions as the valve element. It will be noted that both the plates 741 and the flap member 743 have a small perimeter cut-out at 751 which fit around a locating tab 753 in the lower part of the housing portion 734, and this tab 753 with the cut-out 751 provide an alignment function for the plate 741 and the flap member 743.

The retaining ring 734 has either a snap fit, friction fit, a threaded connection or a bonded connection, to fit within the lower end of the cylinder portion 735 and retains the plate 741 and flap member 743 in the bottom part of the cylinder portion 735. The flap member 750 functions as a check valve element so that it permits the biofluids to descend through the tubular portion 738 into the container, while preventing a reverse flow of the biofluids back up the tubular member 734.

The plug and manifold assembly 716 comprises a top cap 754, having a cylindrical configuration. This cap 754 has a lower perimeter portion 755 formed with four arcuate recesses 756 and four arcuate, inwardly projecting portions 758. These protruding portions 758 enable the plug and manifold assembly 716 to be securely connected to the valve connecting assembly 706, by inserting the housing portion 734 downwardly through the valve passageway 736, with the protruding portions 758 passing between laterally through the gaps between the outwardly extending tabs 759 positioned at four evenly spaced locations around the top portion of the valve housing 724.

Figure 45:
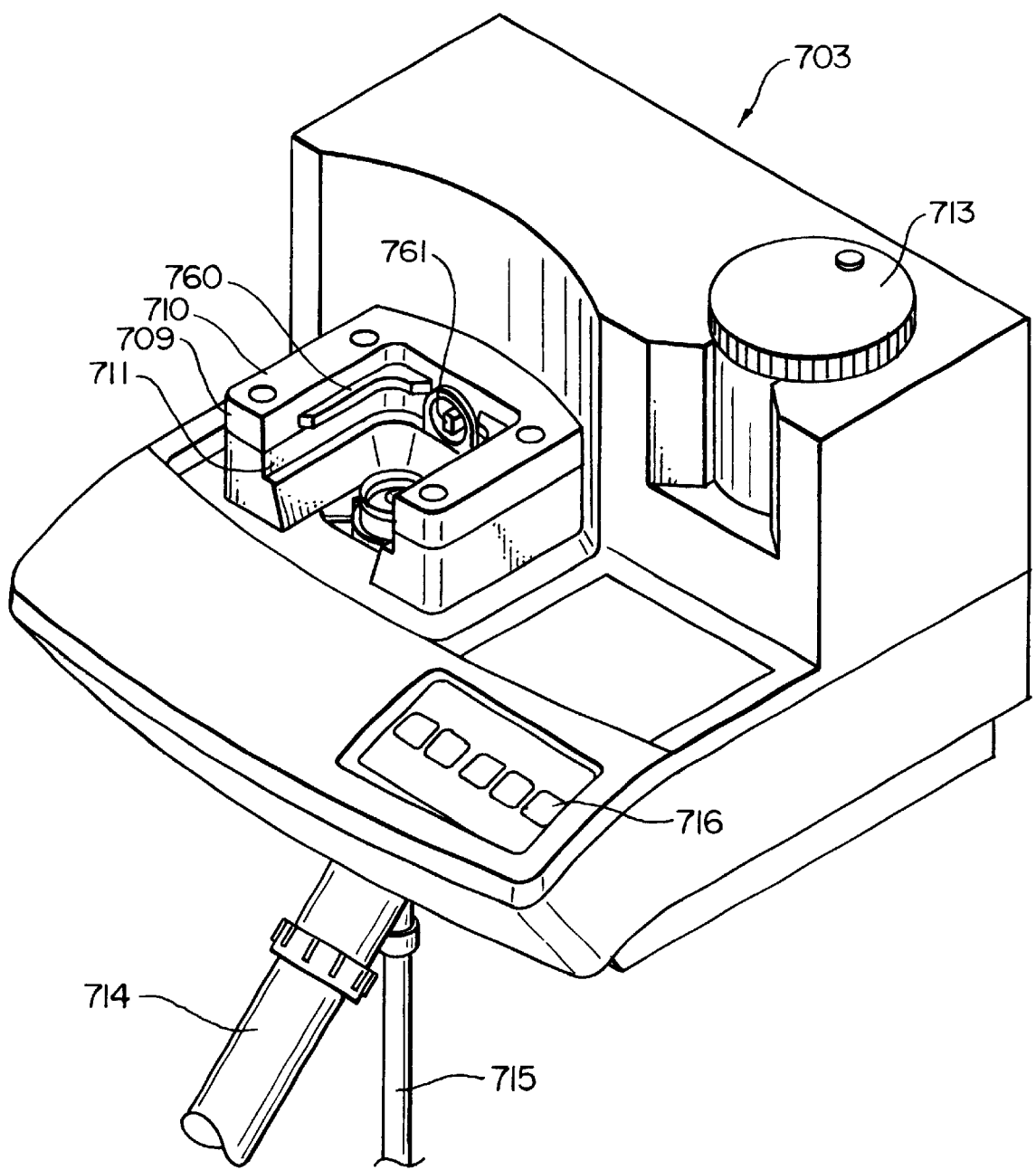
FIGS. 45A, 45B and 45C are isometric views showing upper, middle and lower portions of the base assembly, with these being exploded views.

FIG. 45 is an isometric view substantially the same as FIG. 40, but differing in that it shows only the base assembly 703 without the container assembly 701 mounted thereto. In addition to showing the components shown in FIG. 40, FIG. 45 also illustrates one of the upper member 760 defining the upper part of the slideway 711, and further shows a drive member 761 that interfits with the drive connector 729 that connects to the ball valve element 723 of the valve 721.

Figure 45A:
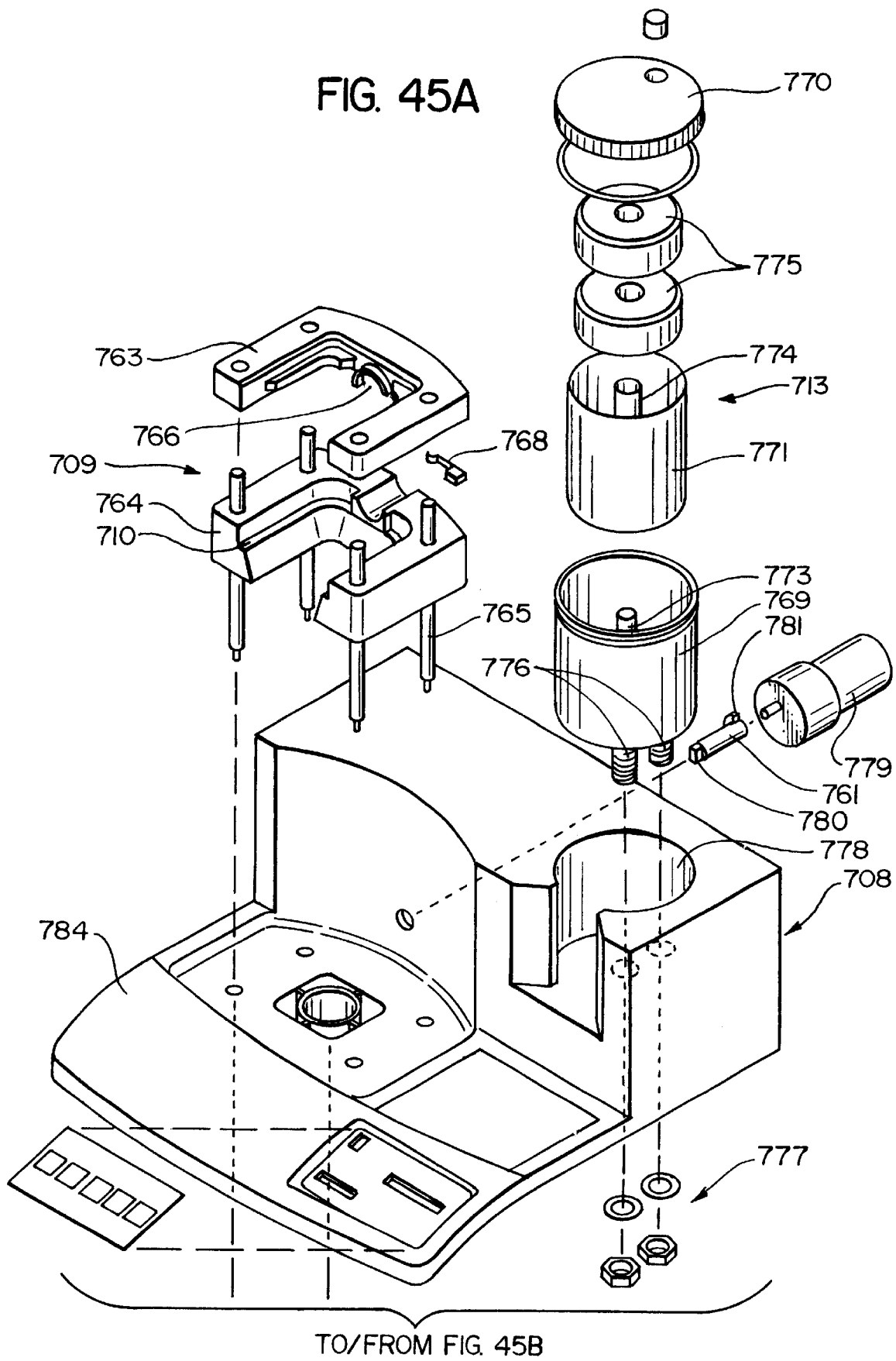

To describe the base assembly 703 in more detail, reference is now made to the three sheets showing three isometric exploded views of the base assembly 703, in FIGS. 45A, 45B and 45C.

The mounting structure 709 is shown as comprising upper and lower U shaped sections 763 and 764 joined to one another by suitable connecting members 765 that in term connect to the base housing 708. Also, these members 761 and 763 define at their rear portions a cylindrical opening 766 to receive the drive member 761.

There is a micro switch 768 positioned at the rear part of the mounting section 709. This switch 768 is part of the control circuitry and is positioned.to engage the valve and connecting assembly 706 of the container assembly 701 when the container assembly 701 is located in its position interconnecting with the connecting section 709.

The disinfectant assembly 713 comprises a cylindrical container 769 having a lid 770 and a removable cylindrical insert 771. The container 769 has a central locating and water inlet tube at 773 which engages a locating tube member at 774 connecting to the insert 771. Several wafers 775 made of a dissolvable disinfectant material are placed over the locating member 774 and into the insert 771.

At the lower end of the container 769, there are two threaded connecting fittings 776, one connected to an inflow water line and the other to an outflow water line. A pair of retaining nuts and associated washers generally designated 777 connect to the fittings at 776 and retain the container 769 in place. The container 769 fits within a cylindrical recess 778 formed in the housing 703.

There is an electric motor 779 which rotates the aforementioned actuating member 761 to rotate the ball valve element 723. This can also be done manually. More specifically, the actuating member 761 has a male drive member 780 which fits in a matching recess in the valve actuating element 729.

There is a stop member 781 mounted to the actuating member 761, and this engages stationary stop members on the housing to limit the rotation of the actuating members 761 to 90° of rotation. When either of the stop members are engaged, an overload circuit simply cuts off power to the motor 779. The reason for this is to limit the rotation of the member 761 to move the ball valve element 723 only through 90° of rotation over the same path so that the ball valve element 73 moves only from the closed position to the open position, and then back over the same path to the closed position.

In FIGS. 45B and 45C, there is shown the entire drain assembly 783. This drain assembly 783 is positioned immediately below a top cover portion 784 of the base housing 708, and is located in a lower housing section 785 of this base housing 708. The drain assembly 783 comprises a discharge passageway section 786 and a motorized lever actuating mechanism 787.

Reference is first made to FIG. 45B and also FIG. 45A. There is an upper drain section 788 which is an integral structure and comprises an upper cylindrical tube portion 789 having an upper edge surface 790 that in operation engages a lower perimeter surface portion 791 that surrounds a through opening 792 which is a discharge opening of the valve 721. The upper perimeter edge surface 790 has an inwardly and downwardly slanting frusto-conical upper surface configuration, and the aforementioned valve housing perimeter surface portion 791 has a matching upwardly and outwardly slanting perimeter surface so that these press against one another to make a fluid tight connection.

Surrounding the tubular section 788, is a scupper member 793 spaced outwardly from the tubular section 788. This scupper member 793 slants downwardly and inwardly to join at its lower end to a lower cylindrical tubular housing section 794. This lower tubular section 794 has at its upper part a circumferential lip 795 against which is positioned a compression spring 796 which surrounds the middle part of the tubular portion 794.

Surrounding the lower part of he tubular portion 794 is an actuating ring 797 operably engaged to a lever portion of the motorized lever section 787. As will be described later herein, and this ring 797 acts to move the upper drain section 788 upwardly so that the upper tubular portion 789 comes into sealing engagement with the lower valve housing section 726.

The aforementioned lever section 787 comprises a lever member 798 which has a middle pivot location 799 at which the lever 798 is mounted to a pair of brackets 800 by a pin 801. One end 802 of the lever 798 is connected to a threaded nut 803 which in turn is connected to an actuating screw 804 driven from a motor 805. The end of the lever 798 opposite the end 802 is formed with two laterally spaced arms 806 which fit on opposite sides of the aforementioned actuating and positioning ring 797. Each arm 806 has an inwardly projecting lifting stub 807 that engages a lower edge of the ring 797. It is apparent that by rotating the screw 804 by means of the motor 805, the actuating end 802 the lever arm 798 can be lowered or raised, and by lowering the actuating arm end 802, the two arms 806 are caused to move upwardly, to in turn move the actuating ring 797 upwardly to press against the spring 796 and thus urge the upper discharge section 788 upwardly to cause engagement of the upper perimeter surface 790 of a tubular portion 789 against the aforementioned surface 791 of the lower valve housing section 726 and thus form a sealed fluid passageway.

Also, in FIG. 45B, there are shown two components 811 and 813 of the aforementioned control panel 716. These provide the contact points to control the operation of the two motors 805 and 779.

Reference is now made to FIG. 45C to describe the lower drain passageway section 814. This lower passageway section comprises a tubular section 815 having in cross section a circular configuration with a larger diameter upper portion 816 positioned within a lower portion of the tubular section 794, with a close sliding fit, and a lower tubular section 818 of a smaller diameter. The lower section 818 is removably connected to the upper end 819 of the aforementioned sewer disposal line 714 by means of a conventional connection indicated at 820. More particularly, this connection 820 comprises an interiorly threaded collar 821 which threads onto the upper threaded end 819 of the disposal line 714, and there is a seal ring 824 which fits between the collar 821 and the upper tubular end 819. The sewer disposal line 714 also has an elbow connecting section 825 which in turn connects to the main line 714 through another connecting device 826 which is the same as, or similar to, the connecting device 821. The drain passageway could lead to a sewer or other disposal container or location.

Figure 50:
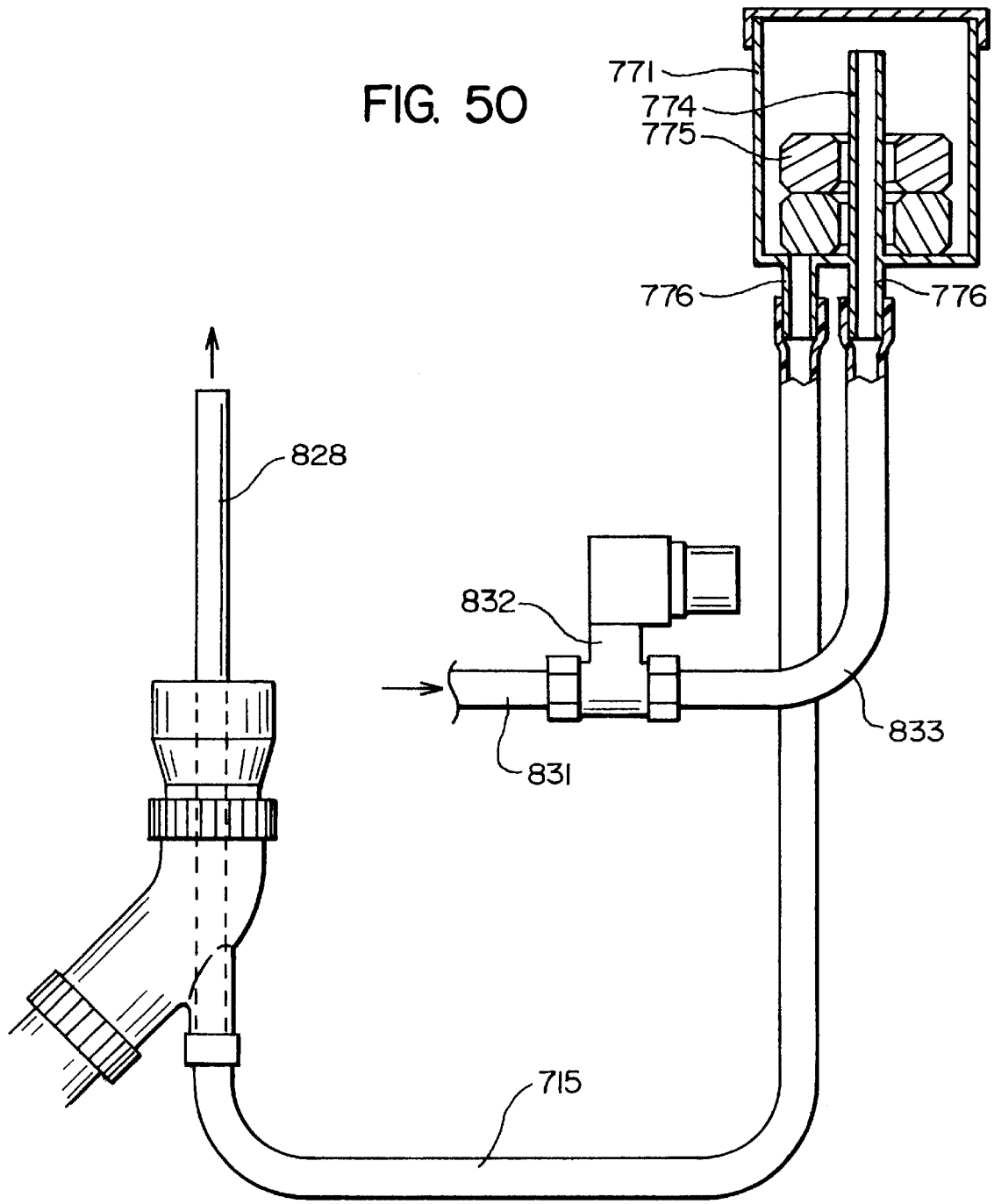
FIG. 50 is an elevational view, partly in section, showing the disinfecting/irrigating assembly.

An irrigating/disinfecting tube 828 connects to the water line 715 and extends in a seal tight arrangement through the elbow 819 and extends upwardly to have its upper end 829 positioned at about the top perimeter edge 790 of the tubular member 789. As can be seen in FIG. 50, this tubular member 828 connects to the water line 715 that in turn connects to one of the fittings 776. A water supply tube 831 is connected to an external source of water, and connects to a motor controlled on/off valve 832 which in turn connects to a tube 833 connected to the other fitting 776 to direct water upwardly through the locating and water supply tube 774. Thus, after the biofluid in the container 704 has completely drained from the container 704, the water valve 832 is turned on to cause water to flow through the inlet tube 833 and through the tube 774 into the interior of the container 771 to flow downwardly through the disinfecting wafers 775 and through the fitting 776 to the tube 830 to in turn be directed through the irrigating/disinfecting tube 828.

Figure 51:
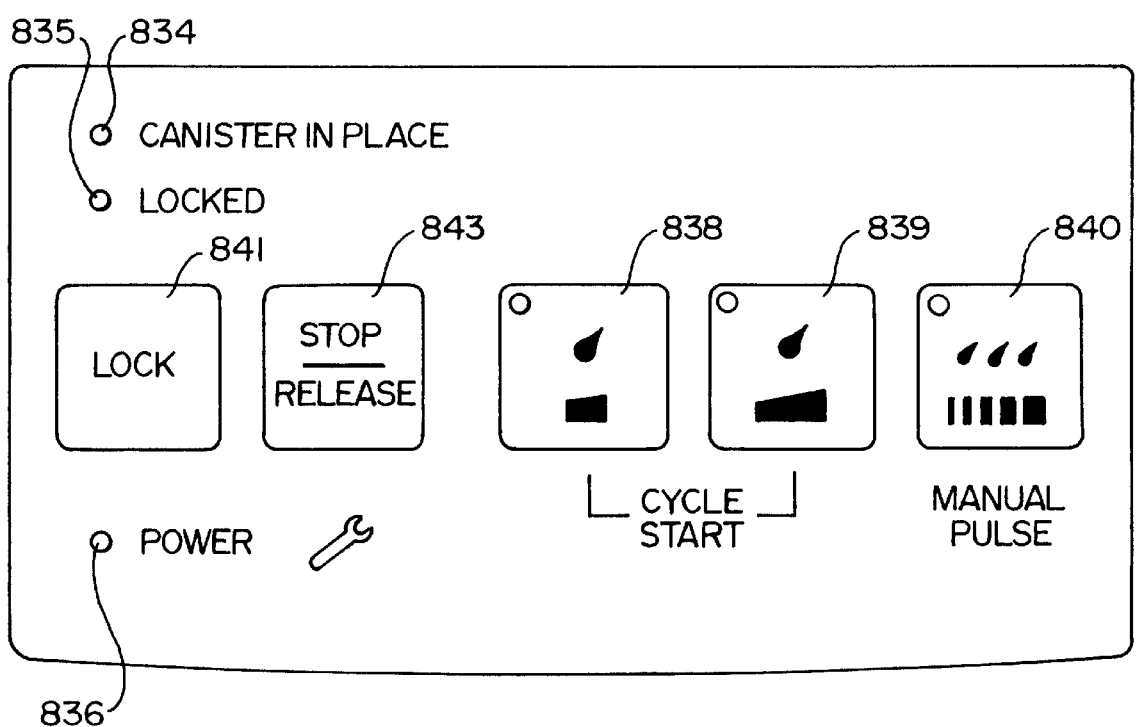
FIG. 51 is a plan view of the control panel.

The control panel is shown in FIG. 51. There are indicator lights 834, 835 and 836 to indicate, respectively, whether the container assembly 701 is in place, whether the container assembly 701 is locked in place, and whether the power is on. There are two pressure contact switches 838 and 839 which start the cycle, switch 838 for a shorter cycle and switch 839 for a longer cycle. There is also the manual pulsing switch 840 (operated by servo mechanisms) which can be operated to open the irrigating valve 832 for shorter or longer periods for additional washing/disinfecting of the interior of the container 704 and the other interior surfaces exposed to the biofluid. Further, there is a lock switch 841 to lock the container assembly, and a stop/release switch 843 by which a cycle can be stopped and the container assembly 701 released from its engaged position in the base assembly 703.

To describe the overall operation of the present invention, reference is first made to FIG. 41. Initially, the valve 721 should be in the open position, and if it is not, then the manual valve handle 728 is rotated to the position of FIG. 41 so that the valve passageway 736 is vertically oriented.

In the normal mode of operation, the valve and connecting assembly 706 remains connected to the container 704 and is usually removed only for maintenance or periodic sanitization of the system. On the other hand, the plug and manifold assembly is used only for a single filling of the container 704, and is thereafter disposed of as a contaminated waste object, or collected and taken to a sanitizing and disinfecting location, so that it could be used again.

Then the plug and manifold assembly 716 is inserted downwardly through the upper open end of the valve and connection assembly 706, and secured in place, this being accomplished by positioning the cap 743 so that the open areas 756 pass over the protrusions 759 (see FIG. 44A), after which the cap 74 is rotated 45° to be in the lock position. This action forms a seal at the lower end of the body 735.

After that, the two or more suction tubes 718, and also the vacuum line 719 are inserted into the related upper openings defined by the tubular members 738 and 739, respectively.

Thus, with the installation of the plug and manifold assembly 716 being accomplished, and with the tube 718 and 719 in place, the container 704 is positioned at a location near the patient, and the suctioning proceeds as described previously in this text.

When the container 704 is filled to a predetermined level, then the vacuum source is turned off so that the pressure within the container 704 rises toward atmospheric level. The tube 718 and 719 are detached from the plug and manifold assembly 716, and thereafter either reconnected to another container assembly 702 or removed from the patient and moved to some other location to be washed and sterilized.

The operation of the plug and manifold assembly 716 was described previously herein, but to review this briefly, the action of the flap member 750, acting as a check valve, permits the biofluid to flow through the openings 745 in the plate 741 and into the container. The air and other gaseous substances in the container are withdrawn through the opening 747 and into the vacuum tube member 739 that is in turn connected to the vacuum line 719.

After the tubes 718 and 719 have been removed, the plug and manifold assembly 716 is removed by rotating the cap 754 45° and lifting the plug and manifold assembly 716 out of engagement with the valve and connecting assembly 706. The plug and manifold assembly 716 can simply be treated as a disposable item and discarded as contaminated material. Alternatively, these plug and manifold assemblies 716 could be collected to a washing and sanitizing location to be reused.

Then, the valve handle 728 is manually rotated 90° to move the ball valve element 723 to its closed position. The container 704 is then grasped by the handles 705 and moved to the disposal location where the base assembly 703 is located.

The containing assembly 701, with its valve 721 closed, is then taken to the location of the base assembly 703, inverted 180°, and then positioned so that the two side connecting elements 733 are aligned with the slideway 710, and also so that the valve handle 738 is positioned forwardly and the actuating member 729 is located rearwardly. Thus, as can be seen in FIG. 45, as the container 704 is moved rearwardly into the slideway mounting 709, the valve actuating member 729 comes into engagement with the protruding end portion 780 of the valve actuator 761 that is positioned in the base housing 708 and connected to the valve actuating motor 779. In this position, the valve 721 still remains closed.

Figure 46A:
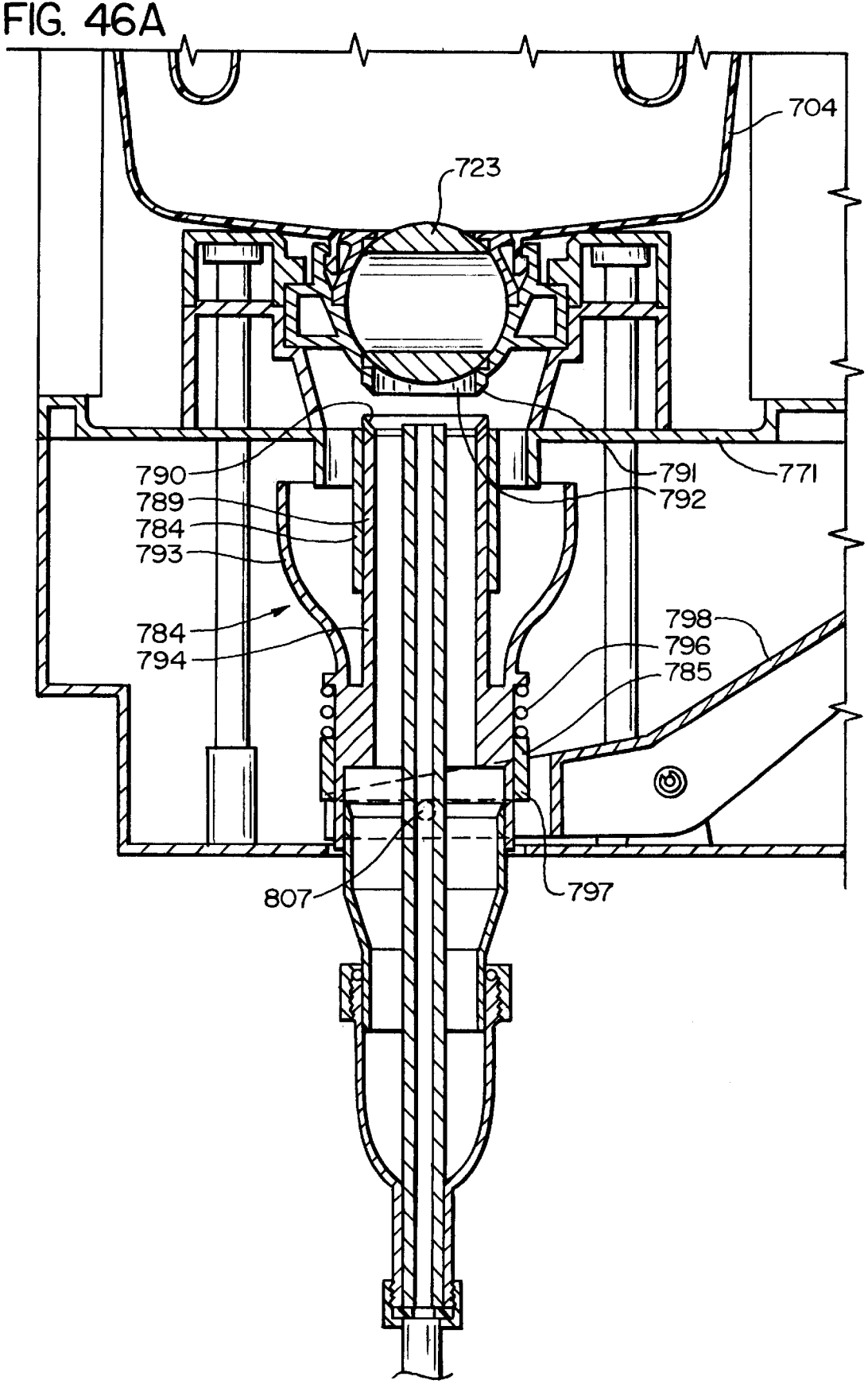
FIG. 46A is a sectional view showing the container in its disposal position but with the valve closed.
Figure 46B:
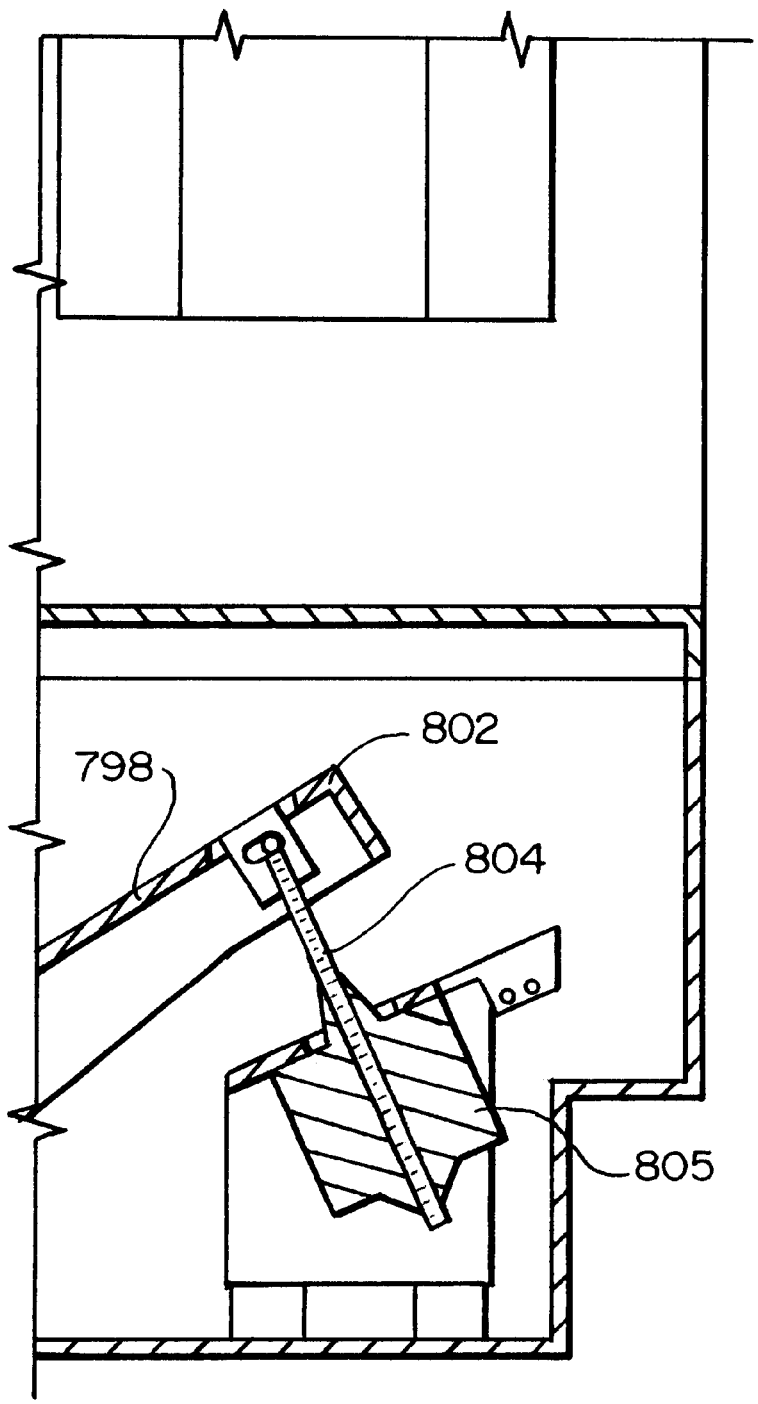
FIG. 46B is an elevational view, partly in section, of a motorized lever portion of the disposal section.

Also, the contact switch 768 senses when the valve and connecting assembly 706 is located fully into its connected position, and this is transmitted to the control apparatus to indicate that the draining, and cleaning/disinfecting cycle can be initiated. At this time the power light 836, and also the canister in place light 834 would be lit. However, the "locked" button 835 is not yet lit. Before the cycle is initiated, the upper drain section 788 in the base assembly 703 is in the position as shown in 46A and 46B. More specifically, the positioning lever 798 is in the disengaging position, where the end 802 of the lever is raised, and the two arms 806 are in a lowered position, as illustrated in FIGS. 46A and 46B.

As soon as one of the cycle switches 838 or 839 is activated, the first thing that happens is that the positioning motor 805 starts operating to rotate the locating screw 804 to move the end 802 of the lever arm 798 downwardly, thus raising the two arms 806 and causing these to lift the actuating ring 797. The ring 797 in turn acts against the compression spring 796 to engage the lip 794 and raise the upper drain section 788 upwardly. This causes the upper slanted sealing surface 790 of the upper tube 789 to come into engagement with the matching surface 791 of the perimeter portion of the lower valve housing section 726 surrounding the opening 792 to form a fluid tight seal. At this time, the upper drain section 788 is in the position shown in FIG. 48A, and because of the engagement of the tubular section 788 with the valve housing 724, the containing assembly 701 is now locked in place in its position of FIG. 40 with respect to the base assembly 703.

Figure 48A:
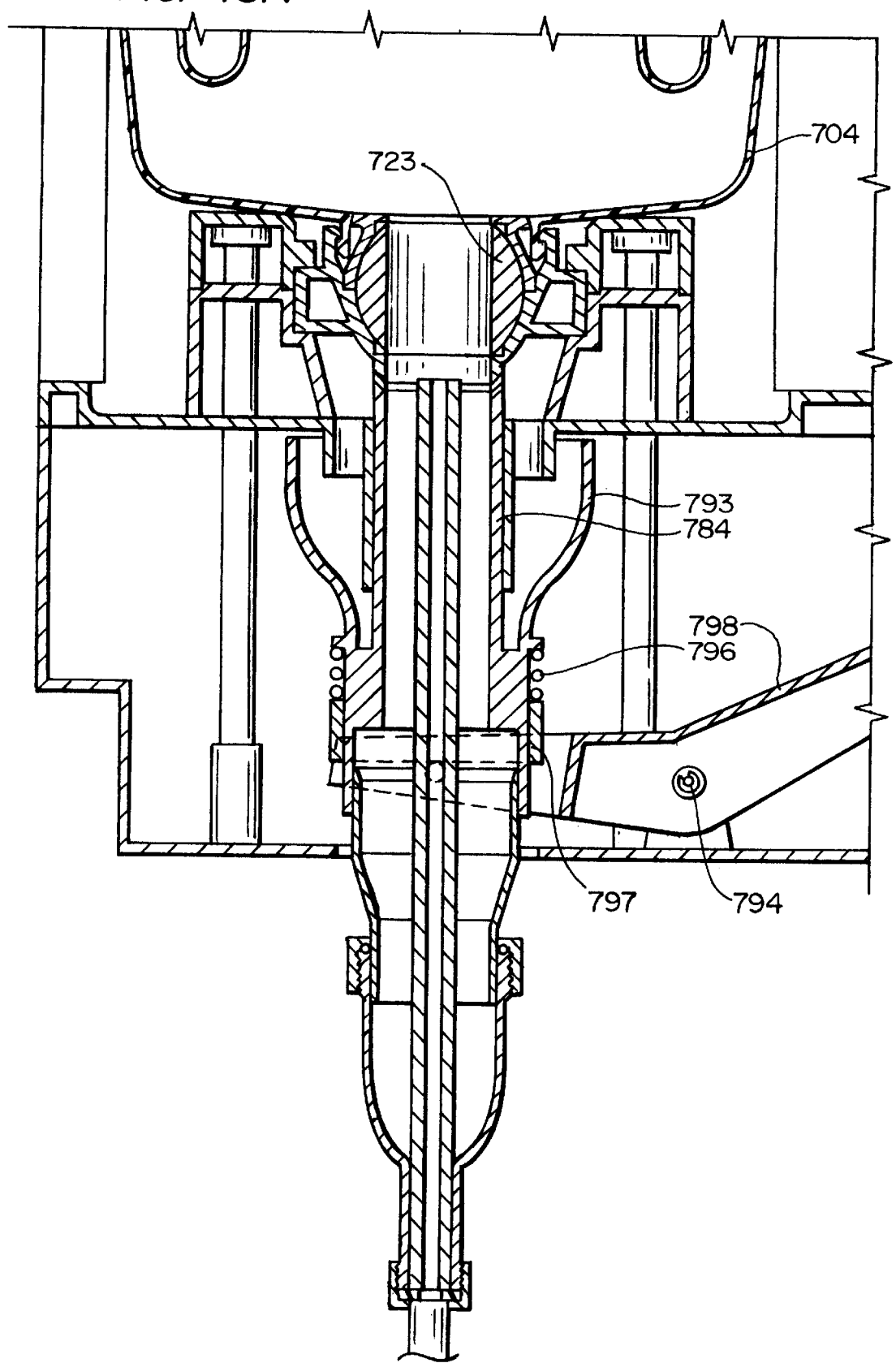
FIG. 48A is a sectional view similar to 46A, but showing the valve in its open position.
Figure 48B:
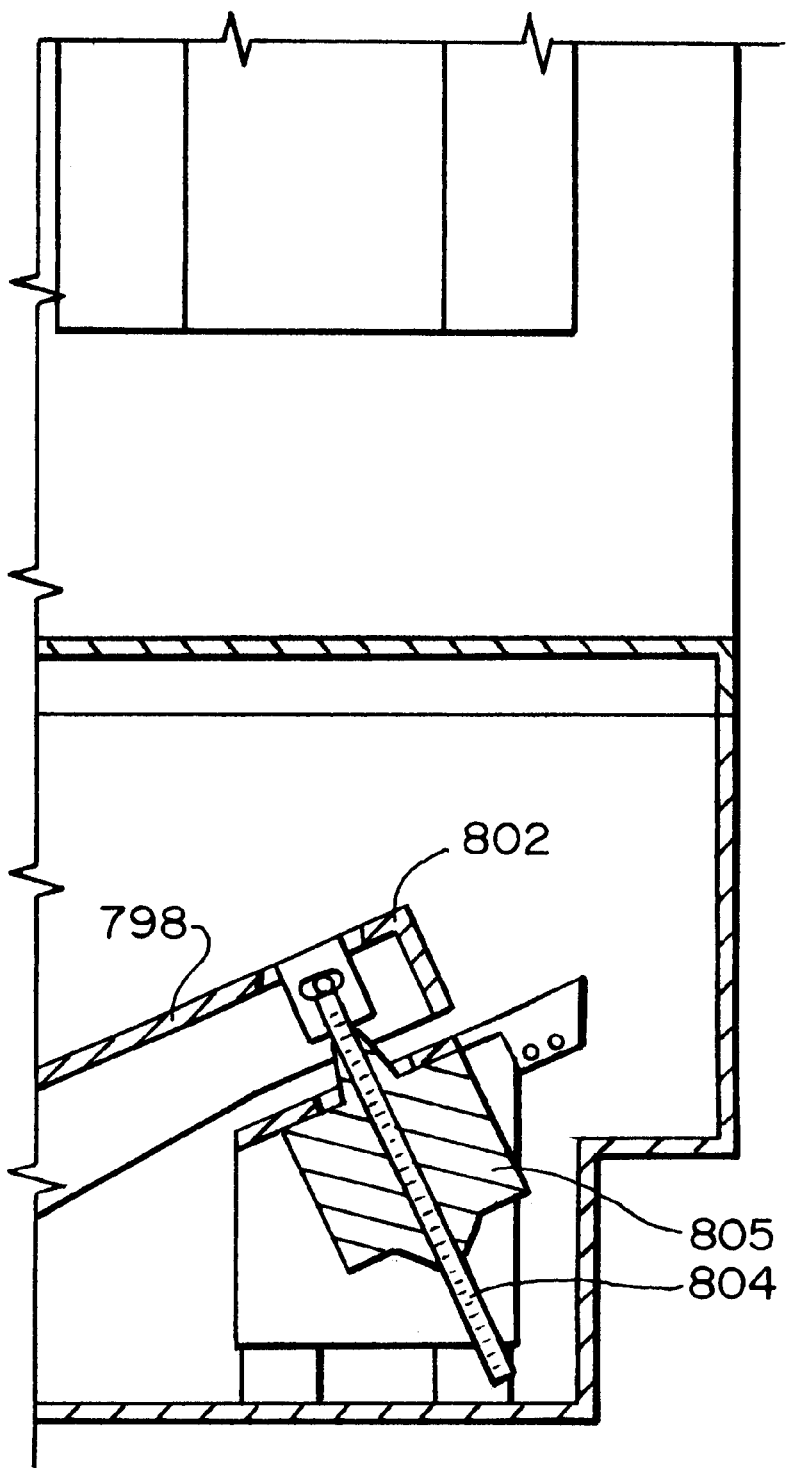
FIG. 48B is a view similar to 46B, but showing the motorized lever section in a different operating position.
Figure 49:
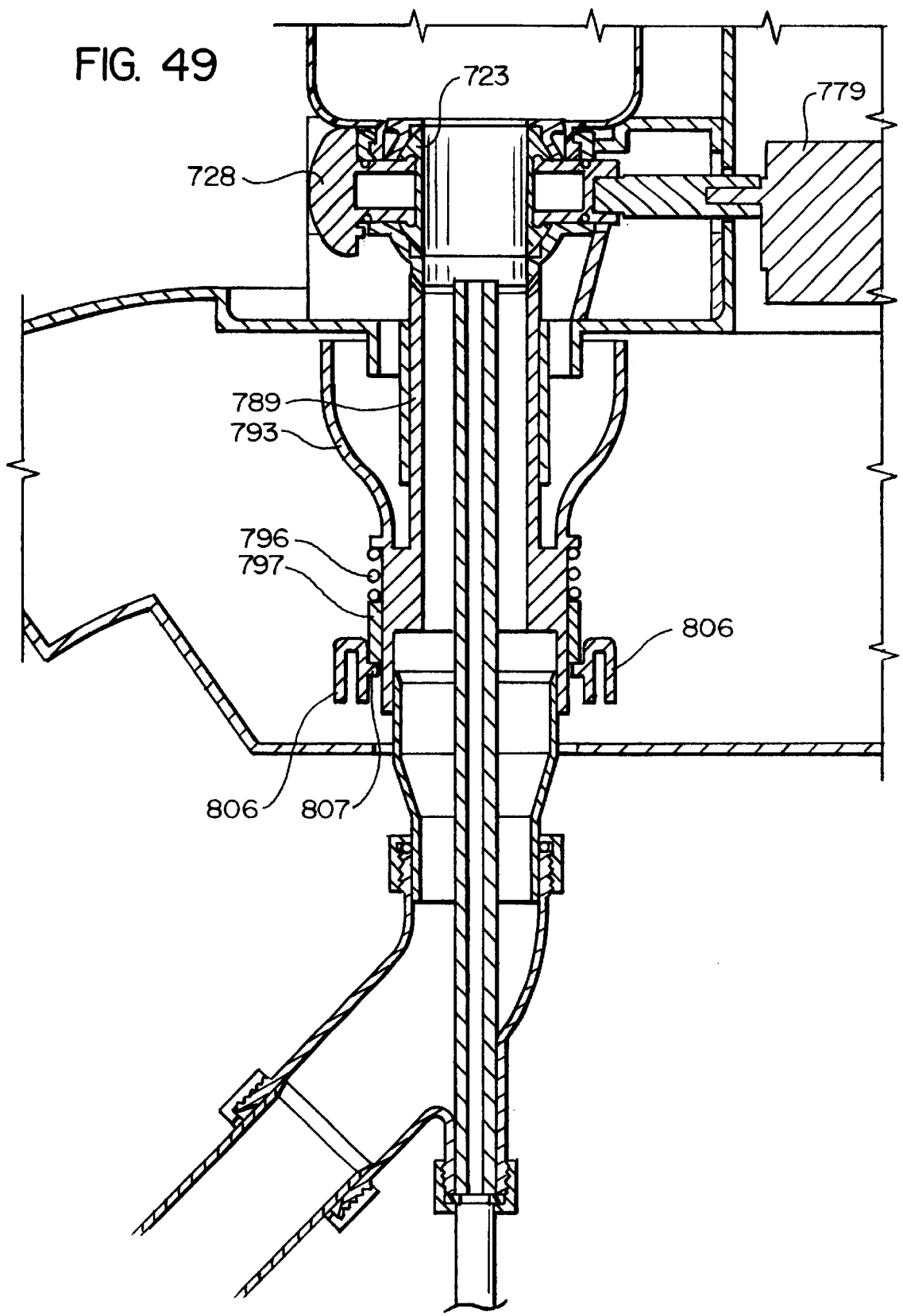
FIG. 49 is a sectional view similar to FIG. 47, but showing the valve in the open position.

Next, the control mechanism causes the valve motor 779 to operate to rotate the actuating member 761 90° to in turn cause the valve element 723 to rotate 90° to the open position shown in FIG. 48A. Also, it can be seen in FIG. 48B that the arm portion 802 of the lever arm 798 has been rotated downwardly to the position of FIG. 48B.

After a period of time adequate for the container 704 to have its contents totally emptied into the drainage system, the control mechanism opens the water valve 832 to cause the water to flow upwardly through the line 833 into the container 771 to come in contact with the wafers 775 which dissolve gradually into the water. The water with the disinfectant thus flows through the line 715 upwardly through the tube 828, through the valve passageway 836 and into the container 704. If additional washing is desired, then the manual pulse switch 840 is activated to cause the water valve 832 to open for predetermined periods of time to cause additional wash/disinfecting liquid to be directed upwardly into the container 704 for further washing. The wash/disinfecting liquid simply passes out the sewer drain 74.

When the washing/disinfecting operation has been completed, then the stop release switch 843 is activated.

This first causes the valve motor 779 to rotate the actuating member 761 to its closed position. When the valve element 723 has moved to its fully closed position, thus insuring that no further liquid will flow from the container 704, the control system then starts the positioning motor 805 which raises the lever arm portion 801 to lower the upper drain section 786, causing it to come out of engagement with the valve housing 724. Then the container assembly 701 can be removed from the base assembly and reused as indicated above.

l) Twelfth Embodiment

This twelfth embodiment of the present invention will be described with reference to FIGS. 52–59. The overall configuration of this twelfth embodiment is rather similar to the eleventh embodiment described immediately before. Two of the main differences are that the interconnecting means between the container assembly and the base assembly is different, in that instead of having a slide connection, there is a "twist in" connection. Also, in this twelfth embodiment, the motorized lever assembly of the eleventh embodiment is not included. Rather, the seal tight connection is made by the valve and connecting portion of the container assembly moving downwardly to engage the movable tubular member of the drain assembly to press it downwardly and form a tight seal. A further difference is the manner in which the valve element is engaged by the valve motor to cause rotation of the valve.element in the container assembly.

Components of this twelfth embodiment which are similar to those of the eleventh embodiment will be given like numerical designations, with an "a" suffix distinguishing those of this twelfth embodiment.

Figure 52:
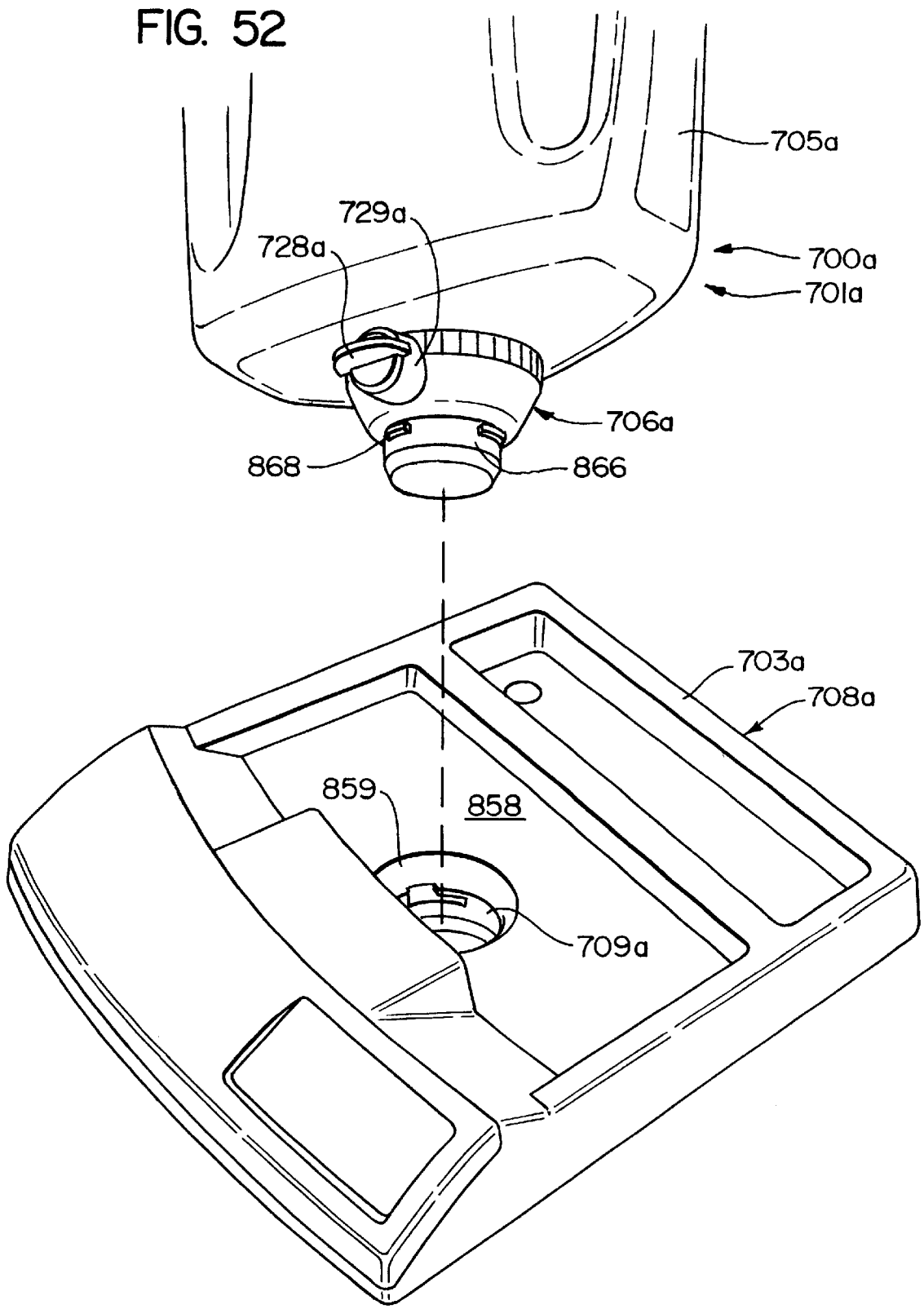
FIG. 52 is an isometric view of an twelfth embodiment of the present invention showing the container assembly positioned above the base assembly.

With reference to FIG. 52, it can be seen that the system 700*a* comprises a container assembly 701*a* and a base assembly 703a. As in the eleventh embodiment, the container 704a has two side handles 705a and also a valve and connecting assembly 706a. The base assembly 703a also has a container connecting portion 709a, but this functions in a different manner than the mounting section of the eleventh embodiment.

A disinfecting/irrigating tube is also provided corresponding to the tube 715 of the eleventh embodiment, but this is not shown in FIGS. 52–59. Rather, the fitting 850 by which this connection is made is shown (see FIG. 58).

Figure 58:
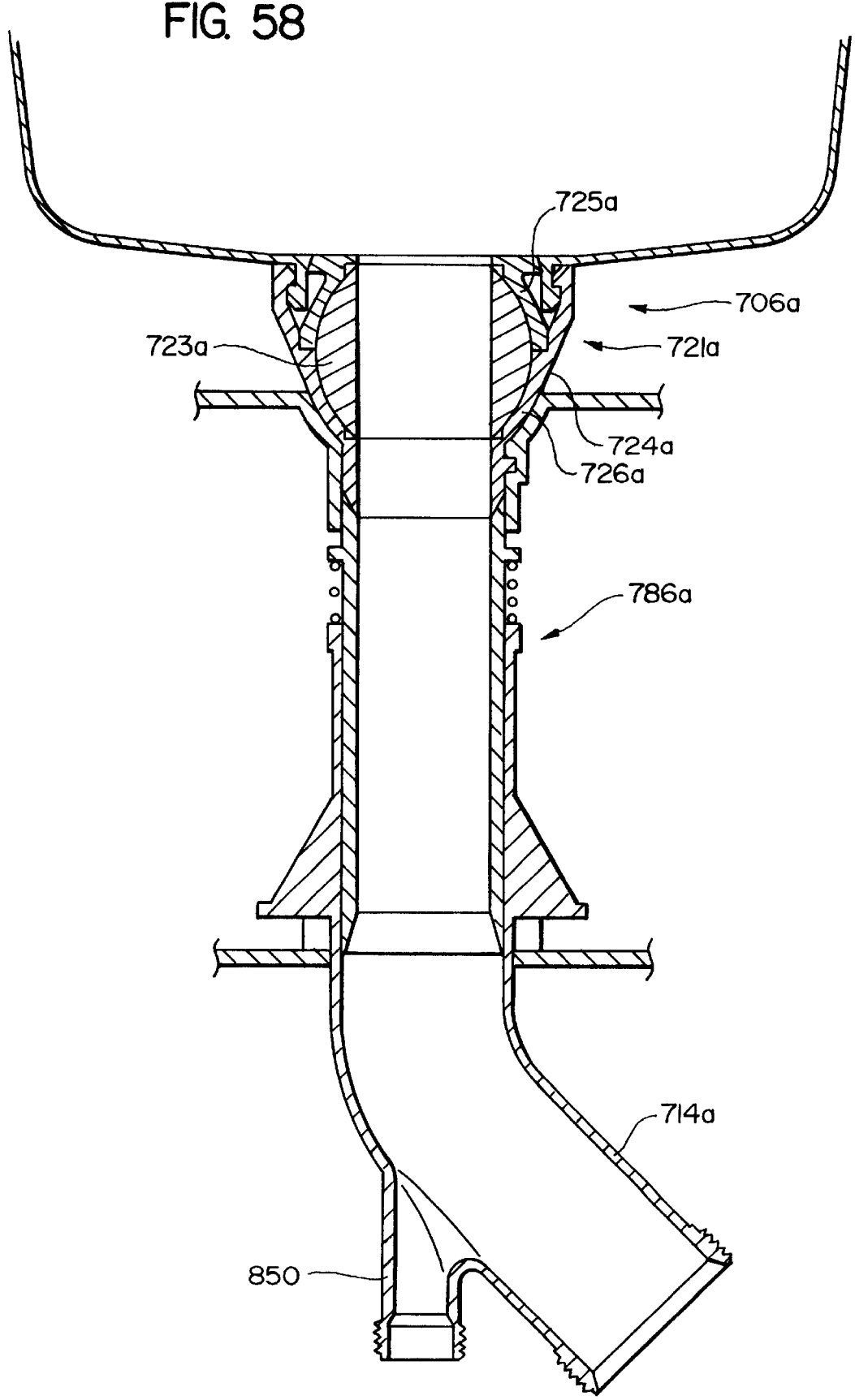
FIG. 58 is a view similar to FIG. 57, but showing the container assembly mounted to the base assembly.
Figure 59:
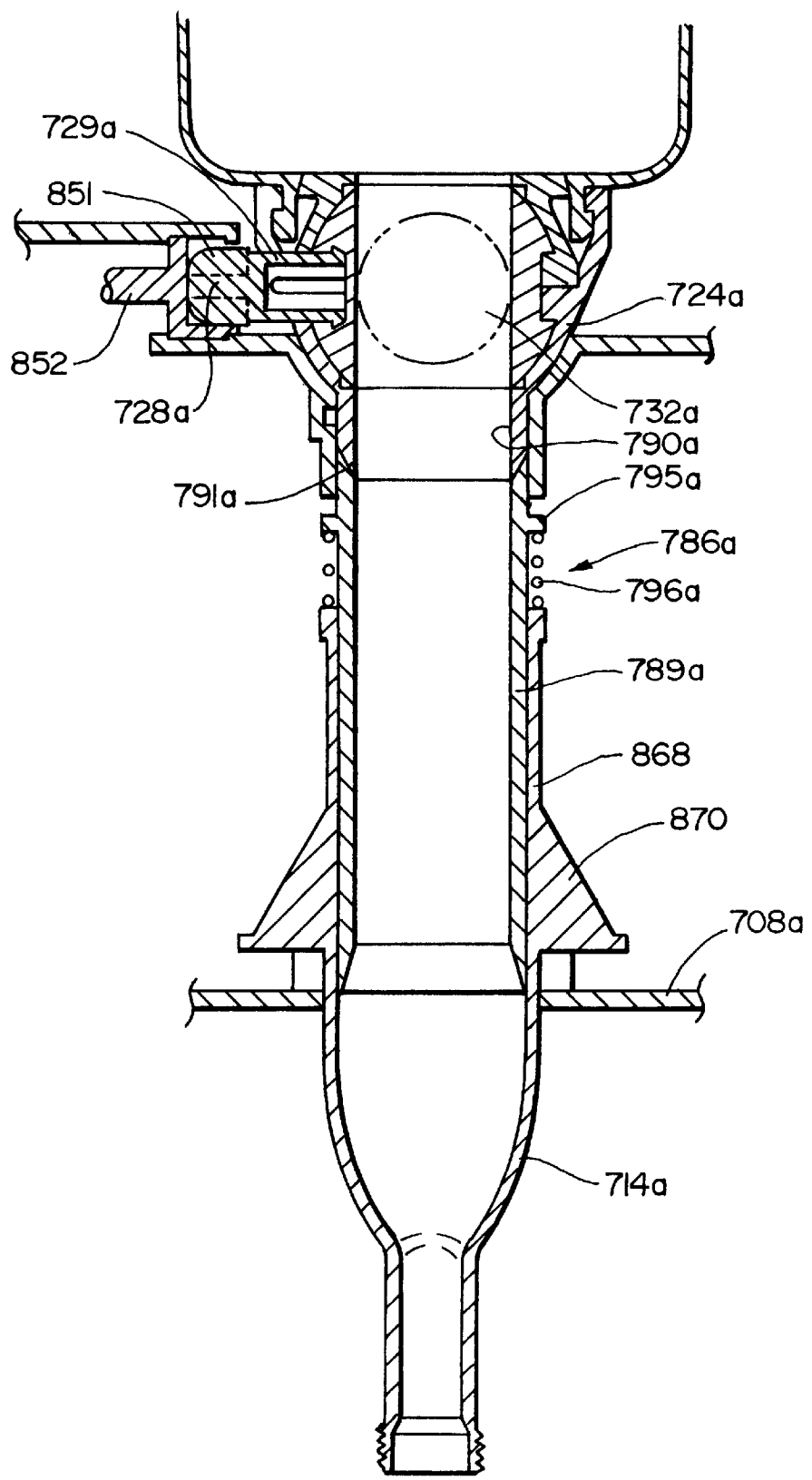
FIG. 59 is a sectional view similar to FIG. 58, but with the section plane rotated 90° from FIG. 58.

With reference to FIGS. 58 and 59, there is shown the valve 721a of the valve and connecting assembly 706a. As in the eleventh embodiment, this valve 721a comprises a ball valve element 723a, positioned within a valve housing 724a made up of upper and lower housing sections 725a and 726a. As can be seen in FIG. 52, there is a valve handle 728a, but instead of having this connected to the valve element 723a as simply a manual operated handle, this is interconnected to the valve element 723a by a valve drive connector 729a, and the valve handle 728a interconnects with a drive connector 851, which is in turn connected to a motor located in a housing portion 853.

It can be seen (see FIGS. 53 and 54) that the housing section 853 has a horizontal slot 854 having a curved backwall 855. It can be seen that this slot 854 is aligned with an interior slot 856 in the drive member 851. As will be described hereinafter with respect to the method of mounting the container assembly 701a, when the valve and connecting assembly 706a is inserted into the base mounting portion 709 of the base assembly 703a, the handle 728a at its lowermost location is at the same level as the slot 854 in the housing section 853. Then when the container assembly 701a is rotated into its fully engaged position, the valve handle 728a moves through the slot 584 and into the actuating slot 856.(See FIGS. 55 and 56). Then when the cycle is started, the electric motor contained in the housing section 853 rotates the actuating member 851 90° to the position of FIG. 54, thus opening the ball valve element 723a. In addition to opening the ball valve element 723a, the actuating member 851 also locks the container assembly 701a in place since, with the actuator 851 in the position of FIG. 54, it is not possible to rotate the container assembly 701a to come out interconnecting engagement with the base interconnecting means 709a.

FIG. 52 shows the base mounting portion 709a more clearly. This mounting portion 709a, is positioned at an upper plate surface 858 of the base housing 708a. This base mounting portion 709a comprises a downwardly and inwardly cylindrically curved mounting surface 859 that in turns leads into a lower cylindrical section 860. The cylindrical member 860 is formed with four bayonet shaped slots 861 each having a vertical entry portion 864 and a horizontally curved portion 865. In FIG. 52, it can be seen that the valve and connecting assembly 706a has a cylindrical portion 866 which has four protrusions 868l.

To interconnect the container assembly 701a with the base assembly 703a, the container assembly is inverted to the position of FIG. 52, and at this time the valve handle 728a is disposed horizontally relative to the container 704a so that the ball valve element 723a is closed. The container assembly 701a is lowered, with the protrusions 868 in alignment with the vertical slot portions 864. When the protrusions 868 reach the level of the horizontal slot portions 865, the container assembly 701a is rotated about 45° so that the protrusions 868 become positioned within the horizontal slot portion 865, so that in that position it is not possible to lift the container assembly 701a upwardly. As indicated previously, at the start of the cycle, the actuating member 851 rotates to move the handle 728a vertically, thus opening the valve element 723a and also retaining the container assembly 704a in its interconnecting position.

As indicated earlier in the introductory portion of this text relating to this twelfth embodiment, another difference between this twelfth embodiment and the eleventh embodiment is that the motorized lever mechanism of the drainage assembly of the eleventh embodiment is eliminated. To explain how the drainage connection is made between the container assembly 701a and the base assembly 703a, reference is made to FIGS. 58 and 59 where there is shown in cross section the drainage section 786a.

There is a tubular member 789a, having an upwardly facing slanted contact surface 790a which engages the matching contact surface 791a of a lower perimeter portion of the valve housing 724a. Also, this tubular member 789a has at its upper portion a circumferential lip 795a which engages a compression spring 796a surrounding the middle portion of the tubular portion 789a. This spring 796a bears against a stationary sleeve 868 that is fixedly connected to the base housing 708a. The lower end of the tubular member 789a is slide mounted within this sleeve 868, and this sleeve 868 in turn is either made integrally with, or connected to the aforementioned drainage member 714a. As shown herein, this sleeve 868 has several radially extending mounting fins 870 which serve to stabilize the sleeve 868 relative to the base housing 708a.

It is believed that the operation of this twelfth embodiment can readily be understood from reading the operation of the eleventh embodiment, but this mode of operation will be described briefly at this time.

Initially, the container assembly 701a is positioned in an upright position, and a plug and manifold assembly, such as the assembly 716 of the eleventh embodiment, is positioned in the valve and connecting assembly 706 and connected to the appropriate suction tubes and vacuum tube to withdraw the biofluid from the patient. The plug and manifold assembly is then removed, and the valve handle 728 is manually moved to the closed position. The container assembly 700a is then moved to the location of the base assembly, inverted, and then lowered toward the base connecting portion 709a, with the connecting protrusions 768 aligned with the vertical slot portions 864.

In a non-engaged position, the sleeve 789a is in an up position where the aforementioned lip 795a engages a sleeve 869 that is made integral with and is connected to the housing wall 859. This contact with this sleeve 869 properly position the tubular member 859a in its upwardly position. Then, as shown in FIG. 58, when the container assembly 701a is lowered into its connecting position, the slanted contact surface 791a of the lower perimeter portion of the valve housing 724a contacts the matching upper edge surface 790a of the tubular member 789a and pushes the tubular member 789a downwardly against the urging of the compression spring 796a, thus making a fluid tight contact between the surfaces 790a and 791a.

At this time, the operating cycle is initiated, and the motor (not shown for ease of illustration) corresponding to the motor 789 of the first embodiment turns the actuating member 851 90° to rotate the valve handle 728a 90° to move the valve element 723a to its open position, as shown in FIGS. 58 and 59. Then the biofluid in the container 704a flows downwardly through the valve passageway 732a through the tubular member 789a, and downwardly into the sewer discharge line 714a. After the emptying of the container 704a is completed, then an irrigating and disinfecting cycle can be accomplished as described previously in this text.

Figure 53:
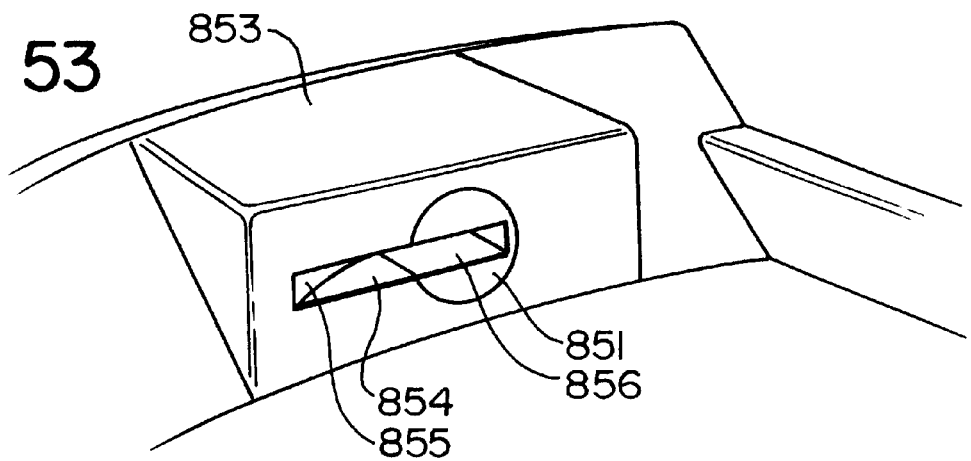
FIGS. 53 and 54 are isometric views showing a portion of the base assembly which interconnects with the valve of the container assembly.

When the irrigating and disinfecting step is completed, the valve actuating motor (corresponding to the motor 789 of the eleventh embodiment) is rotated in reverse 90° to return the valve actuator 851 back to its horizontal position of FIG. 53. This permits the container handles 705*a* to be grasped to rotate the container assembly 701*a* 45°, so that the connecting protrusions 868 are aligned with the vertical slot opening 865. At this time, the valve element 723*a* is in its closed position, and the container 701*a* can be lifted free of the base assembly 703*a* and returned to its collecting position where the plug and manifold assembly could be inserted into the valve and connecting assembly 706*a* so that further suctioning of the patient can be accomplished.

m) Thirteenth Embodiment

The thirteenth embodiment of the present invention will now be described with reference to FIGS. 60–76. Components of this thirteenth embodiment which are similar to components in the eleventh and twelfth embodiment will be given like numerical designations, with a "b" suffix added to distinguish those of the thirteenth embodiment.

This thirteenth embodiment is rather similar to the twelfth embodiment, but with some modified design features. Among these modifications are the following. There is a modified design for the plug and manifold assembly 619*b*. The configuration of the valve 721*b* is changed. Also, the configuration of the biofluid container is modified to permit initial small quantities of biofluid that flow into the container to be measured more accurately, and also so that the container can be mounted more conveniently, to a wall bracket.

Figure 60:
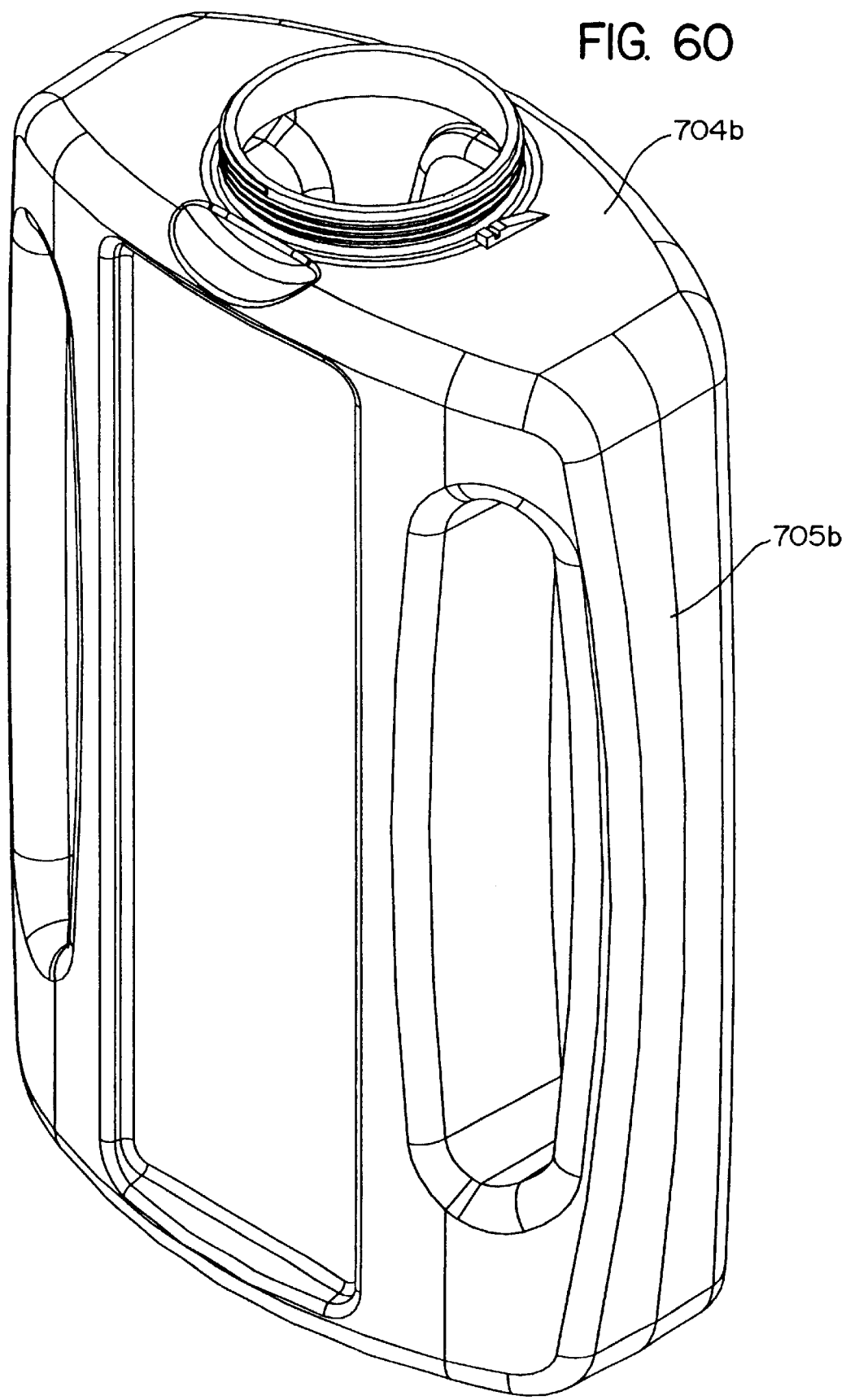
FIG. 60 is an isometric view of the container of the present invention, without the valve and connecting assembly.
Figure 61:
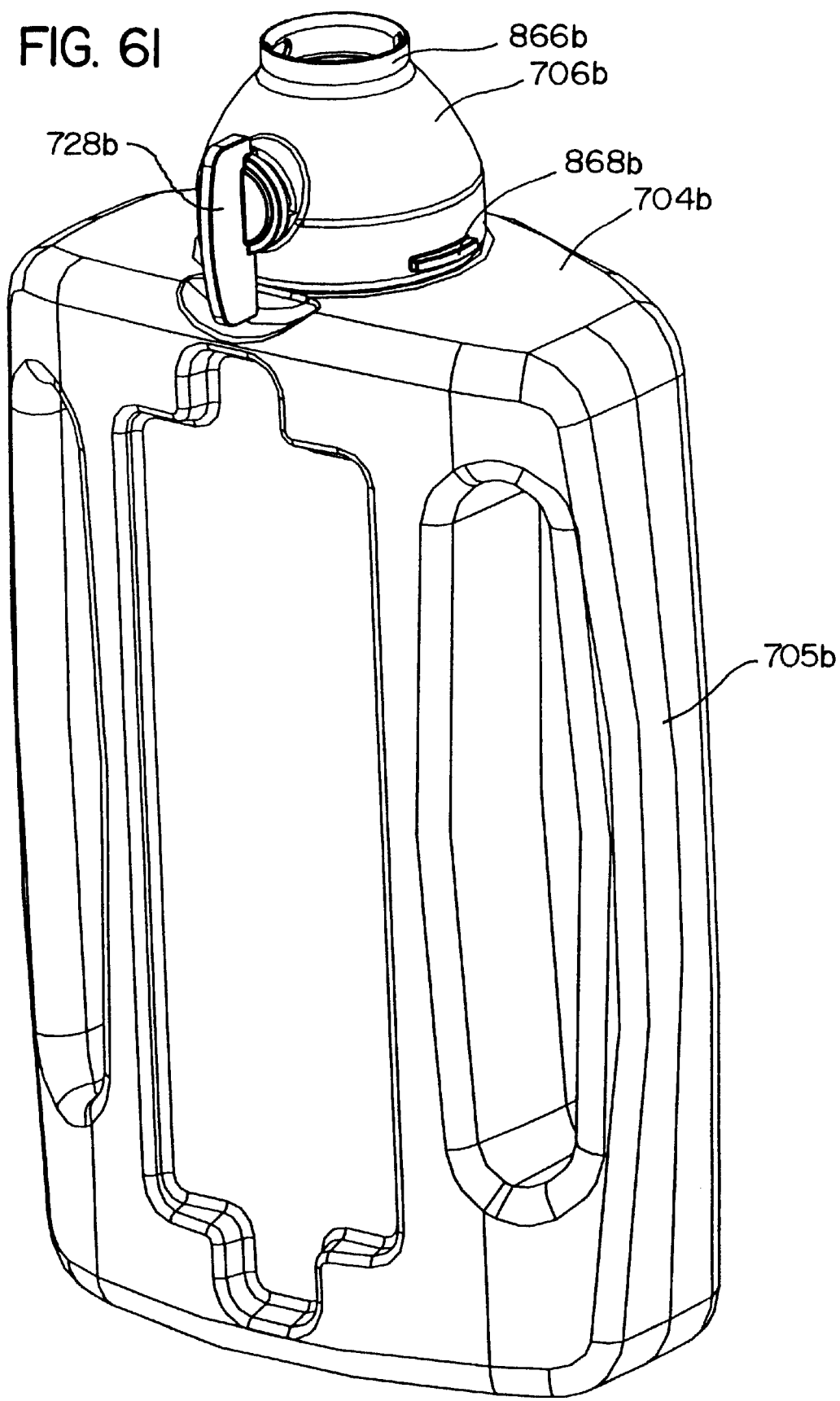
FIG. 61 is an isometric view similar to FIG. 60, but with the container having the valve and connecting assembly mounted thereto.

With reference to FIG. 60, there is shown the container 704*b*, with substantially the same configuration as the container 704*a*. In FIG. 61, the container 704*b* is again shown, but with the valve and connecting assembly 706*b* mounted to the container 704*b*. The upper perimeter portion 866*b* is modified in that the connecting protrusions 868*b* are positioned at a lower location on the valve and connecting assembly 706*b*.

Figure 62:
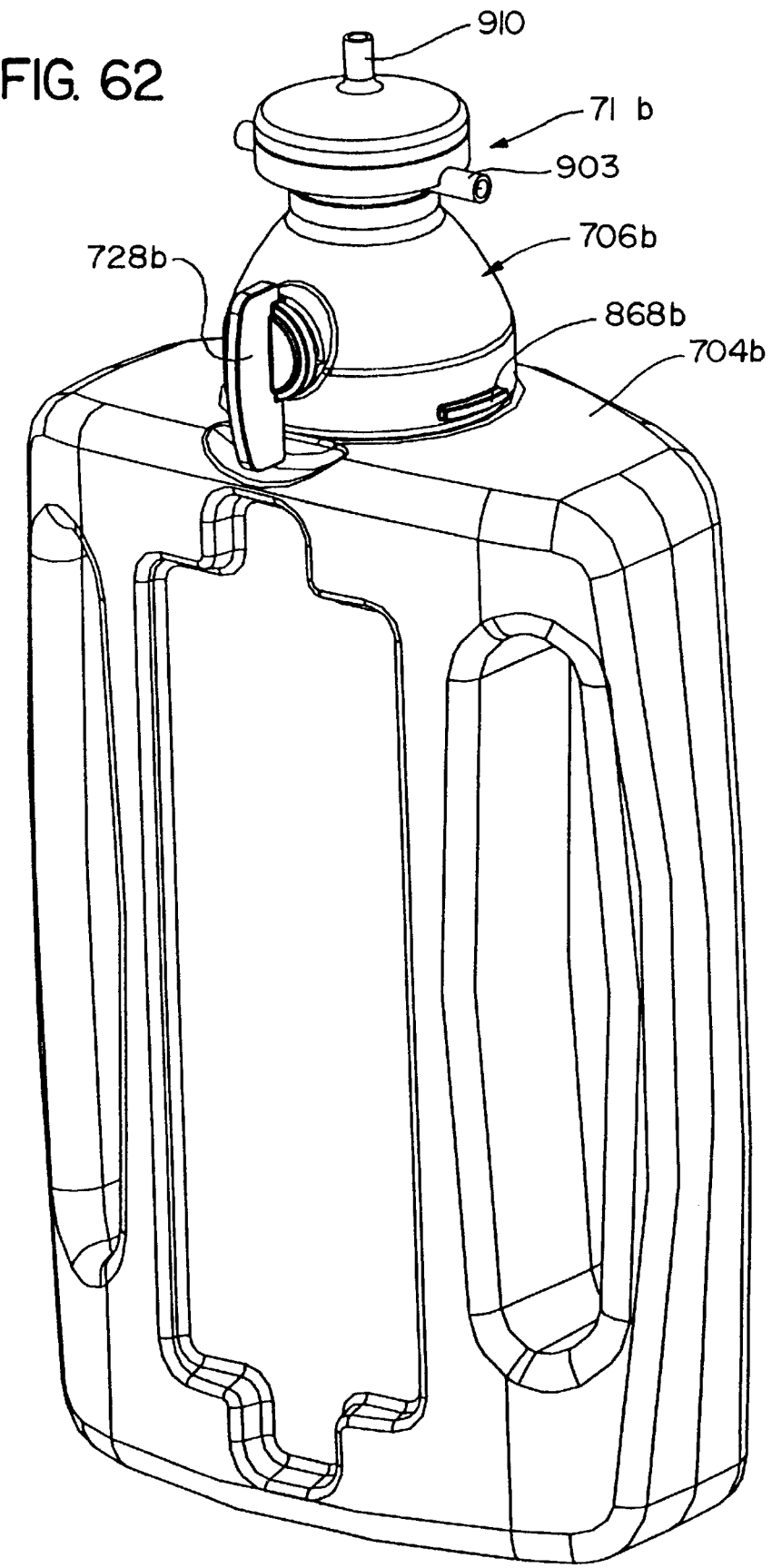
FIG. 62 is an isometric view similar to FIG. 61, showing the plug and manifold assembly mounted to the valve and connecting assembly.

FIG. 62 again shows the container 704*b*, but with the plug and manifold assembly 716*b* mounted in the valve and connecting assembly 706*b*. It can be seen that the configuration of the plug and manifold assembly 716*b* has a modified design in several respects. As can be seen in FIG. 62, one of the changes is that there is a central vertically extending fitting 870 adapted to be connected to the vacuum line, and two radially extending diametrically opposed fittings 871 to be connected to the suction line. Also the interlock elements 868*b* are located to interconnect in slots within the valve housing. This plug and manifold assembly 716*a* will be described more particularly with reference to FIGS. 69 and 70.

Figure 63:
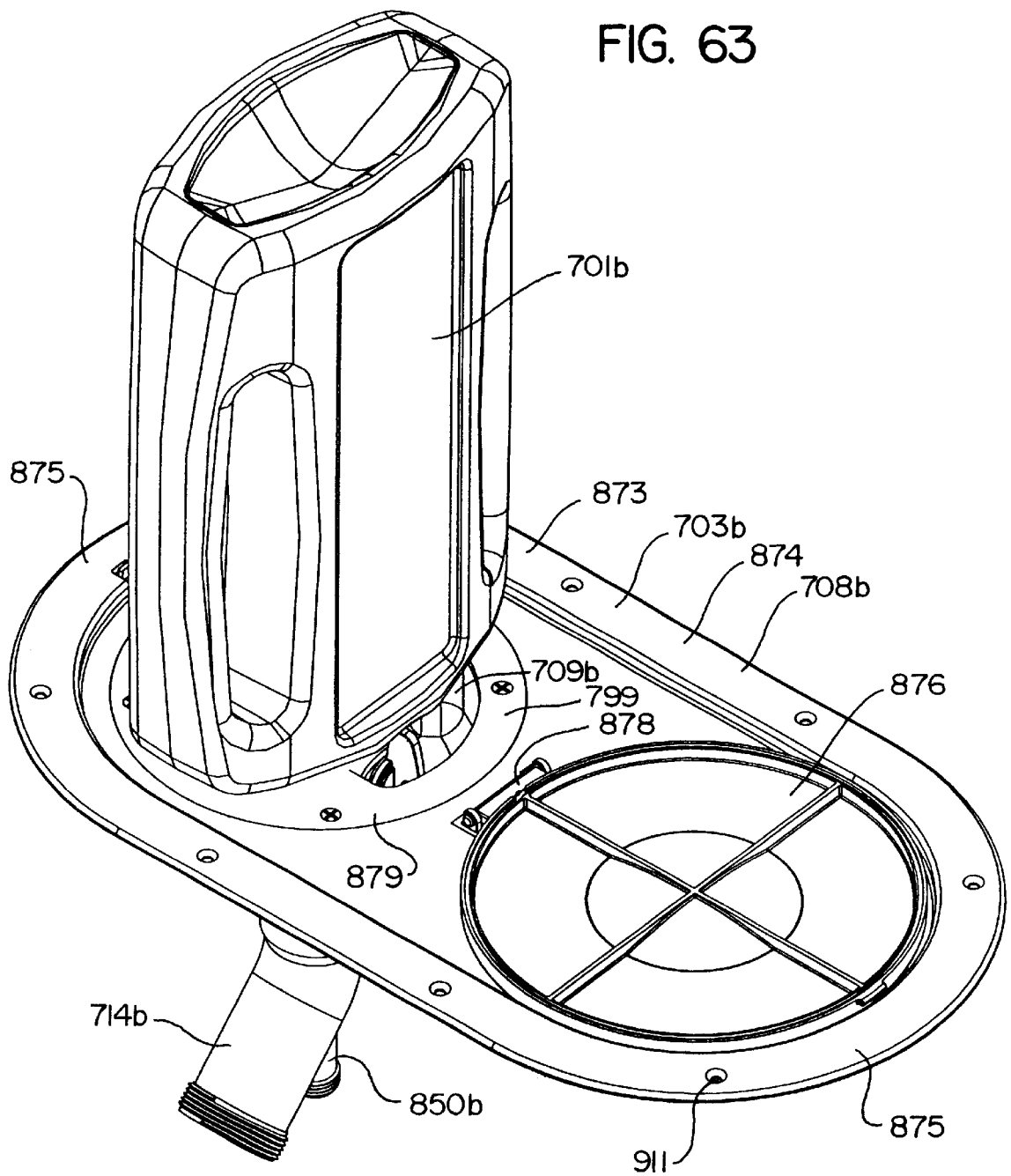
FIG. 63 is an isometric view showing the containing assembly mounted to the base assembly.

In FIG. 63, the container assembly 701*b* is shown in its connecting position to the base assembly 703*b*. It can be seen that the base housing 708*b* had a somewhat modified configuration, in that it has an upper housing plate 873 having a "race trace", configuration where there are two parallel straight edges 874 connected by two 180° curved portions 875. There is a base mounting portion 709*b* at one side of the plate 873, and a closure lid 876 having a circular configuration and hinge mounted at 878. When the container assembly 701*b* is removed from the base assembly 703*b*, this lid 876 is swung over to cover the base mounting portion 709*b* and forms a perimeter fluid tight circumferential seal. As also can be seen in FIG. 63, there is a sewer discharge line 714*b*, and also the connector 850*b* for the irrigating/disinfectant tube.

Figure 64:
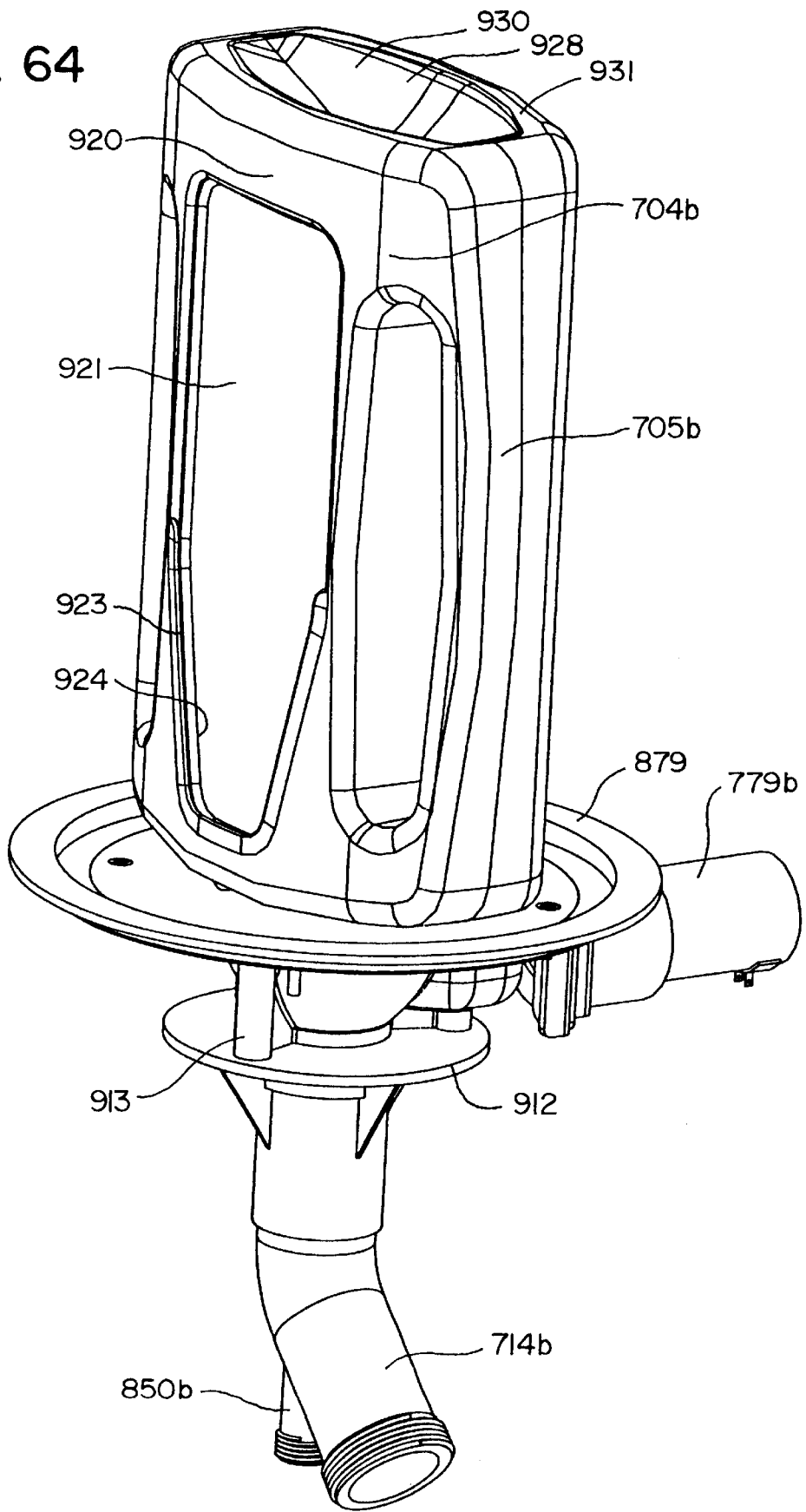
FIG. 64 is an isometric view showing the container assembly mounted to the base assembly, but showing only certain components of the base assembly.
Figure 65:
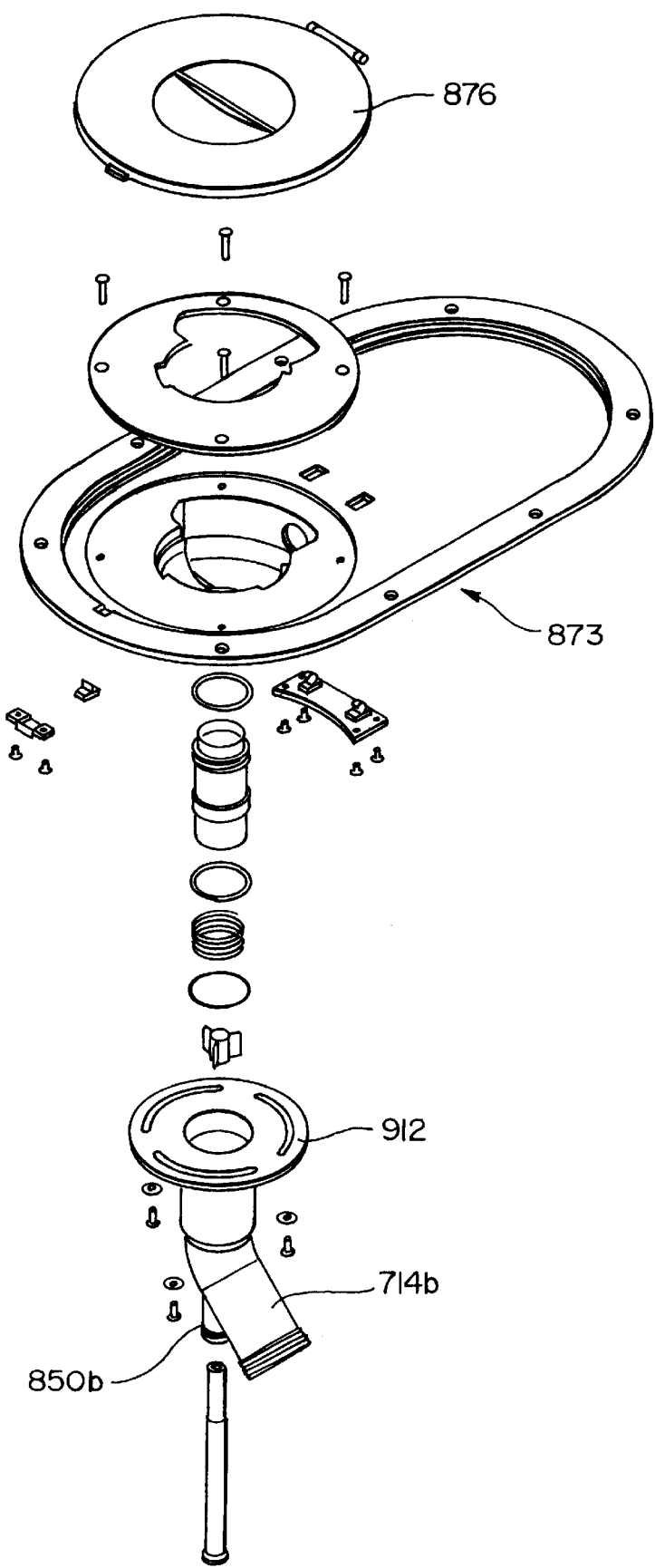
FIG. 65 is an exploded view showing various components of the base assembly.

In FIG. 64, the container 704*b* is shown in its interconnected operating position, mounted to a base plate 879 of the base housing 708*b*, but not showing the rest of the housing plate 873. Also in FIG. 65 there is shown the valve actuating motor 779*b*. FIG. 65 is an exploded view showing various components of the base assembly 703*b*.

Figure 66:
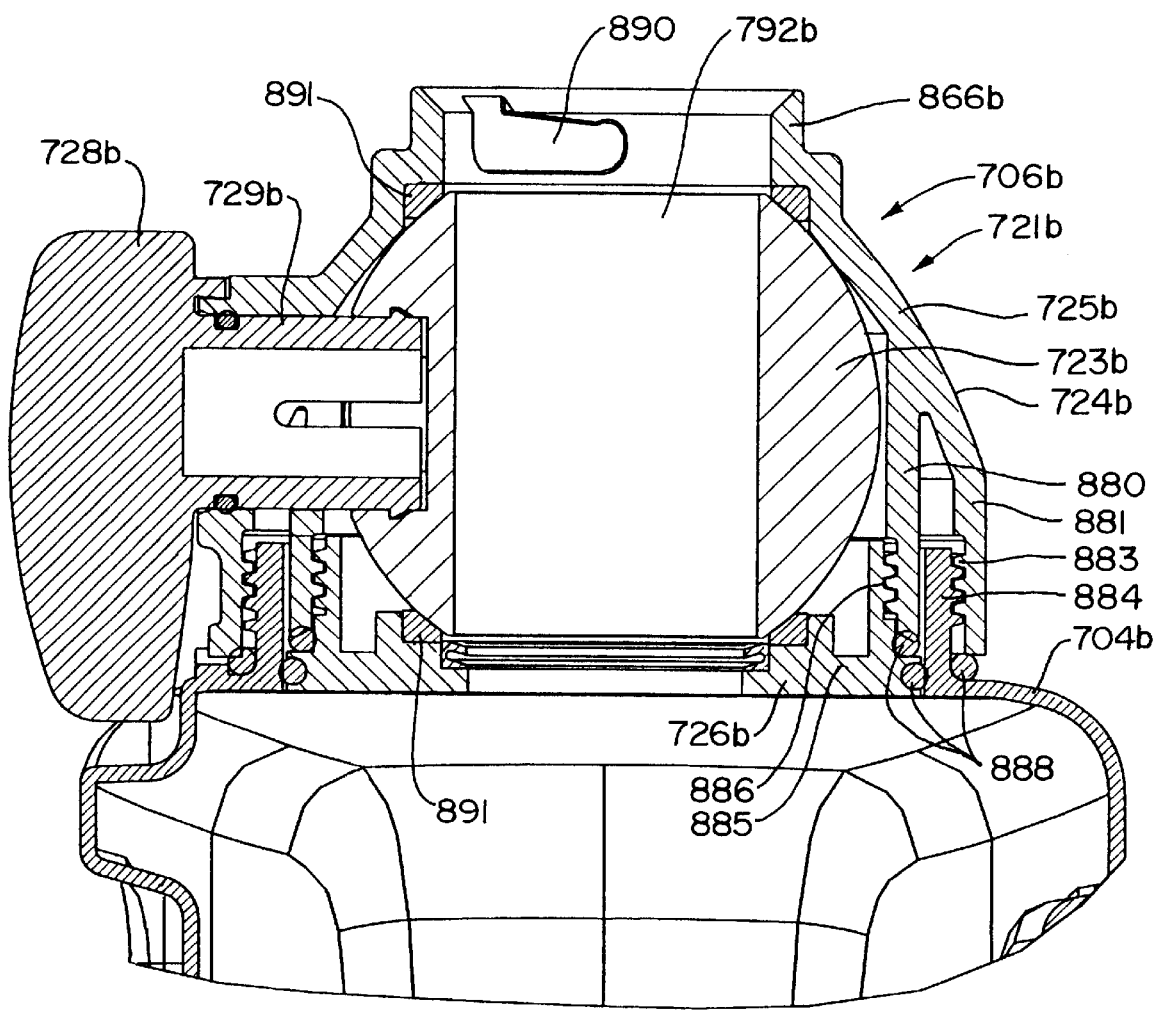
FIG. 66 is a sectional view of the top part of the container, and showing the valve in its open position.
Figure 67:
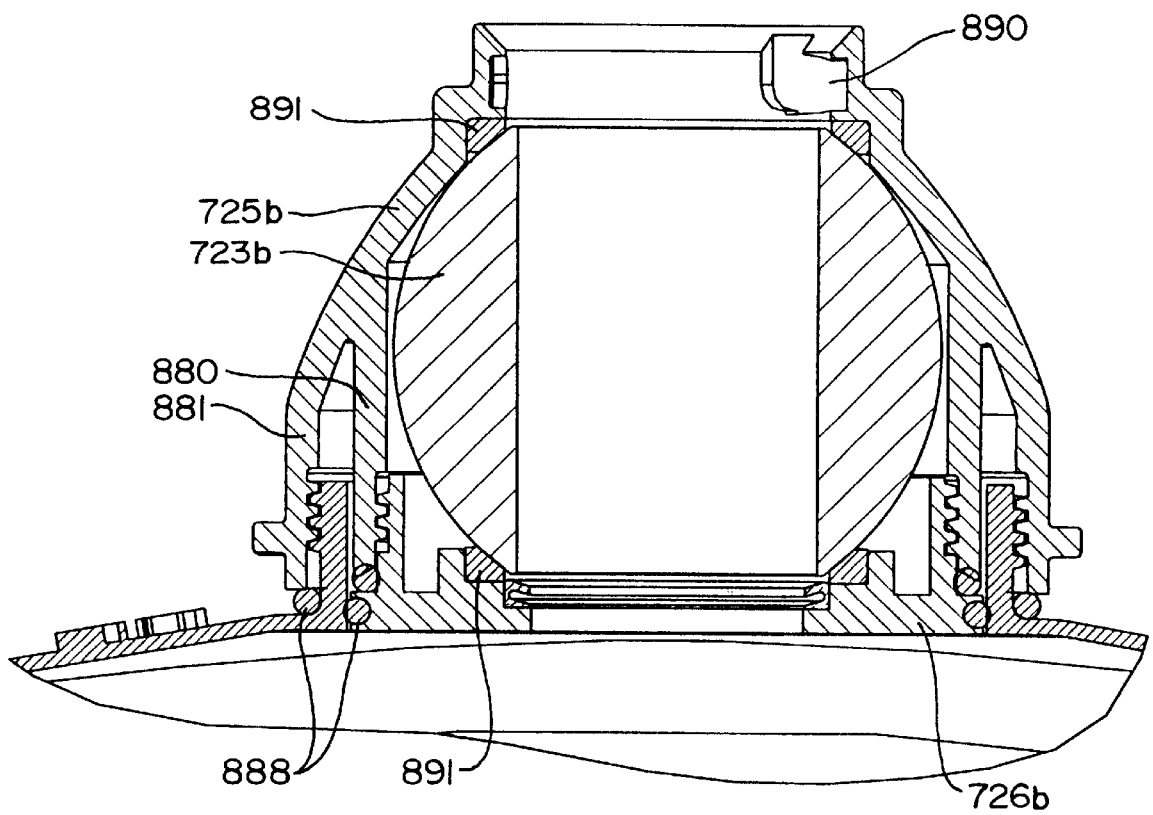
FIG. 67 is a sectional view similar to FIG. 66, but with the section plane rotated 90°.

In FIG. 66, the valve and connecting assembly 706*b* is shown, this comprising the valve 721*b* and the interconnecting portion 866*b*. The valve 721*b* is substantially the same as the valve 721*a*, in that there is the valve element 723*b*, and the valve housing 724*b*, comprising the upper housing section 725*b* and the lower housing section 726*b*. Further, there is the valve handle 728*b* connected to the actuating interconnecting member 729*b*. However, the valve housing 724*b* is modified from the housing 724*a* of the twelfth embodiment in that the lower circumferential part of the upper housing section 725*b* has its lower edge formed as two concentric cylindrical walls 880 and 881. The outer concentric wall 881 has interior threads at 883 to engage matching threads of an upstanding cylindrical mounting flange 884 formed integrally with the container 704*b*. The inner wall 880 also has interior threads 885 to engage external threads of an outer cylindrical housing portion 886 of the lower valve housing section 736*b*. Seals 888 are provided at the three locations shown in FIG. 66. Thus, the valve and connecting section 706*b* is connected to the upper end of the container 704*b* simply by threading the outer circumferential wall 881 onto the upstanding mounting flange 884.

Also, it will be noted in FIG. 66 that there is one of two bayonet type connecting slots 890 formed in the interior surface of the connecting member 866 to connect to the plug and manifold assembly 716*b*.

Upper and lower circumferential valve seals 891 are provided to engage upper and lower spherical surface portions of the valve element 723*b*. As can be seen in FIG. 66, with the valve element 723 in its open position, these two seals 891 surround the upper and lower surface portions of the valve element 723 that are immediately adjacent to the through opening 792*b* of the valve element 723*b*. In the open position of FIG. 66, these two seals 891 close the space inside the valve housing 724*b* from the biofluid. When the valve element 723 is in its closed position, and when the container 704*b* is inverted to be placed in its disposal position, biofluid within the container 704*b* comes into contact with the adjacent spherical valve surface portion. Then during the disposal operation, when the valve element 723*b* is moved to its open position, the seal 891 adjacent to the container 704*b* serves a wiping function to wipe the biofluid on the surface of the valve element 723*b* off so that this biofluid also flows through the passageway 792*b* to the disposal location.

Figure 69:
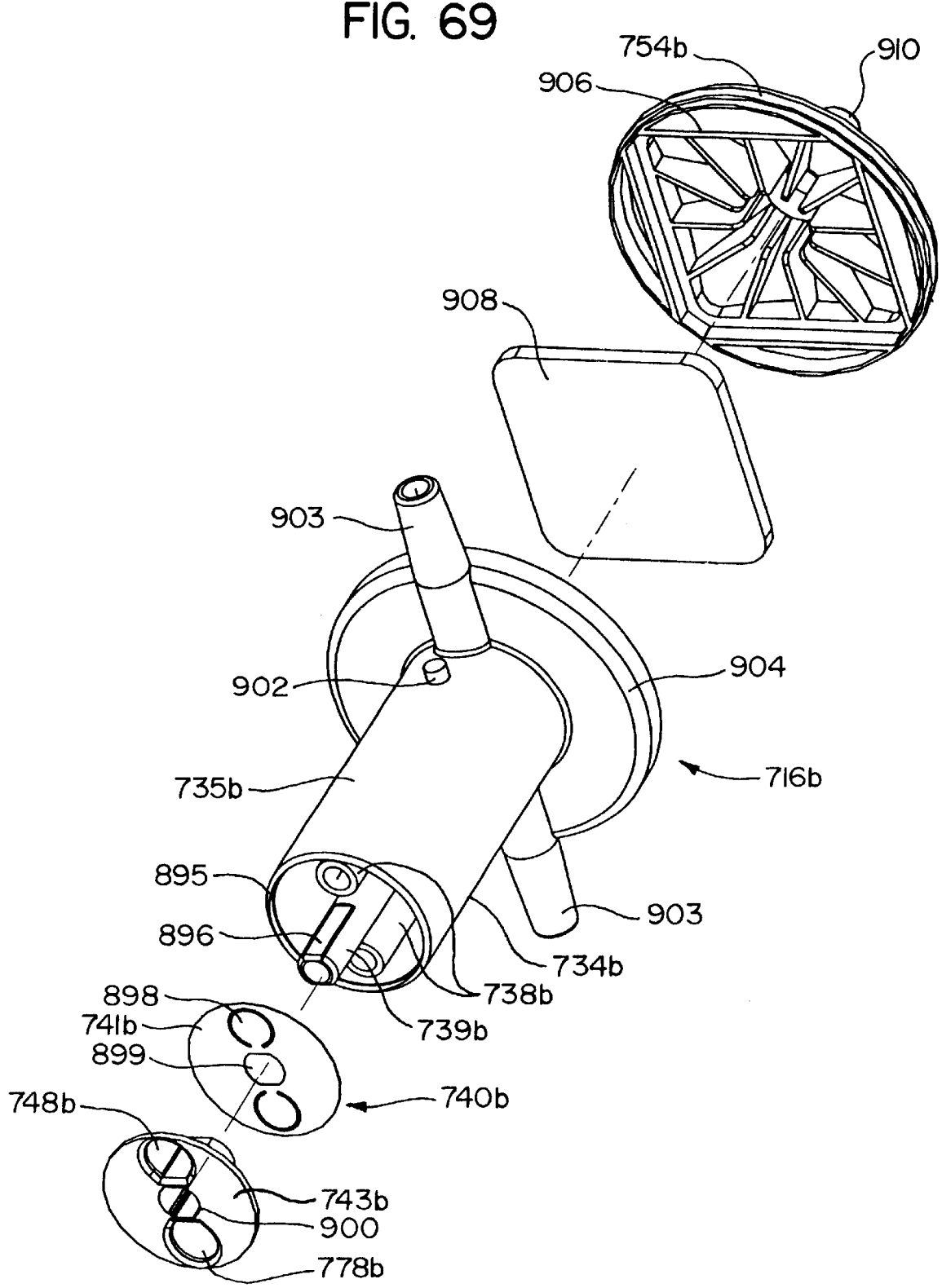
FIG. 69 is an exploded isometric view showing the closure and manifold assembly.
Figure 70:
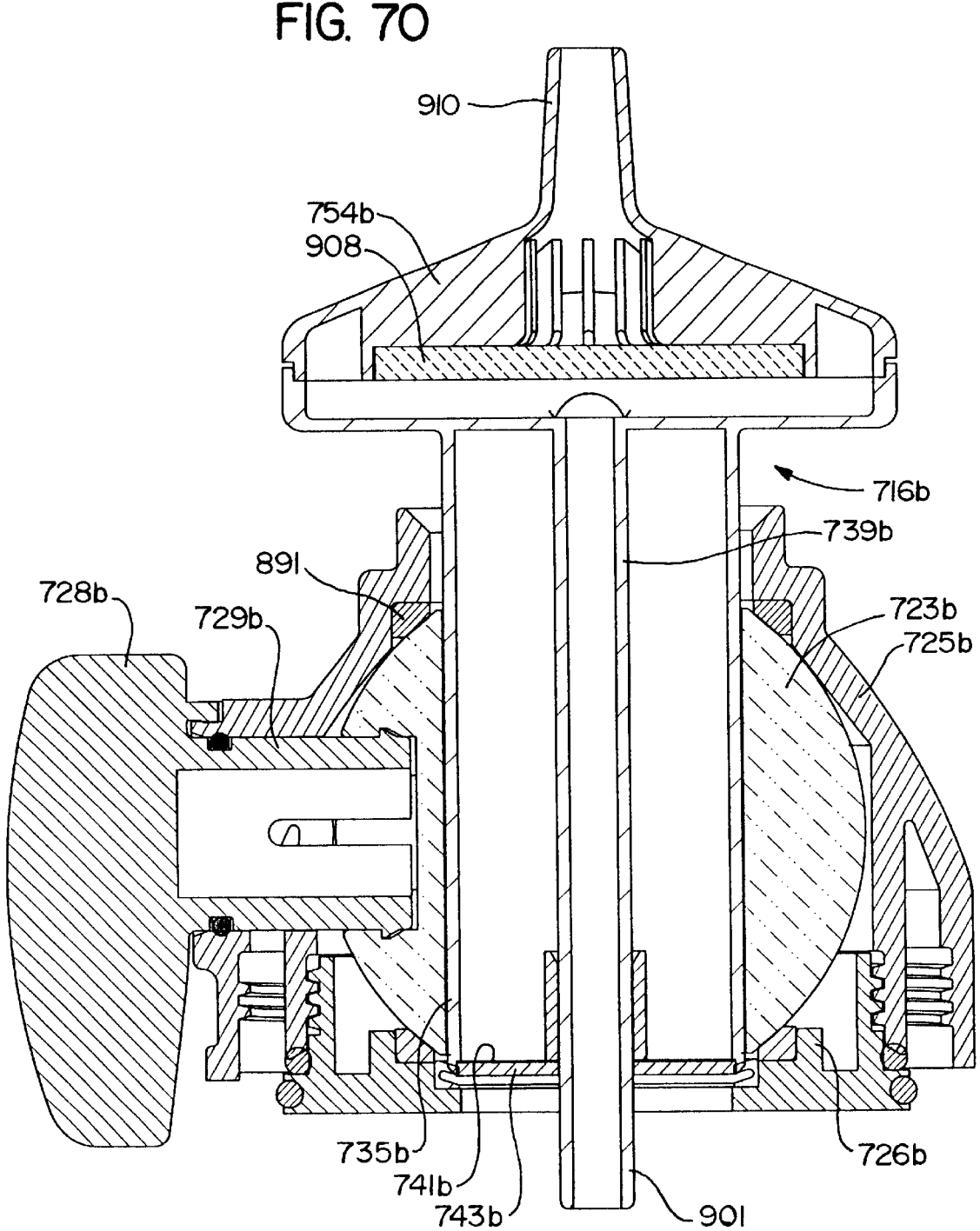
FIG. 70 is a sectional view showing the closure and manifold assembly being mounted in the valve and connecting section.

The plug and manifold assembly 719*b* is shown in an exploded view in FIG. 69, and also shown in a cross sectional view in FIG. 70, where the plug and manifold assembly 716*b* is positioned within the valve and connector assembly 706*b*. As in the eleventh embodiment, this assembly 716*b* comprises a body 734*b* having the cylindrical outside portion 735*b*, a check valve assembly 740*b*, and a cap 754*b*.

However, instead of having the check valve arrangement of the eleventh embodiment, where there is the plate member 741, flap 743 and retaining ring 744, the plate member 743*b* also serves the function of a retaining member. There the two tubular members 738*b* that receive fluid from their respective suction tubes, but the tubular portion 739*b* is constructed somewhat differently, in that it is positioned at the center of a cylindrical member 735*b*, and extends downwardly below the lower edge 895 of the cylindrical member 735*b*. Further, the lower part of the tubular member 739*b* has flattened surfaces 896 to serve a locating function.

The flap member 741*b* has two circular flaps 898 of a circular configuration, and these are positioned to be immediately adjacent the outlets of the suction tubes 738*b*. Then the flap member 741*b* is formed with a center opening 899 that is aligned with, and fits over, the lower end 896 of the center tube 739*b*, and also fits through a matching opening 90° in the plate member 734*b*. The plate member 734*b* has two openings 748*b* aligned with the flap elements 898. The flap member 741*b* is inserted onto the lower end of the center tube 739*b*, and the plate member 743*b* is then positioned over the flap member 741*b* and retained in the end of the cylindrical member 735*b*, as in the eleventh embodiment. It can be seen that the flap elements 898 are able to deflect downwardly to permit the inflow of the biofluid.

It will be noted in FIG. 70 that the lower portion of the tube 793, indicated at 901, extends downwardly below the location of the flap elements 898. Further, the two flap elements 898 are positioned so that these open toward the perimeter of the flap member 741*b*, thus tending to deflect the biofluids passing through the plug and manifold member 716*b* away from the intake to the lower tube portion 901. At the upper end of the cylindrical portion 735*b*, there is a pair of diametrically opposed connecting protrusions 902. These fit in the matching slots 890 (see FIGS. 66 and 67).

The body 734*b* has at its top end two laterally extending and diametrically opposed intake fittings 903 adapted to be attached to the patient suction tubes, and also connecting to the tubular member 738*b*. Also at the top of the body member 734*b* there is a circular mounting plate 904 having a diameter greater than the cylindrical body portion 735*b*. Positioned within the interior of the cap 754*b*, there is a square retaining frame 906 in which fits a square filter 908, to protect the vacuum line from contamination and filter out particulate matter. There are a number of radially extending ribs 909 positioned within the cap 754*b* for reinforcing and also to permit the gases to pass through the filter, and thence into a top tube 910 that extends upwardly from the cap 754*b*.

The basic operation of the plug and manifold assembly 716*b* is quite similar to that of the assembly 716 of the first embodiment. In the fluid collecting mode of operation of system 700*b*, the body portion 734*b* is positioned to extend downwardly through the ball valve element 723*b*, and the suction tubes and vacuum tubes are connected to the assembly 716*b*, in this instance, by the fittings 903 and 910. The suctioning proceeds as indicated previously in this text, with the biofluids entering through the fittings 903 and exiting down through the tube 738*b* and through the flap elements 898.

The filter 908 is made of a material which expands, when it comes in contact with the biofluid. Thus, as the biofluid raises in the chamber of the container 704*b* and reaches the level of the lower end 901 of the central tube 739*b*, the biofluid rises in the tube 739*b* to come in contact with the filter 908. The filter expands, thus blocking the vacuum passageway in the tube 739*b*, thus causing the biofluid to stop flowing into the container 704*b*. This signals the operator that the container 704*b* is sufficiently full, so that it can be disconnected.

Figure 71:
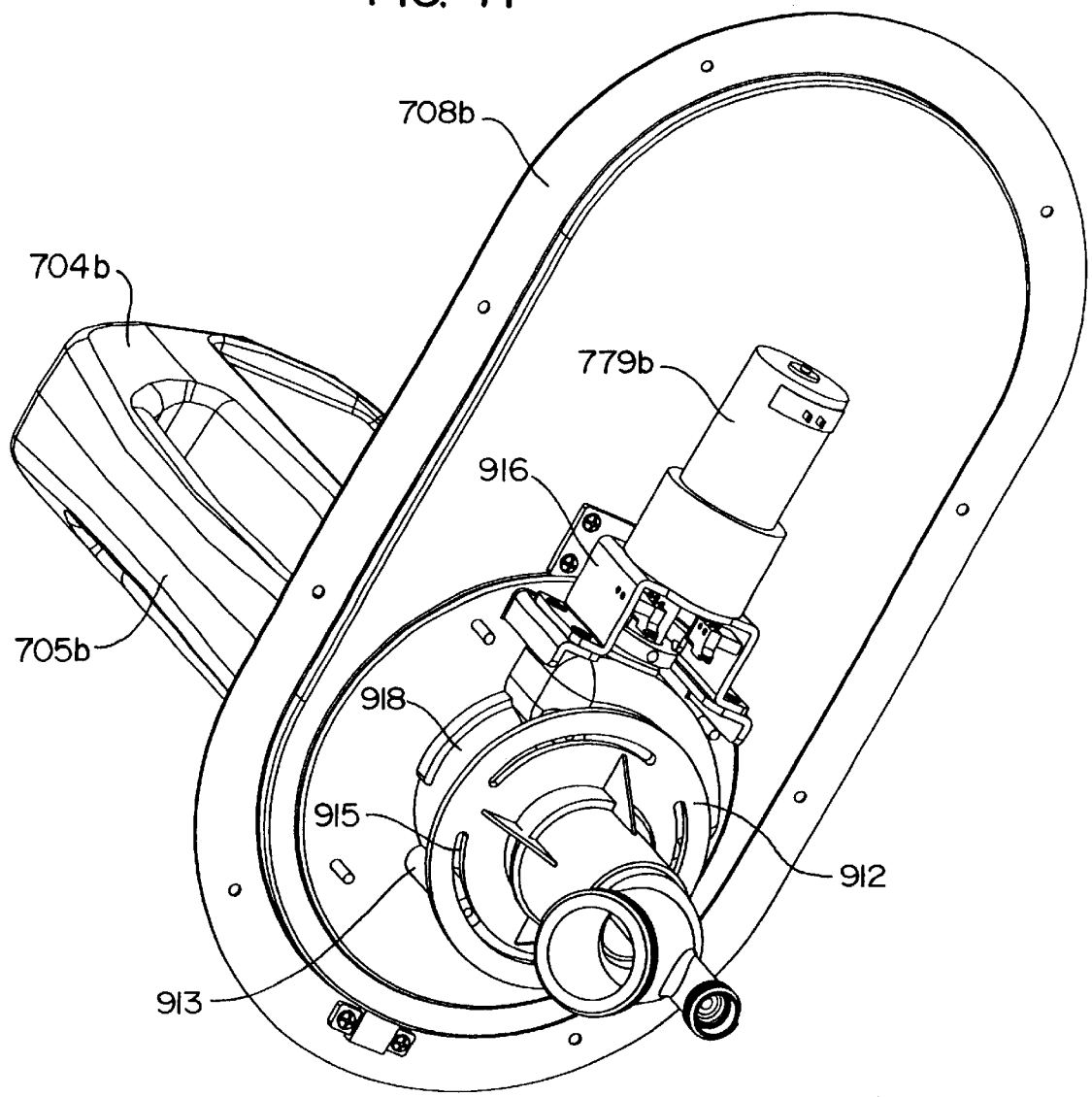
FIG. 71 is an isometric view showing the container assembly mounted to the base assembly, and showing base assembly components from a lower location.
Figure 72:
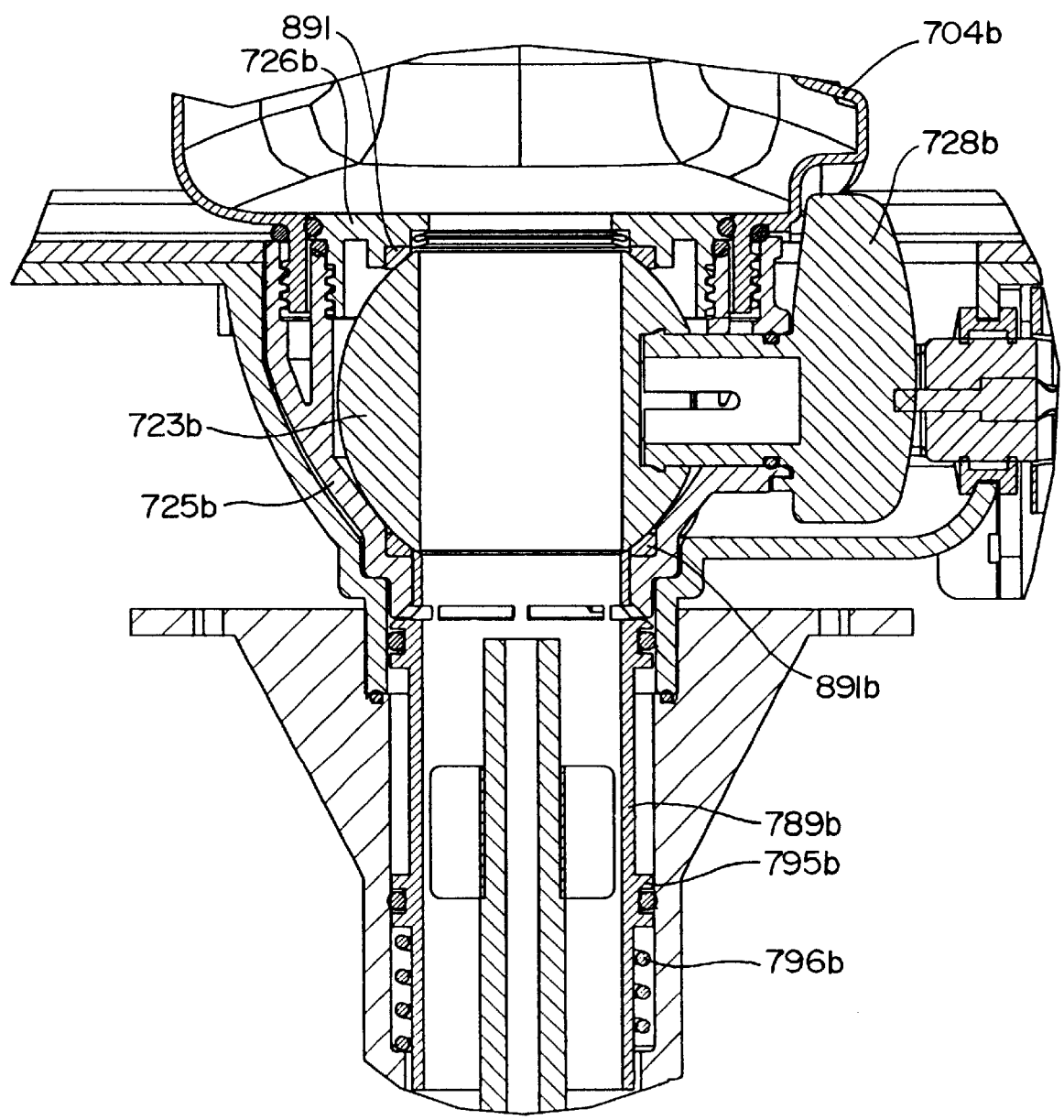
FIG. 72 is a sectional view of the valve and connecting assembly mounted to the base assembly, and also showing an upper portion of the disposal section.
Figure 73:
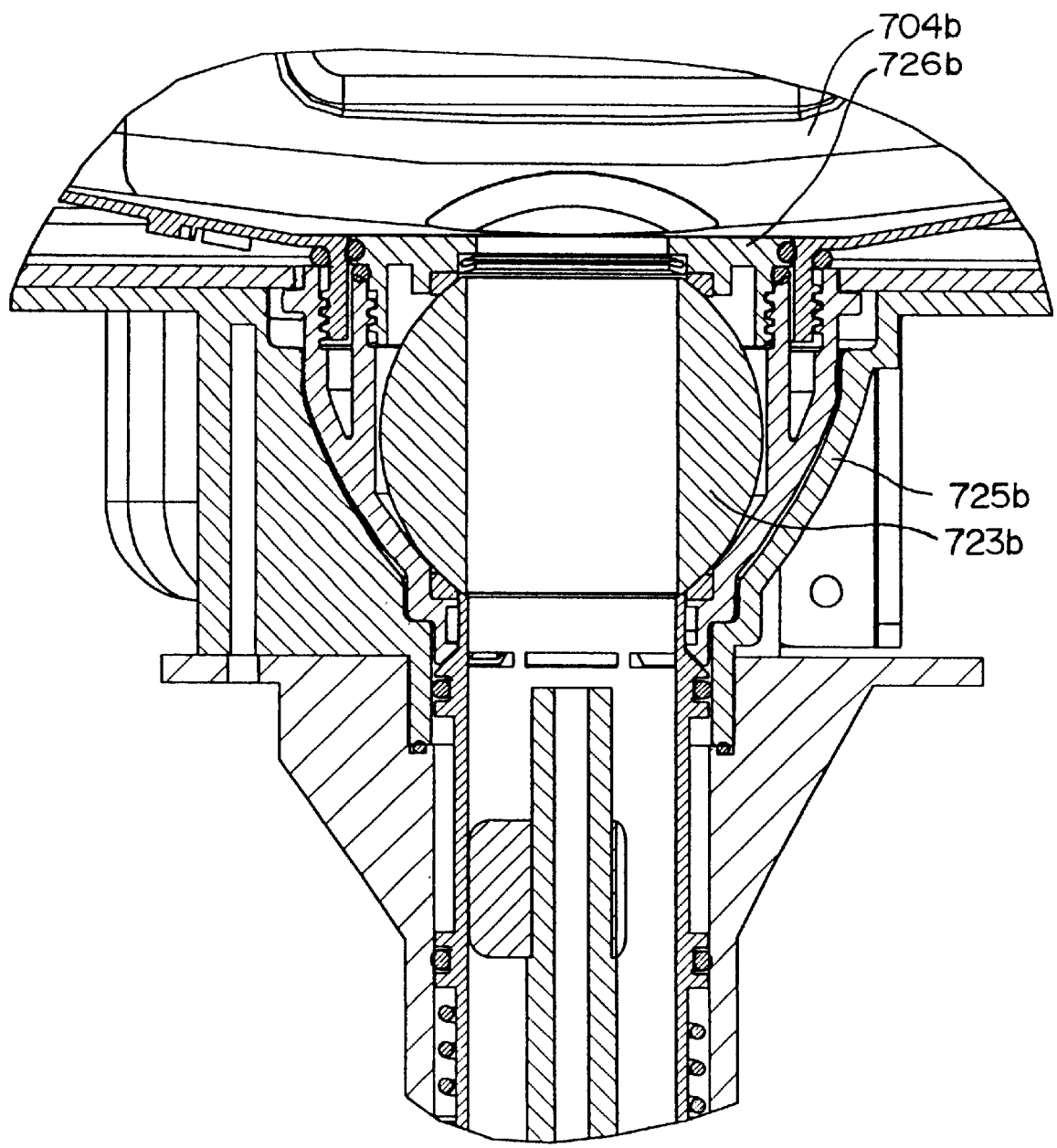
FIG. 73 is a sectional view similar to FIG. 72, but with the section plane being rotated 90°.
Figure 74:
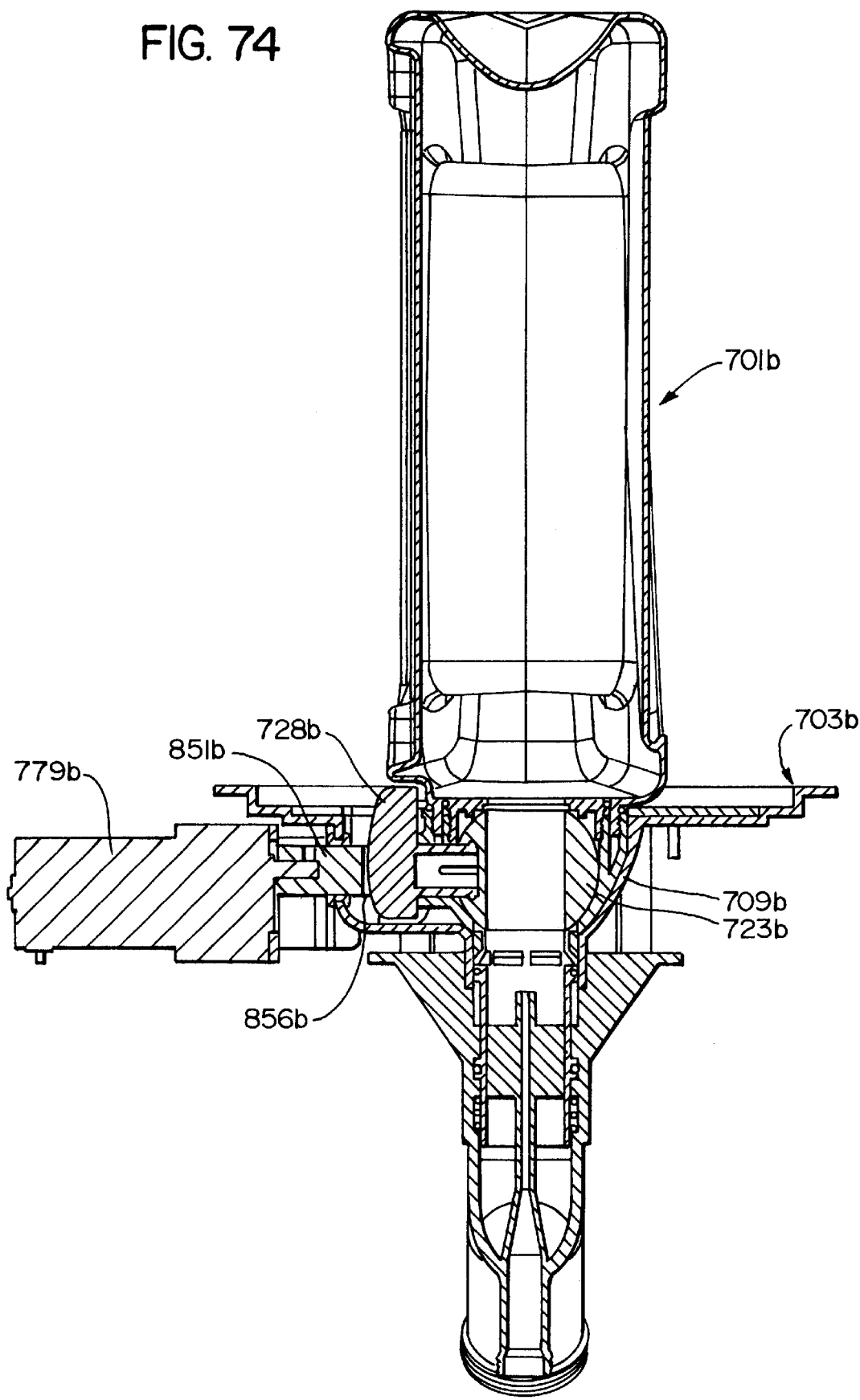
FIG. 74 is a sectional view showing the container assembly mounted to the base assembly, with the valve open.
Figure 75:
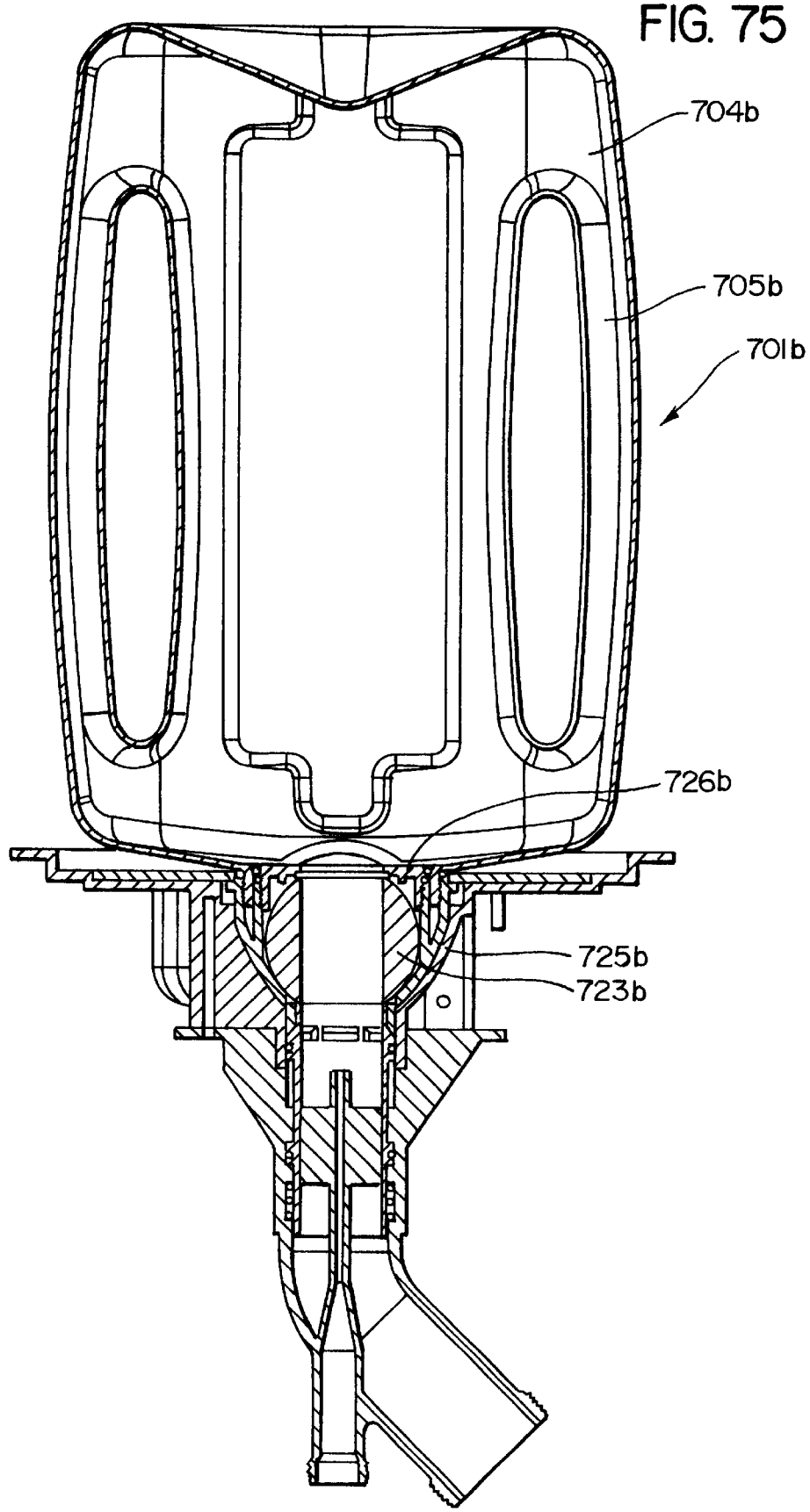
FIG. 75 is a view similar to FIG. 74? but with the section plane rotated 90°

With regard to the overall construction of the base housing 708*b*, as indicated above, there is a main housing plate 873, and this can be placed over a matching opening in a suitable planar support member, such as a counter top, and connected thereto by screws or the like, the openings 911 in the plate being provided for that purpose. As can be seen in FIG. 71, there is a lower support plate 912 which bears against support posts 913 extending downwardly from the aforementioned mounting plate section 879. Connecting bolts can be inserted through the support posts 913 and connect to the support plate 912 by extending through the arcuate slots 915 provided in the support plate 912 (see FIG. 71). The motor 779*b* is mounted by a suitable bracket 916 to a side housing portion 918 that is connected to the aforementioned mounting plate 879.

Figure 54:
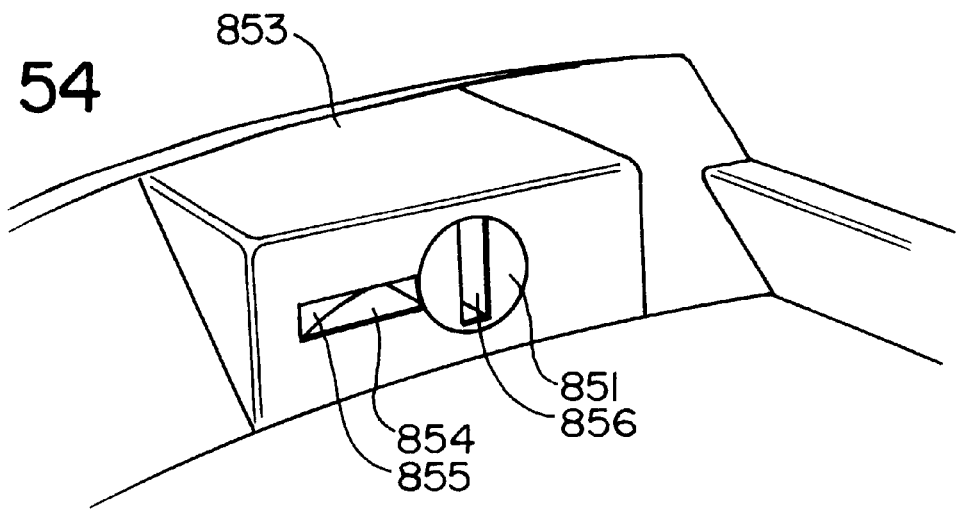
Figure 55:
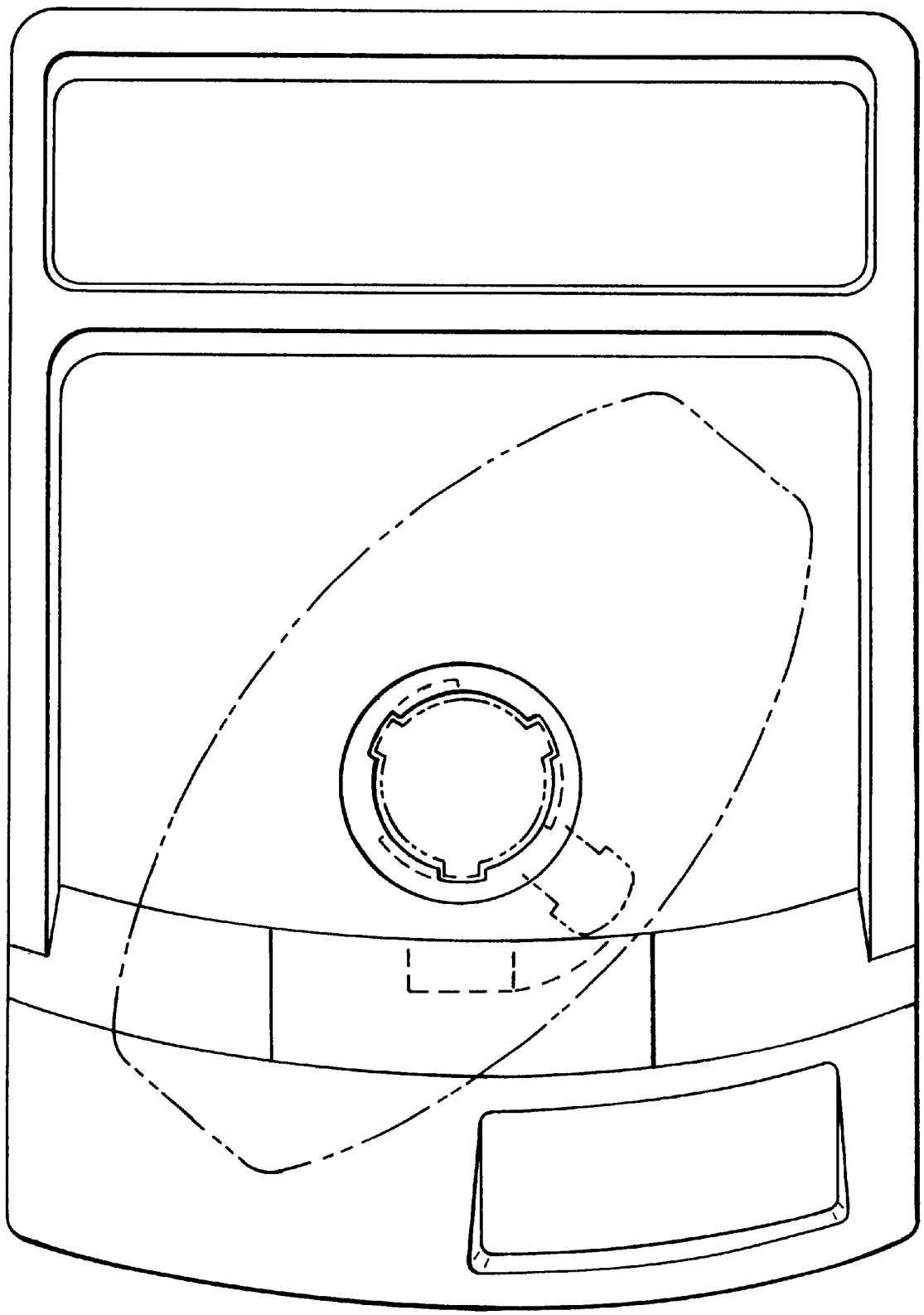
FIGS. 55 and 56 are top plan views of the base assembly showing the manner in which the container assembly is moved to its interconnecting position in the base assembly.
Figure 56:
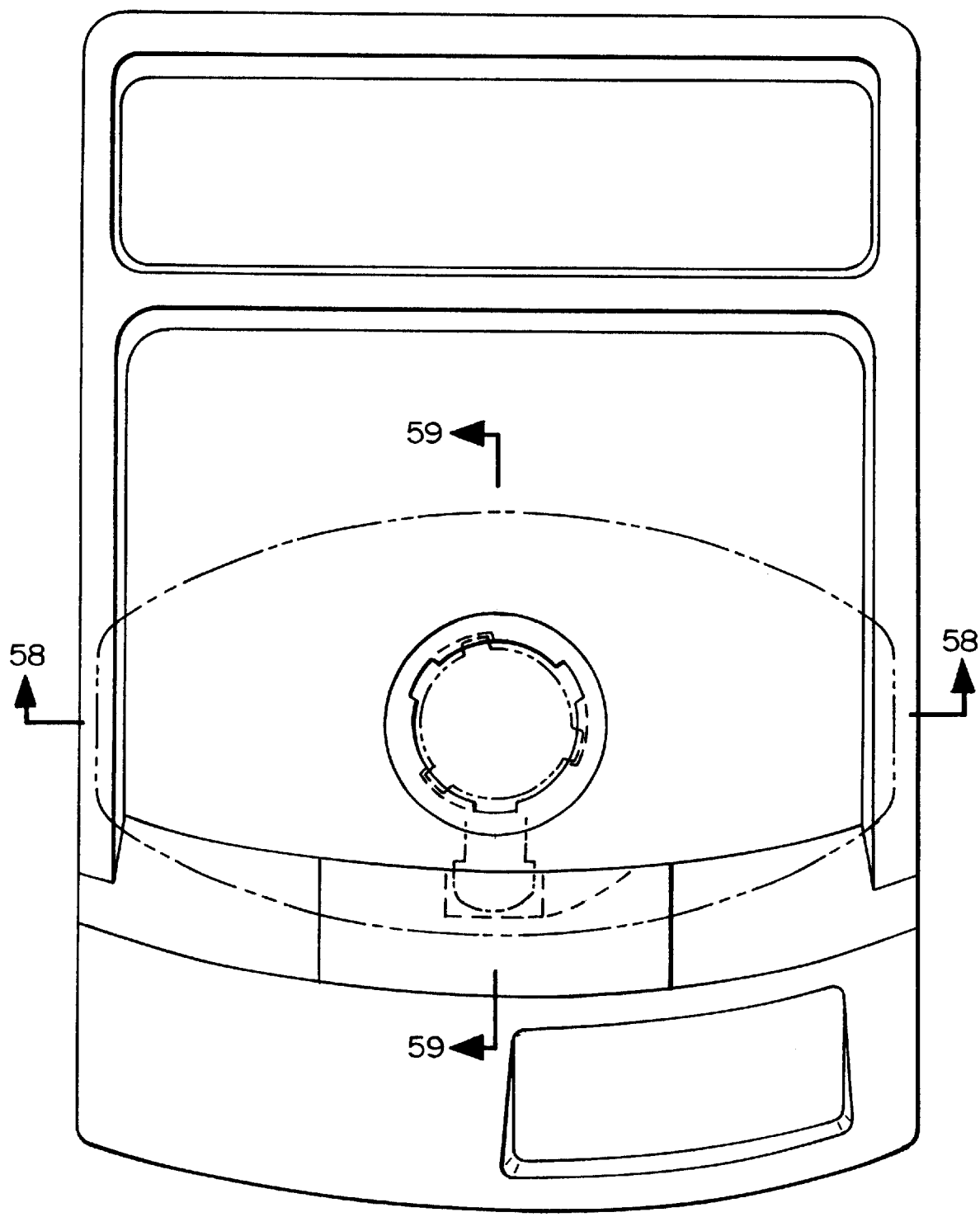
Figure 57:
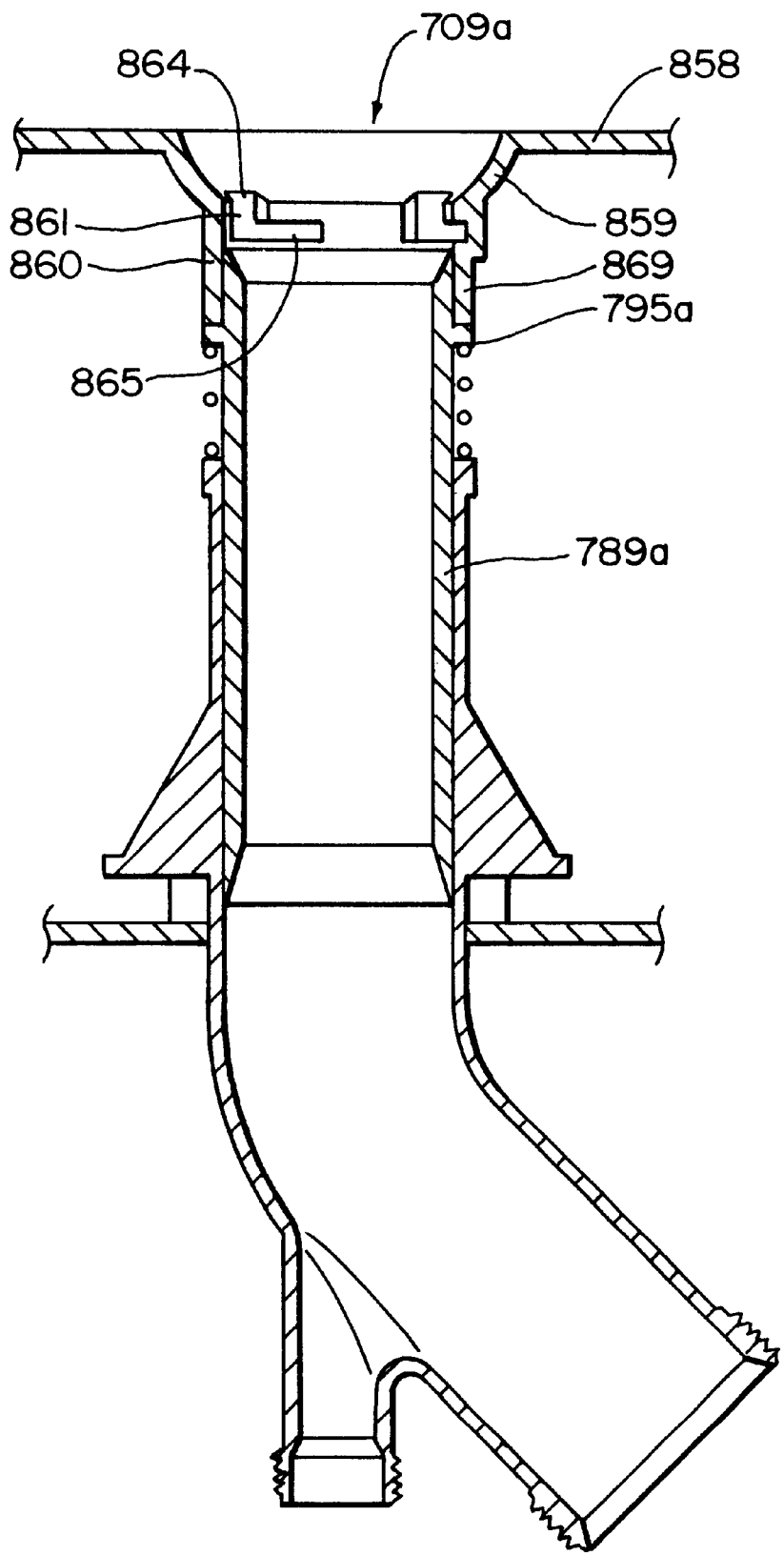
FIG. 57 is a vertical longitudinal sectional view of a portion of the disposing section of the base assembly.
Figure 76:
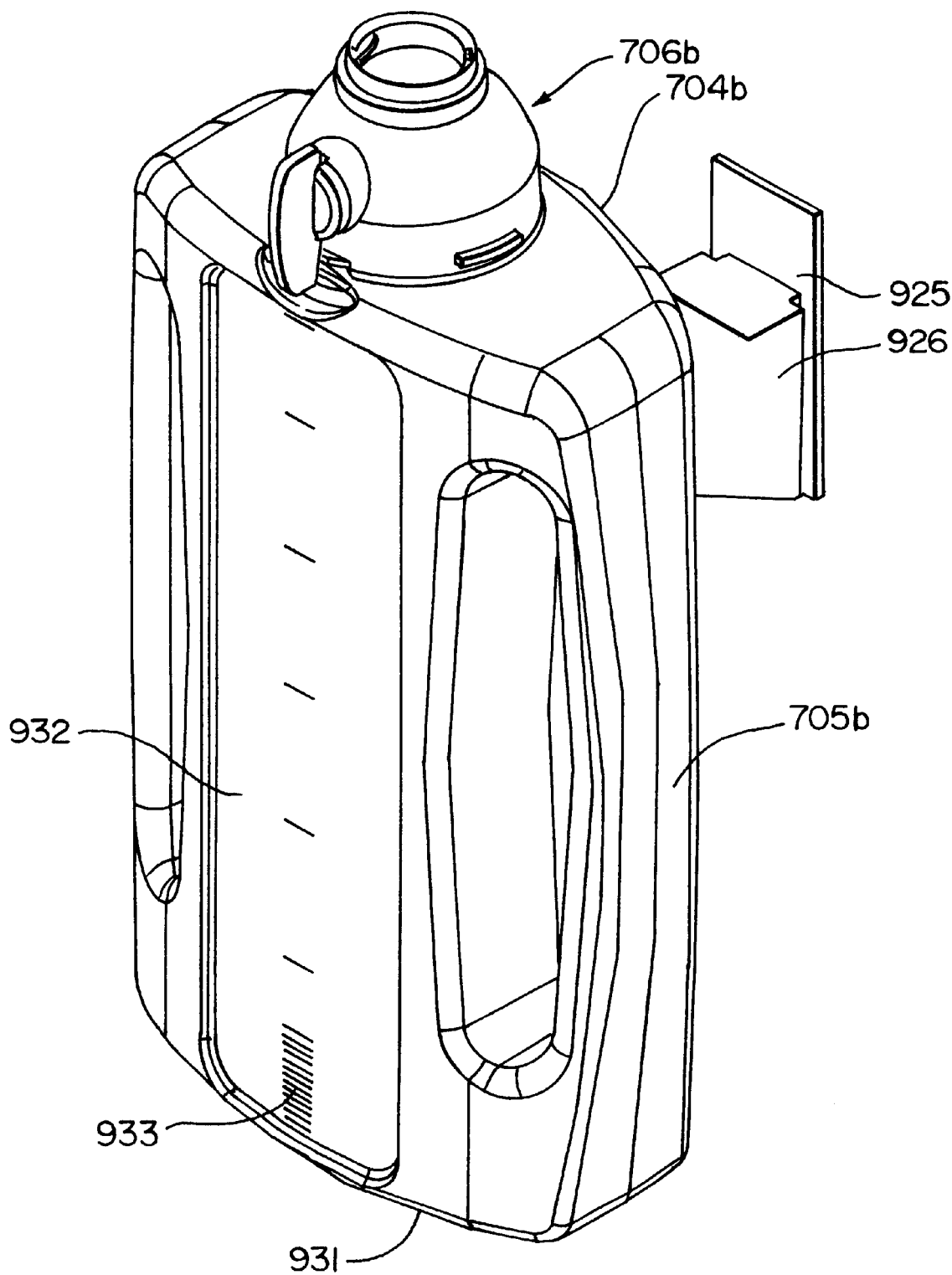
FIG. 76 is an isometric view of the container assembly mounted to a wall bracket.

The mounting portion 709*b* of the base assembly 703*b* has an arrangement similar to that shown in FIGS. 53 and 54 of the twelfth embodiment, in that the drive member 851*b* (see FIG. 74) has the slot 856*b* to receive the valve handle 728*b*. Thus, when the valve and connecting assembly 706*b* is connected to the base assembly 703*b*, and after the motor 779*b* has rotated the valve handle 728*b* to the vertical position of FIG. 74B so as to move the valve element 723*b* to its open position, the container assembly 701*b* remains locked in place. It is only after the motor 779*b* has been operated to rotate the actuating member 851*b* and the handle 728*b* 90° so that the handle 728*b* is back to a horizontal position, that the container assembly 701*b* can be rotated to its release position. Insert at end As indicated previously in this text, the container 704*b* has several additional features in this thirteenth embodiment. First, with reference to FIG. 64, it can be seen that the container 704*b* has one sidewall 920 formed with a shallow planar recess 921 extending over a substantial area of the wall 920. At the upper end of this recess 921, there is a perimeter flange or lip 923 which extends inwardly over the adjacent edge portion of the recess 921 to form a U shaped slot 924. This recess 921 with the slot 924 provides a means by which the container 704*b* can be mounted to a wall fitting, as shown in FIG. 76, where there is a wall mounted bracket 925 having an outwardly projecting portion 926. At the end of the mounting protruding portion 926, there is a matching plate member (not visible in FIG. 76) which is configured to fit within the recess portion defined by the U shaped slot 924.

Figure 68:
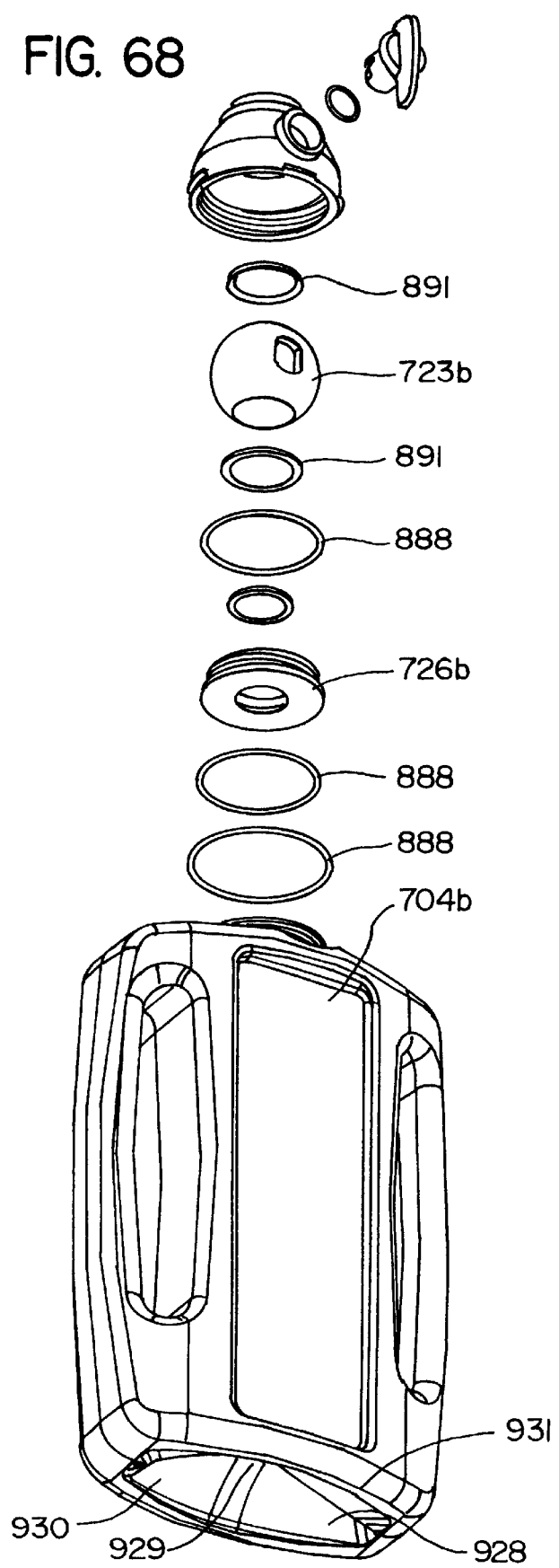
FIG. 68 is an isometric exploded view showing the container and the valve and connecting assembly.

To describe another feature of the container 704*b*, reference is made first to FIG. 68. It can be seen that the bottom wall 928 of the container 704*b* has what might be termed a raised pyramid configuration, in that there is a raised center or apex point 929, and the bottom wall 928 slopes outwardly and downwardly as at 930 to join to the lower perimeter portion 931 of the container 704.

Reference is now made to FIG. 76 which shows the sidewall 932 which is opposite the sidewall 921 having a plurality of fluid level markings 933. It can be seen that at the lower part of the container 704, these markings 933 are spaced closely together, and spaced further apart at the upper end. The reason for this is that it is sometimes desirable that the initial quantities of biofluids flowing from the patient should be measured in very small quantities. With the pyramid shaped bottom wall portion 928, the area of the volume of the container 704*b* taken in a horizontal section closely adjacent to the lower perimeter wall portion 931 of the container 704 is very small. Thus, with a very small amount of biofluid flowing into the container, the fluid level in the container would rise to a measurable level. As the flow increases, the net cross sectional area of the volume inside the container increases. Thus, there is a greater flow level required to raise the level of fluid by equal increments. When substantial amounts of biofluid are flowing, it becomes less critical to measure the exact volume, and thus the fluid level indicating lines 933 are spaced further apart.

The pyramid shaped bottom wall 928 has another advantage in cooperating with the irrigating system of this thirteenth embodiment. In FIGS. 72 through 75, there is shown the irrigating tube 934, which functions in this thirteenth embodiment in substantially the same way as in the prior embodiments, and has its own irrigating system with a control valve, a disinfectant system, such as one of those described previously herein, and the other tubes, connectors, and components associated with the irrigating system.

When the irrigating tube 934 directs its fluid upwardly into the container, the irrigating fluid (water, or water plus disinfectant and/or cleaning solution) strikes against the raised apex portion 929 of the bottom wall 928. This causes the irrigating fluid to disburse laterally over the bottom wall 928, to flow along the sidewalls of the container back toward the container exit opening, and also to flow upwardly through the hollow areas formed in the container handle 705*b*, thus cleaning the entire inside surface of the container 704*b* exposed to the biofluid.

It should also be noted that the hand grips 705*b*, being vertically aligned and spaced at equal distances from the vertical center axis of the container 704*b*, these handles 705*b* are ideally suited for the operator to conveniently grasp the container, move it to its upside down position, and then push the container downwardly and in a twisting motion to interconnect the container 704*b* with the base assemblies 703*b*.

Figure 77:
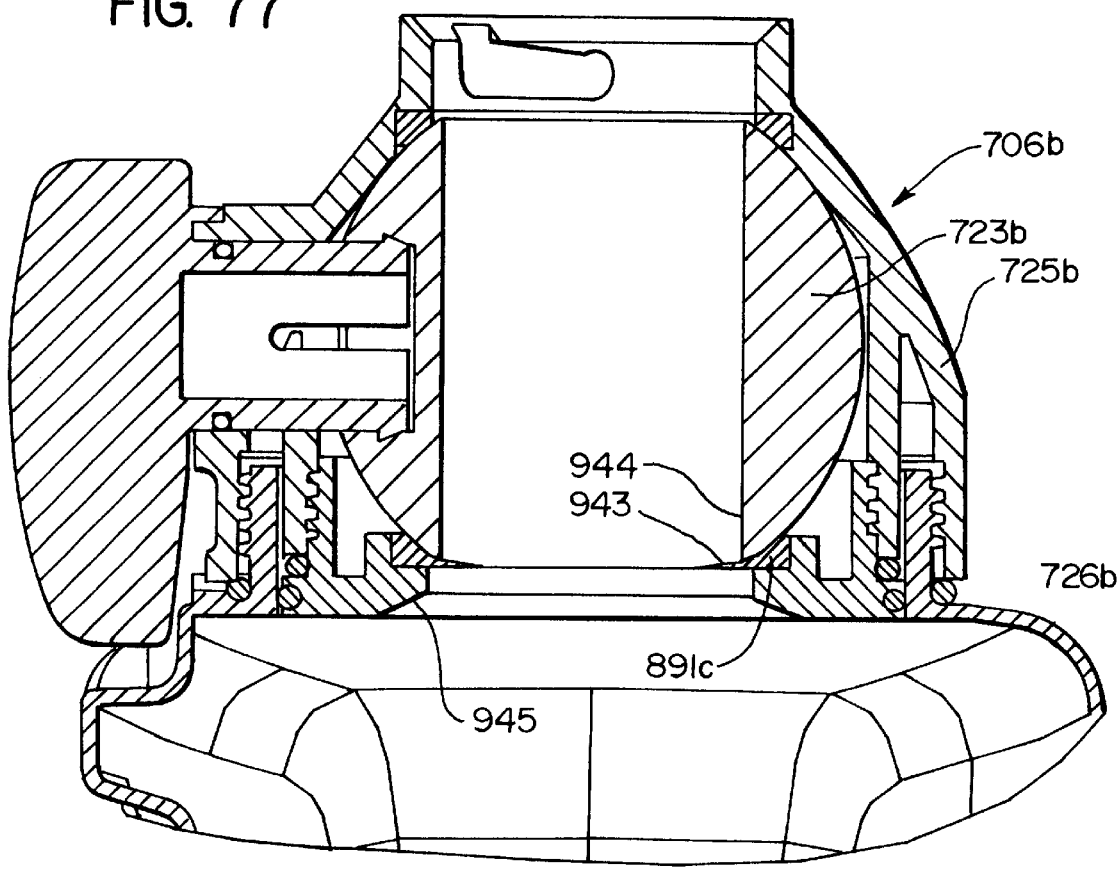
FIG. 77 is a sectional view of a modified form of the valve and connecting assembly.
Figure 77A:
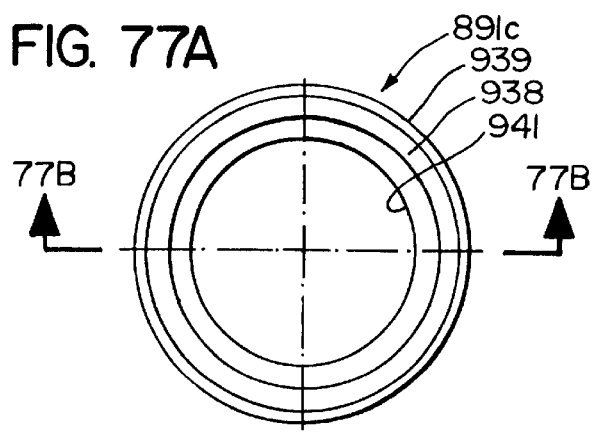
FIGS. 77A, 77B and 77C are additional views of the seal.
Figure 77B:
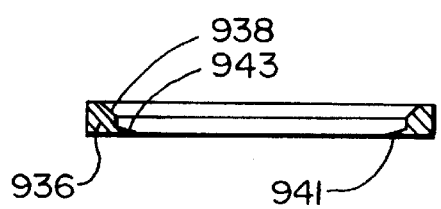

Reference is now made to FIGS. 77, and 77A, B and C to illustrate a modified lower seal arrangement for the valve and connecting section 706*b*. This particular improvement relates to the lower seal which in this improvement will be labeled 891*c*. In FIG. 77A, the seal 891 seal is shown in plan view, and FIGS. 77B and 77C are cross sectional views.

Figure 77C:
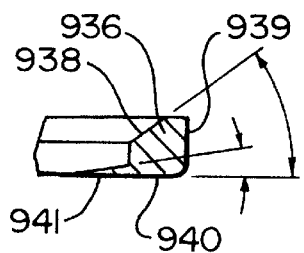

As shown in FIG. 77C, the seal 891 comprises a main perimeter portion 936 which has an upwardly and inwardly facing slanted seal surface 938 that engages the exterior surface of the valve element 723*b*. The seal also has a circumferential outside surface 939 and a bottom surface 940 which fit against adjacent portions of the lower housing section 726*b*.

In addition, the seal 891*c* comprises a radially inwardly extending lip 941, the lower part of which is co-planar with the bottom seal surface 940. This lip 941 is made relatively thin, and as can be seen in FIG. 77 the inner edge portion 943 of the lip 941 extends beyond the adjacent surface 944 that defines the through passageway of the valve element 723*b*.

Thus, when the plug and manifold assembly 716*b* is inserted into the through passageway of the ball element 723*b* the lower edge portion 895 comes into engagement with the inwardly extending seal portion 943. The effect of this is that a single seal 891*c* seals not only against the adjacent surface of the valve element 723*b*, but also engages the lower edge portion 895*c* of the body section 735*b* of the plug and manifold device 734*b*.

Another modification made in the valve and connecting assembly 706*b* is that the perimeter portion of the lower housing section 726*b* that extends around the through opening of the valve element 723*b* has its lower inner edge cut away to form a frusto-conical surface at 945 that slants away from the valve opening. Thus, when the plug and manifold assembly 716*b* is inserted within the valve element 723*b*, the lower ends of the inlet tubes 738*b* that discharge the biofluid through the flap valve elements 898 are positioned so that the biofluid is deflected laterally and radially outwardly away from the inlet end of the vacuum intake tube 739*b*. Thus, the valve housing surface 945 does not interfere with this flow of the biofluid in a radially outward direction.

Figure 78:
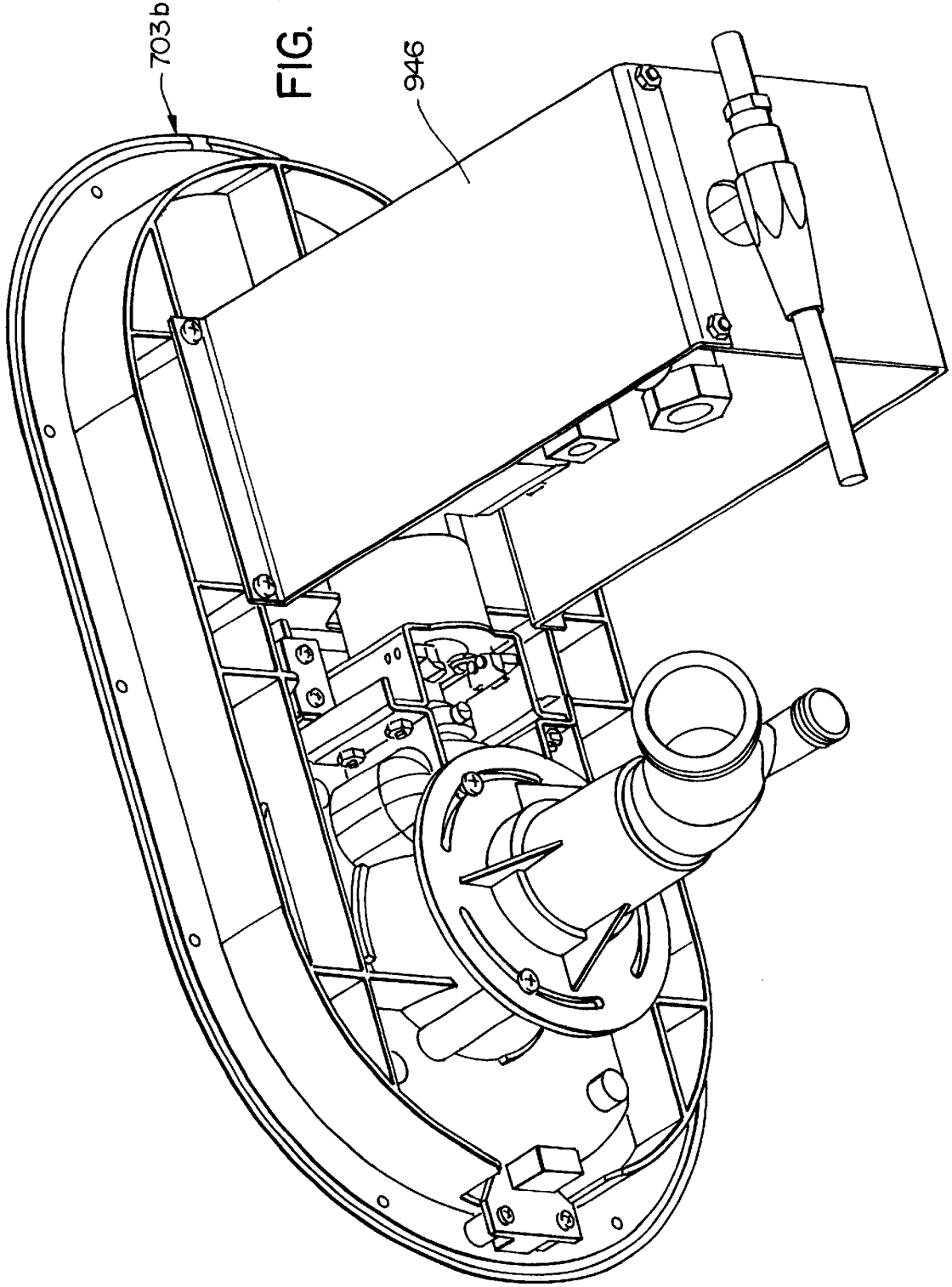
FIG. 78 is an isometric view of the lower portion of the base assembly.

FIG. 78 shows a bottom plan view of the base assembly 703*b*, is given to show the location of additional operating components which are located in a downwardly extending U shape bracket 946. Located within this bracket 946 are such things as the valve for the irrigating/disinfectant system, associated servo controls and components, and other items.

Figure 79:
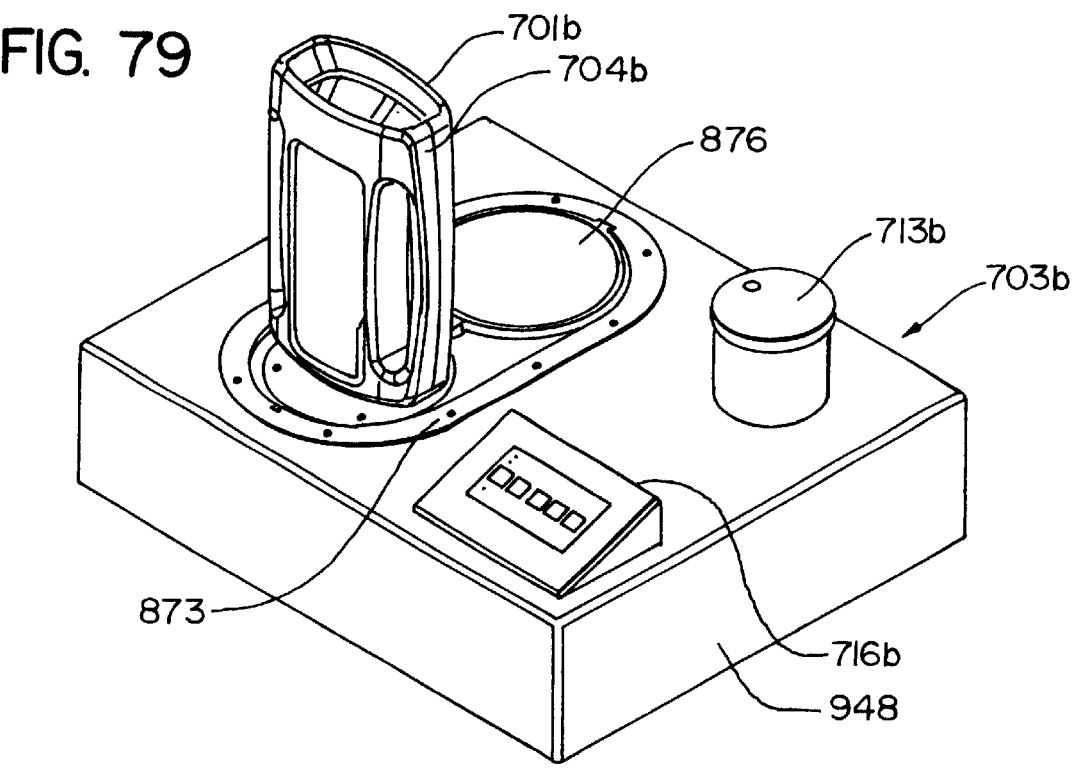
FIG. 79 is an isometric view of the entire system.
Figure 80:
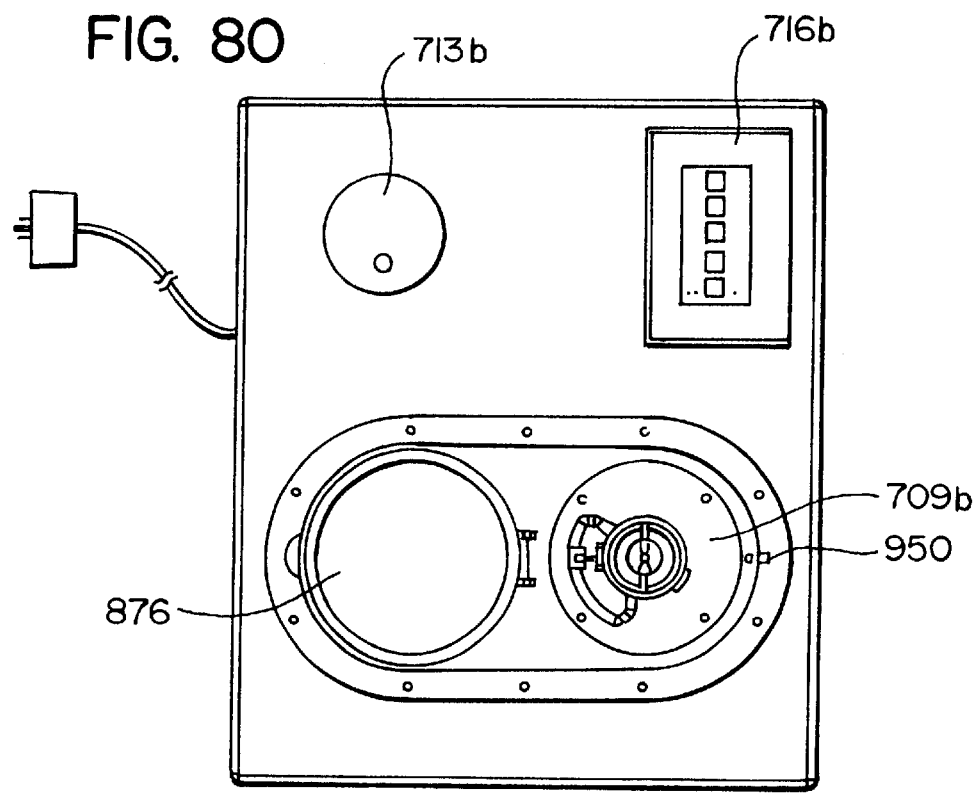
FIG. 80 is a top plan view of the base assembly.

FIG. 79 shows the thirteenth embodiment more completely, where the base assembly 704 further comprises a rectangular container 948, with the control panel 716*b* and the disinfectant container 713*b*. FIG. 80 is a top plan view of the base assembly portion 703*b* as shown in FIG. 79.

Another feature of the present invention is that when the lid 876 is swung over to close the base mounting section 709*b*, there is an interlock mechanism 950 which engages the lid 876 to hold it in place. This interlock mechanism 950 also comprises a switch enabling element that is operably connected to the valve for the irrigating system. Thus, after the biofluid disposal operation has been completed, and after the container assembly has been removed from the base assembly, and the lid 876 closed and locked in place, the enabling mechanism permits the irrigating valve to be opened to wash the interior surfaces of the base assembly that are exposed to the biofluid. The lid 876 is provided with a fluid tight circumferential seal to prevent the escape of any irrigating fluid.

Figure 81:
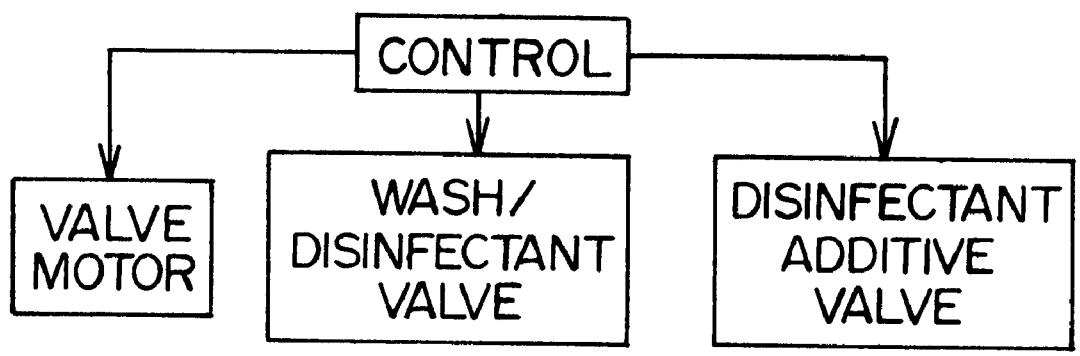
FIG. 81 is a schematic view of the control circuitry.

FIG. 81 shows a control circuit useable in this thirteenth embodiment, and also in a number of the earlier embodiments. There is a central control which in turn operates the valve motor, the wash disinfectant valve, and the disinfectant additive valve (if that is present in the system). In addition, the control mechanism is made responsive to the inputs from the control panel, and also the contact made with our other switch signaling devices in the assembly. For example, a contact switch to ascertain if the container assembly is in its interengaged position with the base assembly would input into the control mechanism. Also, the aforementioned enabling switch with the interlock mechanism 950 would provide input to the control mechanism.

It is believed that the overall operation of this thirteenth embodiment is readily apparent from the descriptions of the earlier embodiments. However, a few items will be summarized briefly at this point.

The container assembly 704*b* is positioned in its collecting location adjacent to the patient, and the plug and manifold assembly 716*b* is positioned in the valve and connecting section 706*b*. As there is an inflow in the suction tubes, through the plug and manifold assembly 716*b* and into the container 704*b*, as indicated previously, the arrangement of the plug and manifold assembly permits the biofluid to be directed from the exit ends of the inlet tube 738*b* radially outwardly to alleviate the problem of possible ingestion of particles of biofluid entering the suction tube and thus be drawn out of the container. Also, as indicated earlier, with the position of the lower end of the vacuum tube, in combination with the filter 908 that expands with contact with the biofluid, the level of the biofluid in the container 704*b* can be determined when it is at a sufficiently high level so that the container 704*b* should be changed.

Also, as indicated above with reference to FIG. 76, the pyramid shape of the bottom wall 728 of the container 704*b* enhances the washing operation, and also permits liquid level markings 933 to measure even very small quantities of biofluid that enter into the container 704*b*.

It should also be pointed out that if large amounts of biofluid are to be extracted from the patient (this could happen, for example, when orthoscopic surgery is being performed and a washing fluid is directed through the patient and to the container), the container 704*b* could be,changed, and the plug and manifold assembly 716*b* could remain connected to the suction tubes and the vacuum line, which in turn would be connected to the patient and the vacuum source, so that another container 704b could be put into place without disturbing the tubes already in the patient.

An alternative procedure would be that quite possibly the plug and manifold container could be connected directly to a disposal line which would in turn go to the disposal location, thus by-passing the need of the container 704b.

After the plug and manifold assembly 716b is removed from the container 704b, small caps are desirably placed upon the ends of the tubes 738b and the tube 739b to prevent possible leakage of biofluid.

The container 704b is then mounted to the base assembly 703b in the manner described above and placed securely in the interlocking position. The disposal operation can be performed completely by the control system, as indicated in FIG. 81, and this control system could be mechanical or electromechanical. Alternatively, the operation could be performed totally manually or a combination of the same. As indicated previously with the containing assembly 701b in its interconnected position, and with the valve element 723b open, the container 704b is locked in place so that it can not be removed for accidental spilling of the liquid.

Also as described previously with regard to the various seals and interface of the components, the passageway from the patient, through the tubes, through the plug and manifold assembly 716b, and into the container 704b is accomplished in a manner to avoid splashing, leakage, or aerosolization of the biofluid. Also, the engagement and interconnection of the container assembly 701b with a base assembly 703b and the subsequent operation is such that there is a totally sealed, fluid tight passageway, again to avoid any splashing, leakage, and/or aerosolization. Further, the washing/disinfecting/irrigating of the interior surfaces exposed to the biofluid can be accomplished without any splashing or leakage of the irrigating/wash/disinfecting fluid. Further, with the interlock of the lid 709b, and the lid 709b making a circumferential seal, the washing of the interior surfaces of the base assembly that come in contact with the biofluid can be washed separately.

It is apparent that various modifications can be made to the present invention without departing from the basic teachings thereof.

What is claimed is:

1. A system for collecting, transporting and disposing of biofluids in a manner to protect an operator and related support devises and systems from contact with potentially hazardous biofluids, said system comprising:
   a) a containing assembly comprising:
      i. a portable container defining a biofluid containing chamber;
      ii. a fluid inlet and outlet section having an intake/outlet opening and having a valve to selectively close said intake/outlet passageway;
      iii. a container assembly interconnecting section;
   b. a base assembly comprising:
      i. a base structure having a receiving area to receive said container in an operating position;
      ii. base interconnecting section arranged to interconnect with the container interconnecting section with the container in said operating position;
      iii. disposal portion defining a disposal passageway leading toward a disposal location;
   c. said containing assembly and said base assembly being arranged so that with said container in said operating position, and with interconnection of said container interconnecting section and said base interconnecting section, said containing assembly and said base assembly provide a discharge passageway from said chamber to said disposal passageway whereby said containing assembly can be positioned at a collecting location to receive biofluid, the container can be moved to the base assembly, the container interconnecting section and the base interconnecting section can be interconnected, and the biofluid delivered toward the disposal location.

2. The system as recited in claim 1, wherein said fluid inlet and outlet section comprises an inlet portion which defines at least one inlet passageway by which biofluid can be moved from a location exterior of said container into said containing chamber.

3. The system as recited in claim 1, wherein said fluid inlet and outlet section comprises a closure and fluid inlet device which has a closure housing configured and arranged to be positioned in a valve passageway when said valve is in its open position and having at least one inlet passageway therein for inflow of biofluid into said chamber.

4. The system as recited in claim 3, wherein said closure and fluid inlet device comprises a check valve to permit flow from an exterior location through said at least one passageway into said containing chamber, but to block flow from said containing chamber outwardly to said inlet passageway.

5. The system as recited in claim 4, wherein said closure and fluid inlet device comprises an outlet passageway permitting gaseous flow outwardly from said containing chamber to a suction source.

6. The system as recited in claim 1, comprising:
   a. said container defining a through opening leading from an exterior location through said container to said containing chamber;
   b. a closure and fluid inlet device comprising:
      i. a closure housing configured and arranged to fit into said through opening in sealing relationship;
      ii. an inlet positioned in said closure housing and defining an inlet passageway having an inlet end and an outlet end communicating with said chamber;
      iii. said inlet end having a connecting portion adapted to be connected to a biofluid tube [means] to carry biofluid;
   c. said closure and fluid inlet device and said container being arranged so that said closure and fluid inlet device can be removably mounted in container in a manner that in an operating mode where said closure and fluid inlet device is connected to said biofluid tube, said closure and fluid inlet device seals said through opening while permitting inflow of biofluids into said chamber, and said closure and fluid inlet device can be removed from said through opening with or without a suction tube connected thereto for disposal at a disposal location, whereby said containing assembly with said closure and fluid inlet device mounted in the container, and with at least one biofluid tube connected to said closure and fluid inlet device, collection of biofluids can be accomplished while isolating the biofluids from an area outside the containing assembly, and after collection, said closure and fluid inlet device can be removed from said container to another location for disposal or washing and sanitization for reuse.

7. The system as recited in claim 6, wherein said closure and fluid inlet device has an outlet leading from said chamber to an exterior location, said outlet being adapted to be connected to a suction tube that in turn would be connected to a vacuum source.

8. The system as recited in claim 7, wherein said closure and fluid inlet device has check valve operatively positioned with respect to said inlet to permit flow through said inlet into said chamber, but to prevent outflow through said inlet.

9. The system as recited in claim 8, wherein said closure housing has an outer housing section adapted to fit in sealing engagement with said through opening, and said inlet and outlet are provided as a tubular passageway inlet and a tubular passageway outlet in said housing.

10. The system as recited in claim 9, wherein a lower inlet portion of said tubular passageway outlet is positioned below a lower outlet end of said tubular passageway inlet, and said check valve is located at the lower end portion of the tubular passageway inlet, whereby biofluid flowing through said tubular passageway inlet is discharged into said container in a manner to alleviate possible outflow of biofluid particles into said tubular passageway outlet.

11. The system as recited in claim 10, wherein said check valve comprises a flexible generally planar flap member positioned at a lower end portion of said outer housing, with said flap member having an opening aligned with said tubular passageway outlet, but extending over the outlet end of the tubular passageway inlet, and being retained in a manner so as to be movable away from outlet end of the tubular passageway inlet means to permit inflow of biofluid.

12. The system as recited in claim 7, wherein said outlet has an outlet end, said closure and fluid inlet device further comprising a filter positioned within said closure and fluid inlet device proximate to the outlet end of said outer to collect biofluid possibly passing through said outlet means.

13. The system as recited in claim 12, wherein said filter is arranged so that when biofluid comes into contact with said filter, said filter expands to block said outlet.

14. The system as recited in claim 1, wherein said container has a through opening, and said fluid inlet and outlet section and said container assembly interconnecting section comprises a valve and connecting portion mounted in operative engagement with the through opening of said container, said valve and connecting portion comprising:
   a. a valve comprising:
      i. a valve housing;
      ii. a valve element bring moveable relative to said valve housing between an open position to provide a valve through opening from said connecting chamber, and a closed position closing said valve through opening;
   b. said container assembly interconnecting section arranged to come into interconnecting engagement with said base interconnecting section, with said container interconnecting mechanism of said valve and connecting portion being arranged to position the valve so that the valve through opening is in communication with the disposal passageway of the base assembly.

15. The system as recited in claim 14, wherein said valve element is rotatably mounted in said valve housing, said valve further comprising a valve actuator by which said valve element can be moved between said open position and closed position.

16. The system as recited in claim 15, wherein said valve element and said valve are arranged, relative to said base assembly in a manner that with the valve and connecting portion being interconnected with the base interconnecting section in an operating position, and with said valve element in its open position, the valve and connecting portion is not able to be moved toward a release position until said valve element has been moved to its closed position.

17. The system as recited in claim 16, wherein said valve actuator comprises at least in part a manually operably valve handle by which said valve element can be manually moved between its open and closed position, and said system is arranged so that with the container assembly interconnecting section in operative engagement with the base interconnecting section, movement of the valve element to the closed position also moves said valve actuator to a position preventing disengagement of said interconnecting mechanism.

18. The system as recited in claim 17, wherein said valve handle becomes positioned to prevent disengagement of said interconnecting portion.

19. The system as recited in claim 17, wherein movement of said container from an interconnecting position is blocked by said valve actuator coming into interlocking engagement with said base assembly to prevent movement of the container from the interconnecting position.

20. The system as recited in claim 17, wherein at least a portion of said valve actuator is positioned in said base assembly, and said valve handle is arranged so that when the container interconnecting portion into operative engagement with the base assembly, said valve handle comes into operative engagement with said portion of said valve actuator, said portion of said valve actuator and said valve handle being arranged so that when said valve actuator rotates the valve element to the open position, said valve actuator is moved to an interlocking position to prevent movement of the container from its interconnecting position to a disengaged position.

21. The system as recited in claim 17, wherein said container assembly interconnecting sections and the base interconnecting sections are arranged with a recess/protrusion interconnecting means, where one of said interconnecting section of the container interconnecting section and the base interconnecting section is provided with a recess, and the other of the container interconnecting sections and the base interconnecting section is provided with a protruding portion which comes into operative interconnecting engagement with the recess, whereby said valve and connecting means is moved rotatably relative to said base assembly to come into and out of interconnecting engagement.

22. The system as recited in claim 21, wherein said container interconnecting sections and said base interconnecting sections are arranged so that interconnecting movement of the container interconnecting section has a component of travel toward said base assembly, said container interconnecting section being arranged relative to said disposal portion of the base assembly so that said movement said container assembly interconnecting section causes it to come into sealing inter-engagement with said disposal portion so that the discharge opening is connected with the disposal passageway of the disposal portion in a sealing isolated relationship to provide a sealed disposal path.

23. The system as recited in claim 1, wherein said valve and said container interconnecting portion are arranged so that when said container interconnecting portion is moved into interconnecting engagement along an interconnecting path of travel, an interlocking device blocks movement of container along said interconnecting path to move out of interconnecting engagement.

24. The system as recited in claim 1, wherein:
   a) said valve comprises a valve housing having first and second housing openings on first and second sides of said valve housing;
   b) said valve element being rotatably mounted in said valve housing between an open position where said valve opening is aligned with said valve housing openings, and a closed position where said opening is out of alignment with said valve housing openings;
   c) first and second circumferential seals positioned around, respectively, said first and second housing openings so as to form a seal around each of said housing openings, said first and second seals also being in sealing engagement with said valve element, whereby with said valve element in its open position, said first and second seals form a fluid tight passageway through said valve, and when said valve element is in its closed position, a surface portion of said valve element is positioned in its related housing opening so as to come into contact with said biofluid in the container, and with said valve element being moved form its closed position to the open position, the valve element surface portion exposed to said biofluid moves by its related circumferential seal to wipe said seal surface portion clean of the biofluid, and thus preventing biofluid from leaking into said valve housing.

25. A removable closure and inlet device particularly adapted to be used in a system for collecting and disposing of biofluids from a patient, where said system comprises:
   a. a containing assembly comprising:
      i. a portable container having an upper end and a lower end and defining a biofluid containing chamber;
      ii. an inlet and outlet section located at the upper end of the container having a container opening to receive biofluid from the patient and direct the biofluid into the containing chamber, and to discharge the biofluid from the chamber, said inlet and outlet section comprising a valve positioned at the upper end and having a through valve passageway, leading said valve comprising a valve housing and a valve element;
      iii. a container interconnecting portion.
   b. a base collecting section comprising:
      i. base structure having a receiving area to receive said container in operating discharge position;
      ii. a base interconnecting portion arranged to interconnect with the container, interconnecting portion with the container in said operating discharged position;
      iii. a disposal portion defining a disposal passageway leading toward a disposal location;
   said closure and inlet device comprising:
      a. a closure housing configured and arranged to be positioned in the container opening in sealing relationship to close said container opening;
      b. at least one inlet passageway extending through said closure housing from a location exterior of said container to said containing chamber, thus permitting fluid from an exterior location to flow into said containing chamber
   whereby said closure and inlet device can be positioned in said through passageway to block said through passageway and prevent escape of fluid in said container while permitting an inflow of biofluid from the patient into the containing chamber, and said closure and inlet device can be removed from the through passageway to permit the container to be placed in the operating position to permit flow of biofluid from the container into the disposal passageway.

26. A method for collecting and disposing of biofluids from a patient, said system comprising:
   a. locating a containing assembly at a collecting location relative to said patient, wherein said containing assembly comprises a portable container defining a biofluid containing chamber;
   b. directing biofluid from the patient through an inlet and outlet section of said containing assembly into the containing chamber;
   c. providing a base assembly which comprises a base structure having a receiving area to receive said container in an operating position, and providing a disposal passageway leading to a disposal location;
   d. with a valve of said inlet and outlet section closed, placing said container at said receiving area and interconnecting said container with said base assembly with the container in said operating position;
   e. opening said valve and causing said biofluid in said containing chamber to move through said inlet and outlet section into said base assembly and through said disposal passageway toward said disposal location.

27. The method as recited in claim 26, wherein when the containing assembly is placed in the operating position in a manner that the biofluid flows by gravity-flow from the containing chamber to the disposal passageway.

28. The method as recited in claim 26, wherein the containing assembly has an upper end portion and a lower end portion, said method further comprising locating the container assembly in a collecting position in which biofluid is received into the collecting chamber, and the upper end portion of the containing assembly is positioned above the lower end portion of the containing assembly and then positioning the container unit in a discharge position so that the upper end of the containing assembly is positioned at a lower elevation than the lower end portion of the containing unit, with said discharge passageway being positioned at the upper end portion f the containing assembly so that in the discharge position, the biofluid flows by gravity through the discharge passageway tot he disposal passageway.

29. The method as recited in claim 26, further comprising placing a removable closure and fluid inlet device in a discharge opening of said inlet and outlet section and directing said biofluid through inlet opening of said closure and inlet device into the containing chamber.

30. The method as recited in claim 29, further comprising having the valve in its open position when the closure and fluid inlet device is positioned in the discharge passageway, and with said closure and fluid inlet device out of said discharge passageway, then closing the valve member.

31. The method as recited in claim 29, further providing said closure and fluid inlet device with an outlet passageway removing gaseous material from said container unit by suction.

32. The method as recited in claim 29, further comprising providing a plurality of said closure and fluid inlet devices, and using one of said closure and inlet devices to collect biofluid, and after discharge of the biofluid using another of the closure and inlet devices for collection of a second quantity of biofluid.

33. The closure and inlet device as recited in claim 25, wherein:
   a) said closure housing has lengthwise axis, a predetermined length dimension, an upper portion, and a lower portion, the lengthwise dimension of the closure housing being such that a lower end portion of the closure housing extends into the discharge passageway downwardly at least to said valve element;
   b) said closure housing having a sealing surface portion positioned and arranged to be in sealing engagement with an interior sealing surface portion of the container unit at a location at least as low as the valve passageway with the valve element in the open position to provide a seal to substantially isolate a portion of the said container opening above said valve element from said biofluid in said chamber,
   whereby with the closure and inlet device isolates the biofluid in the container so that the closure and inlet device can be removed form the container, the valve can be closed, and the container safely moved to the base assembly for disposal of the fluid.

34. The closure and inlet device of claim 33, wherein said closure housing extends through said valve passageway when in its container closing position, and the sealing surface portion of the closure housing is positioned at least as low as a lower portion of the valve passageway.

35. The closure and inlet device as recited in claim 33 wherein the closure housing has a positioning device which, with the closure and inlet device being placed in its container closing position, positions the closure and inlet device to cause the sealing surface portion of the closure housing to be in proper sealing engagement with the interior sealing surface portion of the container.

36. The closure and inlet device as recited in claim 35, wherein said positioning device comprises an interengaging component mounted to the closure housing and positioned to engage a matching interconnecting component mounted to the container in a manner to cause the closure and inlet device to be axially positioned so that it is in its proper sealing position.

37. The closure and inlet device as recited in claim 36, wherein said positioning device is at a location above a location of said sealing surface portion of the closure housing to substantially isolate said positioning device from the biofluid, and said closure housing extends through said valve passageway when in its container closing position, and the sealing surface portion of the closure housing is positioned at least as low as a lower portion of the valve passageway.

38. The closure and inlet device as recited in claim 37, wherein said positioning device is at a location above a location of said valve element when the closure and inlet device is in its container closing position.

39. The closure and inlet device as recited in claim 38, wherein said positioning device comprises an interengaging component mounted to the closure housing and positioned to engage a matching interconnecting component mounted of the container in a manner to cause the closure and inlet device to be axially positioned so that the closure and inlet device is in its proper sealing position.

40. The closure and inlet device as recited in claim 37, wherein said positioning device comprises an interengaging component mounted to the closure housing and positioned to engage a matching interconnecting component mounted of the container in a manner to cause the closure and inlet device to be axially positioned so that the closure and inlet device is in its proper sealing position.

41. The closure and inlet device as recited in claim 33, wherein said closure and inlet device is arranged so that the positioned device comes into interengagement by rotation of the closure and inlet device.

42. The closure and inlet device as recited in claim 41, wherein said closure and inlet device is arranged, relative tot he container so that rotation of the closure housing causes a cam action to cause axial movement of the closure and inlet device to its proper sealing position.

43. The closure and inlet device as recited in claim 42, wherein said positioning device is at a location above a location of said sealing surface portion of the closure housing to substantially isolate said positioning device from the biofluid.

44. The closure and inlet device as recited in claim 43, wherein said positioning device is at a location above a location of said valve element when the closure and inlet device is in its container closing position.

45. The closure and inlet device as recited in claim 33, wherein said sealing surface of the closure housing comprises at least in part a sealing surface portion positioned at a lower perimeter and portion of the closure housing and said sealing surface portion has at least in part a downwardly facing directional component to come into engagement with a laterally and inwardly extending annular surface portion of the interior sealing surface portion of the container positioned at least as low as a lower portion of said valve element.

46. The closure and inlet device as recited in claim 45, wherein the closure and inlet device has a positioning device which, with the closure and inlet device being placed in its container closing position, positions the closure and inlet device to cause the sealing surface portion of, the closure housing to be in proper sealing engagement with the interior sealing surface portion of the container, said positioning device comprising one of two interengaging components which become interengaged to cause axial movement of the closure and inlet device downwardly to cause the sealing surface portion of the closure housing to come into sealing engagement with the inwardly extending surface portion of the interior sealing surface portion of the container.

47. A system for collecting, transporting and disposing of biofluids in a manner to protect an operator and related support devises and systems from contact with potentially hazardous biofluids, said system comprising:
   a) at least one containing assembly comprising:
      i. a portable container defining a biofluid containing chamber;
      ii. a fluid inlet and outlet section having an inlet/outlet opening to receive biofluids from a patient and direct the biofluid into the containing chamber, and to discharge the biofluid from the chamber;
      iii. a container assembly interconnecting section.
   b) a plurality of recyclable and/or disposable closure and fluid inlet devices, each of which has a closure housing adapted to be removably positioned to close said intake/discharge opening and having at least one inlet passageway therein for inflow of biofluid into said container valve operable closure selectively close and open said inlet/outlet opening;
   c) a base assembly comprising:
      i. a base structure having a receiving area to receive said container in an operating position;
      ii. base interconnecting section arranged to interconnect with the container interconnecting section with the container in said operating position;
      iii. a disposal portion defining a disposal passageway leading toward a disposal location;
   d) said containing assembly and said base assembly being arranged so that with said container in said operating position, and with interconnection of said container interconnecting section and said base interconnecting section, said containing assembly and said base assembly provide a discharge passageway from said chamber to said disposal passageway whereby said containing assembly with a selected one of said closure and fluid inlet device in said inlet/outlet opening can be positioned at a collecting location to receive biofluid, the closure and fluid inlet device can be removed from the container, the container can be moved to the base assembly, the container interconnecting section and the base interconnecting section can be interconnected, the biofluid delivered toward the disposal location, a second closure and fluid inlet device can be positioned in the inlet/outlet opening and additional biofluid be directed into the container.

48. A combination for collecting, transporting and disposing of biofluids in a manner to protect an operator and related support devises and systems from contact with potentially hazardous biofluids, said combination comprising:
  a) at least one containing assembly comprising:
    i. a portable container defining a biofluid containing chamber;
    ii. a fluid inlet and outlet section having an inlet/discharge to receive biofluids from a patient and direct the biofluid into the containing chamber, and to discharge the biofluid from the chamber;
    iii. a selectively operable closure valve to close and open said inlet/discharge opening.
  b) closure and fluid inlet device which has a closure housing adapted to be removably positioned to said inlet/discharge opening and having at least one inlet passageway therein for inflow of biofluid into said container;
  c) said valve, said inlet discharge opening and said closure and fluid inlet device being arranged so that with the valve in the open position, the closure and fluid inlet device is able to be positioned in the inlet discharge opening to close an outlet passageway of the valve, and with the closure and fluid inlet device removed from the inlet/discharge opening the valve can be closed to close the inlet/discharge opening and safely contain the biofluid in the chamber during movement of the container to a disposal location, and then with the container in a desired disposal position the valve can be opened and cause discharge of the biofluid into a desired disposal inlet.

49. A system for collecting transporting and disposing of biofluids in a manner to protect an operator and related support devises and systems from contact with potentially hazardous biofluids, said system comprising:
  a) a containing assembly comprising:
    i. a portable container which has a biofluid inlet at an upper portion of the container defining a biofluid containing chamber;
    ii. a fluid inlet and outlet section and which, with the container in a generally upright position receives biofluid from a patient and directs the biofluid into the containing chamber, from the chamber;
    iii. container assembly interconnecting section;
  b) a base assembly comprising:
    i. a base structure having a receiving area to receive said container in a generally inverted operating position;
    ii. base interconnecting section arranged to interconnect with the container interconnecting section is with the container in said generally inverted operating position;
    iii. a disposal portion defining a disposal passageway leading toward a disposal location;
  c) said containing assembly and said base assembly being arranged so that with said container in said generally inverted operating position, and with interconnection of said container interconnecting section and said base interconnecting section, said containing assembly and said base assembly provide a discharge passageway from said chamber to said disposal passageway whereby said containing assembly can be positioned in a said generally upright position at a collecting location to receive biofluid, and the container can be moved to the base assembly, and in said generally inverted position the container interconnecting section and the base interconnecting section can be interconnected, and the biofluid delivered toward the disposal passageway.

50. A method for collecting and disposing of biofluids from a patient, said system comprising:
  a) locating a containing section at a collection location relative to said patient in a generally upright intake position, wherein said containing section comprises a portable container having an inlet at an upper portion thereof and defining a biofluid containing chamber;
  b) directing biofluid from the patient through said inlet of said containing section into the: containing chamber;
  c) providing a base section which comprises a base structure having a receiving area to receive said container in a generally inverted discharge position, and providing a base disposal passageway leading to a disposal location;
  d) placing said container at said receiving area in its inverted discharge position and interengaging said container with said base assembly with the container;
  e) causing said biofluid in said containing chamber to move through a discharge opening of said container into said base section and through said base disposal passageway to said disposal location.

51. A method for collecting and disposing of biofluids from a patient, said system comprising:
  a) locating a portable container at a collecting location relative to said patient, wherein said container has a biofluid containing chamber and an outlet opening leading from said chamber;
  b) positioning a closure and fluid inlet device in said outlet opening and directing biofluid from the patient through an inlet of said closure and inlet device into the containing chamber;
  c) removing said closure and inlet device from said outlet opening and operating a closure valve of said container to close said outlet opening'
  d) providing a base assembly which comprises a base structure having a receiving area to receive said container in an operating discharge position, and providing a base disposal passageway leading to a disposal location;
  e) placing said container at said receiving area and interengaging said container with said base section with the container in said operating discharge position;
  f) opening said valve and causing said biofluid in said containing chamber to move through said discharge opening into said base assembly and through said disposal passageway to said disposal location.

52. A method for collecting and disposing of biofluids from a patient, said system comprising:
  a) locating a containing assembly at a collecting location relative to said patient, wherein said containing assembly comprises a portable container defining a biofluid containing chamber and having an intake/discharge opening;
  b) providing a plurality of removable closure and fluid inlet devices and positioning one of said closure and inlet devices in said intake/discharge opening;
  c) directing biofluid from the patient through said one of said closure and fluid inlet devices into the containing chamber;
  d) removing said one of said closure and fluid inlet devices from said container for disposal or recycling;
  e) closing said intake/discharge opening and moving said container to a receiving area of a base assembly arranged to receive said container in an operating discharge position, and provide a disposal passageway leading to a disposal location;

f) opening said intake/discharge opening and said biofluid said containing chamber to move into said base assembly and through said disposal passageway toward said disposal location;

g) removing the container from the base assembly, placing a second one of said closure and inlet devices in said intake/discharge opening and directing further biofluid into said container for disposal.

53. A method for collecting and disposing of biofluids from a patient, said system comprising:

a) locating a portable container at a collecting location relative to said patient, wherein said container has a biofluid containing chamber, and outlet opening leading from said chamber, and a valve to selectively close said outlet opening;

b) positioning a closure and fluid inlet device in said outlet opening and directing biofluid from the patient through an inlet of said closure and fluid inlet device into the containing chamber;

c) removing said closure and inlet device from said outlet opening and operating said valve to close the outlet opening;

d) positioning the container in a disposal position at a disposal inlet of a disposal structure, and opening said valve and causing the biofluid to move through the outlet opening tot he disposal inlet.

* * * * *

UNITED STATES PATENT AND TRADEMARK OFFICE
CERTIFICATE OF CORRECTION

PATENT NO. : 6,488,675 B1  Page 1 of 1
APPLICATION NO. : 09/418895
DATED : December 3, 2002
INVENTOR(S) : Fred R. Radford et al.

It is certified that error appears in the above-identified patent and that said Letters Patent is hereby corrected as shown below:

On the title page item (76), line 7, add inventor, --Wayne Willich 14150 NE 20$^{th}$ Street, #371 Bellevue, WA (US) 98007--.

Signed and Sealed this

Second Day of January, 2007

JON W. DUDAS
*Director of the United States Patent and Trademark Office*